US008226945B2

(12) United States Patent
Ebens, Jr. et al.

(10) Patent No.: US 8,226,945 B2
(45) Date of Patent: Jul. 24, 2012

(54) ANTIBODIES AND IMMUNOCONJUGATES AND USES THEREFOR

(75) Inventors: Allen J. Ebens, Jr., San Carlos, CA (US); Alane M. Gray, Brisbane, CA (US); Wei-Ching Liang, Foster City, CA (US); Yan Wu, Foster City, CA (US); Shang-Fan Yu, Milpitas, CA (US)

(73) Assignee: Genentech, Inc., South San Francisco, CA (US)

( * ) Notice: Subject to any disclaimer, the term of this patent is extended or adjusted under 35 U.S.C. 154(b) by 68 days.

(21) Appl. No.: 12/939,533

(22) Filed: Nov. 4, 2010

(65) Prior Publication Data

US 2011/0142859 A1 Jun. 16, 2011

Related U.S. Application Data

(63) Continuation of application No. 11/754,899, filed on May 29, 2007.

(60) Provisional application No. 60/809,328, filed on May 30, 2006, provisional application No. 60/908,941, filed on Mar. 29, 2007, provisional application No. 60/911,829, filed on Apr. 13, 2007.

(51) Int. Cl.
*A61K 39/395* (2006.01)
*A61K 39/00* (2006.01)
*C07K 16/28* (2006.01)
*C07K 16/46* (2006.01)
*C12P 21/08* (2006.01)

(52) U.S. Cl. ............... 424/130.1; 424/133.1; 424/141.1; 424/142.1; 424/143.1; 424/178.1; 424/179.1; 424/181.1; 424/183.1; 530/387.1; 530/387.3; 530/388.15; 530/388.22; 530/391.1; 530/391.3; 530/391.7; 530/391.9

(58) Field of Classification Search ..................... None
See application file for complete search history.

(56) References Cited

U.S. PATENT DOCUMENTS

| | | | |
|---|---|---|---|
| 4,970,198 A | 11/1990 | Lee et al. |
| 4,975,278 A | 12/1990 | Senter et al. |
| 5,079,233 A | 1/1992 | Lee |
| 5,208,020 A | 5/1993 | Chari et al. |
| 5,416,064 A | 5/1995 | Chari et al. |
| 5,585,089 A | 12/1996 | Queen et al. |
| 5,606,040 A | 2/1997 | McGahren et al. |
| 5,693,762 A | 12/1997 | Queen et al. |
| 5,739,116 A | 4/1998 | Hamann et al. |
| 5,767,237 A | 6/1998 | Sakakibara et al. |
| 5,767,285 A | 6/1998 | Hamann et al. |
| 5,773,001 A | 6/1998 | Hamann et al. |
| 5,789,554 A | 8/1998 | Leung et al. |
| 6,124,431 A | 9/2000 | Sakakibara et al. |
| 6,194,551 B1 | 2/2001 | Idusogie et al. |
| 6,441,163 B1 | 8/2002 | Chari et al. |
| 7,084,257 B2 | 8/2006 | Deshpande |

| | | |
|---|---|---|
| 2004/0001827 A1 | 1/2004 | Dennis |
| 2004/0018194 A1 | 1/2004 | Francisco et al. |
| 2005/0169933 A1 | 8/2005 | Steeves et al. |
| 2005/0238649 A1 | 10/2005 | Doronina et al. |
| 2005/0238650 A1 | 10/2005 | Crowley et al. |
| 2005/0244828 A1 | 11/2005 | Kreitman et al. |
| 2005/0276812 A1 | 12/2005 | Ebens et al. |
| 2008/0050310 A1 | 2/2008 | Ebens et al. |
| 2009/0053226 A1 | 2/2009 | Crowley |
| 2011/0045005 A1 | 2/2011 | Crowley |

FOREIGN PATENT DOCUMENTS

| | | |
|---|---|---|
| EP | 0425235 A2 | 9/1996 |
| EP | 1 391 213 A1 | 2/2004 |
| EP | 1689432 | 12/2009 |
| WO | 99/51642 | 10/1999 |
| WO | 00/12130 | 3/2000 |
| WO | 00/42072 | 7/2000 |
| WO | 01/45746 A2 | 6/2001 |
| WO | 01/74388 | 10/2001 |
| WO | 02/098883 | 12/2002 |
| WO | 03/043583 A2 | 5/2003 |
| WO | 03/062401 | 7/2003 |
| WO | 03/072036 A2 | 9/2003 |
| WO | 03/072736 A2 | 9/2003 |
| WO | 03/074567 | 9/2003 |
| WO | 03/093320 A2 | 11/2003 |
| WO | 2004/010957 | 2/2004 |
| WO | 2005/037992 | 4/2005 |
| WO | 2005/049075 A2 | 6/2005 |
| WO | 2005/081711 A2 | 9/2005 |
| WO | 2005/117986 | 12/2005 |
| WO | WO2005/113003 | 12/2005 |
| WO | 2006/034488 A2 | 3/2006 |
| WO | 2006/042240 A2 | 4/2006 |
| WO | 2007/140371 | 12/2007 |

OTHER PUBLICATIONS

Szatrowski et al. et al., "Lineage specific treatment of adult patients with acute lymphoblastic leukemia in first remission with anti-B4-blocked ricin or high-dose cytarabine: Cancer and Leukemia Group B Study 93" *Cancer* 97(6):1471-1480 (Mar. 15, 2003).

Herrera et al. et al., "Treatment of SCID/human B cell precursor ALL with anti-CD19 and anti-CD22 immunotoxins" *Leukemia* 17(2):334-338 (Feb. 2003).

Bolognesi et al., "Evaluation of immunotoxins containing single-chain ribosome-inactivating proteins and an anti-CD22 monoclonal antibody (OM124): In vitro and in vivo studies" *British Journal of Haematology* 101(1):179-188 (Apr. 1998).

Mattes et al., "The advantage of residualizing radiolabels for targeting b-cell lymphomas with a radiolabeled anti-CD22 monoclonal antibody" *International Journal of Cancer*:429-435 (May 1, 1997).

Miura et al. et al., "Molecular cloning of a human RP105 homologue and chromosomal localization of the mouse and human RP105 genes (Ly64 and LY64" *Genomics* 38(3):299-304 (Dec. 15, 1996).

(Continued)

*Primary Examiner* — Phuong Huynh
(74) *Attorney, Agent, or Firm* — Bonny G. Yeung

(57) ABSTRACT

Anti-CD22 antibodies and immunoconjugates thereof are provided. Methods of using anti-CD22 antibodies and immunoconjugates thereof are provided.

25 Claims, 31 Drawing Sheets

OTHER PUBLICATIONS

Tobinai kensei, "Rituximab and other emerging antibodies as molecular target-based therapy of lymphoma" *Int J Clin Oncol* 8(4):212-223 (Aug. 2003).

Yamashita et al., "Activation mediated by RP105 but not CD40 makes normal B cells susceptible to anti-IgM-induced apoptosis: a role for Fc receptor coligation" *J Exp Med.* 184(1):113-120 (Jul. 1, 1996).

Cesano et al., "CD22 as a target of passive immunotherapy" *Seminars in Oncoloy* 30(2):253-257 (Apr. 1, 2003).

Miyake et al. et al., "RP105, a novel B cell surface molecule implicated in B cell activation, is a member of the leucine-rich repeat protein family" *J Immunol* 154(7):3333-3340 (Apr. 1, 1995).

Polson et al., "Anti-CD22-DM1: an antibody-drug conjugate with a stable linker for the treatment of non-Hodgkin's lymphoma" *Leukemia* 24(9):1566-1573 (Jul. 1, 2010).

"Gemtuzumab Ozogamicin" *Drugs of the Future* 25 (7):686-692 (2000).

Amlot et al., "A phase I study of an anti-CD22-deglycosylated ricin A chain immunotoxin in the treatment of B-cell lymphomas resistant to conventional therapy" *Blood* 82(9):2624-33 (Nov. 1, 1993).

Baldwin et al., "Monoclonal Antibodies in Cancer Treatment" *Lancet* pp. 603-605 (Mar. 15, 1986).

Bhaskar et al., "E-Selectin Up-Regulation Allows for Targeted Drug Delivery in Prostate Cancer" *Cancer Research* 63:6387-6394 (2003).

Carnahan, J., et al., "Epratuzumab, a Humanized Monoclonal Antibody Targeting CD22" *Clinical Cancer Research* 9:3982-3990 (Sep. 1, 2003).

Cesano et al., "Differential Expression of CD22 in Indolent and Aggresive Non-Hodgkin's Lymphoma (NHL): Implications for Targeted Immunotherapy" *Blood* (Abstract #1358) 100:350a (2002).

Chari et al., "Immunoconjugates Containing Novel Maytansinoids: Promising Anticancer Drugs" *Cancer Research* 52:127-131 (Jan. 1992).

Chen et al., "Selection and Analysis of an Optimized Anti-VEGF Antibody: Crystal Structure of an Affinity-matured Fab in Comples with Antigen" *Journal of Molecular Biology* 293 (4) : 865-881 (1999).

De Pascalis et al., "Grafting of "abbreviated" complementarity-determining regions containing specificity-determining residues essential for ligand contact to engineer a less immunogenic humanized monoclonal antibody" *J. Immunol.* 169:3076-3084 (2002).

Dennis et al., "Albumin binding as a general strategy for improving the pharmacokinetics of proteins" *Journal of Biological Chemistry* 277 (38):35035-35043 (Sep. 20, 2002).

DiJoseph et al., "Antibody-targeted chemotherapy with CMC-544: a CD22-targeted immunoconjugate of calicheamicin for the treatment of B-lymphoid malignancies" *Blood* 103:1807-1814 (2004).

Dorken et al., "HD39 (B3), a B lineage-restricted antigen whose cell surface expression is limited to resting and activated human B lymphocytes" *J. Immunol.* 136(12):4470-4479 (Jun. 15, 1986).

Doronina et al., "Development of potent monoclonal antibody auristatin conjugates for cancer therapy" *Nature Biotechnology* 21:778-784 (2003).

Engel et al., "Identification of the Ligand-binding Domains of CD22, a Member of the Immunoglobulin Superfamily that Uniquely Binds a Sialic Acid-dependent Ligand" *Journal of Experimental Medicine* 181(4):1581-1586 (Apr. 1, 1995).

Engel et al., "The same epitope on CD22 of B lymphocytes mediates the adhesion of erythrocytes, T and B lymphocytes, neutrophils, and monocytes" *Journal of Immunology* 150(11):4719-4732 (Jun. 1, 1993).

Fisher et al., "Current therapeutic paradigm for the treatment of non-Hodgkin's lymphoma" *Semin Oncol.* 27(6 Suppl 12):2-8 (2000).

Francisco et al., "cAClO-vcMMAE, an anti-CD30 monomethyl auristatin E conjugate with potent and selective antitumor activity" *Blood* 102:1458-1465 (2003).

Ghetie et al., "Evaluation of ricin A chain-containing immunotoxins directed against CD19 and CD22 antigens on normal and malignant human B-cells as potential reagents for in vivo therapy" *Cancer Research* 48(9):2610-2617 (May 1, 1988).

Griffiths et al., "90Y-DOTA-hLL2: an agent for radioimmunotherapy of non-Hodgkin's lymphoma" *J Nucl Med.* 44(1):77-84 (Jan. 2003).

Grillo-Lopez et al., "Monoclonal antibodies: a new era in the treatment of non-Hodgkin's lymphoma" *Current Pharmaceutical Biotechnology* 2:301-311 (2001).

Harris et al., "The World Health Organization classification of neoplasms of the hematopoietic and lymphoid tissues: report of the Clinical Advisory Committee meeting—Airlie House, Virginia, Nov. 1997" *Hematol J.* 1:53-66 (2000).

Hinman et al., "Preparation and Characterization of Monoclonal Antibody conjugates of the Calicheamicins: A Novel and Potent Family of Antitumor Antibiotics" *Cancer Research* 53:3336-3342 (Jul. 15, 1993).

Holm, et al., "Functional mapping and single chain construction of the anti-cytokeratin 8 monoclonal antibody TS1" *Molucular Immunology* 44:1075-1084 (2007).

Idusogie et al., "Mapping of the Clq Binding Site on Rituxan, A Chimeric Antibody with a Human IgG1 Fc" *J Immunol.* 164(8):4178-4184 (2000).

Jemal et al., "Cancer Statistics, 2002" *CA-A Cancer Journal for Physicians* 52:23-47 (2002).

Juweid et al., "Pharmacokinetics, dosimetry, and initial therapeutic results with 131I- and (111)In- /90Y-labeled humanized LL2 anti-CD22 monoclonal antibody in patients with relapsed, refractory non-Hodgkin's lymphoma" *Clin Cancer Res.* 5(10 Suppl):3292s-3303s (Oct. 1999).

Kerr et al., "Listeriolysin O Potentiates Immunotoxin and Bleomycin Cytotoxicity" *Bioconjugate Chem.* 8 (6):781-784 (Nov. 1997).

Klussman et al., "Secondary mAb-vcMMAE Conjugates Are Highly Sensitive Reporters of Antibody Internalization via the Lysosome Pathway" *Bioconjugate Chemistry* 15(4):765-773 (2004).

Kreitman et al., "Efficacy of the anti-CD22 recombinant immunotoxin BL22 in chemotherapy-resistant hairy-cell leukemia" *N Engl J Med.* 345(4):241-247 (Jul. 26, 2001)

Law et al., "CD70 is expressed on renal cell carcinoma and is a potential target for tumor cell elimination by antibody-drug conjugates" *Proceedings of the American Association for Cancer Research* 45 (2004).

Leonard et al., "Epratuzumab, a Humanized Anti-CD22 Antibody, in Aggressive Non-Hodgkin's Lymphoma: Phase I/II Clinical Trial Results" *Clinical Cancer Research* 10:5327-5334 (Aug. 15, 2004).

Linden et al., "Radioimmunotherapy using 131I-labeled anti-CD22 monoclonal antibody (LL2) in patients with previously treated B-cell lymphomas" *Clin Cancer Res.* 5(10 Suppl):3287s-3291s (Oct. 1999).

Linden, et al., "Dose-Fractionated Radioimmunotherapy in Non-Hodgkin's Lymphoma Using DOTA-Conjugated, 90Y-Radiolabeled, Humanized Anti-CD22 Monoclonal Antibody, Epratuzumab" *Cancer Therapy: Clinical* 11:5215-5222 (Jul. 2005).

Liu et al., "Eradication of Large Colon Tumor Xenografts by Targeted Delivery of Maytansinoids." *Proc. Natl. Acad, Sci, USA* 93:8618-8623 (1996).

Lode et al., "Targeted Therapy with a Novel Enediyene Antibiotic Calicheamicin θII Effectively Suppresses Growth and Dissemination of Liver Metastases in a Syngeneic Model of Murine Neuroblastoma" *Cancer Research* 58:2925-2928 (Jul. 15, 1998).

MacCallum et al., "Antibody-antigen Interactions: Contact Analysis and Binding Site Topography" *J. Mol. Biol.* 262:732-745 (1996).

Mandler et al., "Immunoconjugates of Geldanamycin and Anti-HER2 Monoclonal Antibodies: Antiproliferative Activity on Human Breast Carcinoma Cell Lines" *Journal of the National Cancer Institute* 92(19):1573-1581(Oct. 4, 2000).

Mandler et al., "Modifications in synthesis strategy improve the yield and efficacy of geldanamycin—herceptin immunoconjugates" *Bioconjugate Chem.* 13:786-791 (2002).

Mandler et al., "Synthesis and Evaluation of Antiproliferative Activity of a Geldanamycin-Herceptin(tm) Immunoconjugate" *Bioorganic & Medicinal Chemistry Letters* 10:1025-1028 (2000).

Mansfield et al., "Recombinant RFB4 immunotoxins exhibit potent cytotoxic activity for CD22-bearing cells and tumors" *Blood* 90(5):2020-2026 (Sep. 1, 1997)

Mao et al., "EphB2 as a Therapeutic Antibody Drug Target for the Treatment of Colorectal Cancer" *Cancer Research* 64:781-788 (2004).

May et al., "Selective killing of normal and neoplastic human B cells with anti-CD19- and anti-CD22-ricin A chain immuno-toxins" *Chemical Abstracts* 106:35-36 (1987).

Meyer et al., "Recent Advances in Antibody Drug Conjugates for Cancer Therapy" *Annual Reports in Medicinal Chemistry*, Chapter 23, 38:229-237 (2003).

Nakamura et al., "Stereochemistry and Total Synthesis of Dolastatin E" *Tetrahedron Letters* 36(28):5059-5062 (1995).

Niculescu-Duvaz and Springer, "Antibody-Directed Enzyme Prodrug Therapy (ADEPT): A Review" *Adv. Drg. Del. Rev.* 26:151-172 (1997).

Otipoby et al., "CD22 regulates thymus-independent responses and the lifespan of B cells" *Nature* 384(6610):634-637 (Dec. 19, 1996).

Pawlak-Byczkowska et al., "Two new monoclonal antibodies, EPB-1 and EPB-2, reactive with human lymphoma" *Cancer Research* 49(16):4568-77 (Aug. 15, 1989).

Pettit et al., "Antineoplastic agents 365. Dolastatin 10 SAR probes" *Anti-Cancer Drug Design* 13:243-277 (1998).

Pettit et al., "Isolation of dolastatins 10.15 from the marine mollusc, *Dolabella auricularia*" *Tetrahedron Letters* 49(41):9151-9170 (1993).

Pettit, "The Dolastatins" *Progress in the Chemistry of Organic Natural Products*, W. Hertz at al., SpringerWienNewYork vol. 70:1-79 (1997).

Riemer et al., "Matching of trastuzumab (Herceptin) epitope mimics onto the surface of Her-2/neu—a new method of epitope definition" *Molecular Immunology* 42:1121-1124 (2005).

Roitt et al., "IgG Structure in Relation to Function" *Immunology (second edition), Gower Medical Publishing New York* pp. 5.8 and 5.9 (1989).

Rowland et al., "Drug Localisation and Growth Inhibition Studies of Vindesine-Monoclonal anti-CEA Conjugates in a Human Tumour Xenograft" *Cancer Immunol. Immunother.* 21:183-187 (1986).

Rudikoff, et al:, "Single amino acid substitution altering antigen-binding specificity" *Proc. Natl. Acad. Sci. USA* 79:1979-1983 (1982).

Sanderson et al., "In vivo Drug-Linker Stability of an Anti-CD30 Dipeptide-Linked Auristatin Immunoconjugate" *Clinical Cancer Research* 11:843-852 (Jan. 2005).

Sato et al., "CD22 is both a positive and negative regulator of B lymphocyte antigen receptor signal transduction: altered signaling in CD22-deficient mice" *Immunity* 5(6):551-562 (Dec 1996).

Sato et al., "CD22 negatively and positively regulates signal transduction through the B lymphocyte antigen receptor" *Seminars in Immunology* 10(4):287-297 (Aug. 1998).

Senter et al., "Immunoconjugates comprised of drugs with impaired cellular permeability: a new approach to targeted therapy, Abstract No. 623, presented on Mar. 28, 2004, Proceedings of the American Association for Cancer Research" 45:36 (2004).

Shields et al., "High Resolution Mapping of the Binding Site on Human IgG1 for FcγRI, FcγRII, FcγRIII, and FcRn and Design of IgG1 Variants with Improved Binding to the FcγR" *Journal of Biological Chemistry* 276(9):6591-6604 (2001).

Sone et al., "Dolabellin, a Cytotoxic Bisthiazole Metabolite from the Sea Hare *Dolabella auricularia*: Structural Determination and Synthesis" *Journal Org. Chem.* 60:4474-4781(1995).

Stamenkovic et al., "The B-cell antigen CD22 mediates monocyte and erythrocyte adhesion" *Nature* 345:74-77 (1990).

Stancovski et al., "Mechanistic Aspects of the Opposing Effects of Monoclonal Antibodies to the ERBB2 Receptor on Tumor Growth" *Proc. Natl. Acad. Sci. USA* 88(19):8691-8695 (Oct. 1, 1991).

Stein et al., "Epitope specificity of the anti-(B cell lymphoma) monoclonal antibody, LL2" *Cancer Immunol Immunother.* 37(5):293-298 (Oct. 1993).

Syrigos et al., "Antibody Directed Enzyme Prodrug Therapy (ADEPT): A Review of the Experimental and Clinical Considerations" *Anticancer Research* 19:605-613 (1999).

Thorpe, "Antibody Carriers of Cytotoxic Agents in Cancer Therapy: A Review" *Monoclonal Antibodies 84: Biological and Clinical Applications*, A. Pinchera, G. Doria, F. Dammacco & Bargellesi, Editrice Kurtis s.r.l. pp. 475-506 (1985).

Vajdos et al., "Comprehensive functional maps of the antigen-binding site of an anti-ErbB2 antibody obtained with shotgun scanning mutagenesis" *J Mol Biol.* 320:415-428 (2002).

Wilson et al., "cDNA Cloning of the B Cell Membrane Protein CD22: A Mediator of B-B Cell Interactions" *Journal of Experimental Medicine* 173:137-146 (Jan. 1991).

Wiseman et al, "Ibritumomab tiuxetan radioimmunotherapy for patients with relapsed or refractory non-Hodgkin lymphoma and mild thrombocytopenia: a phase II multicenter trail" *Blood* 99 (12):4336-4342 (Jun. 15, 2002).

Wiseman et al., "Phase I/II 90Y-Zevalin (yttrium-90 ibritumomab tiuxetan, IDEC-Y2B8) radioimmunotherapy dosimetry results in relapsed or refractory non-Hodgkin's lymphoma" *European Journal of Nuclear Medicine* 27(7):766-777 (Jul. 2000).

Witzig et al, "Randomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma" *Journal of Clinical Oncology* 20(10):2453-2463, 2002.

Witzig et al, "Treatment With Ibritumomab Tiuxetan Radioimmunotherapy in Patients With Rituximab-Refractory Follicular Non-Hodgkin's Lymphoma" *Journal of Clinical Oncology* 20(15):3262-3269 (Aug. 1, 2002).

Wu et al., "Humanization of a Murine Monoclonal Antibody by Simultaneous Optimization of Framework and CDR Residues" *J. Mol. Biol.* 294:151-162 (1999).

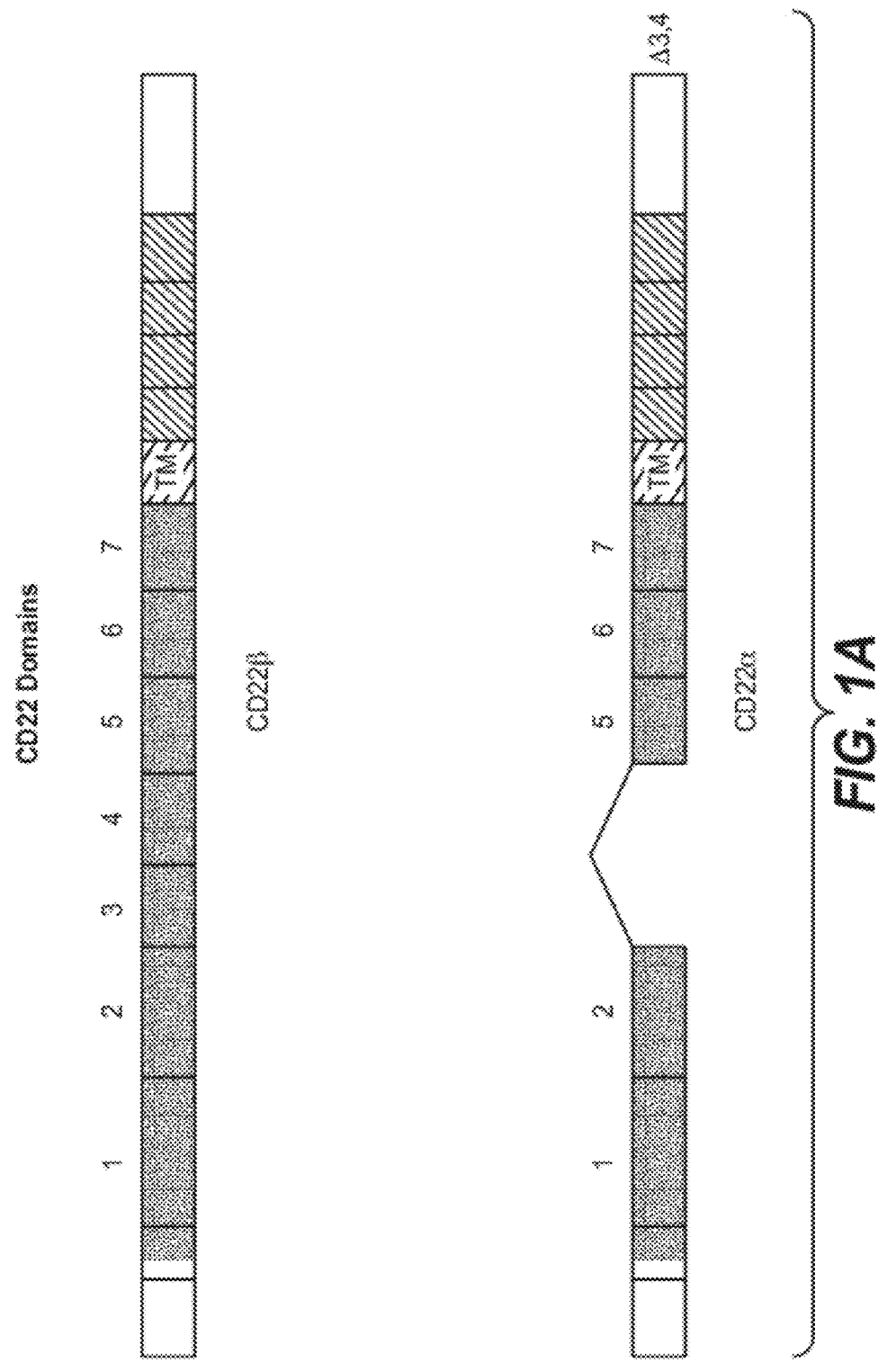

2/31

```
  1 mhllgpwlll lvleylafsd sskwvfehpe tlyawegacv wipctyrald gdlesfilfh
 61 npeynkntsk fdgtrlyest kdgkvpseqk rvqflgdknk nctlsihpvh ldsqqlglr
121 mektekwme rihlnvserp fpphiqlppe iqesqevtlt clinfscygy piqlqwlleg
181 vpmrqaavts teltikavft rselkfspqw shhgkivtcq lqdadgkfls ndtvqlnvkh
241 tpklslkvtp sdaivregds vtmtcsvss npeyttvswl kdgtslkkgn tftlnlrevt
301 kdqsgkycog vsndvgprs esvflgvqya pepstvqllh spaveqsqve flcmslsnpl
361 pthyteyhng kemgqrteek whipkllpwh sgtyscvaen ilgtgqrgpq aseldvqypk
421 kvttviqnpm plregdtvtl scnynasaps vtryewkpbg aweepslgvl klqnvgwdnt
481 tiacarcnsw cswaspvaln vqyaprdvrv rkikplseih sgnsvslqcd fssshpkevq
541 ffweknqrll qkesqlnfds lspedaqsys cwnnsiggt askawtlevl yaprrlvsm
601 spdqvmegk satltcesds nppvshyrwf dwnngslphh sgklrlepvk vqhsgaywcq
661 gtnsvqkqrs plstltvyys petigrrvav glgsclaili laicglklgr rwkrtqsqgq
721 lqenssgqaf fvrnkkvrra plseqphslg cynpsmedgi syttlrfpem slprtqdaes
781 semqrpprtc ddtvtysalh krqvgdyenv ipdfpedeqi hysellqfgv qerpqaqeev
841 dyvilkh  (SEQ ID NO: 27)
```

FIG. 1B

```
  1 mhllgpwlll lvleylafsd sskwvfehpe tlyawegacv wipctyrald gdlesfilfh
 61 npeynkntsk fdgtrlyest kdgkvpseqk rvqflgdknk nctlsihpvh ldsqqlglr
121 mektekwme rihlnvserp fpphiqlppe iqesqevtlt clinfscygy piqlqwlleg
181 vpmrqaavts teltikavft rselkfspqw shhgkivtcq lqdadgkfls ndtvqlnvkh
241 ppkvttvig npmpiregdt vtlscmynss npsvtryewk phgaweepsl qvlkiqnvgw
301 dnttiacaac nswcswaspv alnvqyaprd vrvrkikpls eihsgnsvsl qcdfssshpk
361 evqffweknq rllqkesqln fdslspedag sysewnnsi ggtaskawtl evlyaprrlr
421 vsmspdqvm eqksatltce sdsnppvshy twfdwnnqsl pyhsqklrle pvkvqhsgay
481 wcqgtnsvgk grsplstltv yyspetigrr vavglgscla llllaicglk lqrrwkrtqs
541 qgglqensg qsffvrnkkv rraplseqph slgcynpmme dgisyttlrf pemslprtqd
601 aessemqrpp pdcddtvtys alhkrqvgtm rtsfgifqkm rgfltqs (SEQ ID NO:29)
```

FIG. 1C

```
MHLLGPWLLLLEYLAFSDS SKWVIEHPGTIYAWEGACIWVPCTYRVLDGA
LETFILFHNPEYNQNMSKFEGTRLYESTKIDGKVPSGQKRVQFLGNEINNNC
TLSINPVRVNDSGQLGLRMVSKTEKWMERIHLNVSERPFPPRIQLPPKLQE
SQEVTLTCLINFSCYGYQIQLQWLLEGAPMRQAAVTLTSLSTKSVFTRSEL
KFSPQWSHHGKIVTCELRDVDGRVLSEDTVQLNVKHTFKLTIEVTPNETIV
RKGDSVTMTCKVNSSNPEYTTVSWLKDDIIPLKEQNTLMLTLMEVTRSQTGT
YCCRVSNDVGPATSEKVFLQVQYAPEPSRVQISQSPAVEGSEVNFLCISPA
NPLFTNYTWYRNGKEVQGRTEKQFQIQKILPWHAGTYSCVAENILGSIGERG
PGTELDVQYPPKKVTMVIESPTPIREGDTVTLSCMYSSSNPIVNRYEWRPR
GAWKEPSLGVLKIQHMIGWNNTAVACAACNWWCSWASPVTLNVLYAPRGVRV
RKIKPLSEIHSGNLVSLQCDFSSSHPKEVQFFWEKNGSLLGKESQLNFDSI
SPEDAGSYSCWVNNSIGGTASKAMTLEVLYAPRRLVSNSQGNQVMEGKTA
ILTCESDANPPVYSYAWFDWNNQSLPYSGRMLRLEPVKVQHSGAYWCQGTN
RVGKGRSPLITLTVYYSPETIGRRVAVGLGSCLAILILAMCGFKVQRRWNKR
TQSQGQLQENSSGQSFFVRNKKVRBTPLSEGPHSLGCYNPMMEDGISYATL
RFPETNTPRIGDAKTSELQRLPPDCDDTVTYSVLQKRQVGDYENVIPDFPE
DEGIHYSELIQFGFGERPQAQENVDYVIVEH  (SEQ ID NO:31)
```

```
kv1  DIQMTQSPSSLSASVGDRVTITC -L1- WYQQKPGKAPKLLIY -L2- GVPSRFSGSGSGTDFTLTISSLQP
kv1  DIQMTQSPSSLSASVGDRVTITC -L1- WYQQKPGKAPKLLIQ -L2- GVPSRFSGSGSGTDFTLTISSLQP
kv2  DIVMTQSPLSLPVTPGEPASISC -L1- WYLQKPGQSPQLLIY -L2- GVPDRFSGSGSGTDFTLKISRVEA
kv3  EIVLTQSPGTLSLSPGERATLSC -L1- WYQQKPGQAPRLLIY -L2- GIPDRFSGSGSGTDFTLTISRLEP
kv4  DIVMTQSPDSLAVSLGERATINC -L1- WYQQKPGQPPKLLIY -L2- GVPDRFSGSGSGTDFTLTISSLQA
```

FIG. 4A

```
kv1  EDFATYYC -L3- FGQGTKVEIK   SEQ ID NOs.: 74, 75, 76, 77
kv1  EDFATYYC -L3- FGQGTKVEIK   SEQ ID NOs.: 74, 78, 76, 77
kv2  EDFATYYC -L3- FGGGTKVEIK   SEQ ID NOs.: 49, 79, 80, 77
kv3  EDFGVYYC -L3- FGQGTKVEIK   SEQ ID NOs.: 81, 82, 83, 77
kv4  EDFAVYYC -L3- FGQGTKVEIK   SEQ ID NOs.: 84, 85, 86, 77
```

FIG. 4B

```
              230       240       250       260       270
humIgG1    PAPELLGGPSVFLFPPKPKDTLMISRTPEVTCVVVDVSHEDPEVKFNWYV
humIgG2    PAP-PVAGPSVFLFPPKPKDTLMISRTPEVTCVVVDVSHEDPEVQFNWYV
humIgG3    PAPELLGGPSVFLFPPKPKDTLMISRTPEVTCVVVDVSHEDPEVQFKWYV
humIgG4    PAPEFLGGPSVFLFPPKPKDTLMISRTPEVTCVVVDVSQEDPEVQFNWYV
           * * * *                                *    *  *

280       290       300       310       320
humIgG1    DGVEVHNAKTKPREEQYNSTYRVVSVLTVLHQDWLNGKEYKCKVSNKALP
humIgG2    DGVEVHNAKTKPREEQFNSTFRVVSVLTVVHQDWLNGKEYKCKVSNKGLP
humIgG3    DGVEVHNAKTKPREEQFNSTFRVVSVLTVLHQDWLNGKEYKCKVSNKALP
humIgG4    DGVEVHNAKTKPREEQFNSTYRVVSVLTVLHQDWLNGKEYKCKVSNKGLP
                            *  *                            *

330       340       350       360       370
humIgG1    APIEKTISKAKGQPREPQVYTLPPSREEMTKNQVSLTCLVKGFYPSDIAV
                          D  L
humIgG2    APIEKTISKTKGQPREPQVYTLPPSREEMTKNQVSLTCLVKGFYPSDIAV
humIgG3    APIEKTISKTKGQPREPQVYTLPPSREEMTKNQVSLTCLVKGFYPSDIAV
humIgG4    SSIEKTISKAKGQPREPQVYTLPPSQEEMTKNQVSLTCLVKGFYPSDIAV
           **         *                *

380       390       400       410       420
humIgG1    EWESNGQPENNYKTTPPVLDSDGSFFLYSKLTVDKSRWQQGNVFSCSVMH
humIgG2    EWESNGQPENNYKTTPPMLDSDGSFFLYSKLTVDKSRWQQGNVFSCSVMH
humIgG3    EWESSGQPENNYNTTPPMLDSDGSFFLYSKLTVDKSRWQQGNIFSCSVMH
humIgG4    EWESNGQPENNYKTTPPVLDSDGSFFLYSRLTVDKSRWQEGNVFSCSVMH
               *        *    *                *      *   *

430       440
humIgG1    EALHNHYTQKSLSLSPGK  SEQ ID NO: 38
humIgG2    EALHNHYTQKSLSLSPGK  SEQ ID NO: 39
humIgG3    EALHNRFTQKSLSLSPGK  SEQ ID NO: 40
humIgG4    EALHNHYTQKSLSLSLGK  SEQ ID NO: 41
                * *      *
```

A Kappa Light Chain Constant Region Consensus Sequence:

RTVAAPSVFIFPPSDEQLKSGTASVVCLLNNFYPREAKVQWK
VDNALQSGNSQESVTEQDSKDSTYSLSSTLTLSKADYEKHKV
YACEVTHQGLSSPVTKSFNRGEC    SEQ ID NO: 37

*FIG. 5A*

Anti-CD22 h10F4v2 Light Chain

DIQMTQSPSSLSASVGDRVTITCRSSQSIVHSVGNTFLEWYQQKPGKAPKLLI
YKVSNRFSGVPSRFSGSGSGTDFTLTISSLQPEDFATYYCFQGSQFPYTFGQG
TKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTK
SFNRGEC   (SEQ ID NO:87)

Anti-CD22 h10F4v2 Heavy Chain

EVQLVESGGGLVQPGGSLRLSCAASGYEFSRSWMNWVRQAPGKGLEWVGRIYP
GDGDTNYSGKFKGRFTISADTSKNTAYLQMNSLRAEDTAVYYCARDGSSWDWY
FDVWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK   (SEQ ID NO:88)

FIG. 5B

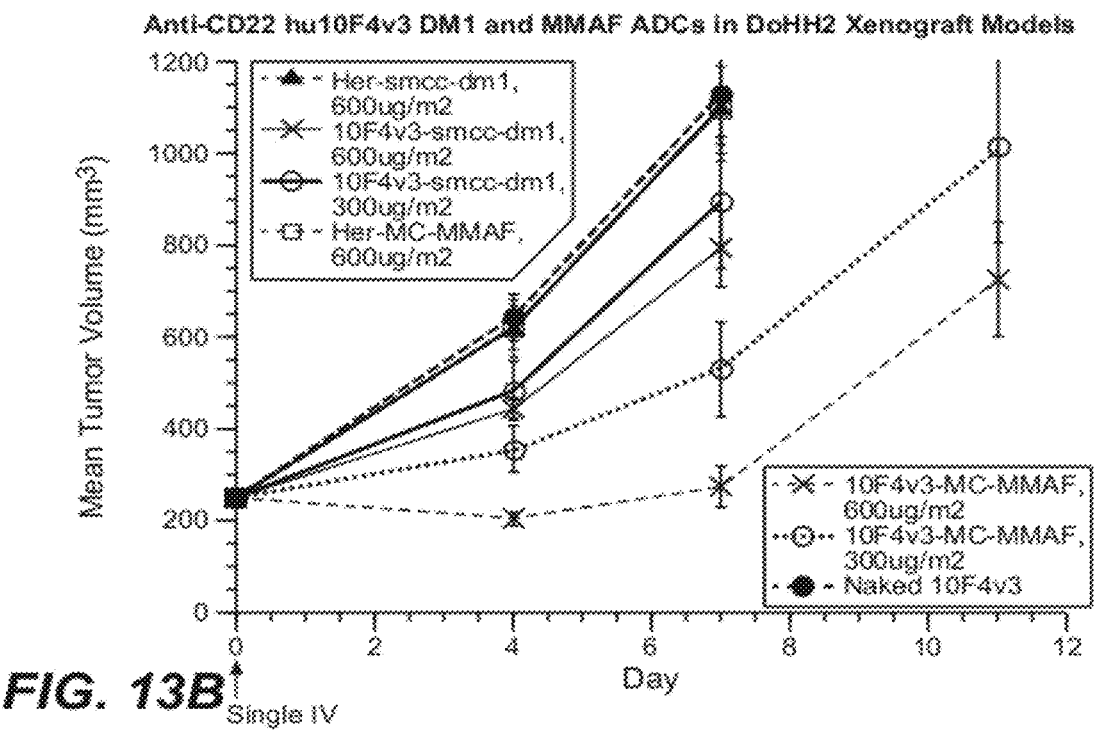
FIG. 13B Single IV
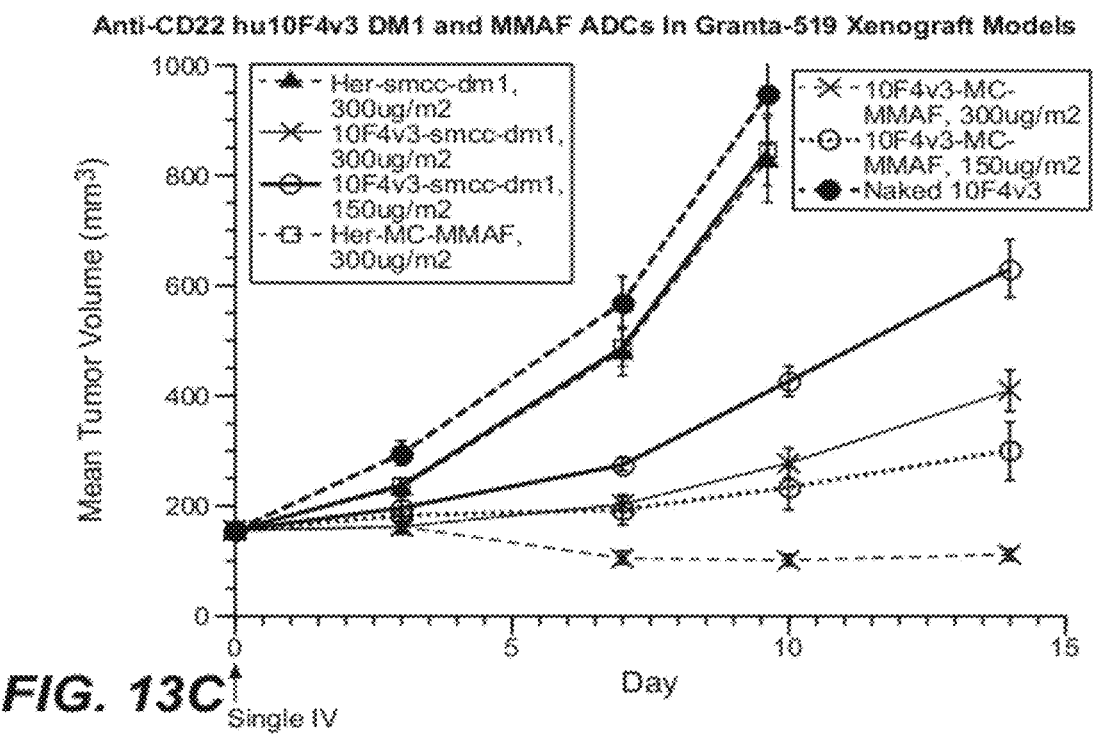
FIG. 13C Single IV

Anti-CD22 V205C h10F4v3 Cysteine Engineered Light Chain

DIQMTQSPSSLSASVGDRVTITCRSSQSIVHSVGNTFLEWYQQKPGKAPKLLI
YKVSNRFSGVPSRFSGSGSGTDFTLTISSLQPEDFATYYCFQGSQFPYTFGQG
TKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPCTK
SFNRGEC (SEQ ID NO:91)

*FIG. 17A*

Anti-CD22 A118C h10F4v3 Cysteine Engineered Heavy Chain

EVQLVESGGGLVQPGGSLRLSCAASGYEFSRSWMNWVRQAPGKGLEWVGRIYP
GDGDTNYSGKFKGRFTISADTSKNTAYLQMNSLRAEDTAVYYCARDGSSWDWY
FDVWGQGTLVTVSSCSTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK (SEQ ID NO:92)

*FIG. 17B*

Anti-CD22 S400C h10F4v3 Cysteine Engineered Fc Region

EVQLVESGGGLVQPGGSLRLSCAASGYEFSRSWMNWVRQAPGKGLEWVGRIYP
GDGDTNYSGKFKGRFTISADTSKNTAYLQMNSLRAEDTAVYYCARDGSSWDWY
FDVWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCL
VKGFYPSDIAVEWESNGQPENNYKTTPPVLDCDGSFFLYSKLTVDKSRWQQGN
VFSCSVMHEALHNHYTQKSLSLSPGK (SEQ ID NO:93)

*FIG. 17C*

FIG. 25B
Ki-67 Staining
(Dividing Cells)
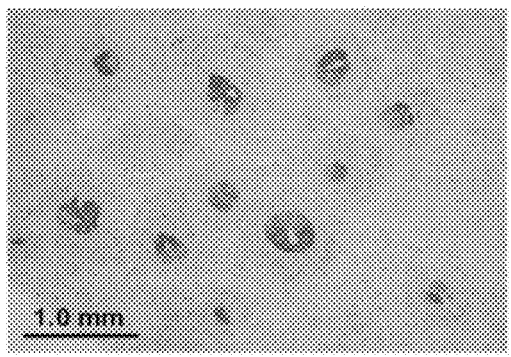
Vehicle
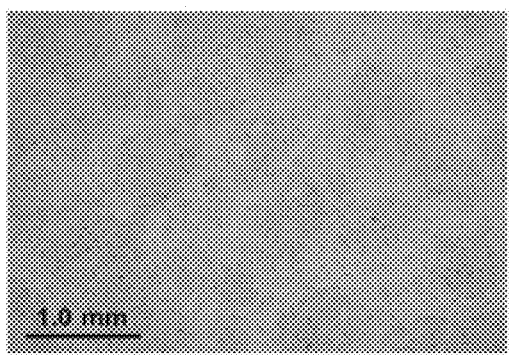
Anti-CD22-MC-MMAF
(10 mg/kg)
FIG. 25C
FIG. 25D
Anti-IgD Staining
(Naive B-Cells)
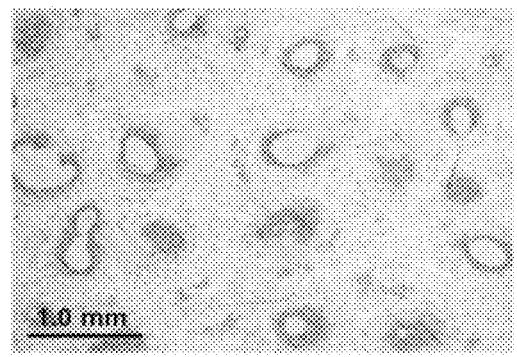
Vehicle
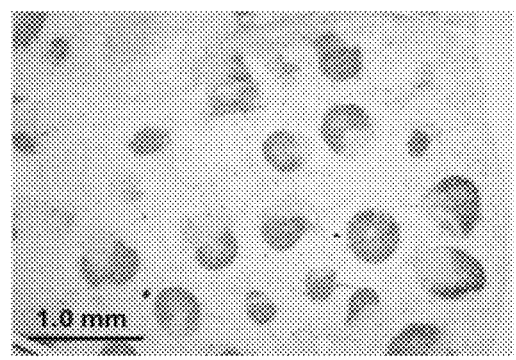
Anti-CD22-MC-MMAF
(10 mg/kg)
FIG. 25E

SEQUENCE LISTING

```
<160> NUMBER OF SEQ ID NOS: 93

<210> SEQ ID NO 1
<211> LENGTH: 25
<212> TYPE: PRT
<213> ORGANISM: Artificial sequence
<220> FEATURE:
<223> OTHER INFORMATION: sequence is synthesized

<400> SEQUENCE: 1

Glu Val Gln Leu Val Glu Ser Gly Gly Gly Leu Val Gln Pro Gly
  1               5                  10                  15

Gly Ser Leu Arg Leu Ser Cys Ala Ala Ser
                 20                  25

<210> SEQ ID NO 2
<211> LENGTH: 10
<212> TYPE: PRT
<213> ORGANISM: Artificial sequence
<220> FEATURE:
<223> OTHER INFORMATION: sequence is synthesized

<400> SEQUENCE: 2

Gly Tyr Glu Phe Ser Arg Ser Trp Met Asn
                 5                  10

<210> SEQ ID NO 3
<211> LENGTH: 13
<212> TYPE: PRT
<213> ORGANISM: Artificial sequence
<220> FEATURE:
<223> OTHER INFORMATION: sequence is synthesized

<400> SEQUENCE: 3
```

```
Trp Val Arg Gln Ala Pro Gly Lys Gly Leu Glu Trp Val
                5                   10

<210> SEQ ID NO 4
<211> LENGTH: 18
<212> TYPE: PRT
<213> ORGANISM: Artificial sequence
<220> FEATURE:
<223> OTHER INFORMATION: sequence is synthesized

<400> SEQUENCE: 4

Gly Arg Ile Tyr Pro Gly Asp Gly Asp Thr Asn Tyr Ser Gly Lys
 1               5                   10                  15

Phe Lys Gly

<210> SEQ ID NO 5
<211> LENGTH: 30
<212> TYPE: PRT
<213> ORGANISM: Artificial sequence
<220> FEATURE:
<223> OTHER INFORMATION: sequence is synthesized

<400> SEQUENCE: 5

Arg Phe Thr Ile Ser Ala Asp Thr Ser Lys Asn Thr Ala Tyr Leu
 1               5                   10                  15

Gln Met Asn Ser Leu Arg Ala Glu Asp Thr Ala Val Tyr Tyr Cys
                20                  25                  30

<210> SEQ ID NO 6
<211> LENGTH: 11
<212> TYPE: PRT
<213> ORGANISM: Artificial sequence
<220> FEATURE:
<223> OTHER INFORMATION: sequence is synthesized

<400> SEQUENCE: 6

Asp Gly Ser Ser Trp Asp Trp Tyr Phe Asp Val
 1               5                   10

<210> SEQ ID NO 7
<211> LENGTH: 11
<212> TYPE: PRT
<213> ORGANISM: Artificial sequence
<220> FEATURE:
<223> OTHER INFORMATION: sequence is synthesized

<400> SEQUENCE: 7

Trp Gly Gln Gly Thr Leu Val Thr Val Ser Ser
 1               5                   10

<210> SEQ ID NO 8
<211> LENGTH: 23
<212> TYPE: PRT
<213> ORGANISM: Artificial sequence
<220> FEATURE:
<223> OTHER INFORMATION: sequence is synthesized

<400> SEQUENCE: 8

Asp Ile Gln Met Thr Gln Ser Pro Ser Ser Leu Ser Ala Ser Val
 1               5                   10                  15

Gly Asp Arg Val Thr Ile Thr Cys
                20

<210> SEQ ID NO 9
<211> LENGTH: 16
```

```
<212> TYPE: PRT
<213> ORGANISM: Artificial sequence
<220> FEATURE:
<223> OTHER INFORMATION: sequence is synthesized

<400> SEQUENCE: 9

Arg Ser Ser Gln Ser Ile Val His Ser Asn Gly Asn Thr Phe Leu
 1               5                  10                  15

Glu

<210> SEQ ID NO 10
<211> LENGTH: 16
<212> TYPE: PRT
<213> ORGANISM: Artificial sequence
<220> FEATURE:
<223> OTHER INFORMATION: sequence is synthesized

<400> SEQUENCE: 10

Arg Ser Ser Gln Ser Ile Val His Ser Val Gly Asn Thr Phe Leu
 1               5                  10                  15

Glu

<210> SEQ ID NO 11
<211> LENGTH: 15
<212> TYPE: PRT
<213> ORGANISM: Artificial sequence
<220> FEATURE:
<223> OTHER INFORMATION: sequence is synthesized

<400> SEQUENCE: 11

Trp Tyr Gln Gln Lys Pro Gly Lys Ala Pro Lys Leu Leu Ile Tyr
 1               5                  10                  15

<210> SEQ ID NO 12
<211> LENGTH: 7
<212> TYPE: PRT
<213> ORGANISM: Artificial sequence
<220> FEATURE:
<223> OTHER INFORMATION: sequence is synthesized

<400> SEQUENCE: 12

Lys Val Ser Asn Arg Phe Ser
                  5

<210> SEQ ID NO 13
<211> LENGTH: 32
<212> TYPE: PRT
<213> ORGANISM: Artificial sequence
<220> FEATURE:
<223> OTHER INFORMATION: sequence is synthesized

<400> SEQUENCE: 13

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                 20                  25                  30

Tyr Cys

<210> SEQ ID NO 14
<211> LENGTH: 9
<212> TYPE: PRT
<213> ORGANISM: Artificial sequence
<220> FEATURE:
<223> OTHER INFORMATION: sequence is synthesized

<400> SEQUENCE: 14
```

```
Phe Gln Gly Ser Gln Phe Pro Tyr Thr
                 5

<210> SEQ ID NO 15
<211> LENGTH: 10
<212> TYPE: PRT
<213> ORGANISM: Artificial sequence
<220> FEATURE:
<223> OTHER INFORMATION: sequence is synthesized

<400> SEQUENCE: 15

Phe Gly Gln Gly Thr Lys Val Glu Ile Lys
                 5                  10

<210> SEQ ID NO 16
<211> LENGTH: 120
<212> TYPE: PRT
<213> ORGANISM: Artificial sequence
<220> FEATURE:
<223> OTHER INFORMATION: sequence is synthesized

<400> SEQUENCE: 16

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Glu Phe Ser
                20                  25                  30

Arg Ser Trp Met Asn Trp Val Arg Gln Ala Pro Gly Lys Gly Leu
                35                  40                  45

Glu Trp Val Gly Arg Ile Tyr Pro Gly Asp Gly Asp Thr Asn Tyr
                50                  55                  60

Ser Gly Lys Phe Lys Gly Lys Ala Thr Leu Thr Ala Asp Lys Ser
                65                  70                  75

Ser Ser Thr Ala Tyr Leu Gln Met Asn Ser Leu Arg Ala Glu Asp
                80                  85                  90

Thr Ala Val Tyr Tyr Cys Ala Arg Asp Gly Ser Ser Trp Asp Trp
                95                 100                 105

Tyr Phe Asp Tyr Trp Gly Gln Gly Thr Leu Val Thr Val Ser Ser
               110                 115                 120

<210> SEQ ID NO 17
<211> LENGTH: 113
<212> TYPE: PRT
<213> ORGANISM: Artificial sequence
<220> FEATURE:
<223> OTHER INFORMATION: sequence is synthesized

<400> SEQUENCE: 17

Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Ser Ile Val
                20                  25                  30

His Ser Asn Gly Asn Thr Phe Leu Glu Trp Tyr Gln Gln Lys Pro
                35                  40                  45

Gly Lys Ala Pro Lys Leu Leu Ile Tyr Lys Val Ser Asn Arg Phe
                50                  55                  60

Ser Gly Val Pro Ser Arg Phe Ser Gly Ser Arg Ser Gly Thr Asp
                65                  70                  75

Phe Thr Leu Thr Ile Ser Ser Leu Gln Pro Glu Asp Phe Ala Thr
                80                  85                  90

Tyr Tyr Cys Phe Gln Gly Ser Gln Phe Pro Tyr Thr Phe Gly Gln
```

```
                    95                 100                 105
Gly Thr Lys Val Glu Ile Lys Arg
                110

<210> SEQ ID NO 18
<211> LENGTH: 113
<212> TYPE: PRT
<213> ORGANISM: Artificial sequence
<220> FEATURE:
<223> OTHER INFORMATION: sequence is synthesized

<400> SEQUENCE: 18

Asp Ile Gln Met Thr Gln Ser Pro Ser Ser Leu Ser Ala Ser Val
  1               5                  10                  15

Gly Asp Arg Val Thr Ile Thr Cys Arg Ser Ser Gln Ser Ile Val
                 20                  25                  30

His Ser Val Gly Asn Thr Phe Leu Glu Trp Tyr Gln Gln Lys Pro
                 35                  40                  45

Gly Lys Ala Pro Lys Leu Leu Ile Tyr Lys Val Ser Asn Arg Phe
                 50                  55                  60

Ser Gly Val Pro Ser Arg Phe Ser Gly Ser Arg Ser Gly Thr Asp
                 65                  70                  75

Phe Thr Leu Thr Ile Ser Ser Leu Gln Pro Glu Asp Phe Ala Thr
                 80                  85                  90

Tyr Tyr Cys Phe Gln Gly Ser Gln Phe Pro Tyr Thr Phe Gly Gln
                 95                 100                 105

Gly Thr Lys Val Glu Ile Lys Arg
                110

<210> SEQ ID NO 19
<211> LENGTH: 16
<212> TYPE: PRT
<213> ORGANISM: Artificial sequence
<220> FEATURE:
<223> OTHER INFORMATION: sequence is synthesized

<400> SEQUENCE: 19

Arg Ser Ser Gln Ser Ile Val His Ser Ala Gly Asn Thr Phe Leu
  1               5                  10                  15
Glu

<210> SEQ ID NO 20
<211> LENGTH: 16
<212> TYPE: PRT
<213> ORGANISM: Artificial sequence
<220> FEATURE:
<223> OTHER INFORMATION: sequence is synthesized

<400> SEQUENCE: 20

Arg Ser Ser Gln Ser Ile Val His Ser Gln Gly Asn Thr Phe Leu
  1               5                  10                  15
Glu

<210> SEQ ID NO 21
<211> LENGTH: 16
<212> TYPE: PRT
<213> ORGANISM: Artificial sequence
<220> FEATURE:
<223> OTHER INFORMATION: sequence is synthesized

<400> SEQUENCE: 21

Arg Ser Ser Gln Ser Ile Val His Ser Ser Gly Asn Thr Phe Leu
```

Glu

<210> SEQ ID NO 22
<211> LENGTH: 16
<212> TYPE: PRT
<213> ORGANISM: Artificial sequence
<220> FEATURE:
<223> OTHER INFORMATION: sequence is synthesized

<400> SEQUENCE: 22

Arg Ser Ser Gln Ser Ile Val His Ser Asp Gly Asn Thr Phe Leu
1               5                   10                  15

Glu

<210> SEQ ID NO 23
<211> LENGTH: 16
<212> TYPE: PRT
<213> ORGANISM: Artificial sequence
<220> FEATURE:
<223> OTHER INFORMATION: sequence is synthesized

<400> SEQUENCE: 23

Arg Ser Ser Gln Ser Ile Val His Ser Ile Gly Asn Thr Phe Leu
1               5                   10                  15

Glu

<210> SEQ ID NO 24
<211> LENGTH: 113
<212> TYPE: PRT
<213> ORGANISM: Artificial sequence
<220> FEATURE:
<223> OTHER INFORMATION: sequence is synthesized

<400> SEQUENCE: 24

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ser Val Ile Ser Gly Asp Gly Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Phe Asp Tyr Trp Gly Gln
                95                  100                 105

Gly Thr Leu Val Thr Val Ser Ser
                110

<210> SEQ ID NO 25
<211> LENGTH: 107
<212> TYPE: PRT
<213> ORGANISM: Artificial sequence
<220> FEATURE:
<223> OTHER INFORMATION: sequence is synthesized

<400> SEQUENCE: 25

Asp Ile Gln Met Thr Gln Ser Pro Ser Ser Leu Ser Ala Ser Val
1               5                   10                  15

```
Gly Asp Arg Val Thr Ile Thr Cys Arg Ala Ser Gln Ser Ile Ser
             20                  25                  30

Asn Tyr Leu Ala Trp Tyr Gln Gln Lys Pro Gly Lys Ala Pro Lys
             35                  40                  45

Leu Leu Ile Tyr Ala Ala Ser Ser Leu Glu Ser Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

Tyr Asn Ser Leu Pro Trp Thr Phe Gly Gln Gly Thr Lys Val Glu
             95                  100                 105

Ile Lys

<210> SEQ ID NO 26
<211> LENGTH: 30
<212> TYPE: PRT
<213> ORGANISM: Artificial sequence
<220> FEATURE:
<223> OTHER INFORMATION: sequence is synthesized

<400> SEQUENCE: 26

Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
             20                  25                  30

<210> SEQ ID NO 27
<211> LENGTH: 847
<212> TYPE: PRT
<213> ORGANISM: Homo sapiens

<400> SEQUENCE: 27

Met His Leu Leu Gly Pro Trp Leu Leu Leu Val Leu Glu Tyr
 1               5                  10                  15

Leu Ala Phe Ser Asp Ser Ser Lys Trp Val Phe Glu His Pro Glu
             20                  25                  30

Thr Leu Tyr Ala Trp Glu Gly Ala Cys Val Trp Ile Pro Cys Thr
             35                  40                  45

Tyr Arg Ala Leu Asp Gly Asp Leu Glu Ser Phe Ile Leu Phe His
             50                  55                  60

Asn Pro Glu Tyr Asn Lys Asn Thr Ser Lys Phe Asp Gly Thr Arg
             65                  70                  75

Leu Tyr Glu Ser Thr Lys Asp Gly Lys Val Pro Ser Glu Gln Lys
             80                  85                  90

Arg Val Gln Phe Leu Gly Asp Lys Asn Lys Asn Cys Thr Leu Ser
             95                  100                 105

Ile His Pro Val His Leu Asn Asp Ser Gly Gln Leu Gly Leu Arg
             110                 115                 120

Met Glu Ser Lys Thr Glu Lys Trp Met Glu Arg Ile His Leu Asn
             125                 130                 135

Val Ser Glu Arg Pro Phe Pro Pro His Ile Gln Leu Pro Pro Glu
             140                 145                 150

Ile Gln Glu Ser Gln Glu Val Thr Leu Thr Cys Leu Leu Asn Phe
             155                 160                 165

Ser Cys Tyr Gly Tyr Pro Ile Gln Leu Gln Trp Leu Leu Glu Gly
             170                 175                 180
```

```
Val Pro Met Arg Gln Ala Ala Val Thr Ser Thr Ser Leu Thr Ile
            185                 190                 195

Lys Ser Val Phe Thr Arg Ser Glu Leu Lys Phe Ser Pro Gln Trp
            200                 205                 210

Ser His His Gly Lys Ile Val Thr Cys Gln Leu Gln Asp Ala Asp
            215                 220                 225

Gly Lys Phe Leu Ser Asn Asp Thr Val Gln Leu Asn Val Lys His
            230                 235                 240

Thr Pro Lys Leu Glu Ile Lys Val Thr Pro Ser Asp Ala Ile Val
            245                 250                 255

Arg Glu Gly Asp Ser Val Thr Met Thr Cys Glu Val Ser Ser Ser
            260                 265                 270

Asn Pro Glu Tyr Thr Thr Val Ser Trp Leu Lys Asp Gly Thr Ser
            275                 280                 285

Leu Lys Lys Gln Asn Thr Phe Thr Leu Asn Leu Arg Glu Val Thr
            290                 295                 300

Lys Asp Gln Ser Gly Lys Tyr Cys Cys Gln Val Ser Asn Asp Val
            305                 310                 315

Gly Pro Gly Arg Ser Glu Glu Val Phe Leu Gln Val Gln Tyr Ala
            320                 325                 330

Pro Glu Pro Ser Thr Val Gln Ile Leu His Ser Pro Ala Val Glu
            335                 340                 345

Gly Ser Gln Val Glu Phe Leu Cys Met Ser Leu Ala Asn Pro Leu
            350                 355                 360

Pro Thr Asn Tyr Thr Trp Tyr His Asn Gly Lys Glu Met Gln Gly
            365                 370                 375

Arg Thr Glu Glu Lys Val His Ile Pro Lys Ile Leu Pro Trp His
            380                 385                 390

Ala Gly Thr Tyr Ser Cys Val Ala Glu Asn Ile Leu Gly Thr Gly
            395                 400                 405

Gln Arg Gly Pro Gly Ala Glu Leu Asp Val Gln Tyr Pro Pro Lys
            410                 415                 420

Lys Val Thr Thr Val Ile Gln Asn Pro Met Pro Ile Arg Glu Gly
            425                 430                 435

Asp Thr Val Thr Leu Ser Cys Asn Tyr Asn Ser Ser Asn Pro Ser
            440                 445                 450

Val Thr Arg Tyr Glu Trp Lys Pro His Gly Ala Trp Glu Glu Pro
            455                 460                 465

Ser Leu Gly Val Leu Lys Ile Gln Asn Val Gly Trp Asp Asn Thr
            470                 475                 480

Thr Ile Ala Cys Ala Arg Cys Asn Ser Trp Cys Ser Trp Ala Ser
            485                 490                 495

Pro Val Ala Leu Asn Val Gln Tyr Ala Pro Arg Asp Val Arg Val
            500                 505                 510

Arg Lys Ile Lys Pro Leu Ser Glu Ile His Ser Gly Asn Ser Val
            515                 520                 525

Ser Leu Gln Cys Asp Phe Ser Ser Ser His Pro Lys Glu Val Gln
            530                 535                 540

Phe Phe Trp Glu Lys Asn Gly Arg Leu Leu Gly Lys Glu Ser Gln
            545                 550                 555

Leu Asn Phe Asp Ser Ile Ser Pro Glu Asp Ala Gly Ser Tyr Ser
            560                 565                 570

Cys Trp Val Asn Asn Ser Ile Gly Gln Thr Ala Ser Lys Ala Trp
```

```
                575                 580                 585
Thr Leu Glu Val Leu Tyr Ala Pro Arg Arg Leu Arg Val Ser Met
                590                 595                 600

Ser Pro Gly Asp Gln Val Met Glu Gly Lys Ser Ala Thr Leu Thr
                605                 610                 615

Cys Glu Ser Asp Ala Asn Pro Pro Val Ser His Tyr Thr Trp Phe
                620                 625                 630

Asp Trp Asn Asn Gln Ser Leu Pro His His Ser Gln Lys Leu Arg
                635                 640                 645

Leu Glu Pro Val Lys Val Gln His Ser Gly Ala Tyr Trp Cys Gln
                650                 655                 660

Gly Thr Asn Ser Val Gly Lys Gly Arg Ser Pro Leu Ser Thr Leu
                665                 670                 675

Thr Val Tyr Tyr Ser Pro Glu Thr Ile Gly Arg Arg Val Ala Val
                680                 685                 690

Gly Leu Gly Ser Cys Leu Ala Ile Leu Ile Leu Ala Ile Cys Gly
                695                 700                 705

Leu Lys Leu Gln Arg Arg Trp Lys Arg Thr Gln Ser Gln Gln Gly
                710                 715                 720

Leu Gln Glu Asn Ser Ser Gly Gln Ser Phe Phe Val Arg Asn Lys
                725                 730                 735

Lys Val Arg Arg Ala Pro Leu Ser Glu Gly Pro His Ser Leu Gly
                740                 745                 750

Cys Tyr Asn Pro Met Met Glu Asp Gly Ile Ser Tyr Thr Thr Leu
                755                 760                 765

Arg Phe Pro Glu Met Asn Ile Pro Arg Thr Gly Asp Ala Glu Ser
                770                 775                 780

Ser Glu Met Gln Arg Pro Pro Arg Thr Cys Asp Asp Thr Val Thr
                785                 790                 795

Tyr Ser Ala Leu His Lys Arg Gln Val Gly Asp Tyr Glu Asn Val
                800                 805                 810

Ile Pro Asp Phe Pro Glu Asp Glu Gly Ile His Tyr Ser Glu Leu
                815                 820                 825

Ile Gln Phe Gly Val Gly Glu Arg Pro Gln Ala Gln Glu Asn Val
                830                 835                 840

Asp Tyr Val Ile Leu Lys His
                845

<210> SEQ ID NO 28
<211> LENGTH: 660
<212> TYPE: PRT
<213> ORGANISM: Homo sapiens

<400> SEQUENCE: 28

Ser Lys Trp Val Phe Glu His Pro Glu Thr Leu Tyr Ala Trp Glu
  1               5                  10                  15

Gly Ala Cys Val Trp Ile Pro Cys Thr Tyr Arg Ala Leu Asp Gly
                 20                  25                  30

Asp Leu Glu Ser Phe Ile Leu Phe His Asn Pro Glu Tyr Asn Lys
                 35                  40                  45

Asn Thr Ser Lys Phe Asp Gly Thr Arg Leu Tyr Glu Ser Thr Lys
                 50                  55                  60

Asp Gly Lys Val Pro Ser Glu Gln Lys Arg Val Gln Phe Leu Gly
                 65                  70                  75

Asp Lys Asn Lys Asn Cys Thr Leu Ser Ile His Pro Val His Leu
```

-continued

```
                    80                  85                  90
Asn Asp Ser Gly Gln Leu Gly Leu Arg Met Glu Ser Lys Thr Glu
                    95                 100                 105
Lys Trp Met Glu Arg Ile His Leu Asn Val Ser Glu Arg Pro Phe
                   110                 115                 120
Pro Pro His Ile Gln Leu Pro Pro Glu Ile Gln Glu Ser Gln Glu
                   125                 130                 135
Val Thr Leu Thr Cys Leu Leu Asn Phe Ser Cys Tyr Gly Tyr Pro
                   140                 145                 150
Ile Gln Leu Gln Trp Leu Leu Glu Gly Val Pro Met Arg Gln Ala
                   155                 160                 165
Ala Val Thr Ser Thr Ser Leu Thr Ile Lys Ser Val Phe Thr Arg
                   170                 175                 180
Ser Glu Leu Lys Phe Ser Pro Gln Trp Ser His His Gly Lys Ile
                   185                 190                 195
Val Thr Cys Gln Leu Gln Asp Ala Asp Gly Lys Phe Leu Ser Asn
                   200                 205                 210
Asp Thr Val Gln Leu Asn Val Lys His Thr Pro Lys Leu Glu Ile
                   215                 220                 225
Lys Val Thr Pro Ser Asp Ala Ile Val Arg Glu Gly Asp Ser Val
                   230                 235                 240
Thr Met Thr Cys Glu Val Ser Ser Ser Asn Pro Glu Tyr Thr Thr
                   245                 250                 255
Val Ser Trp Leu Lys Asp Gly Thr Ser Leu Lys Lys Gln Asn Thr
                   260                 265                 270
Phe Thr Leu Asn Leu Arg Glu Val Thr Lys Asp Gln Ser Gly Lys
                   275                 280                 285
Tyr Cys Cys Gln Val Ser Asn Asp Val Gly Pro Gly Arg Ser Glu
                   290                 295                 300
Glu Val Phe Leu Gln Val Gln Tyr Ala Pro Glu Pro Ser Thr Val
                   305                 310                 315
Gln Ile Leu His Ser Pro Ala Val Glu Gly Ser Gln Val Glu Phe
                   320                 325                 330
Leu Cys Met Ser Leu Ala Asn Pro Leu Pro Thr Asn Tyr Thr Trp
                   335                 340                 345
Tyr His Asn Gly Lys Glu Met Gln Gly Arg Thr Glu Glu Lys Val
                   350                 355                 360
His Ile Pro Lys Ile Leu Pro Trp His Ala Gly Thr Tyr Ser Cys
                   365                 370                 375
Val Ala Glu Asn Ile Leu Gly Thr Gly Gln Arg Gly Pro Gly Ala
                   380                 385                 390
Glu Leu Asp Val Gln Tyr Pro Pro Lys Lys Val Thr Val Ile
                   395                 400                 405
Gln Asn Pro Met Pro Ile Arg Glu Gly Asp Thr Val Thr Leu Ser
                   410                 415                 420
Cys Asn Tyr Asn Ser Ser Asn Pro Ser Val Thr Arg Tyr Glu Trp
                   425                 430                 435
Lys Pro His Gly Ala Trp Glu Glu Pro Ser Leu Gly Val Leu Lys
                   440                 445                 450
Ile Gln Asn Val Gly Trp Asp Asn Thr Thr Ile Ala Cys Ala Arg
                   455                 460                 465
Cys Asn Ser Trp Cys Ser Trp Ala Ser Pro Val Ala Leu Asn Val
                   470                 475                 480
```

Gln Tyr Ala Pro Arg Asp Val Arg Val Arg Lys Ile Lys Pro Leu
                485                 490                 495

Ser Glu Ile His Ser Gly Asn Ser Val Ser Leu Gln Cys Asp Phe
                500                 505                 510

Ser Ser Ser His Pro Lys Glu Val Gln Phe Phe Trp Glu Lys Asn
                515                 520                 525

Gly Arg Leu Leu Gly Lys Glu Ser Gln Leu Asn Phe Asp Ser Ile
                530                 535                 540

Ser Pro Glu Asp Ala Gly Ser Tyr Ser Cys Trp Val Asn Asn Ser
                545                 550                 555

Ile Gly Gln Thr Ala Ser Lys Ala Trp Thr Leu Glu Val Leu Tyr
                560                 565                 570

Ala Pro Arg Arg Leu Arg Val Ser Met Ser Pro Gly Asp Gln Val
                575                 580                 585

Met Glu Gly Lys Ser Ala Thr Leu Thr Cys Glu Ser Asp Ala Asn
                590                 595                 600

Pro Pro Val Ser His Tyr Thr Trp Phe Asp Trp Asn Asn Gln Ser
                605                 610                 615

Leu Pro His His Ser Gln Lys Leu Arg Leu Glu Pro Val Lys Val
                620                 625                 630

Gln His Ser Gly Ala Tyr Trp Cys Gln Gly Thr Asn Ser Val Gly
                635                 640                 645

Lys Gly Arg Ser Pro Leu Ser Thr Leu Thr Val Tyr Tyr Ser Pro
                650                 655                 660

<210> SEQ ID NO 29
<211> LENGTH: 647
<212> TYPE: PRT
<213> ORGANISM: Homo sapiens

<400> SEQUENCE: 29

Met His Leu Leu Gly Pro Trp Leu Leu Leu Val Leu Glu Tyr
  1               5                  10                  15

Leu Ala Phe Ser Asp Ser Ser Lys Trp Val Phe Glu His Pro Glu
                20                  25                  30

Thr Leu Tyr Ala Trp Glu Gly Ala Cys Val Trp Ile Pro Cys Thr
                35                  40                  45

Tyr Arg Ala Leu Asp Gly Asp Leu Glu Ser Phe Ile Leu Phe His
                50                  55                  60

Asn Pro Glu Tyr Asn Lys Asn Thr Ser Lys Phe Asp Gly Thr Arg
                65                  70                  75

Leu Tyr Glu Ser Thr Lys Asp Gly Lys Val Pro Ser Glu Gln Lys
                80                  85                  90

Arg Val Gln Phe Leu Gly Asp Lys Asn Lys Asn Cys Thr Leu Ser
                95                  100                 105

Ile His Pro Val His Leu Asn Asp Ser Gly Gln Leu Gly Leu Arg
                110                 115                 120

Met Glu Ser Lys Thr Glu Lys Trp Met Glu Arg Ile His Leu Asn
                125                 130                 135

Val Ser Glu Arg Pro Phe Pro Pro His Ile Gln Leu Pro Pro Glu
                140                 145                 150

Ile Gln Glu Ser Gln Glu Val Thr Leu Thr Cys Leu Leu Asn Phe
                155                 160                 165

Ser Cys Tyr Gly Tyr Pro Ile Gln Leu Gln Trp Leu Leu Glu Gly
                170                 175                 180

-continued

```
Val Pro Met Arg Gln Ala Ala Val Thr Ser Thr Ser Leu Thr Ile
            185                 190                 195

Lys Ser Val Phe Thr Arg Ser Glu Leu Lys Phe Ser Pro Gln Trp
            200                 205                 210

Ser His His Gly Lys Ile Val Thr Cys Gln Leu Gln Asp Ala Asp
            215                 220                 225

Gly Lys Phe Leu Ser Asn Asp Thr Val Gln Leu Asn Val Lys His
            230                 235                 240

Pro Pro Lys Lys Val Thr Thr Val Ile Gln Asn Pro Met Pro Ile
            245                 250                 255

Arg Glu Gly Asp Thr Val Thr Leu Ser Cys Asn Tyr Asn Ser Ser
            260                 265                 270

Asn Pro Ser Val Thr Arg Tyr Glu Trp Lys Pro His Gly Ala Trp
            275                 280                 285

Glu Glu Pro Ser Leu Gly Val Leu Lys Ile Gln Asn Val Gly Trp
            290                 295                 300

Asp Asn Thr Thr Ile Ala Cys Ala Ala Cys Asn Ser Trp Cys Ser
            305                 310                 315

Trp Ala Ser Pro Val Ala Leu Asn Val Gln Tyr Ala Pro Arg Asp
            320                 325                 330

Val Arg Val Arg Lys Ile Lys Pro Leu Ser Glu Ile His Ser Gly
            335                 340                 345

Asn Ser Val Ser Leu Gln Cys Asp Phe Ser Ser Ser His Pro Lys
            350                 355                 360

Glu Val Gln Phe Phe Trp Glu Lys Asn Gly Arg Leu Leu Gly Lys
            365                 370                 375

Glu Ser Gln Leu Asn Phe Asp Ser Ile Ser Pro Glu Asp Ala Gly
            380                 385                 390

Ser Tyr Ser Cys Trp Val Asn Asn Ser Ile Gly Gln Thr Ala Ser
            395                 400                 405

Lys Ala Trp Thr Leu Glu Val Leu Tyr Ala Pro Arg Arg Leu Arg
            410                 415                 420

Val Ser Met Ser Pro Gly Asp Gln Val Met Glu Gly Lys Ser Ala
            425                 430                 435

Thr Leu Thr Cys Glu Ser Asp Ala Asn Pro Pro Val Ser His Tyr
            440                 445                 450

Thr Trp Phe Asp Trp Asn Asn Gln Ser Leu Pro Tyr His Ser Gln
            455                 460                 465

Lys Leu Arg Leu Glu Pro Val Lys Val Gln His Ser Gly Ala Tyr
            470                 475                 480

Trp Cys Gln Gly Thr Asn Ser Val Gly Lys Gly Arg Ser Pro Leu
            485                 490                 495

Ser Thr Leu Thr Val Tyr Tyr Ser Pro Glu Thr Ile Gly Arg Arg
            500                 505                 510

Val Ala Val Gly Leu Gly Ser Cys Leu Ala Ile Leu Ile Leu Ala
            515                 520                 525

Ile Cys Gly Leu Lys Leu Gln Arg Arg Trp Lys Arg Thr Gln Ser
            530                 535                 540

Gln Gln Gly Leu Gln Glu Asn Ser Ser Gly Gln Ser Phe Phe Val
            545                 550                 555

Arg Asn Lys Lys Val Arg Arg Ala Pro Leu Ser Glu Gly Pro His
            560                 565                 570

Ser Leu Gly Cys Tyr Asn Pro Met Met Glu Asp Gly Ile Ser Tyr
            575                 580                 585
```

```
Thr Thr Leu Arg Phe Pro Glu Met Asn Ile Pro Arg Thr Gly Asp
            590                 595                 600

Ala Glu Ser Ser Glu Met Gln Arg Pro Pro Asp Cys Asp Asp
            605                 610                 615

Thr Val Thr Tyr Ser Ala Leu His Lys Arg Gln Val Gly Thr Met
            620                 625                 630

Arg Thr Ser Phe Gln Ile Phe Gln Lys Met Arg Gly Phe Ile Thr
            635                 640                 645

Gln Ser

<210> SEQ ID NO 30
<211> LENGTH: 483
<212> TYPE: PRT
<213> ORGANISM: Homo sapiens

<400> SEQUENCE: 30

Ser Lys Trp Val Phe Glu His Pro Glu Thr Leu Tyr Ala Trp Glu
  1               5                  10                  15

Gly Ala Cys Val Trp Ile Pro Cys Thr Tyr Arg Ala Leu Asp Gly
             20                  25                  30

Asp Leu Glu Ser Phe Ile Leu Phe His Asn Pro Glu Tyr Asn Lys
             35                  40                  45

Asn Thr Ser Lys Phe Asp Gly Thr Arg Leu Tyr Glu Ser Thr Lys
             50                  55                  60

Asp Gly Lys Val Pro Ser Glu Gln Lys Arg Val Gln Phe Leu Gly
             65                  70                  75

Asp Lys Asn Lys Asn Cys Thr Leu Ser Ile His Pro Val His Leu
             80                  85                  90

Asn Asp Ser Gly Gln Leu Gly Leu Arg Met Glu Ser Lys Thr Glu
             95                  100                 105

Lys Trp Met Glu Arg Ile His Leu Asn Val Ser Glu Arg Pro Phe
             110                 115                 120

Pro Pro His Ile Gln Leu Pro Pro Glu Ile Gln Glu Ser Gln Glu
             125                 130                 135

Val Thr Leu Thr Cys Leu Leu Asn Phe Ser Cys Tyr Gly Tyr Pro
             140                 145                 150

Ile Gln Leu Gln Trp Leu Leu Glu Gly Val Pro Met Arg Gln Ala
             155                 160                 165

Ala Val Thr Ser Thr Ser Leu Thr Ile Lys Ser Val Phe Thr Arg
             170                 175                 180

Ser Glu Leu Lys Phe Ser Pro Gln Trp Ser His His Gly Lys Ile
             185                 190                 195

Val Thr Cys Gln Leu Gln Asp Ala Asp Gly Lys Phe Leu Ser Asn
             200                 205                 210

Asp Thr Val Gln Leu Asn Val Lys His Pro Pro Lys Lys Val Thr
             215                 220                 225

Thr Val Ile Gln Asn Pro Met Pro Ile Arg Glu Gly Asp Thr Val
             230                 235                 240

Thr Leu Ser Cys Asn Tyr Asn Ser Ser Asn Pro Ser Val Thr Arg
             245                 250                 255

Tyr Glu Trp Lys Pro His Gly Ala Trp Glu Glu Pro Ser Leu Gly
             260                 265                 270

Val Leu Lys Ile Gln Asn Val Gly Trp Asp Asn Thr Thr Ile Ala
             275                 280                 285
```

```
Cys Ala Ala Cys Asn Ser Trp Cys Ser Trp Ala Ser Pro Val Ala
            290                 295                 300

Leu Asn Val Gln Tyr Ala Pro Arg Asp Val Arg Val Arg Lys Ile
            305                 310                 315

Lys Pro Leu Ser Glu Ile His Ser Gly Asn Ser Val Ser Leu Gln
            320                 325                 330

Cys Asp Phe Ser Ser His Pro Lys Glu Val Gln Phe Phe Trp
            335                 340                 345

Glu Lys Asn Gly Arg Leu Leu Gly Lys Glu Ser Gln Leu Asn Phe
            350                 355                 360

Asp Ser Ile Ser Pro Glu Asp Ala Gly Ser Tyr Ser Cys Trp Val
            365                 370                 375

Asn Asn Ser Ile Gly Gln Thr Ala Ser Lys Ala Trp Thr Leu Glu
            380                 385                 390

Val Leu Tyr Ala Pro Arg Arg Leu Arg Val Ser Met Ser Pro Gly
            395                 400                 405

Asp Gln Val Met Glu Gly Lys Ser Ala Thr Leu Thr Cys Glu Ser
            410                 415                 420

Asp Ala Asn Pro Pro Val Ser His Tyr Thr Trp Phe Asp Trp Asn
            425                 430                 435

Asn Gln Ser Leu Pro Tyr His Ser Gln Lys Leu Arg Leu Glu Pro
            440                 445                 450

Val Lys Val Gln His Ser Gly Ala Tyr Trp Cys Gln Gly Thr Asn
            455                 460                 465

Ser Val Gly Lys Gly Arg Ser Pro Leu Ser Thr Leu Thr Val Tyr
            470                 475                 480

Tyr Ser Pro

<210> SEQ ID NO 31
<211> LENGTH: 846
<212> TYPE: PRT
<213> ORGANISM: Pan troglodytes

<400> SEQUENCE: 31

Met His Leu Leu Gly Pro Trp Leu Leu Leu Glu Tyr Leu Ala
 1               5                  10                  15

Phe Ser Asp Ser Ser Lys Trp Asn Ile Glu His Pro Gly Thr Ile
            20                  25                  30

Tyr Ala Trp Glu Gly Ala Cys Ile Trp Val Pro Cys Thr Tyr Arg
            35                  40                  45

Val Leu Asp Gly Ala Leu Glu Thr Phe Ile Leu Phe His Asn Pro
            50                  55                  60

Glu Tyr Asn Gln Asn Met Ser Lys Phe Glu Gly Thr Arg Leu Tyr
            65                  70                  75

Glu Ser Thr Lys Asp Gly Lys Val Pro Ser Gly Gln Lys Arg Val
            80                  85                  90

Gln Phe Leu Gly Asn Lys Ile Asn Asn Cys Thr Leu Ser Ile
            95                  100                 105

His Pro Val His Val Asn Asp Ser Gly Gln Leu Gly Leu Arg Met
            110                 115                 120

Val Ser Lys Thr Glu Lys Trp Met Glu Arg Ile His Leu Asn Val
            125                 130                 135

Ser Glu Arg Pro Phe Pro Pro Arg Ile Gln Leu Pro Pro Lys Leu
            140                 145                 150

Gln Glu Ser Gln Glu Val Thr Leu Thr Cys Leu Leu Asn Phe Ser
```

-continued

```
                155                 160                 165
Cys Tyr Gly Tyr Gln Ile Gln Leu Gln Trp Leu Leu Glu Gly Ala
                170                 175                 180
Pro Met Arg Gln Ala Ala Val Thr Leu Thr Ser Leu Ser Thr Lys
                185                 190                 195
Ser Val Phe Thr Arg Ser Glu Leu Lys Phe Ser Pro Gln Trp Ser
                200                 205                 210
His His Gly Lys Ile Val Thr Cys Glu Leu His Asp Val Asp Gly
                215                 220                 225
Lys Val Leu Ser Glu Asp Thr Val Gln Leu Asn Val Lys His Thr
                230                 235                 240
Pro Lys Leu Thr Ile Glu Val Thr Pro Asn Glu Thr Ile Val Arg
                245                 250                 255
Lys Gly Asp Ser Val Thr Met Thr Cys Lys Val Asn Ser Ser Asn
                260                 265                 270
Pro Glu Tyr Thr Thr Val Ser Trp Leu Lys Asp Asp Ile Pro Leu
                275                 280                 285
Lys Glu Gln Asn Thr Leu Met Leu Thr Leu His Glu Val Thr Lys
                290                 295                 300
Ser Gln Thr Gly Thr Tyr Cys Cys Arg Val Ser Asn Asp Val Gly
                305                 310                 315
Pro Ala Thr Ser Glu Lys Val Phe Leu Gln Val Gln Tyr Ala Pro
                320                 325                 330
Glu Pro Ser Arg Val Gln Ile Ser Gln Ser Pro Ala Val Glu Gly
                335                 340                 345
Ser Glu Val Asn Phe Leu Cys Ile Ser Pro Ala Asn Pro Leu Pro
                350                 355                 360
Thr Asn Tyr Thr Trp Tyr His Asn Gly Lys Glu Val Gln Gly Arg
                365                 370                 375
Thr Glu Lys Gln Phe Gln Ile Gln Lys Ile Leu Pro Trp His Ala
                380                 385                 390
Gly Thr Tyr Ser Cys Val Ala Glu Asn Ile Leu Gly Ile Gly Glu
                395                 400                 405
Arg Gly Pro Gly Thr Glu Leu Asp Val Gln Tyr Pro Pro Lys Lys
                410                 415                 420
Val Thr Met Val Ile Glu Asn Pro Thr Pro Ile Arg Glu Gly Asp
                425                 430                 435
Thr Val Thr Leu Ser Cys Asn Tyr Ser Ser Ser Asn Pro Ile Val
                440                 445                 450
Asn His Tyr Glu Trp Arg Pro Arg Gly Ala Trp Glu Glu Pro Ser
                455                 460                 465
Leu Gly Val Leu Lys Ile Gln Asn Ile Gly Trp Asn Asn Thr Ala
                470                 475                 480
Val Ala Cys Ala Ala Cys Asn Asn Trp Cys Ser Trp Ala Ser Pro
                485                 490                 495
Val Thr Leu Asn Val Leu Tyr Ala Pro Arg Gly Val Arg Val Arg
                500                 505                 510
Lys Ile Lys Pro Leu Ser Glu Ile His Ser Gly Asn Leu Val Ser
                515                 520                 525
Leu Gln Cys Asp Phe Ser Ser Ser His Pro Lys Glu Val Gln Phe
                530                 535                 540
Phe Trp Glu Lys Asn Gly Ser Leu Leu Gly Lys Glu Ser Gln Leu
                545                 550                 555
```

```
Asn Phe Asp Ser Ile Ser Pro Glu Asp Ala Gly Ser Tyr Ser Cys
            560                 565                 570
Trp Val Asn Asn Ser Ile Gly Gln Thr Ala Ser Lys Ala Trp Thr
        575                 580                 585
Leu Glu Val Leu Tyr Ala Pro Arg Arg Leu Arg Val Ser Met Ser
            590                 595                 600
Gln Gly Asn Gln Val Met Glu Gly Lys Thr Ala Ile Leu Thr Cys
            605                 610                 615
Glu Ser Asp Ala Asn Pro Pro Val Tyr Ser Tyr Ala Trp Phe Asp
            620                 625                 630
Trp Asn Asn Gln Ser Leu Pro Tyr Ser Gly Arg Met Leu Arg Leu
            635                 640                 645
Glu Pro Val Lys Val Gln His Ser Gly Ala Tyr Trp Cys Gln Gly
            650                 655                 660
Thr Asn Arg Val Gly Lys Gly His Ser Pro Leu Ile Thr Leu Thr
            665                 670                 675
Val Tyr Tyr Ser Pro Glu Thr Ile Gly Arg Arg Val Ala Val Gly
            680                 685                 690
Leu Gly Ser Cys Leu Ala Ile Leu Ile Leu Ala Met Cys Gly Phe
            695                 700                 705
Lys Val Gln Arg Arg Trp Lys Arg Thr Gln Ser Gln Gln Gly Leu
            710                 715                 720
Gln Glu Asn Ser Ser Gly Gln Ser Phe Phe Val Arg Asn Lys Lys
            725                 730                 735
Val Arg Arg Thr Pro Leu Ser Glu Gly Pro His Ser Leu Gly Cys
            740                 745                 750
Tyr Asn Pro Met Met Glu Asp Gly Ile Ser Tyr Ala Thr Leu Arg
            755                 760                 765
Phe Pro Glu Thr Asn Thr Pro Arg Thr Gly Asp Ala Glu Thr Ser
            770                 775                 780
Glu Leu Gln Arg Leu Pro Pro Asp Cys Asp Asp Thr Val Thr Tyr
            785                 790                 795
Ser Val Leu Gln Lys Arg Gln Val Gly Asp Tyr Glu Asn Val Ile
            800                 805                 810
Pro Asp Phe Pro Glu Asp Glu Gly Ile His Tyr Ser Glu Leu Ile
            815                 820                 825
Gln Phe Gly Phe Gly Glu Arg Pro Gln Ala Gln Glu Asn Val Asp
            830                 835                 840
Tyr Val Ile Val Lys His
            845

<210> SEQ ID NO 32
<211> LENGTH: 16
<212> TYPE: PRT
<213> ORGANISM: Artificial sequence
<220> FEATURE:
<223> OTHER INFORMATION: sequence is synthesized

<400> SEQUENCE: 32

Arg Ser Ser Gln Ser Ile Val His Ser Ile Gly Ala Thr Phe Leu
 1               5                  10                  15
Glu

<210> SEQ ID NO 33
<211> LENGTH: 16
<212> TYPE: PRT
<213> ORGANISM: Artificial sequence
```

<220> FEATURE:
<223> OTHER INFORMATION: sequence is synthesized

<400> SEQUENCE: 33

Arg Ser Ser Gln Ser Ile Val His Ser Ile Gly Gln Thr Phe Leu
1               5                   10                  15

Glu

<210> SEQ ID NO 34
<211> LENGTH: 120
<212> TYPE: PRT
<213> ORGANISM: Artificial sequence
<220> FEATURE:
<223> OTHER INFORMATION: sequence is synthesized

<400> SEQUENCE: 34

Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Glu Phe Ser
                20                  25                  30

Arg Ser Trp Met Asn Trp Val Lys Gln Arg Pro Gly Gln Gly Arg
            35                  40                  45

Glu Trp Ile Gly Arg Ile Tyr Pro Gly Asp Gly Asp Thr Asn Tyr
        50                  55                  60

Ser Gly Lys Phe Lys Gly Lys Ala Thr Leu Thr Ala Asp Lys Ser
65                  70                  75

Ser Ser Thr Ala Tyr Met Gln Leu Ser Ser Leu Thr Ser Val Asp
                80                  85                  90

Ser Ala Val Tyr Phe Cys Ala Arg Asp Gly Ser Ser Trp Asp Trp
                95                  100                 105

Tyr Phe Asp Val Trp Gly Ala Gly Thr Thr Val Thr Val Ser Ser
            110                 115                 120

<210> SEQ ID NO 35
<211> LENGTH: 112
<212> TYPE: PRT
<213> ORGANISM: Artificial sequence
<220> FEATURE:
<223> OTHER INFORMATION: sequence is synthesized

<400> SEQUENCE: 35

Asp Ile Leu Met Thr Gln Thr Pro Leu Ser Leu Pro Val Ser Leu
1               5                   10                  15

Gly Asp Gln Ala Ser Ile Ser Cys Arg Ser Ser Gln Ser Ile Val
                20                  25                  30

His Ser Asn Gly Asn Thr Phe Leu Glu Trp Tyr Leu Gln Lys Pro
            35                  40                  45

Gly Gln Ser Pro Lys Leu Leu Ile Tyr Lys Val Ser Asn Arg Phe
        50                  55                  60

Ser Gly Val Pro Asp Arg Phe Ser Gly Ser Gly Ser Gly Thr Asp
65                  70                  75

Phe Thr Leu Lys Ile Ser Arg Val Glu Ala Glu Asp Leu Gly Val
                80                  85                  90

Tyr Tyr Cys Phe Gln Gly Ser Gln Phe Pro Tyr Thr Phe Gly Gly
                95                  100                 105

Gly Thr Lys Val Glu Ile Lys
            110

<210> SEQ ID NO 36

```
<211> LENGTH: 847
<212> TYPE: PRT
<213> ORGANISM: Homo sapiens

<400> SEQUENCE: 36

Met His Leu Leu Gly Pro Trp Leu Leu Leu Val Leu Glu Tyr
1               5                   10                  15

Leu Ala Phe Ser Asp Ser Ser Lys Trp Val Phe Glu His Pro Glu
                20                  25                  30

Thr Leu Tyr Ala Trp Glu Gly Ala Cys Val Trp Ile Pro Cys Thr
                35                  40                  45

Tyr Arg Ala Leu Asp Gly Asp Leu Glu Ser Phe Ile Leu Phe His
                50                  55                  60

Asn Pro Glu Tyr Asn Lys Asn Thr Ser Lys Phe Asp Gly Thr Arg
                65                  70                  75

Leu Tyr Glu Ser Thr Lys Asp Gly Lys Val Pro Ser Glu Gln Lys
                80                  85                  90

Arg Val Gln Phe Leu Gly Asp Lys Asn Lys Asn Cys Thr Leu Ser
                95                  100                 105

Ile His Pro Val His Leu Asn Asp Ser Gly Gln Leu Gly Leu Arg
                110                 115                 120

Met Glu Ser Lys Thr Glu Lys Trp Met Glu Arg Ile His Leu Asn
                125                 130                 135

Val Ser Glu Arg Pro Phe Pro Pro His Ile Gln Leu Pro Pro Glu
                140                 145                 150

Ile Gln Glu Ser Gln Glu Val Thr Leu Thr Cys Leu Leu Asn Phe
                155                 160                 165

Ser Cys Tyr Gly Tyr Pro Ile Gln Leu Gln Trp Leu Leu Glu Gly
                170                 175                 180

Val Pro Met Arg Gln Ala Ala Val Thr Ser Thr Ser Leu Thr Ile
                185                 190                 195

Lys Ser Val Phe Thr Arg Ser Glu Leu Lys Phe Ser Pro Gln Trp
                200                 205                 210

Ser His His Gly Lys Ile Val Thr Cys Gln Leu Gln Asp Ala Asp
                215                 220                 225

Gly Lys Phe Leu Ser Asn Asp Thr Val Gln Leu Asn Val Lys His
                230                 235                 240

Thr Pro Lys Leu Glu Ile Lys Val Thr Pro Ser Asp Ala Ile Val
                245                 250                 255

Arg Glu Gly Asp Ser Val Thr Met Thr Cys Glu Val Ser Ser Ser
                260                 265                 270

Asn Pro Glu Tyr Thr Thr Val Ser Trp Leu Lys Asp Gly Thr Ser
                275                 280                 285

Leu Lys Lys Gln Asn Thr Phe Thr Leu Asn Leu Arg Glu Val Thr
                290                 295                 300

Lys Asp Gln Ser Gly Lys Tyr Cys Cys Gln Val Ser Asn Asp Val
                305                 310                 315

Gly Pro Gly Arg Ser Glu Glu Val Phe Leu Gln Val Gln Tyr Ala
                320                 325                 330

Pro Glu Pro Ser Thr Val Gln Ile Leu His Ser Pro Ala Val Glu
                335                 340                 345

Gly Ser Gln Val Glu Phe Leu Cys Met Ser Leu Ala Asn Pro Leu
                350                 355                 360

Pro Thr Asn Tyr Thr Trp Tyr His Asn Gly Lys Glu Met Gln Gly
                365                 370                 375
```

-continued

Arg Thr Glu Glu Lys Val His Ile Pro Lys Ile Leu Pro Trp His
                380                 385                 390

Ala Gly Thr Tyr Ser Cys Val Ala Glu Asn Ile Leu Gly Thr Gly
                395                 400                 405

Gln Arg Gly Pro Gly Ala Glu Leu Asp Val Gln Tyr Pro Pro Lys
                410                 415                 420

Lys Val Thr Thr Val Ile Gln Asn Pro Met Pro Ile Arg Glu Gly
                425                 430                 435

Asp Thr Val Thr Leu Ser Cys Asn Tyr Asn Ser Ser Asn Pro Ser
                440                 445                 450

Val Thr Arg Tyr Glu Trp Lys Pro His Gly Ala Trp Glu Glu Pro
                455                 460                 465

Ser Leu Gly Val Leu Lys Ile Gln Asn Val Gly Trp Asp Asn Thr
                470                 475                 480

Thr Ile Ala Cys Ala Arg Cys Asn Ser Trp Cys Ser Trp Ala Ser
                485                 490                 495

Pro Val Ala Leu Asn Val Gln Tyr Ala Pro Arg Asp Val Arg Val
                500                 505                 510

Arg Lys Ile Lys Pro Leu Ser Glu Ile His Ser Gly Asn Ser Val
                515                 520                 525

Ser Leu Gln Cys Asp Phe Ser Ser Ser His Pro Lys Glu Val Gln
                530                 535                 540

Phe Phe Trp Glu Lys Asn Gly Arg Leu Leu Gly Lys Glu Ser Gln
                545                 550                 555

Leu Asn Phe Asp Ser Ile Ser Pro Glu Asp Ala Gly Ser Tyr Ser
                560                 565                 570

Cys Trp Val Asn Asn Ser Ile Gly Gln Thr Ala Ser Lys Ala Trp
                575                 580                 585

Thr Leu Glu Val Leu Tyr Ala Pro Arg Arg Leu Arg Val Ser Met
                590                 595                 600

Ser Pro Gly Asp Gln Val Met Glu Gly Lys Ser Ala Thr Leu Thr
                605                 610                 615

Cys Glu Ser Asp Ala Asn Pro Pro Val Ser His Tyr Thr Trp Phe
                620                 625                 630

Asp Trp Asn Asn Gln Ser Leu Pro His His Ser Gln Lys Leu Arg
                635                 640                 645

Leu Glu Pro Val Lys Val Gln His Ser Gly Ala Tyr Trp Cys Gln
                650                 655                 660

Gly Thr Asn Ser Val Gly Lys Gly Arg Ser Pro Leu Ser Thr Leu
                665                 670                 675

Thr Val Tyr Tyr Ser Pro Glu Thr Ile Gly Arg Arg Val Ala Val
                680                 685                 690

Gly Leu Gly Ser Cys Leu Ala Ile Leu Ile Leu Ala Ile Cys Gly
                695                 700                 705

Leu Lys Leu Gln Arg Arg Trp Lys Arg Thr Gln Ser Gln Gln Gly
                710                 715                 720

Leu Gln Glu Asn Ser Ser Gly Gln Ser Phe Phe Val Arg Asn Lys
                725                 730                 735

Lys Val Arg Arg Ala Pro Leu Ser Glu Gly Pro His Ser Leu Gly
                740                 745                 750

Cys Tyr Asn Pro Met Met Glu Asp Gly Ile Ser Tyr Thr Thr Leu
                755                 760                 765

Arg Phe Pro Glu Met Asn Ile Pro Arg Thr Gly Asp Ala Glu Ser

```
                        770                 775                 780
Ser Glu Met Gln Arg Pro Pro Arg Thr Cys Asp Asp Thr Val Thr
                    785                 790                 795

Tyr Ser Ala Leu His Lys Arg Gln Val Gly Asp Tyr Glu Asn Val
                    800                 805                 810

Ile Pro Asp Phe Pro Glu Asp Glu Gly Ile His Tyr Ser Glu Leu
                    815                 820                 825

Ile Gln Phe Gly Val Gly Glu Arg Pro Gln Ala Gln Glu Asn Val
                    830                 835                 840

Asp Tyr Val Ile Leu Lys His
                    845

<210> SEQ ID NO 37
<211> LENGTH: 42
<212> TYPE: PRT
<213> ORGANISM: Homo sapiens

<400> SEQUENCE: 37

Arg Thr Val Ala Ala Pro Ser Val Phe Ile Phe Pro Pro Ser Asp
  1               5                  10                  15

Glu Gln Leu Lys Ser Gly Thr Ala Ser Val Val Cys Leu Leu Asn
                 20                  25                  30

Asn Phe Tyr Pro Arg Glu Ala Lys Val Gln Trp Lys
                 35                  40

<210> SEQ ID NO 38
<211> LENGTH: 218
<212> TYPE: PRT
<213> ORGANISM: Homo sapiens

<400> SEQUENCE: 38

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys
                 35                  40                  45

Phe Asn Trp Tyr Val Asp Gly Val Glu Val His Asn Ala Lys Thr
                 50                  55                  60

Lys Pro Arg Glu Glu Gln Tyr Asn Ser Thr Tyr Arg Val Val Ser
                 65                  70                  75

Val Leu Thr Val Leu His Gln Asp Trp Leu Asn Gly Lys Glu Tyr
                 80                  85                  90

Lys Cys Lys Val Ser Asn Lys Ala Leu Pro Ala Pro Ile Glu Lys
                 95                 100                 105

Thr Ile Ser Lys Ala Lys Gly Gln Pro Arg Glu Pro Gln Val Tyr
                110                 115                 120

Thr Leu Pro Pro Ser Arg Glu Glu Met Thr Lys Asn Gln Val Ser
                125                 130                 135

Leu Thr Cys Leu Val Lys Gly Phe Tyr Pro Ser Asp Ile Ala Val
                140                 145                 150

Glu Trp Glu Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Lys
                170                 175                 180

Leu Thr Val Asp Lys Ser Arg Trp Gln Gln Gly Asn Val Phe Ser
                185                 190                 195
```

```
Cys Ser Val Met His Glu Ala Leu His Asn His Tyr Thr Gln Lys
            200                 205                 210

Ser Leu Ser Leu Ser Pro Gly Lys
            215

<210> SEQ ID NO 39
<211> LENGTH: 217
<212> TYPE: PRT
<213> ORGANISM: Homo sapiens

<400> SEQUENCE: 39

Pro Ala Pro Pro Val Ala Gly Pro Ser Val Phe Leu Phe Pro Pro
  1               5                  10                  15

Lys Pro Lys Asp Thr Leu Met Ile Ser Arg Thr Pro Glu Val Thr
                 20                  25                  30

Cys Val Val Val Asp Val Ser His Glu Asp Pro Glu Val Gln Phe
                 35                  40                  45

Asn Trp Tyr Val Asp Gly Val Glu Val His Asn Ala Lys Thr Lys
                 50                  55                  60

Pro Arg Glu Glu Gln Phe Asn Ser Thr Phe Arg Val Val Ser Val
                 65                  70                  75

Leu Thr Val Val His Gln Asp Trp Leu Asn Gly Lys Glu Tyr Lys
                 80                  85                  90

Cys Lys Val Ser Asn Lys Gly Leu Pro Ala Pro Ile Glu Lys Thr
                 95                 100                 105

Ile Ser Lys Thr Lys Gly Gln Pro Arg Glu Pro Gln Val Tyr Thr
                110                 115                 120

Leu Pro Pro Ser Arg Glu Glu Met Thr Lys Asn Gln Val Ser Leu
                125                 130                 135

Thr Cys Leu Val Lys Gly Phe Tyr Pro Ser Asp Ile Ala Val Glu
                140                 145                 150

Trp Glu Ser Asn Gly Gln Pro Glu Asn Asn Tyr Lys Thr Thr Pro
                155                 160                 165

Pro Met Leu Asp Ser Asp Gly Ser Phe Phe Leu Tyr Ser Lys Leu
                170                 175                 180

Thr Val Asp Lys Ser Arg Trp Gln Gln Gly Asn Val Phe Ser Cys
                185                 190                 195

Ser Val Met His Glu Ala Leu His Asn His Tyr Thr Gln Lys Ser
                200                 205                 210

Leu Ser Leu Ser Pro Gly Lys
            215

<210> SEQ ID NO 40
<211> LENGTH: 217
<212> TYPE: PRT
<213> ORGANISM: Homo sapiens

<400> SEQUENCE: 40

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Gln Phe
                 35                  40                  45

Lys Trp Tyr Val Asp Gly Val Glu Val His Asn Ala Lys Thr Lys
                 50                  55                  60
```

```
Pro Arg Glu Glu Gln Phe Asn Ser Thr Phe Arg Val Val Ser Val
            65                  70                  75

Leu Thr Val Leu His Gln Asp Trp Leu Asn Gly Lys Glu Tyr Lys
            80                  85                  90

Cys Lys Val Ser Asn Lys Ala Leu Pro Ala Pro Ile Glu Lys Thr
            95                 100                 105

Ile Ser Lys Thr Lys Gly Gln Pro Arg Glu Pro Gln Val Tyr Thr
           110                 115                 120

Leu Pro Pro Ser Arg Glu Glu Met Thr Lys Asn Gln Val Ser Leu
           125                 130                 135

Thr Cys Leu Val Lys Gly Phe Tyr Pro Ser Asp Ile Ala Val Glu
           140                 145                 150

Trp Glu Ser Ser Gly Gln Pro Glu Asn Asn Tyr Asn Thr Thr Pro
           155                 160                 165

Pro Met Leu Asp Ser Asp Gly Ser Phe Phe Leu Tyr Ser Lys Leu
           170                 175                 180

Thr Val Asp Lys Ser Arg Trp Gln Gln Gly Asn Ile Phe Ser Cys
           185                 190                 195

Ser Val Met His Glu Ala Leu His Asn Arg Phe Thr Gln Lys Ser
           200                 205                 210

Leu Ser Leu Ser Pro Gly Lys
           215

<210> SEQ ID NO 41
<211> LENGTH: 218
<212> TYPE: PRT
<213> ORGANISM: Homo sapiens

<400> SEQUENCE: 41

Pro Ala Pro Glu Phe Leu Gly Gly Pro Ser Val Phe Leu Phe Pro
  1               5                  10                  15

Pro Lys Pro Lys Asp Thr Leu Met Ile Ser Arg Thr Pro Glu Val
             20                  25                  30

Thr Cys Val Val Val Asp Val Ser Gln Glu Asp Pro Glu Val Gln
             35                  40                  45

Phe Asn Trp Tyr Val Asp Gly Val Glu Val His Asn Ala Lys Thr
             50                  55                  60

Lys Pro Arg Glu Glu Gln Phe Asn Ser Thr Tyr Arg Val Val Ser
             65                  70                  75

Val Leu Thr Val Leu His Gln Asp Trp Leu Asn Gly Lys Glu Tyr
             80                  85                  90

Lys Cys Lys Val Ser Asn Lys Gly Leu Pro Ser Ser Ile Glu Lys
             95                 100                 105

Thr Ile Ser Lys Ala Lys Gly Gln Pro Arg Glu Pro Gln Val Tyr
            110                 115                 120

Thr Leu Pro Pro Ser Gln Glu Glu Met Thr Lys Asn Gln Val Ser
            125                 130                 135

Leu Thr Cys Leu Val Lys Gly Phe Tyr Pro Ser Asp Ile Ala Val
            140                 145                 150

Glu Trp Glu Ser Asn Gly Gln Pro Glu Asn Asn Tyr Lys Thr Thr
            155                 160                 165

Pro Pro Val Leu Asp Ser Asp Gly Ser Phe Phe Leu Tyr Ser Arg
            170                 175                 180

Leu Thr Val Asp Lys Ser Arg Trp Gln Glu Gly Asn Val Phe Ser
            185                 190                 195
```

```
Cys Ser Val Met His Glu Ala Leu His Asn His Thr Tyr Gln Lys
            200                 205                 210

Ser Leu Ser Leu Ser Leu Gly Lys
            215

<210> SEQ ID NO 42
<211> LENGTH: 30
<212> TYPE: PRT
<213> ORGANISM: Artificial sequence
<220> FEATURE:
<223> OTHER INFORMATION: sequence is synthesized

<400> SEQUENCE: 42

Cys Asp Lys Thr His Thr Gly Gly Gly Ser Gln Arg Leu Met Glu
  1               5                  10                  15

Asp Ile Cys Leu Pro Arg Trp Gly Cys Leu Trp Glu Asp Asp Phe
                 20                  25                  30

<210> SEQ ID NO 43
<211> LENGTH: 20
<212> TYPE: PRT
<213> ORGANISM: Artificial sequence
<220> FEATURE:
<223> OTHER INFORMATION: sequence is synthesized

<400> SEQUENCE: 43

Gln Arg Leu Met Glu Asp Ile Cys Leu Pro Arg Trp Gly Cys Leu
  1               5                  10                  15

Trp Glu Asp Asp Phe
                 20

<210> SEQ ID NO 44
<211> LENGTH: 20
<212> TYPE: PRT
<213> ORGANISM: Artificial sequence
<220> FEATURE:
<223> OTHER INFORMATION: sequence is synthesized

<400> SEQUENCE: 44

Gln Arg Leu Ile Glu Asp Ile Cys Leu Pro Arg Trp Gly Cys Leu
  1               5                  10                  15

Trp Glu Asp Asp Phe
                 20

<210> SEQ ID NO 45
<211> LENGTH: 18
<212> TYPE: PRT
<213> ORGANISM: Artificial sequence
<220> FEATURE:
<223> OTHER INFORMATION: sequence is synthesized

<400> SEQUENCE: 45

Arg Leu Ile Glu Asp Ile Cys Leu Pro Arg Trp Gly Cys Leu Trp
  1               5                  10                  15

Glu Asp Asp

<210> SEQ ID NO 46
<211> LENGTH: 11
<212> TYPE: PRT
<213> ORGANISM: Artificial sequence
<220> FEATURE:
<223> OTHER INFORMATION: sequence is synthesized

<400> SEQUENCE: 46

Asp Ile Cys Leu Pro Arg Trp Gly Cys Leu Trp
```

<210> SEQ ID NO 47
<211> LENGTH: 14
<212> TYPE: PRT
<213> ORGANISM: Homo sapiens

<400> SEQUENCE: 47

Trp Val Arg Arg Ala Pro Gly Gln Gly Leu Glu Trp Met Gly
                 5                  10

<210> SEQ ID NO 48
<211> LENGTH: 32
<212> TYPE: PRT
<213> ORGANISM: Homo sapiens

<400> SEQUENCE: 48

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
                 20                  25                  30

Ala Arg

<210> SEQ ID NO 49
<211> LENGTH: 23
<212> TYPE: PRT
<213> ORGANISM: Homo sapiens

<400> SEQUENCE: 49

Asp Ile Val Met Thr Gln Ser Pro Leu Ser Leu Pro Val Thr Pro
 1               5                  10                  15

Gly Glu Pro Ala Ser Ile Ser Cys
                 20

<210> SEQ ID NO 50
<211> LENGTH: 25
<212> TYPE: PRT
<213> ORGANISM: Homo sapiens

<400> SEQUENCE: 50

Gln Val Gln Leu Val Gln Ser Gly Ala Glu Val Lys Lys Pro Gly
 1               5                  10                  15

Ala Ser Val Lys Val Ser Cys Lys Ala Ser
                 20                  25

<210> SEQ ID NO 51
<211> LENGTH: 13
<212> TYPE: PRT
<213> ORGANISM: Homo sapiens

<400> SEQUENCE: 51

Trp Val Arg Gln Ala Pro Gly Gln Gly Leu Glu Trp Met
                 5                  10

<210> SEQ ID NO 52
<211> LENGTH: 31
<212> TYPE: PRT
<213> ORGANISM: Homo sapiens

<400> SEQUENCE: 52

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys

```
                    20                  25                  30

Ala

<210> SEQ ID NO 53
<211> LENGTH: 30
<212> TYPE: PRT
<213> ORGANISM: Homo sapiens

<400> SEQUENCE: 53

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
                20                  25                  30

<210> SEQ ID NO 54
<211> LENGTH: 30
<212> TYPE: PRT
<213> ORGANISM: Homo sapiens

<400> SEQUENCE: 54

Gln Val Gln Leu Gln Glu Ser Gly Pro Gly Leu Val Lys Pro Ser
 1               5                  10                  15

Gln Thr Leu Ser Leu Thr Cys Thr Val Ser Gly Gly Ser Val Ser
                20                  25                  30

<210> SEQ ID NO 55
<211> LENGTH: 14
<212> TYPE: PRT
<213> ORGANISM: Homo sapiens

<400> SEQUENCE: 55

Trp Ile Arg Gln Pro Pro Gly Lys Gly Leu Glu Trp Ile Gly
                 5                  10

<210> SEQ ID NO 56
<211> LENGTH: 32
<212> TYPE: PRT
<213> ORGANISM: Homo sapiens

<400> SEQUENCE: 56

Arg Val Thr Ile Ser Val Asp Thr Ser Lys Asn Gln Phe Ser Leu
 1               5                  10                  15

Lys Leu Ser Ser Val Thr Ala Ala Asp Thr Ala Val Tyr Tyr Cys
                20                  25                  30

Ala Arg

<210> SEQ ID NO 57
<211> LENGTH: 25
<212> TYPE: PRT
<213> ORGANISM: Homo sapiens

<400> SEQUENCE: 57

Gln Val Gln Leu Gln Glu Ser Gly Pro Gly Leu Val Lys Pro Ser
 1               5                  10                  15

Gln Thr Leu Ser Leu Thr Cys Thr Val Ser
                20                  25

<210> SEQ ID NO 58
<211> LENGTH: 13
<212> TYPE: PRT
<213> ORGANISM: Homo sapiens

<400> SEQUENCE: 58
```

Trp Ile Arg Gln Pro Pro Gly Lys Gly Leu Glu Trp Ile
    5                   10

<210> SEQ ID NO 59
<211> LENGTH: 31
<212> TYPE: PRT
<213> ORGANISM: Homo sapiens

<400> SEQUENCE: 59

Arg Val Thr Ile Ser Val Asp Thr Ser Lys Asn Gln Phe Ser Leu
1               5                   10                  15

Lys Leu Ser Ser Val Thr Ala Ala Asp Thr Ala Val Tyr Tyr Cys
                20                  25                  30

Ala

<210> SEQ ID NO 60
<211> LENGTH: 30
<212> TYPE: PRT
<213> ORGANISM: Homo sapiens

<400> SEQUENCE: 60

Arg Val Thr Ile Ser Val Asp Thr Ser Lys Asn Gln Phe Ser Leu
1               5                   10                  15

Lys Leu Ser Ser Val Thr Ala Ala Asp Thr Ala Val Tyr Tyr Cys
                20                  25                  30

<210> SEQ ID NO 61
<211> LENGTH: 30
<212> TYPE: PRT
<213> ORGANISM: Homo sapiens

<400> SEQUENCE: 61

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

<210> SEQ ID NO 62
<211> LENGTH: 14
<212> TYPE: PRT
<213> ORGANISM: Homo sapiens

<400> SEQUENCE: 62

Trp Val Arg Gln Ala Pro Gly Lys Gly Leu Glu Trp Val Ser
    5                   10

<210> SEQ ID NO 63
<211> LENGTH: 32
<212> TYPE: PRT
<213> ORGANISM: Homo sapiens

<400> SEQUENCE: 63

Arg Phe Thr Ile Ser Arg Asp Asn Ser Lys Asn Thr Leu Tyr Leu
1               5                   10                  15

Gln Met Asn Ser Leu Arg Ala Glu Asp Thr Ala Val Tyr Tyr Cys
                20                  25                  30

Ala Arg

<210> SEQ ID NO 64
<211> LENGTH: 25
<212> TYPE: PRT
<213> ORGANISM: Homo sapiens

```
<400> SEQUENCE: 64

Glu Val Gln Leu Val Glu Ser Gly Gly Leu Val Gln Pro Gly
  1               5                  10                 15

Gly Ser Leu Arg Leu Ser Cys Ala Ala Ser
             20                  25

<210> SEQ ID NO 65
<211> LENGTH: 13
<212> TYPE: PRT
<213> ORGANISM: Homo sapiens

<400> SEQUENCE: 65

Trp Val Arg Gln Ala Pro Gly Lys Gly Leu Glu Trp Val
             5                  10

<210> SEQ ID NO 66
<211> LENGTH: 31
<212> TYPE: PRT
<213> ORGANISM: Homo sapiens

<400> SEQUENCE: 66

Arg Phe Thr Ile Ser Arg Asp Asn Ser Lys Asn Thr Leu Tyr Leu
  1               5                  10                 15

Gln Met Asn Ser Leu Arg Ala Glu Asp Thr Ala Val Tyr Tyr Cys
             20                  25                      30

Ala

<210> SEQ ID NO 67
<211> LENGTH: 30
<212> TYPE: PRT
<213> ORGANISM: Homo sapiens

<400> SEQUENCE: 67

Arg Phe Thr Ile Ser Arg Asp Asn Ser Lys Asn Thr Leu Tyr Leu
  1               5                  10                 15

Gln Met Asn Ser Leu Arg Ala Glu Asp Thr Ala Val Tyr Tyr Cys
             20                  25                      30

<210> SEQ ID NO 68
<211> LENGTH: 30
<212> TYPE: PRT
<213> ORGANISM: Homo sapiens

<400> SEQUENCE: 68

Glu Val Gln Leu Val Glu Ser Gly Gly Leu Val Gln Pro Gly
  1               5                  10                 15

Gly Ser Leu Arg Leu Ser Cys Ala Ala Ser Gly Phe Asn Ile Lys
             20                  25                      30

<210> SEQ ID NO 69
<211> LENGTH: 32
<212> TYPE: PRT
<213> ORGANISM: Homo sapiens

<400> SEQUENCE: 69

Arg Phe Thr Ile Ser Ala Asp Thr Ser Lys Asn Thr Ala Tyr Leu
  1               5                  10                 15

Gln Met Asn Ser Leu Arg Ala Glu Asp Thr Ala Val Tyr Tyr Cys
             20                  25                      30

Ser Arg
```

```
<210> SEQ ID NO 70
<211> LENGTH: 31
<212> TYPE: PRT
<213> ORGANISM: Homo sapiens

<400> SEQUENCE: 70

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ser

<210> SEQ ID NO 71
<211> LENGTH: 32
<212> TYPE: PRT
<213> ORGANISM: Homo sapiens

<400> SEQUENCE: 71

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala Arg

<210> SEQ ID NO 72
<211> LENGTH: 31
<212> TYPE: PRT
<213> ORGANISM: Homo sapiens

<400> SEQUENCE: 72

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 73
<211> LENGTH: 30
<212> TYPE: PRT
<213> ORGANISM: Homo sapiens

<400> SEQUENCE: 73

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

<210> SEQ ID NO 74
<211> LENGTH: 23
<212> TYPE: PRT
<213> ORGANISM: Homo sapiens

<400> SEQUENCE: 74

Asp Ile Gln Met Thr Gln Ser Pro Ser Ser Leu Ser Ala Ser Val
 1               5                  10                  15

Gly Asp Arg Val Thr Ile Thr Cys
                20

<210> SEQ ID NO 75
<211> LENGTH: 15
<212> TYPE: PRT
```

<213> ORGANISM: Homo sapiens

<400> SEQUENCE: 75

Trp Tyr Gln Gln Lys Pro Gly Lys Ala Pro Lys Leu Leu Ile Tyr
1               5                   10                  15

<210> SEQ ID NO 76
<211> LENGTH: 32
<212> TYPE: PRT
<213> ORGANISM: Homo sapiens

<400> SEQUENCE: 76

Gly Val Pro Ser Arg Phe Ser Gly Ser Gly Ser Gly Thr Asp Phe
1               5                   10                  15

Thr Leu Thr Ile Ser Ser Leu Gln Pro Glu Asp Phe Ala Thr Tyr
                20                  25                  30

Tyr Cys

<210> SEQ ID NO 77
<211> LENGTH: 10
<212> TYPE: PRT
<213> ORGANISM: Homo sapiens

<400> SEQUENCE: 77

Phe Gly Gln Gly Thr Lys Val Glu Ile Lys
                5                   10

<210> SEQ ID NO 78
<211> LENGTH: 14
<212> TYPE: PRT
<213> ORGANISM: Homo sapiens

<400> SEQUENCE: 78

Trp Tyr Gln Gln Lys Pro Gly Lys Ala Pro Lys Leu Leu Ile
                5                   10

<210> SEQ ID NO 79
<211> LENGTH: 15
<212> TYPE: PRT
<213> ORGANISM: Homo sapiens

<400> SEQUENCE: 79

Trp Tyr Leu Gln Lys Pro Gly Gln Ser Pro Gln Leu Leu Ile Tyr
1               5                   10                  15

<210> SEQ ID NO 80
<211> LENGTH: 32
<212> TYPE: PRT
<213> ORGANISM: Homo sapiens

<400> SEQUENCE: 80

Gly Val Pro Asp Arg Phe Ser Gly Ser Gly Ser Gly Thr Asp Phe
1               5                   10                  15

Thr Leu Lys Ile Ser Arg Val Glu Ala Glu Asp Val Gly Val Tyr
                20                  25                  30

Tyr Cys

<210> SEQ ID NO 81
<211> LENGTH: 23
<212> TYPE: PRT
<213> ORGANISM: Homo sapiens

<400> SEQUENCE: 81

Glu Ile Val Leu Thr Gln Ser Pro Gly Thr Leu Ser Leu Ser Pro
1               5                   10                  15

Gly Glu Arg Ala Thr Leu Ser Cys
                20

<210> SEQ ID NO 82
<211> LENGTH: 15
<212> TYPE: PRT
<213> ORGANISM: Homo sapiens

<400> SEQUENCE: 82

Trp Tyr Gln Gln Lys Pro Gly Gln Ala Pro Arg Leu Leu Ile Tyr
1               5                   10                  15

<210> SEQ ID NO 83
<211> LENGTH: 32
<212> TYPE: PRT
<213> ORGANISM: Homo sapiens

<400> SEQUENCE: 83

Gly Ile Pro Asp Arg Phe Ser Gly Ser Gly Ser Gly Thr Asp Phe
1               5                   10                  15

Thr Leu Thr Ile Ser Arg Leu Glu Pro Glu Asp Phe Ala Val Tyr
                20                  25                  30

Tyr Cys

<210> SEQ ID NO 84
<211> LENGTH: 23
<212> TYPE: PRT
<213> ORGANISM: Homo sapiens

<400> SEQUENCE: 84

Asp Ile Val Met Thr Gln Ser Pro Asp Ser Leu Ala Val Ser Leu
1               5                   10                  15

Gly Glu Arg Ala Thr Ile Asn Cys
                20

<210> SEQ ID NO 85
<211> LENGTH: 15
<212> TYPE: PRT
<213> ORGANISM: Homo sapiens

<400> SEQUENCE: 85

Trp Tyr Gln Gln Lys Pro Gly Gln Pro Pro Lys Leu Leu Ile Tyr
1               5                   10                  15

<210> SEQ ID NO 86
<211> LENGTH: 32
<212> TYPE: PRT
<213> ORGANISM: Homo sapiens

<400> SEQUENCE: 86

Gly Val Pro Asp Arg Phe Ser Gly Ser Gly Ser Gly Thr Asp Phe
1               5                   10                  15

Thr Leu Thr Ile Ser Ser Leu Gln Ala Glu Asp Val Ala Val Tyr
                20                  25                  30

Tyr Cys

<210> SEQ ID NO 87
<211> LENGTH: 219
<212> TYPE: PRT
<213> ORGANISM: Artificial sequence
<220> FEATURE:

<223> OTHER INFORMATION: sequence is synthesized

<400> SEQUENCE: 87

```
Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Ser Ile Val
             20                  25                  30

His Ser Val Gly Asn Thr Phe Leu Glu Trp Tyr Gln Gln Lys Pro
         35                  40                  45

Gly Lys Ala Pro Lys Leu Leu Ile Tyr Lys Val Ser Asn Arg Phe
     50                  55                  60

Ser Gly Val Pro Ser Arg Phe Ser Gly Ser Gly Ser Gly Thr Asp
 65                  70                  75

Phe Thr Leu Thr Ile Ser Ser Leu Gln Pro Glu Asp Phe Ala Thr
             80                  85                  90

Tyr Tyr Cys Phe Gln Gly Ser Gln Phe Pro Tyr Thr Phe Gly Gln
         95                 100                 105

Gly Thr Lys Val Glu Ile Lys Arg Thr Val Ala Ala Pro Ser Val
    110                 115                 120

Phe Ile Phe Pro Pro Ser Asp Glu Gln Leu Lys Ser Gly Thr Ala
125                 130                 135

Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
        155                 160                 165

Glu Ser Val Thr Glu Gln Asp Ser Lys Asp Ser Thr Tyr Ser Leu
    170                 175                 180

Ser Ser Thr Leu Thr Leu Ser Lys Ala Asp Tyr Glu Lys His Lys
185                 190                 195

Val Tyr Ala Cys Glu Val Thr His Gln Gly Leu Ser Ser Pro Val
            200                 205                 210

Thr Lys Ser Phe Asn Arg Gly Glu Cys
        215
```

<210> SEQ ID NO 88
<211> LENGTH: 450
<212> TYPE: PRT
<213> ORGANISM: Artificial sequence
<220> FEATURE:
<223> OTHER INFORMATION: sequence is synthesized

<400> SEQUENCE: 88

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Glu Phe Ser
             20                  25                  30

Arg Ser Trp Met Asn Trp Val Arg Gln Ala Pro Gly Lys Gly Leu
         35                  40                  45

Glu Trp Val Gly Arg Ile Tyr Pro Gly Asp Gly Asp Thr Asn Tyr
     50                  55                  60

Ser Gly Lys Phe Lys Gly Arg Phe Thr Ile Ser Ala Asp Thr Ser
 65                  70                  75

Lys Asn Thr Ala Tyr Leu Gln Met Asn Ser Leu Arg Ala Glu Asp
             80                  85                  90

Thr Ala Val Tyr Tyr Cys Ala Arg Asp Gly Ser Ser Trp Asp Trp
         95                 100                 105
```

```
Tyr Phe Asp Val Trp Gly Gln Gly Thr Leu Val Thr Val Ser Ser
            110                 115                 120

Ala Ser Thr Lys Gly Pro Ser Val Phe Pro Leu Ala Pro Ser Ser
            125                 130                 135

Lys Ser Thr Ser Gly Gly Thr Ala Ala Leu Gly Cys Leu Val Lys
            140                 145                 150

Asp Tyr Phe Pro Glu Pro Val Thr Val Ser Trp Asn Ser Gly Ala
            155                 160                 165

Leu Thr Ser Gly Val His Thr Phe Pro Ala Val Leu Gln Ser Ser
            170                 175                 180

Gly Leu Tyr Ser Leu Ser Ser Val Val Thr Val Pro Ser Ser Ser
            185                 190                 195

Leu Gly Thr Gln Thr Tyr Ile Cys Asn Val Asn His Lys Pro Ser
            200                 205                 210

Asn Thr Lys Val Asp Lys Lys Val Glu Pro Lys Ser Cys Asp Lys
            215                 220                 225

Thr His Thr Cys Pro Pro Cys Pro Ala Pro Glu Leu Leu Gly Gly
            230                 235                 240

Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp
            305                 310                 315

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly Lys
            440                 445                 450

<210> SEQ ID NO 89
<211> LENGTH: 120
<212> TYPE: PRT
<213> ORGANISM: Artificial sequence
<220> FEATURE:
<223> OTHER INFORMATION: sequence is synthesized

<400> SEQUENCE: 89

Gln Val Gln Leu Gln Gln Ser Gly Pro Glu Leu Val Lys Pro Gly
```

```
               1               5              10              15
Ala Ser Val Lys Ile Ser Cys Lys Ala Ser Gly Tyr Glu Phe Ser
                   20              25              30

Arg Ser Trp Met Asn Trp Val Lys Gln Arg Pro Gly Gln Gly Arg
                   35              40              45

Glu Trp Ile Gly Arg Ile Tyr Pro Gly Asp Gly Asp Thr Asn Tyr
                   50              55              60

Ser Gly Lys Phe Lys Gly Lys Ala Thr Leu Thr Ala Asp Lys Ser
                   65              70              75

Ser Ser Thr Ala Tyr Met Gln Leu Ser Ser Leu Thr Ser Val Asp
                   80              85              90

Ser Ala Val Tyr Phe Cys Ala Arg Asp Gly Ser Ser Trp Asp Trp
                   95             100             105

Tyr Phe Asp Val Trp Gly Ala Gly Thr Thr Val Thr Val Ser Ser
                  110             115             120

<210> SEQ ID NO 90
<211> LENGTH: 112
<212> TYPE: PRT
<213> ORGANISM: Artificial sequence
<220> FEATURE:
<223> OTHER INFORMATION: sequence is synthesized

<400> SEQUENCE: 90

Asp Ile Leu Met Thr Gln Thr Pro Leu Ser Leu Pro Val Ser Leu
  1               5              10              15

Gly Asp Gln Ala Ser Ile Ser Cys Arg Ser Ser Gln Ser Ile Val
                   20              25              30

His Ser Asn Gly Asn Thr Phe Leu Glu Trp Tyr Leu Gln Lys Pro
                   35              40              45

Gly Gln Ser Pro Lys Leu Leu Ile Tyr Lys Val Ser Asn Arg Phe
                   50              55              60

Ser Gly Val Pro Asp Arg Phe Ser Gly Ser Gly Ser Gly Thr Asp
                   65              70              75

Phe Thr Leu Lys Ile Ser Arg Val Glu Ala Glu Asp Leu Gly Val
                   80              85              90

Tyr Tyr Cys Phe Gln Gly Ser Gln Phe Pro Tyr Thr Phe Gly Gly
                   95             100             105

Gly Thr Lys Val Glu Ile Lys
                  110

<210> SEQ ID NO 91
<211> LENGTH: 219
<212> TYPE: PRT
<213> ORGANISM: Artificial sequence
<220> FEATURE:
<223> OTHER INFORMATION: sequence is synthesized

<400> SEQUENCE: 91

Asp Ile Gln Met Thr Gln Ser Pro Ser Ser Leu Ser Ala Ser Val
  1               5              10              15

Gly Asp Arg Val Thr Ile Thr Cys Arg Ser Ser Gln Ser Ile Val
                   20              25              30

His Ser Val Gly Asn Thr Phe Leu Glu Trp Tyr Gln Gln Lys Pro
                   35              40              45

Gly Lys Ala Pro Lys Leu Leu Ile Tyr Lys Val Ser Asn Arg Phe
                   50              55              60

Ser Gly Val Pro Ser Arg Phe Ser Gly Ser Gly Ser Gly Thr Asp
```

```
              65                  70                  75
Phe Thr Leu Thr Ile Ser Ser Leu Gln Pro Glu Asp Phe Ala Thr
              80                  85                  90

Tyr Tyr Cys Phe Gln Gly Ser Gln Phe Pro Tyr Thr Phe Gly Gln
              95                 100                 105

Gly Thr Lys Val Glu Ile Lys Arg Thr Val Ala Ala Pro Ser Val
             110                 115                 120

Phe Ile Phe Pro Pro Ser Asp Glu Gln Leu Lys Ser Gly Thr Ala
             125                 130                 135

Ser Val Val Cys Leu Leu Asn Asn Phe Tyr Pro Arg Glu Ala Lys
             140                 145                 150

Val Gln Trp Lys Val Asp Asn Ala Leu Gln Ser Gly Asn Ser Gln
             155                 160                 165

Glu Ser Val Thr Glu Gln Asp Ser Lys Asp Ser Thr Tyr Ser Leu
             170                 175                 180

Ser Ser Thr Leu Thr Leu Ser Lys Ala Asp Tyr Glu Lys His Lys
             185                 190                 195

Val Tyr Ala Cys Glu Val Thr His Gln Gly Leu Ser Ser Pro Cys
             200                 205                 210

Thr Lys Ser Phe Asn Arg Gly Glu Cys
             215

<210> SEQ ID NO 92
<211> LENGTH: 450
<212> TYPE: PRT
<213> ORGANISM: Artificial sequence
<220> FEATURE:
<223> OTHER INFORMATION: sequence is synthesized

<400> SEQUENCE: 92

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Glu Phe Ser
              20                  25                  30

Arg Ser Trp Met Asn Trp Val Arg Gln Ala Pro Gly Lys Gly Leu
              35                  40                  45

Glu Trp Val Gly Arg Ile Tyr Pro Gly Asp Gly Asp Thr Asn Tyr
              50                  55                  60

Ser Gly Lys Phe Lys Gly Arg Phe Thr Ile Ser Ala Asp Thr Ser
              65                  70                  75

Lys Asn Thr Ala Tyr Leu Gln Met Asn Ser Leu Arg Ala Glu Asp
              80                  85                  90

Thr Ala Val Tyr Tyr Cys Ala Arg Asp Gly Ser Ser Trp Asp Trp
              95                 100                 105

Tyr Phe Asp Val Trp Gly Gln Gly Thr Leu Val Thr Val Ser Ser
             110                 115                 120

Cys Ser Thr Lys Gly Pro Ser Val Phe Pro Leu Ala Pro Ser Ser
             125                 130                 135

Lys Ser Thr Ser Gly Gly Thr Ala Ala Leu Gly Cys Leu Val Lys
             140                 145                 150

Asp Tyr Phe Pro Glu Pro Val Thr Val Ser Trp Asn Ser Gly Ala
             155                 160                 165

Leu Thr Ser Gly Val His Thr Phe Pro Ala Val Leu Gln Ser Ser
             170                 175                 180

Gly Leu Tyr Ser Leu Ser Ser Val Val Thr Val Pro Ser Ser Ser
             185                 190                 195
```

```
Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp
                305                 310                 315

Trp Leu Asn Gly Lys Glu Tyr Lys Cys Lys Val Ser Asn Lys Ala
                320                 325                 330

Leu Pro Ala Pro Ile Glu Lys Thr Ile Ser Lys Ala Lys Gly Gln
                335                 340                 345

Pro Arg Glu Pro Gln Val Tyr Thr Leu Pro Pro Ser Arg Glu Glu
                350                 355                 360

Met Thr Lys Asn Gln Val Ser Leu Thr Cys Leu Val Lys Gly Phe
                365                 370                 375

Tyr Pro Ser Asp Ile Ala Val Glu Trp Glu Ser Asn Gly Gln Pro
                380                 385                 390

Glu Asn Asn Tyr Lys Thr Thr Pro Pro Val Leu Asp Ser Asp Gly
                395                 400                 405

Ser Phe Phe Leu Tyr Ser Lys Leu Thr Val Asp Lys Ser Arg Trp
                410                 415                 420

Gln Gln Gly Asn Val Phe Ser Cys Ser Val Met His Glu Ala Leu
                425                 430                 435

His Asn His Tyr Thr Gln Lys Ser Leu Ser Leu Ser Pro Gly Lys
                440                 445                 450
```

<210> SEQ ID NO 93
<211> LENGTH: 450
<212> TYPE: PRT
<213> ORGANISM: Artificial sequence
<220> FEATURE:
<223> OTHER INFORMATION: sequence is synthesized

<400> SEQUENCE: 93

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Glu Phe Ser
                 20                  25                  30

Arg Ser Trp Met Asn Trp Val Arg Gln Ala Pro Gly Lys Gly Leu
                 35                  40                  45

Glu Trp Val Gly Arg Ile Tyr Pro Gly Asp Gly Asp Thr Asn Tyr
                 50                  55                  60

Ser Gly Lys Phe Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90
```

-continued

```
Thr Ala Val Tyr Tyr Cys Ala Arg Asp Gly Ser Ser Trp Asp Trp
                95                 100                105
Tyr Phe Asp Val Trp Gly Gln Gly Thr Leu Val Thr Val Ser Ser
               110                 115                120
Ala Ser Thr Lys Gly Pro Ser Val Phe Pro Leu Ala Pro Ser Ser
               125                 130                135
Lys Ser Thr Ser Gly Gly Thr Ala Ala Leu Gly Cys Leu Val Lys
               140                 145                150
Asp Tyr Phe Pro Glu Pro Val Thr Val Ser Trp Asn Ser Gly Ala
               155                 160                165
Leu Thr Ser Gly Val His Thr Phe Pro Ala Val Leu Gln Ser Ser
               170                 175                180
Gly Leu Tyr Ser Leu Ser Ser Val Val Thr Val Pro Ser Ser Ser
               185                 190                195
Leu Gly Thr Gln Thr Tyr Ile Cys Asn Val Asn His Lys Pro Ser
               200                 205                210
Asn Thr Lys Val Asp Lys Lys Val Glu Pro Lys Ser Cys Asp Lys
               215                 220                225
Thr His Thr Cys Pro Pro Cys Pro Ala Pro Glu Leu Leu Gly Gly
               230                 235                240
Pro Ser Val Phe Leu Phe Pro Pro Lys Pro Lys Asp Thr Leu Met
               245                 250                255
Ile Ser Arg Thr Pro Glu Val Thr Cys Val Val Val Asp Val Ser
               260                 265                270
His Glu Asp Pro Glu Val Lys Phe Asn Trp Tyr Val Asp Gly Val
               275                 280                285
Glu Val His Asn Ala Lys Thr Lys Pro Arg Glu Glu Gln Tyr Asn
               290                 295                300
Ser Thr Tyr Arg Val Val Ser Val Leu Thr Val Leu His Gln Asp
               305                 310                315
Trp Leu Asn Gly Lys Glu Tyr Lys Cys Lys Val Ser Asn Lys Ala
               320                 325                330
Leu Pro Ala Pro Ile Glu Lys Thr Ile Ser Lys Ala Lys Gly Gln
               335                 340                345
Pro Arg Glu Pro Gln Val Tyr Thr Leu Pro Pro Ser Arg Glu Glu
               350                 355                360
Met Thr Lys Asn Gln Val Ser Leu Thr Cys Leu Val Lys Gly Phe
               365                 370                375
Tyr Pro Ser Asp Ile Ala Val Glu Trp Glu Ser Asn Gly Gln Pro
               380                 385                390
Glu Asn Asn Tyr Lys Thr Thr Pro Pro Val Leu Asp Cys Asp Gly
               395                 400                405
Ser Phe Phe Leu Tyr Ser Lys Leu Thr Val Asp Lys Ser Arg Trp
               410                 415                420
Gln Gln Gly Asn Val Phe Ser Cys Ser Val Met His Glu Ala Leu
               425                 430                435
His Asn His Tyr Thr Gln Lys Ser Leu Ser Leu Ser Pro Gly Lys
               440                 445                450
```

ANTIBODIES AND IMMUNOCONJUGATES AND USES THEREFOR

This application is a continuation of application U.S. Ser. No. 11/754,899 filed on May 29, 2007 which claims priority under 35 USC Section 119(e) to U.S. Provisional Application Ser. Nos. 60/809,328, filed 30 May 2006, 60/908,941, filed 29 Mar. 2007, and 60/911,829, filed 13 Apr. 2007, the entire contents of which applications are hereby incorporated by reference in their entirety.

FIELD OF THE INVENTION

The present invention relates to anti-CD22 antibodies and immunoconjugates thereof. The invention further relates to methods of using anti-CD22 antibodies and immunoconjugates thereof.

BACKGROUND

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells." Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

B cell-related disorders include, but are not limited to, malignant lymphoma (Non-Hodgkin's Lymphoma, NHL), multiple myeloma, and chronic lymphocytic leukemia (CLL, B cell leukemia (CD5+ B lymphocytes). Non-Hodgkin's lymphomas (NHLs), a heterogeneous group of cancers principally arising from B lymphocytes, represent approximately 4% of all newly diagnosed cancers (Jemal, A. et al., CA-Cancer J Clin, 52: 23-47, (2002)). Aggressive NHL comprises approximately 30-40% of adult NHL (Harris, N. L. et al., Hematol. J. 1:53-66 (2001)) and includes diffuse large B-cell lymphoma (DLBCL), mantle cell lymphoma (MCL), peripheral T-cell lymphoma, and anaplastic large cell lymphoma. Frontline combination chemotherapy cures less than half of the patients with aggressive NHL, and most patients eventually succumb to their disease (Fisher, R. I. Semin. Oncol. 27(suppl 12): 2-8 (2000)).

B cell-related disorders also include autoimmune diseases. Autoimmune diseases remain clinically important diseases in humans. As the name implies, autoimmune diseases act through the body's own immune system. While the pathological mechanisms differ among individual types of autoimmune diseases, one general mechanism involves the binding of certain antibodies (referred to herein as self-reactive antibodies or autoantibodies) to the body's endogenous proteins. Physicians and scientists have identified more than 70 clinically distinct autoimmune diseases, including rheumatoid arthritis, multiple sclerosis, vasculitis, immune-mediated diabetes, and lupus such as systemic lupus erythematosus. While many autoimmune diseases are rare—affecting fewer than 200,000 individuals—collectively, these diseases afflict millions of Americans, an estimated five percent of the population, with women disproportionately affected by most diseases. The chronic nature of these diseases leads to an immense social and financial burden.

Cytotoxic agents which target B cell surface antigens are an important focus of B cell-related cancer therapies. One such B cell surface antigen is CD20. Rituximab (Rituxan; Genentech, Inc. (South San Francisco, Calif.) and IDEC Pharmaceutical Corp. (San Diego, Calif.)), a chimeric (mouse/human) anti-CD20 monoclonal antibody, was the first therapeutic antibody approved by the United States Food and Drug Administration for treatment of relapsed or refractory low-grade or follicular NHL (Leonard, J. P. et al., Clin. Canc. Res. 10:5327-5334 (2004)).

Other B-cell antigens, such as CD19, CD22, and CD52, represent targets of therapeutic potential for treatment of lymphoma (Grillo-Lopez A. J. et al., Curr Pharm Biotechnol, 2:301-11, (2001)). CD22 is a 135-kDa B-cell-restricted sialoglycoprotein expressed on the B-cell surface only at the mature stages of differentiation (Dorken, B. et al., J. Immunol. 136:4470-4479 (1986)). The predominant form of CD22 in humans is CD22beta which contains seven immunoglobulin superfamily domains in the extracellular domain (FIG. 1) (Wilson, G. L. et al., J. Exp. Med. 173:137-146 (1991)). A variant form, CD22 alpha, lacks immunoglobulin superfamily domains 3 and 4 (Stamenkovic, I. and Seed, B., Nature 345:74-77 (1990)). Ligand-binding to human CD22 has been shown to be associated with immunoglobulin superfamily domains 1 and 2 (also referred to as epitopes 1 and 2) (Engel, P. et al., J. Exp. Med. 181:1581-1586, 1995).

In B-cell NHL, CD22 expression ranges from 91% to 99% in the aggressive and indolent populations, respectively (Cesano, A. et al., Blood 100:350a (2002)). CD22 may function both as a component of the B-cell activation complex (Sato, S. et al., Semin. Immunol. 10:287-296 (1998)) and as an adhesion molecule (Engel, Pl t al., J. Immunol. 150:4719-4732 (1993)). The B cells of CD22-deficient mice have a shorter life span and enhanced apoptosis, which suggests a key role of this antigen in B-cell survival (Otipoby, K. L. et al., Nature (Lond) 384:634-637 (1996)). After binding with its natural ligand(s) or antibodies, CD22 is rapidly internalized, providing a potent costimulatory signal in primary B cells and proapoptotic signals in neoplastic B cells (Sato, S. et al., Immunity 5:551-562 (1996)).

Anti-CD22 antibodies have been studied as potential therapies for B cell cancers and other B cell proliferative diseases. Such anti-CD22 antibodies include RFB4 Mansfield, E. et al., Blood 90:2020-2026 (1997)), CMC-544 (DiJoseph, J. F., Blood 103:1807-1814 (2004)) and LL2 (Pawlak-Byczkowska, E. J. et al., Cancer Res. 49:4568-4577 (1989)). The LL2 antibody (formerly called HPB-2) is an IgG2a mouse monoclonal antibody directed against the CD22 antigen (Pawlak-Byczkowska, E. J. et al. (1989), supra). In vitro immunohistological evaluations demonstrated reactivity of the LL2 antibody with 50 of 51 B-cell NHL specimens tested, but not with other malignancies or normal nonlymphoid tissues (Pawlak-Byczkowska (1989), supra; Stein, R. et al., Cancer Immunol. Immunother. 37:293-298 (1993)).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., Cancer Immunol. Immunother. 21:183-87 (1986)). Toxins used in antibody-toxin conjugates include bacterial toxins such as diphtheria toxin, plant toxins such as ricin, small molecule toxins such as geldanamycin (Kerr et al (1997) Bioconjugate Chem. 8(6):781-784; Mandler et al (2000) Journal of the Nat. Cancer Inst. 92(19):1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition (Meyer, D. L. and Senter, P. D. "Recent Advances in Antibody Drug Conjugates for Cancer Therapy" in Annual Reports in Medicinal Chemistry, Vol 38 (2003) Chapter 23, 229-237). Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is being developed for the treatment of cancers that express CanAg antigen, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The same maytansinoid drug moiety, DM1, was linked through a non-disulfide linker, SMCC, to a mouse murine monoclonal antibody, TA.1 (Chari et al. (1992) Cancer Research 52:127-131). This conjugate was reported to be 200-fold less potent than the corresponding disulfide linker conjugate. The SMCC linker was considered therein to be "noncleavable."

Several short peptidic compounds have been isolated from the marine mollusk, Dolabella auricularia, and found to have biological activity (Pettit et al (1993) Tetrahedron 49:9151; Nakamura et al (1995) Tetrahedron Letters 36:5059-5062; Sone et al (1995) Journal Org Chem. 60:4474). Analogs of these compounds have also been prepared, and some were found to have biological activity (for a review, see Pettit et al (1998) Anti-Cancer Drug Design 13:243-277). For example, auristatin E (U.S. Pat. No. 5,635,483) is a synthetic analogue of the marine natural product Dolastatin 10, an agent that inhibits tubulin polymerization by binding to the same site on tubulin as the anticancer drug vincristine (G. R. Pettit, (1997) Prog. Chem. Org. Nat. Prod. 70:1-79). Dolastatin 10, auristatin PE, and auristatin E are linear peptides having four amino acids, three of which are unique to the dolastatin class of compounds, and a C-terminal amide.

The auristatin peptides, auristain E (AE) and monomethylauristatin (MMAE), synthetic analogs of dolastatin, were conjugated to: (i) chimeric monoclonal antibodies cBR96 (specific to Lewis Y on carcinomas); (ii) cAC10 which is specific to CD30 on hematological malignancies (Klussman, et al (2004), Bioconjugate Chemistry 15(4):765-773; Doronina et al (2003) Nature Biotechnology 21(7):778-784; "Monomethylvaline Compounds Capable of Conjugation to Ligands"; Francisco et al (2003) Blood 102(4): 1458-1465; US 2004/0018194; (iii) anti-CD20 antibodies such as Rituxan® (rituximab) (WO 04/032828) for the treatment of CD20-expressing cancers and immune disorders; (iv) anti-EphB2 antibodies 2H9 and anti-IL-8 for treatment of colorectal cancer (Mao, et al (2004) Cancer Research 64(3):781-788); (v) E-selectin antibody (Bhaskar et al (2003) Cancer Res. 63:6387-6394); and (vi) other anti-CD30 antibodies (WO 03/043583). Monomethylauristatin (MMAE) has also been conjugated to 2H9, an antibody against EphB2R which is a type 1 TM tyrosine kinase receptor with close homology between mouse and human, and is over-expressed in colorectal cancer cells (Mao et al (2004) Cancer Res. 64:781-788).

Monomethylauristatin MMAF, a variant of auristatin E (MMAE) with a phenylalanine at the C-terminus (U.S. Pat. No. 5,767,237; U.S. Pat. No. 6,124,431), has been reported to be less potent than MMAE, but more potent when conjugated to monoclonal antibodies (Senter et al, Proceedings of the American Association for Cancer Research, Volume 45, Abstract Number 623, presented Mar. 28, 2004). Auristatin F phenylene diamine (AFP); a phenylalanine variant of MMAE was linked to an anti-CD70 mAb, 1F6, through the C-terminus of 1F6 via a phenylene diamine spacer (Law et al, Proceedings of the American Association for Cancer Research, Volume 45, Abstract Number 625, presented Mar. 28, 2004).

Anti-CD22 antibody-toxin conjugates have also been studied as potential therapeutic compounds. For example, early reports described ricin A chain-containing immunotoxins directed against anti-CD22 as potential anti-cancer agents (May, R. D. et al., Chemical Abstracts 106(21): 168656x pages 35-36 (1987); Ghetie, M. A. et al., Cancer Research 48:2610-2617 (1988); and Amlot, P. L. et al., Blood 82(9): 2624-2633 (1993)). Where the toxin was a radioisotope, Epratuzumab, the humanized (CDR-grafted) IgG1 version of LL2, has shown evidence of therapeutic activity for the radioimmunoconjugate (Juweid, M. E. et al., Clin. Cancer Res. 5 (Suppl 10):3292s-3303s (1999); Griffiths, G. L. et al., J. Nucl. Med. 44:77-84 (2003); Linden, O. et al., Clin. Cancer Res. 5(suppl 10):3287s-3291s (1999)).

There exists a need in the art for additional drugs to treat various B cell-related cancers such as lymphomas such as non-Hodgkin's lymphoma and other B cell proliferative disorders. Particularly useful drugs for this purpose include B cell targeted anti-CD22 antibody-drug conjugates having a significantly lower toxicity, yet useful therapeutic efficiency.

These and other limitations and problems of the past are addressed by the present invention.

The recitation of any reference in this application is not an admission that the reference is prior art to this application. All references cited herein, including patents, patent applications and publications, are incorporated by reference in their entirety.

SUMMARY

The invention provides anti-CD22 antibodies and methods of using the same.

In one aspect, an antibody that binds to CD22 is provided, wherein the antibody comprises at least one, two, three, four, five, or six HVRs selected from:
(1) an HVR-H1 comprising the amino acid sequence of SEQ ID NO:2;
(2) an HVR-H2 comprising the amino acid sequence of SEQ ID NO:4;
(3) an HVR-H3 comprising the amino acid sequence of SEQ ID NO:6;
(4) an HVR-L1 comprising the amino acid sequence of SEQ ID NO:10;
(5) an HVR-L2 comprising the amino acid sequence of SEQ ID NO:12; and
(6) an HVR-L3 comprising the amino acid sequence of SEQ ID NO:14.

In another aspect, an antibody that binds to CD22 comprises (a) an HVR-L1 comprising the amino acid sequence of SEQ ID NO:10, and (b) at least one, two, three, four or five HVRs selected from:
(1) an HVR-H1 comprising the amino acid sequence of SEQ ID NO:2;
(2) an HVR-H2 comprising the amino acid sequence of SEQ ID NO:4;
(3) an HVR-H3 comprising the amino acid sequence of SEQ ID NO:6;
(4) an HVR-L2 comprising the amino acid sequence of SEQ ID NO:12; and
(6) an HVR-L3 comprising the amino acid sequence of SEQ ID NO:14.

In another aspect, an antibody that binds to CD22 comprises (a) an HVR-L1 comprising the amino acid sequence of SEQ ID NO:9, and (b) at least one, two, three, four or five HVRs selected from:
(1) an HVR-H1 comprising the amino acid sequence of SEQ ID NO:2;
(2) an HVR-H2 comprising the amino acid sequence of SEQ ID NO:4;
(3) an HVR-H3 comprising the amino acid sequence of SEQ ID NO:6;
(4) an HVR-L2 comprising the amino acid sequence of SEQ ID NO:12; and
(6) an HVR-L3 comprising the amino acid sequence of SEQ ID NO:14.

In another aspect, an antibody that binds to CD22 comprises (a) an HVR-H3 comprising the amino acid sequence of SEQ ID NO:6, and (b) at least one, two, three, four, or five HVRs selected from:
(1) an HVR-H1 comprising the amino acid sequence of SEQ ID NO:2;
(2) an HVR-H2 comprising the amino acid sequence of SEQ ID NO:4;
(3) an HVR-L1 comprising the amino acid sequence of SEQ ID NO:9;
(4) an HVR-L2 comprising the amino acid sequence of SEQ ID NO:12; and
(5) an HVR-L3 comprising the amino acid sequence of SEQ ID NO:14.

In another aspect, an antibody that binds to CD22 comprises (a) an HVR-H3 comprising the amino acid sequence of SEQ ID NO:6, and (b) at least one, two, three, four, or five HVRs selected from:
(1) an HVR-H1 comprising the amino acid sequence of SEQ ID NO:2;
(2) an HVR-H2 comprising the amino acid sequence of SEQ ID NO:4;
(3) an HVR-L1 comprising the amino acid sequence of SEQ ID NO:10;
(4) an HVR-L2 comprising the amino acid sequence of SEQ ID NO:12; and
(5) an HVR-L3 comprising the amino acid sequence of SEQ ID NO:14.

In one embodiment, the antibody comprises an HVR-L1 comprising the amino acid sequence of SEQ ID NO:10. In one embodiment, the antibody further comprises an HVR-H1 comprising the amino acid sequence of SEQ ID NO:2 and an HVR-H2 comprising the amino acid sequence of SEQ ID NO:4. In one embodiment, the antibody further comprises an HVR-L2 comprising the amino acid sequence of SEQ NO:12 and an HVR-L3 comprising the amino acid sequence of SEQ ID NO:14.

In certain embodiments, any of the above antibodies further comprises at least one framework selected from a VH subgroup III consensus framework and a VL subgroup I consensus framework.

In one aspect, an antibody that binds to CD22 is provided, wherein the antibody comprises a heavy chain variable domain having at least 90%, at least 91%, at least 92%, at least 93%, at least 94%, at least 95%, at least 96%, at least 97%, at least 98%, or at least 99% sequence identity to an amino acid sequence of SEQ ID NO:16. In one embodiment, the antibody comprises a heavy chain variable domain of SEQ ID NO:16.

In one aspect, the antibody further comprises a light chain variable domain having at least 90%, at least 91%, at least 92%, at least 93%, at least 94%, at least 95%, at least 96%, at least 97%, at least 98%, or at least 99% sequence identity to an amino acid sequence of SEQ ID NO:17. In one embodiment, the antibody comprises a light chain variable domain of SEQ ID NO:17.

In one aspect, the antibody further comprises a light chain variable domain having at least 90%, at least 91%, at least 92%, at least 93%, at least 94%, at least 95%, at least 96%, at least 97%, at least 98%, or at least 99% sequence identity to an amino acid sequence of SEQ ID NO:18. In one embodiment, the antibody comprises a light chain variable domain of SEQ ID NO:18.

In one embodiment, the antibody comprises a heavy chain variable domain having at least 90%, at least 91%, at least 92%, at least 93%, at least 94%, at least 95%, at least 96%, at least 97%, at least 98%, at least 99%, or 100% sequence identity to an amino acid sequence of SEQ ID NO:16 and a light chain variable domain having at least 90%, at least 91%, at least 92%, at least 93%, at least 94%, at least 95%, at least 96%, at least 97%, at least 98%, at least 99%, or 100% sequence identity to an amino acid sequence of SEQ ID NO:17. In one embodiment, the antibody comprises a heavy chain variable domain having at least 90%, at least 91%, at least 92%, at least 93%, at least 94%, at least 95%, at least 96%, at least 97%, at least 98%, at least 99%, or 100% sequence identity to an amino acid sequence of SEQ ID NO:16 and a light chain variable domain having at least 90%, at least 91%, at least 92%, at least 93%, at least 94%, at least 95%, at least 96%, at least 97%, at least 98%, at least 99%, or 100% sequence identity to an amino acid sequence of SEQ ID NO:18. In one embodiment, the heavy chain variable domain comprises the amino acid sequence of SEQ ID NO:16, and the light chain variable domain comprises the amino acid sequence of SEQ ID NO:17. In one embodiment, the heavy chain variable domain comprises the amino acid sequence of SEQ ID NO:16, and the light chain variable domain comprises the amino acid sequence of SEQ ID NO:18.

In certain embodiments, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a Chinese hamster ovary (CHO) cell. In one embodiment, a method of making an anti-CD22 antibody is provided, wherein the method comprises culturing the host cell under conditions suitable for expression of the polynucleotide encoding the antibody, and isolating the antibody.

In one aspect, an antibody that binds to CD22 expressed on the surface of a cell is provided. In one embodiment, the antibody binds to an epitope within a region of human or mouse CD22 comprising domain 1 or domain 2 or domains 1 and 2. In one embodiment, the cell is mammalian cell. In one embodiment, the cell is a human cell. In one embodiment, the cell is a cancer cell. In one embodiment the cell is a B cell. In one embodiment the cancer cell is a B cell.

In certain embodiments, any of the above antibodies is a monoclonal antibody. In one embodiment, the antibody is an antibody fragment selected from a Fab, Fab'-SH, Fv, scFv, or (Fab')$_2$ fragment. In one embodiment, the antibody is humanized. In one embodiment, the antibody is human.

In one aspect, a method of detecting the presence of CD22 in a biological sample is provided, the method comprising contacting the biological sample with any of the above antibodies under conditions permissive for binding of the antibody to CD22, and detecting whether a complex is formed between the antibody and CD22. In one embodiment, the biological sample comprises B cells. In one embodiment, the biological sample is from a mammal experiencing or suspected of experiencing a B cell disorder and/or a B cell proliferative disorder including, but not limited to, lymphoma, non-Hogkins lymphoma (NHL), aggressive NHL, relapsed aggressive NHL, relapsed indolent NHL, refractory NIL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, a method of diagnosing a cell proliferative disorder associated with increased expression of CD22 is provided, the method comprising contacting a test cell with any of the above antibodies; determining the level of expression of CD22 by detecting binding of the antibody to CD22; and comparing the level of expression of CD22 by the test cell with the level of expression of CD22 by a control cell, wherein a higher level of expression of CD22 by the test cell as compared to the control cell indicates the presence of a cell proliferative disorder associated with increased expression of CD22. In one embodiment, the test cell is a cell from a patient suspected of having a cell proliferative disorder, such as a B-cell proliferative disorder. In one embodiment, the cell proliferative disorder is selected from B cell disorders including but not limited to lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. In one embodiment, the method comprises determining the level of expression of CD22 on the surface of the test cell and comparing the level of expression of CD22 on the surface of the test cell with the level of expression of CD22 on the surface of the control cell.

In one aspect, a method of diagnosing a cell proliferative disorder associated with an increase in cells, such as B cells, expressing CD22 is provided, the method comprising contacting a test cells in a biological sample with any of the above antibodies; determining the level of antibody bound to test cells in the sample by detecting binding of the antibody to CD22; and comparing the level of antibody bound to cells in a control sample, wherein the level of antibody bound is normalized to the number of CD22-expressing cells in the test and control samples, and wherein a higher level of antibody bound in the test sample as compared to the control sample indicates the presence of a cell proliferative disorder associated with cells expressing CD22.

In one aspect, a method of detecting soluble CD22 in blood or serum, the method comprising contacting a test sample of blood or serum from a mammal suspected of experiencing a B cell proliferative disorder with an anti-CD22 antibody of the invention and detecting an increase in soluble CD22 in the test sample relative to a control sample of blood or serum from a normal mammal. In an embodiment, the method of detecting is useful as a method of diagnosing a B cell proliferative disorder associated with an increase in soluble CD22 in blood or serum of a mammal.

In one aspect, the antibodies of the invention include cysteine engineered antibodies where one or more amino acids of a parent antibody are replaced with a free cysteine amino acid as disclosed in WO2006/034488 (herein incorporated by reference in its entirety). Any form of anti-CD22 antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered anti-CD22 antibodies of the invention include monoclonal antibodies, humanized or chimeric monoclonal antibodies, and antigen-binding fragments of antibodies, fusion polypeptides and analogs that preferentially bind cell-associated CD22 polypeptides. A cysteine engineered antibody may alternatively comprise an antibody comprising a cysteine at a position disclosed herein in the antibody or Fab, resulting from the sequence design and/or selection of the antibody, without necessarily altering a parent antibody, such as by phage display antibody design and selection or through de novo design of light chain and/or heavy chain framework sequences and constant regions. A cysteine engineered antibody comprises one or more free cysteine amino acids having a thiol reactivity value in the ranges of 0.6 to 1.0; 0.7 to 1.0 or 0.8 to 1.0. A free cysteine amino acid is a cysteine residue which has been engineered into the parent antibody and is not part of a disulfide bridge. Cysteine engineered antibodies are useful for attachment of cytotoxic and/or imaging compounds at the site of the engineered cysteine through, for example, a maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

In an embodiment, a cysteine engineered anti-CD22 antibody of the invention comprises an engineered cysteine at any one of the following positions, where the position is number according to Kabat et al. in the light chain (see Kabat et al (1991) Sequences of Proteins of Immunological Interest, 5th Ed. Public Health Service, National Institutes of Health, Bethesda, Md.) and according to EU numbering in the heavy chain (including the Fc region) (see Kabat et al. (1991), supra), wherein the light chain constant region depicted by underlining in FIG. 17A begins at position 108 (Kabat numbering) and the heavy chain constant region depicted by underling in FIGS. 17B and 17C begins at position 118 (EU numbering). The position may also be referred to by its position in sequential numbering of the amino acids of the full length light chain or heavy chain shown in FIGS. 17A-17C. According to one embodiment of the invention, an anti-CD22 antibody comprises an engineered cysteine at LC-V205C (Kabat number: Val 205; sequential number 210 in FIG. 17A engineered to be Cys at that position). The engineered cysteine in the light chain is shown in bold, double underlined text in FIG. 17A. According to one embodiment, an anti-CD22 antibody comprises an engineered cysteine at HC-A118C (EU number: Ala 118; sequential number 121 in FIG. 17B engineered to be Cys at that position). The engineered cysteine in the heavy chain is shown in bold, double underlined text in FIG. 17B. According to one embodiment, an anti-CD22 antibody comprises an engineered cysteine at Fc-S400C (EU number: Ser 400; sequential number 403 in FIG. 17C engineered to be Cys at that position). The engineered cysteine in the Fc region of the heavy chain is shown in bold, double underlined text in FIG. 17C. In other embodiments, the engineered cysteine of the heavy chain (including the Fc region) is at any one of the following positions (according to EU numbering): 41, 88, 116, 118, 120, 171, 282, 375, or 400. Thus, changes in the amino acid at these positions for a parent anti-CD22 antibody of the invention are: A41C, A88C, S116C, A118C, T120C, A171C, V282C, S375C, or S400C. In other embodiments, the engineered cysteine of the light chain is at any one of the following positions (according to Kabat numbering): 15, 43, 110, 144, 168, 205. Thus, changes in the amino acid at these positions for a parent anti-CD22 antibody of the invention are: V15C, A43C, V110C, A144C, S168C, or V205C.

A cysteine engineered anti-CD22 antibody comprises one or more free cysteine amino acids wherein the cysteine engineered anti-CD22 antibody binds to a CD22 polypeptide and is prepared by a process comprising replacing one or more amino acid residues of a parent anti-CD22 antibody by cysteine wherein the parent antibody comprises at least one HVR sequence selected from:

(a) an HVR-L1 sequence RSSQSIVHSNGNTFLE (SEQ ID NO:9) or sequence RSSQSIVHSVGNTFLE (SEQ ID NO:10) (FIG. 2B);

(b) an HVR-L2 sequence KVSNRFS SEQ ID NO:12 (FIG. 2B);

(c) an HVR-L3 sequence FQGSQFPYT (SEQ ID NO:14) (FIG. 2B);

(d) an HVR-H1 sequence GYEFSRSWMN (SEQ ID NO:2) (FIG. 2A);

(e) an HVR-H2 sequence GRIYPGDGDTNYSGKFKG (SEQ ID NO:4 (FIG. 2A); and (f) an HVR-H3 sequence DGSSWDWYFDV (SEQ ID NO:6) (FIG. 2A).

In a certain aspect, the invention concerns a cysteine engineered anti-CD22 antibody, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a cysteine engineered antibody having a full-length amino acid sequence as disclosed herein, or a cysteine engineered antibody amino acid sequence lacking the signal peptide as disclosed herein.

In a yet further aspect, the invention concerns an isolated cysteine engineered anti-CD22 antibody comprising an amino acid sequence that is encoded by a nucleotide sequence that hybridizes to the complement of a DNA molecule encoding (a) a cysteine engineered antibody having a full-length amino acid sequence as disclosed herein, (b) a cysteine engineered antibody amino acid sequence lacking the signal peptide as disclosed herein, (c) an extracellular domain of a transmembrane cysteine engineered antibody protein, with or without the signal peptide, as disclosed herein, (d) an amino acid sequence encoded by any of the nucleic acid sequences disclosed herein or (e) any other specifically defined fragment of a full-length cysteine engineered antibody amino acid sequence as disclosed herein.

In a specific aspect, the invention provides an isolated cysteine engineered anti-CD22 antibody without the N-terminal signal sequence and/or without the initiating methionine and is encoded by a nucleotide sequence that encodes such an amino acid sequence as described in. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

Another aspect of the invention provides an isolated cysteine engineered anti-CD22 antibody which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

In other embodiments, the invention provides isolated anti-CD22 chimeric cysteine engineered antibodies comprising any of the herein described cysteine engineered antibody fused to a heterologous (non-CD22) polypeptide. Example of such chimeric molecules comprise any of the herein described cysteine engineered antibodies fused to a heterologous polypeptide such as, for example, an epitope tag sequence or a Fc region of an immunoglobulin.

The cysteine engineered anti-CD22 antibody may be a monoclonal antibody, antibody fragment, chimeric antibody, humanized antibody, single-chain antibody or antibody that competitively inhibits the binding of an anti-CD22 polypeptide antibody to its respective antigenic epitope. Antibodies of the present invention may optionally be conjugated to a growth inhibitory agent or cytotoxic agent such as a toxin, including, for example, an auristatin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other embodiments of the present invention, the invention provides vectors comprising DNA encoding any of the herein described anti-CD22 antibodies and anti-CD22 cysteine engineered antibodies. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

Cysteine engineered antibodies may be useful in the treatment of cancer and include antibodies specific for cell surface and transmembrane receptors, and tumor-associated antigens (TAA). Such antibodies may be used as naked antibodies (unconjugated to a drug or label moiety) or as antibody-drug conjugates (ADC). Cysteine engineered antibodies of the invention may be site-specifically and efficiently coupled with a thiol-reactive reagent. The thiol-reactive reagent may be a multifunctional linker reagent, a capture label reagent, a fluorophore reagent, or a drug-linker intermediate. The cysteine engineered antibody may be labeled with a detectable label, immobilized on a solid phase support and/or conjugated with a drug moiety. Thiol reactivity may be generalized to any antibody where substitution of amino acids with reactive cysteine amino acids may be made within the ranges in the light chain selected from amino acid ranges: L-10 to L-20; L-38 to L-48; L-105 to L-115; L-139 to L-149; L-163 to L-173; and within the ranges in the heavy chain selected from amino acid ranges: H-35 to H-45; H-83 to H-93; H-114 to H-127; and H-170 to H-184, and in the Fc region within the ranges selected from H-268 to H-291; H-319 to H-344; H-370 to H-380; and H-395 to H-405, where the numbering of amino acid positions begins at position 1 of the Kabat numbering system (Kabat et al. (1991) Sequences of Proteins of Immunological Interest, 5th Ed. Public Health Service, National Institutes of Health, Bethesda, Md.) and continues sequentially thereafter as disclosed in WO2006034488. Thiol reactivity may also be generalized to certain domains of an antibody, such as the light chain constant domain (CL) and heavy chain constant domains, CH1, CH2 and CH3. Cysteine replacements resulting in thiol reactivity values of 0.6 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2. Such antibodies and their uses are disclosed in WO2006/034488.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein, including but not limited to CD22). Cysteine engineered anti-CD22 antibodies of the invention retain the antigen binding capability of their parent anti-CD22 antibody counterparts. Thus, cysteine engineered anti-CD22 antibodies of the invention are capable of binding, preferably specifically, to CD22 antigens including human anti-CD22 isoforms beta and/or alpha, including when such antigens are expressed on the surface of cells, including, without limitation, B cells.

An antibody of the invention may be conjugated to other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

In one aspect, antibodies of the invention may be conjugated with any label moiety which can be covalently attached to the antibody through a reactive moiety, an activated moiety, or a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9): 1137-1146).

Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Metal-chelate complexes suitable as antibody labels for imaging experiments are disclosed: U.S. Pat. No. 5,342,606; U.S. Pat. No. 5,428,155; U.S. Pat. No. 5,316,757; U.S. Pat. No. 5,480,990; U.S. Pat. No. 5,462,725; U.S. Pat. No. 5,428,139; U.S. Pat. No. 5,385,893; U.S. Pat. No. 5,739,294; U.S. Pat. No. 5,750,660; U.S. Pat. No. 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10: 103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. No. 4,275,149 and U.S. Pat. No. 4,318,980.

A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g.

TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Albumin Binding Peptide-Fab Compounds of the Invention:

In one aspect, the antibody of the invention is fused to an albumin binding protein. Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al. (2002) "Albumin Binding As A General Strategy For Improving The Pharmacokinetics Of Proteins" J Biol Chem. 277:35035-35043; WO 01/45746). Compounds of the invention include ABP sequences taught by: (i) Dennis et al (2002) J Biol Chem. 277:35035-35043 at Tables III and IV, page 35038; (ii) US 20040001827 at [0076] SEQ ID NOS: 9-22; and (iii) WO 01/45746 at pages 12-13, all of which are incorporated herein by reference. Albumin Binding (ABP)-Fabs are engineered by fusing an albumin binding peptide to the C-terminus of Fab heavy chain in 1:1 stoichiometric ratio (1 ABP/1 Fab). It was shown that association of these ABP-Fabs with albumin increased antibody half life by more than 25 fold in rabbits and mice. The above described reactive Cys residues can therefore be introduced in these ABP-Fabs and used for site-specific conjugation with cytotoxic drugs followed by in vivo animal studies.

Exemplary albumin binding peptide sequences include, but are not limited to the amino acid sequences listed in SEQ ID NOS:42-46:

```
CDKTHTGGGSQRLMEDICLPRWGCLWEDDF  SEQ ID NO: 42

QRLMEDICLPRWGCLWEDDF            SEQ ID NO: 43

QRLIEDICLPRWGCLWEDDF            SEQ ID NO: 44

RLIEDICLPRWGCLWEDD              SEQ ID NO: 45

DICLPRWGCLW                     SEQ ID NO: 46
```

Antibody-Drug Conjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-CD22 antibodies covalently attached to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides), and those having modifications at other positions Exemplary maytansinoid drug moieties also include those having modifications such as: C-9-SH (U.S. Pat. No. 4,424,219) (prepared by the reaction of maytansinol with H$_2$S or P$_2$S$_5$); C-14-alkoxymethyl(demethoxy/CH$_2$OR) (U.S. Pat. No. 4,331,598); C-14-hydroxymethyl or acyloxymethyl (CH$_2$OH or CH$_2$OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Exemplary embodiments of maytansinoid drug moieties include: DM1; DM3; and DM4, having the structures:

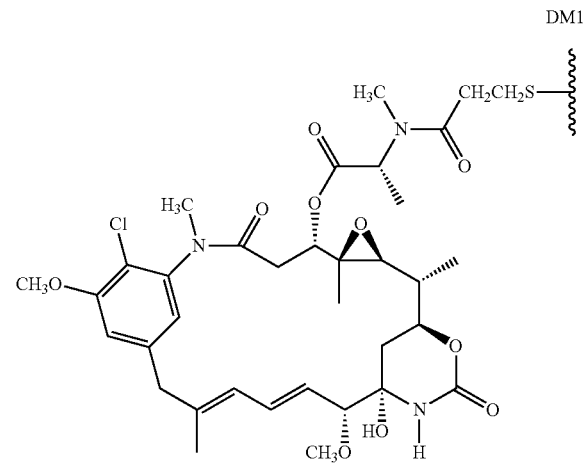

DM1

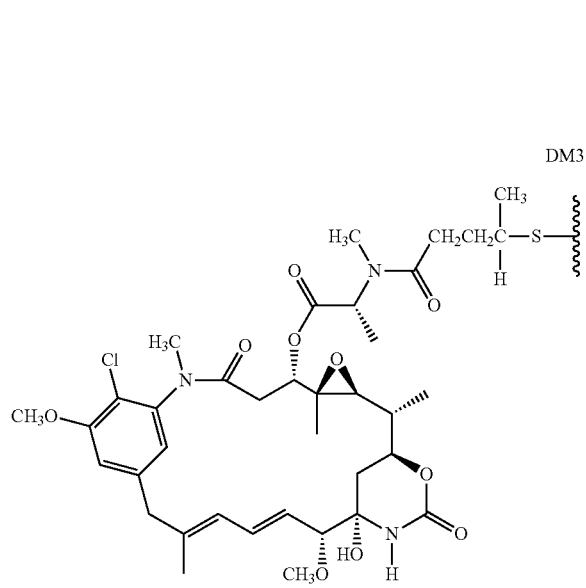

DM3

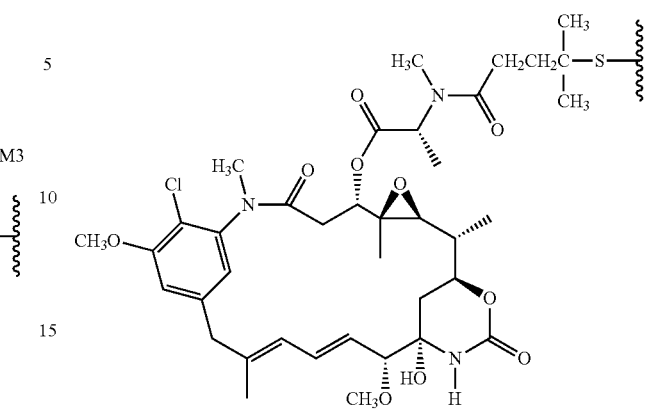

DM4 wherein the wavy line indicates the covalent attachment of the sulfur atom of the drug to a linker (L) of an antibody drug conjugate. HERCEPTIN® (trastuzumab, anti-HER2 antibody) linked by SMCC to DM1 has been reported (WO 2005/037992, which is expressly incorporated herein by reference in its entirety). An antibody drug conjugate of the present invention may be prepared according to the procedures disclosed therein.

Other exemplary maytansinoid antibody drug conjugates have the following structures and abbreviations, (wherein Ab is antibody and p is 1 to about 8):

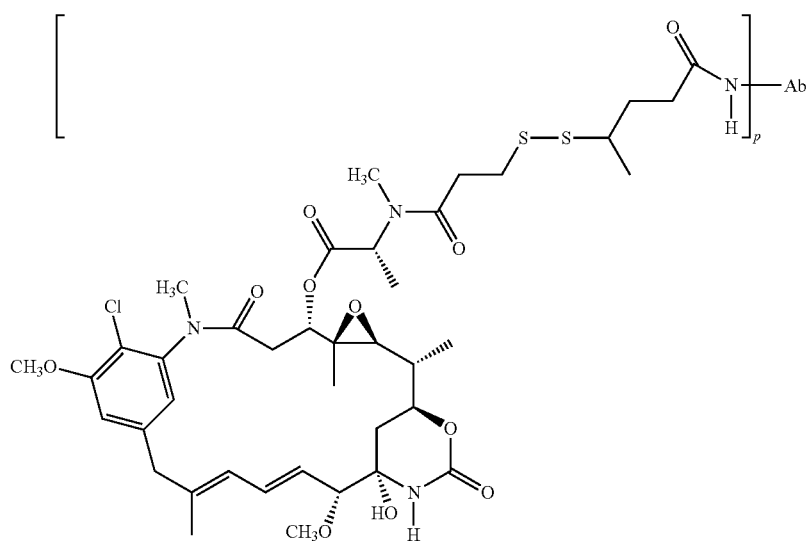

Ab-SPP-DM1

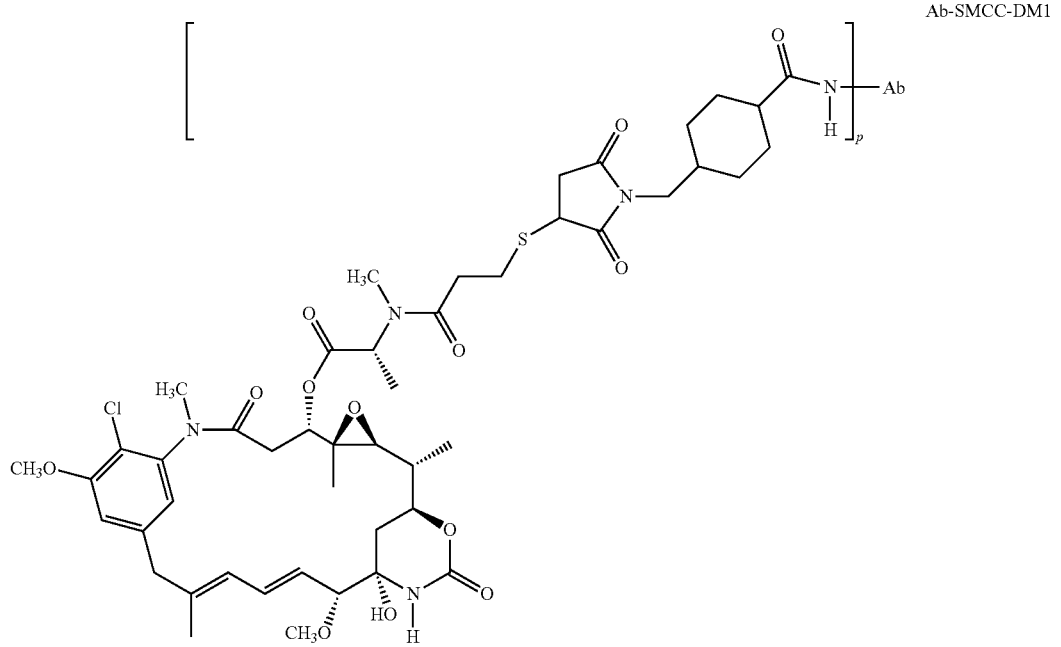

Ab-SMCC-DM1

Exemplary antibody drug conjugates where DM1 is linked through a BMPEO linker to a thiol group of the antibody have the structure and abbreviation:

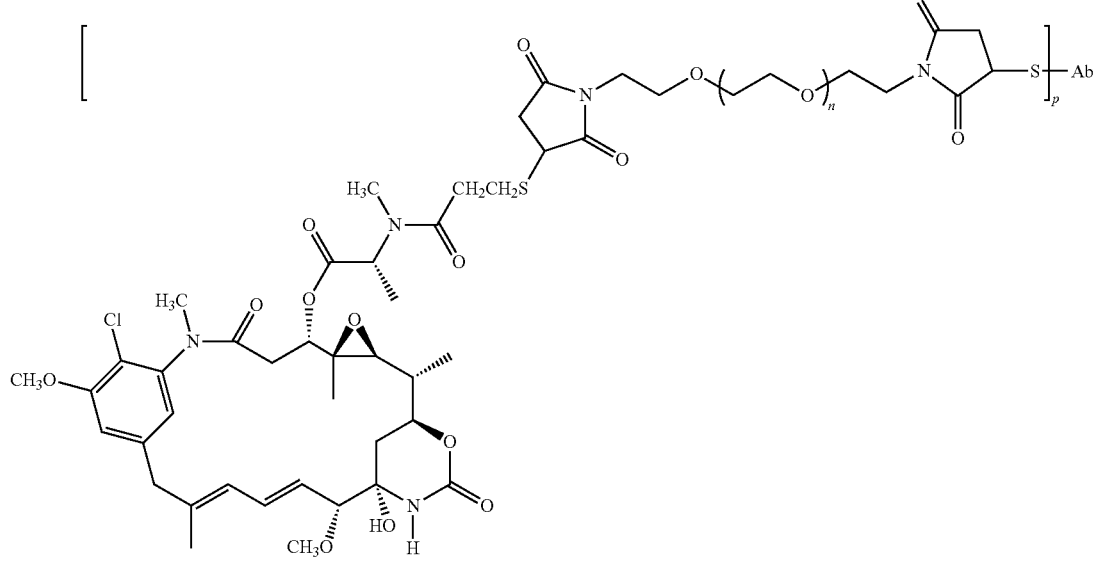

where Ab is antibody; n is 0, 1, or 2; and p is 1, 2, 3, or 4.

Immunoconjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Anti-CD22 antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. Nos. 5,208,020, 6,441,163, or EP Patent 0 425 235 B1, Chari et al., Cancer Research 52:127-131 (1992), and US 2005/0169933 A1, the disclosures of which are hereby expressly incorporated by reference. Antibody-maytansinoid conjugates comprising the linker component SMCC may be prepared as disclosed in U.S. patent application Ser. No. 11/141,344, filed 31 May 2005, "Antibody Drug Conjugates and Methods". The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

In one embodiment, any of the antibodies of the invention (full length or fragment) is conjugated to one or more maytansinoid molecules. In one embodiment of the immunoconjugate, the cytotoxic agent D, is a maytansinoid DM1. In one embodiment of the immunoconjugate, the linker is SMCC. In one embodiment, the antibody-linker-drug conjugate is an anti-CD22 antibody as disclosed herein to which is covalently DM1 cytotoxic agent via the SMCC linker.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE (wherein the wavy line indicates the covalent attachment to a linker (L) of an antibody drug conjugate).

MMAE

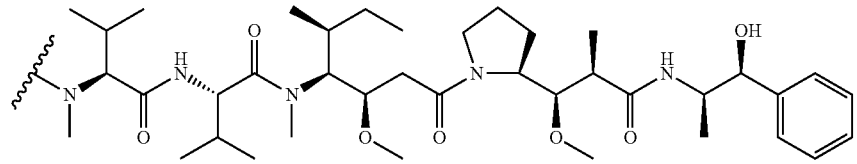

Another exemplary auristatin embodiment is MMAF, wherein the wavy line indicates the covalent attachment to a linker (L) of an antibody drug conjugate (US 2005/0238649):

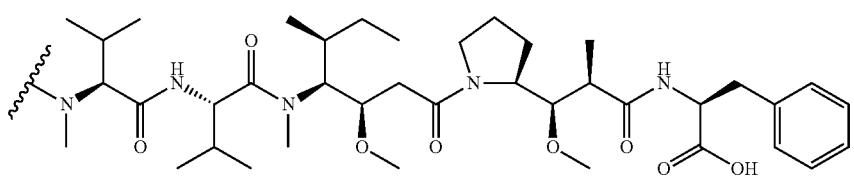

MMAF

Additional exemplary embodiments comprising MMAE or MMAF and various linker components (described further herein) have the following structures and abbreviations (wherein Ab means antibody and p is 1 to about 8):

Calicheamicin

In other embodiments, the immunoconjugate comprises an antibody of the invention conjugated to one or more calicheamicin molecules. The calicheamicin family of antibiotics

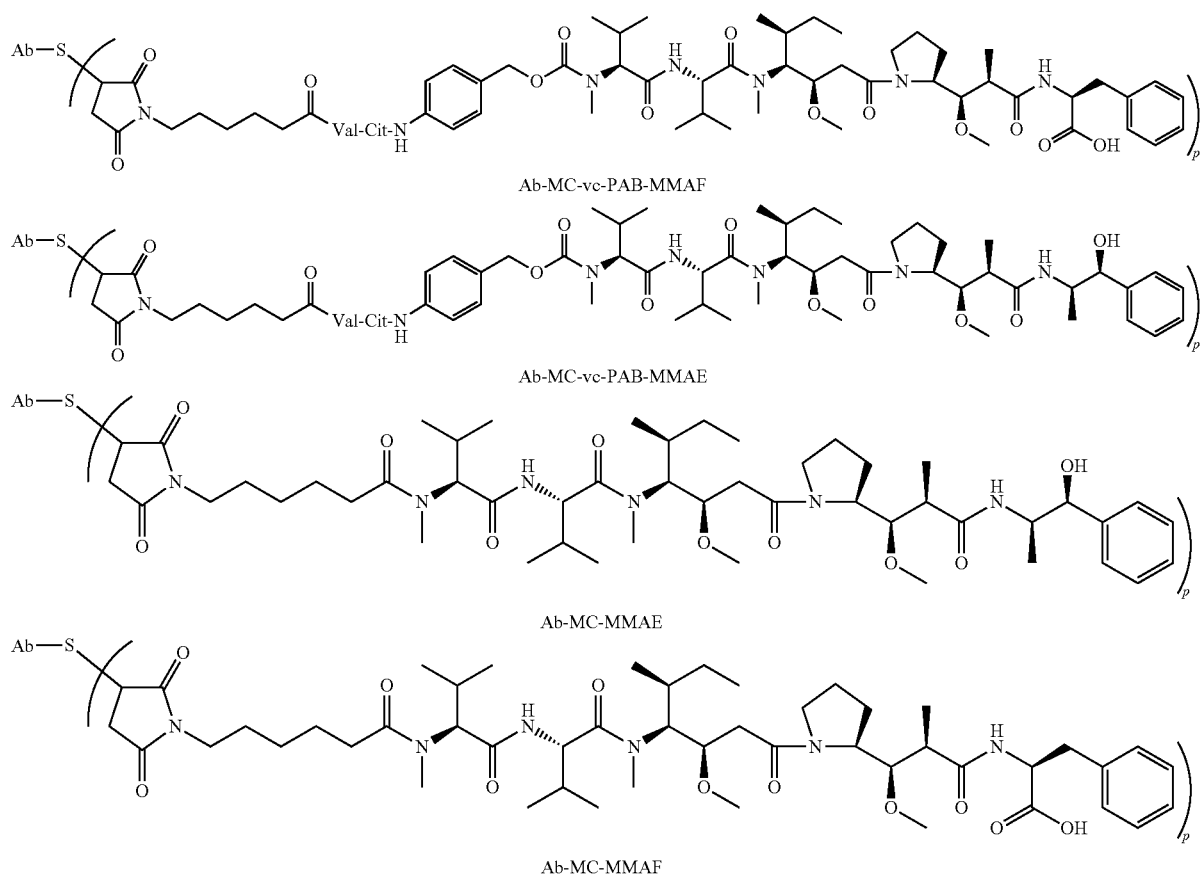

Ab-MC-vc-PAB-MMAF

Ab-MC-vc-PAB-MMAE

Ab-MC-MMAE

Ab-MC-MMAF

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates:

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad \text{Formula I}$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("SIAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Exemplary linker component structures are shown below (wherein the wavy line indicates sites of covalent attachment to other components of the ADC):

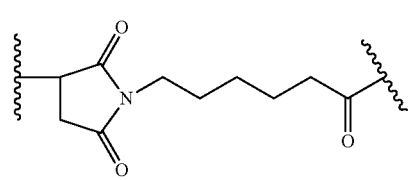

MC

-continued

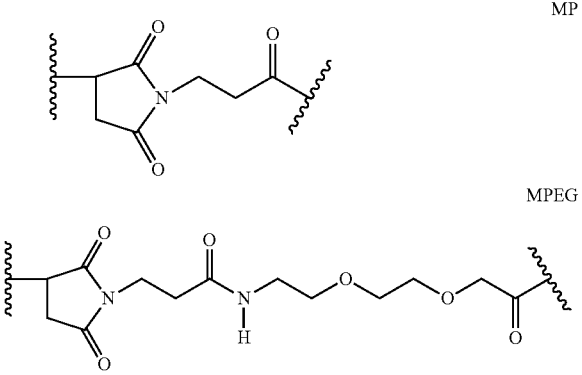

MP

MPEG

Additional exemplary linker components and abbreviations include (wherein the antibody (Ab) and linker are depicted, and p is 1 to about 8):

Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment,

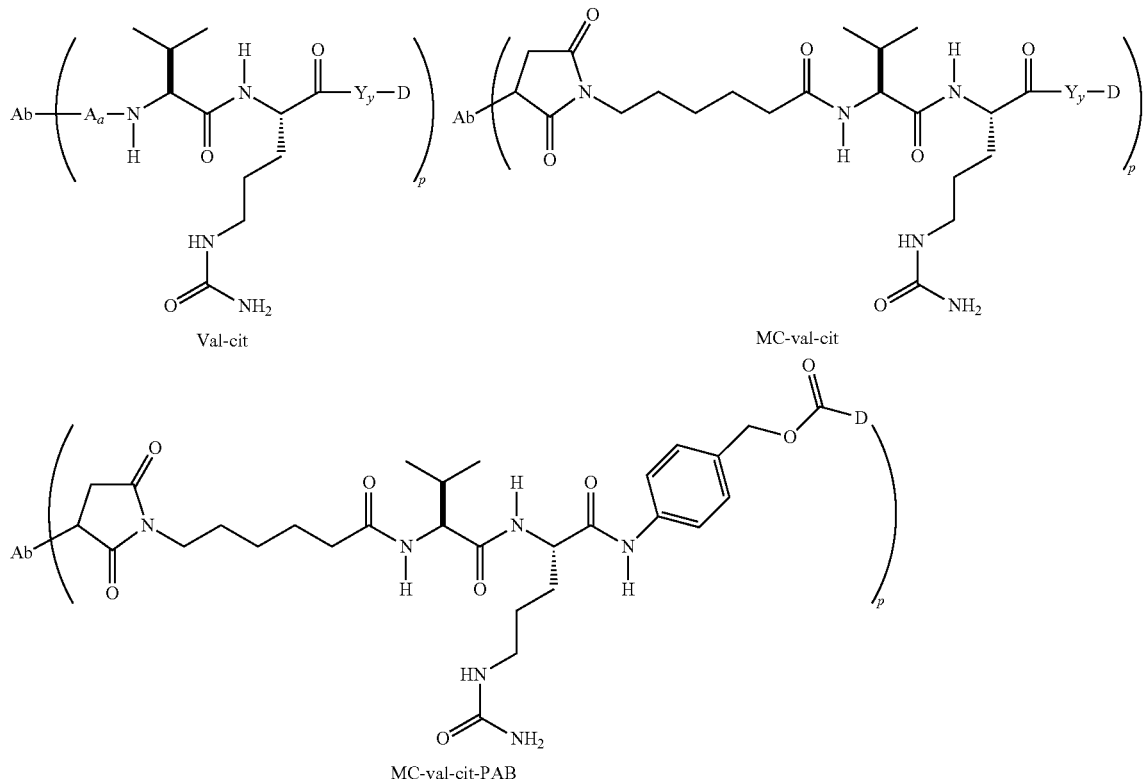

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol).

reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

In yet another aspect, the antibody has one or more lysine residues that can be chemically modified to introduce one or more sulfhydryl groups. The antibody unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the antibody can have one or more carbohydrate groups that can be chemically modified to have one or more sulfhydryl groups. The antibody unit bonds to the Linker Unit, such as the Stretcher Unit, via the sulfhydryl group's sulfur atom, as disclosed herein.

In yet another embodiment, the antibody can have one or more carbohydrate groups that can be oxidized to provide an aldehyde (—CHO) group (see, for e.g., Laguzza, et al., J. Med. Chem. 1989, 32(3), 548-55). The corresponding aldehyde can form a bond with a Reactive Site on a Stretcher. Reactive sites on a Stretcher that can react with a carbonyl group on an antibody include, but are not limited to, hydrazine and hydroxylamine. Other protocols for the modification of proteins for the attachment or association of Drug Units are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. No. 5,208,020; U.S. Pat. No. 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In one embodiment of the immunoconjugate, the cytotoxic agent, D, is an auristatin of formula $D_E$ or $D_F$

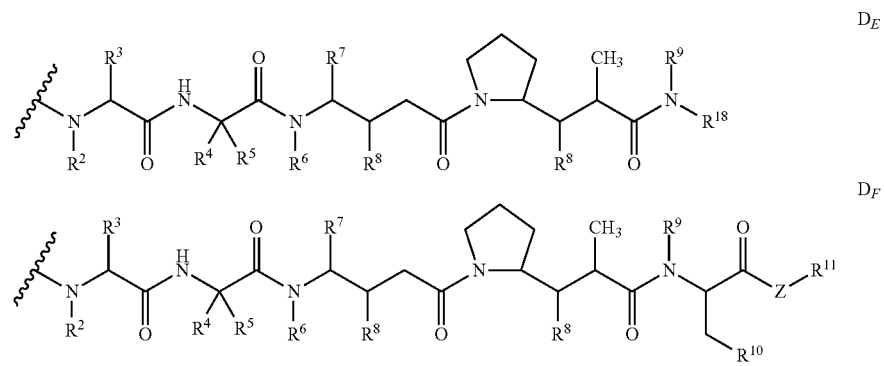

and wherein $R^2$ and $R^6$ are each methyl, $R^3$ and $R^4$ are each isopropyl, $R^7$ is sec-butyl, each $R^8$ is independently selected from $CH_3$, $O—CH_3$, OH, and H; $R^9$ is H; $R^{10}$ is aryl; Z is —O— or —NH—; $R^{11}$ is H, $C_1$-$C_8$ alkyl, or —$(CH_2)_2$—O—$(CH_2)_2$—O—$(CH_2)_2$—O—$CH_3$; and $R^{18}$ is —$C(R^8)_2$—C$(R^8)_2$-aryl; and (d) p ranges from about 1 to 8.

The following embodiments are further provided for any of the above immunoconjugates. In one embodiment, an immunoconjugate has in vitro or in vivo cell killing activity. In one embodiment, the linker is attached to the antibody through a thiol group on the antibody. In one embodiment, the linker is cleavable by a protease. In one embodiment, the linker comprises a val-cit dipeptide. In one embodiment, the linker comprises a p-aminobenzyl unit. In one embodiment, the p-aminobenzyl unit is disposed between the drug and a protease cleavage site in the linker. In one embodiment, the p-aminobenzyl unit is p-aminobenzyloxycarbonyl (PAB). In one embodiment, the linker comprises 6-maleimidocaproyl. In one embodiment, the 6-maleimidocaproyl is disposed between the antibody and a protease cleavage site in the linker. The above embodiments may occur singly or in any combination with one another.

In one embodiment, the drug is selected from MMAE and MMAF. In one embodiment, the immunoconjugate has the formula

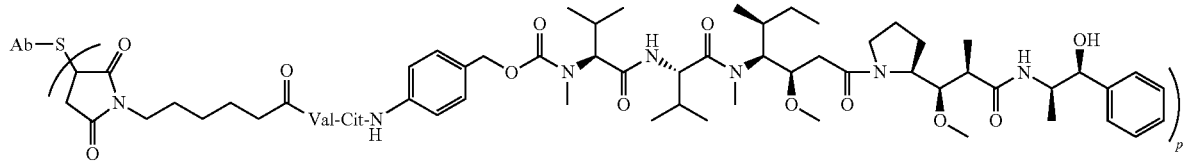

wherein Ab is any of the above anti-CD22 antibodies, S is a sulfur atom, and p ranges from 2 to 5. In one embodiment, the immunoconjugate has the formula

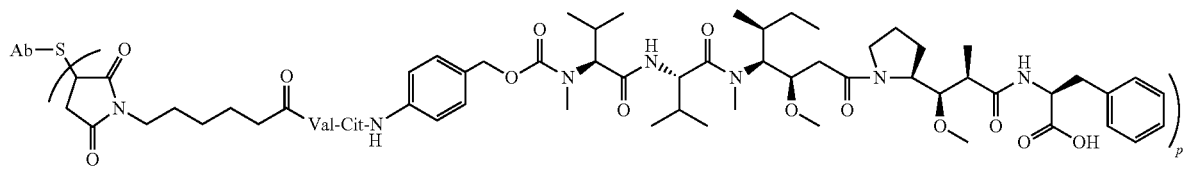

wherein Ab is any of the above anti-CD22 antibodies, S is a sulfur atom, and p ranges from about 1 to about 6, from about 2 to about 5, from about 2 to about 6, from about 2 to about 4, from about 2 to about 3, from about 3 to about 4, from about 3 to about 5, from about 3 to about 6, or from about 4 to about 6.

Labelled Antibody Imaging Methods:

In another embodiment of the invention, cysteine engineered antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture:

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Pharmaceutical Compositions:

In one aspect, a pharmaceutical composition is provided comprising any of the above immunoconjugates and a pharmaceutically acceptable carrier. In one aspect, a method of treating a B cell proliferative disorder is provided, wherein the method comprises administering to an individual the pharmaceutical composition. In one embodiment, the B cell proliferative disorder is selected from lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. In one embodiment, the cell proliferative disorder is associated with increased expression of CD22 on the surface of a cell.

In one aspect, a method of inhibiting cell proliferation is provided, wherein the method comprises exposing a cell to any of the above immunoconjugates under conditions permissive for binding of the immunoconjugate to CD22. In one embodiment, the B cell is a tumor cell. In one embodiment, the tumor cell is a B cell of a mammal experiencing or suspected of experiencing aa B cell proliferative disorder selected from lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma, the cell is a xenograft. In one embodiment, the exposing takes place in vitro. In one embodiment, the exposing takes place in vivo.

In one aspect, a method of using the anti-CD22 antibody of the invention is provided to assay serum soluble CD22 in a mammal experiencing leukemia or lymphoma to diagnose B-cell leukemia or B-cell lymphoma, measuring clinical progression or regression of the diseases, or assess tumor burden or relapse. Such methods are disclosed in US 20050244828 (Kreitman, R. J. et al., the entire contents of which is hereby incorporated by reference) using an anti-CD22 RFB4 antibody PE38 (Pseudomonas exotoxin A fragment 38) toxin conjugate (see Kreitman, R. J. et al., NEJM 345:241-247 (2001)).

BRIEF DESCRIPTION OF THE FIGURES

FIGS. 1A-1D: FIG. 1A is a diagram of CD22 indicating the seven immunoglobulin-like domains of the extracellular domain of the beta isoform. The alpha isoform lacks domains 3 and 4. "TM" refers to transmembrane domain. FIG. 1B depicts the amino acid sequence of the beta form of CD22 (SEQ ID NO:27). The alpha form of CD22 lacks the amino acids shown in italics (encoding domains 3 and 4 of the extracellular domain). The extracellular domain of the mature form of the protein is underlined (SEQ ID NO:28). Amino acids 1-21 depict the signal sequence cleaved from the mature form. FIG. 1C is the amino acid sequence of CD22alpha (SEQ ID NO:29). The ECD of CD22alpha is underlined (SEQ ID NO:30). FIG. 1D is the amino acid sequence of CD22 from cynomolgus monkey (cyno) (SEQ ID NO:31). The first 19 amino acids of cyno CD22 is the signal sequence.

FIGS. 2A-2B: FIG. 2A depicts the amino acid sequence of the heavy chain variable region of murine 10F4 anti-CD22 antibody of the invention (m10F4) aligned with the humanized 10F4 version 1 antibody (h10F4v1) and aligned with the human subgroup III sequence. The HVRs are boxed (HVR-H1, HVR-H2, HVR-H3). The sequences bracketing the HVRs are the framework sequences (FR-H1 to FR-H4). The sequences are numbered according to Kabat numbering. The Kabat, Chothia, and contact CDRs are indicated about the boxed HVRs. FIG. 2B depicts the amino acid sequence of the light chain variable region of murine 10F4 anti-CD22 antibody of the invention (m10F4) aligned with the humanized 10F4 version 1 antibody (h10F4v1) and aligned with the human kappa I sequence. Versions 2 and 3 of the humanized 10F4 antibody (h10F4v2 and h10F4v3) have the same amino acid sequences for the secreted mature form. The antibodies h10F4v2 and h10F4v3 differ from h10F4v1 at amino acid 28 of the HVR-L1 (N28V). The HVRs are boxed. The FR-L1, FR-L2, FR-L3, and FR-L4 sequences bracket the HVRs (HVR-L1, HVR-L2, HVR-L3). The sequences are numbered according to Kabat numbering. The Kabat, Chothia, and contact CDRs are indicated about the boxed HVRs.

human VH subgroup I consensus framework "A" minus Kabat CDRs (SEQ ID NOs:26, 47, 48, 7).

human VH subgroup I consensus frameworks "B," "C," and "D" minus extended hypervariable regions (SEQ ID NOs:50, 51, 52, 7; SEQ ID NOs:50, 51, 52, 7; and SEQ ID NOs:50, 51, 53, 7).

human VH subgroup II consensus framework "A" minus Kabat CDRs (SEQ ID NOs:54, 55, 56, 7).

human VH subgroup II consensus frameworks "B," "C," and "D" minus extended hypervariable regions (SEQ ID NOs:57, 58, 56, 7; SEQ ID NOs:57, 58, 59, 7; and SEQ ID NOs:57, 58, 60, 7).

human VH subgroup III consensus framework "A" minus Kabat CDRs (SEQ ID NOs:61, 62, 63, 7).

human VH subgroup III consensus frameworks "B," "C," and "D" minus extended hypervariable regions (SEQ ID NOs:64, 65, 63, 7; SEQ ID NOs:64, 65, 66, 7; and SEQ ID NOs:64, 65, 67, 7).

human VH acceptor 1 framework "A" minus Kabat CDRs (SEQ ID NOs:68, 62, 69, 7).

human VH acceptor frameworks "B" and "C" minus extended hypervariable regions (SEQ ID NOs:64, 65, 69, 7; and SEQ ID NOs:64, 65, 70, 7).

human VH acceptor 2 framework "A" minus Kabat CDRs (SEQ ID NOs:68, 62, 71, 7).

human VH acceptor 2 framework "B," "C," and "D" minus extended hypervariable regions (SEQ ID NOs:64, 65, 71, 7; SEQ ID NOs:64, 65, 72, 7; and SEQ ID NOs:64, 65, 73, 7).

FIGS. 4A and 4B show exemplary acceptor human variable light (VL) consensus framework sequences for use in practicing the instant invention with sequence identifiers as follows:

human VL kappa subgroup I-1 consensus framework (κv1-1): SEQ ID NOs:74, 75, 76, 77 human VL kappa subgroup I consensus framework (κv1): SEQ ID NOs:74, 78, 76, 77 human VL kappa subgroup II consensus framework (κv2): SEQ ID NOs:49, 79, 80, 77 human VL kappa subgroup III consensus framework (κv3): SEQ ID NOs:81, 82, 83, 77 human VL kappa subgroup IV consensus framework (κv4): SEQ ID NOs:84, 85, 86, 77

FIGS. 5A and 5B: FIG. 5A depicts alignments of native sequence human IgG, Fc region sequences, humIgG1 (non-A allotype, SEQ ID NO:38; and A allotype, where the amino acid sequence SREEM within SEQ ID NO:38 is changed to SRDEL), humIgG2 (SEQ ID NO:39), humIgG3 (SEQ ID NO:40) and humIgG4 (SEQ ID NO:41) with differences between the sequences marked with asterisks. Numbers above the sequences represent the EU numbering system. An exemplary kappa constant region is also shown. FIG. 5B depicts the full length amino acid sequences (variable and constant regions) of the light and heavy chains of humanized anti-CD22 antibody 10F4v2, isotype IgG1. The underlined portions depict the constant domains.

Figure 6A:
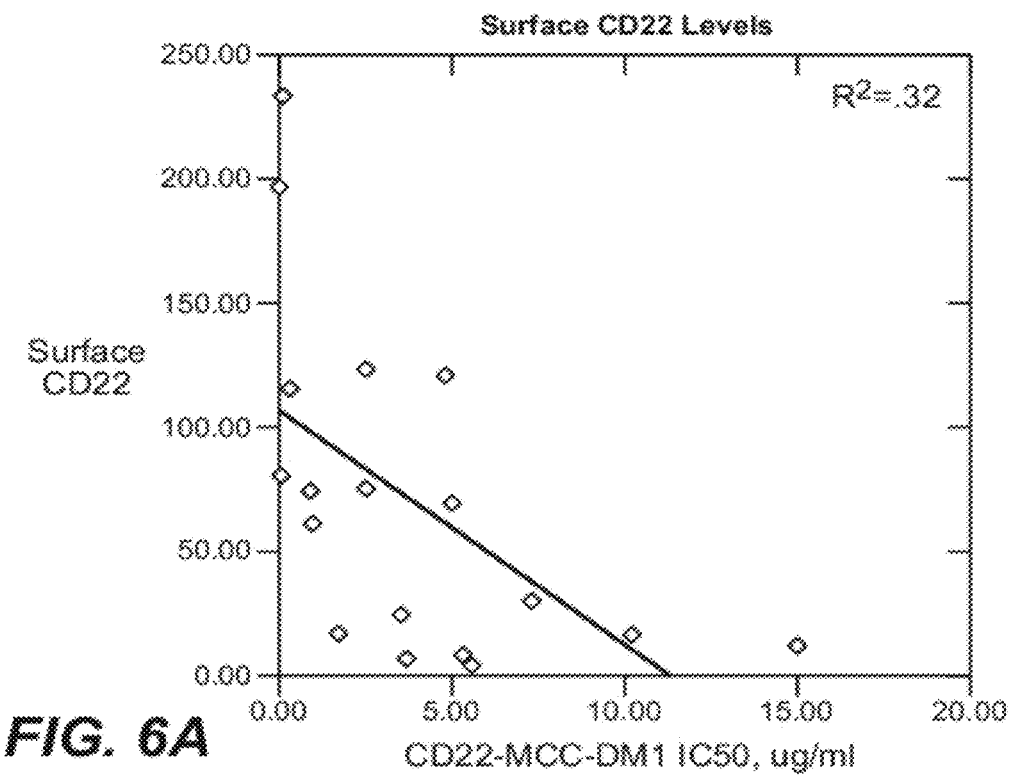
Figure 6B:
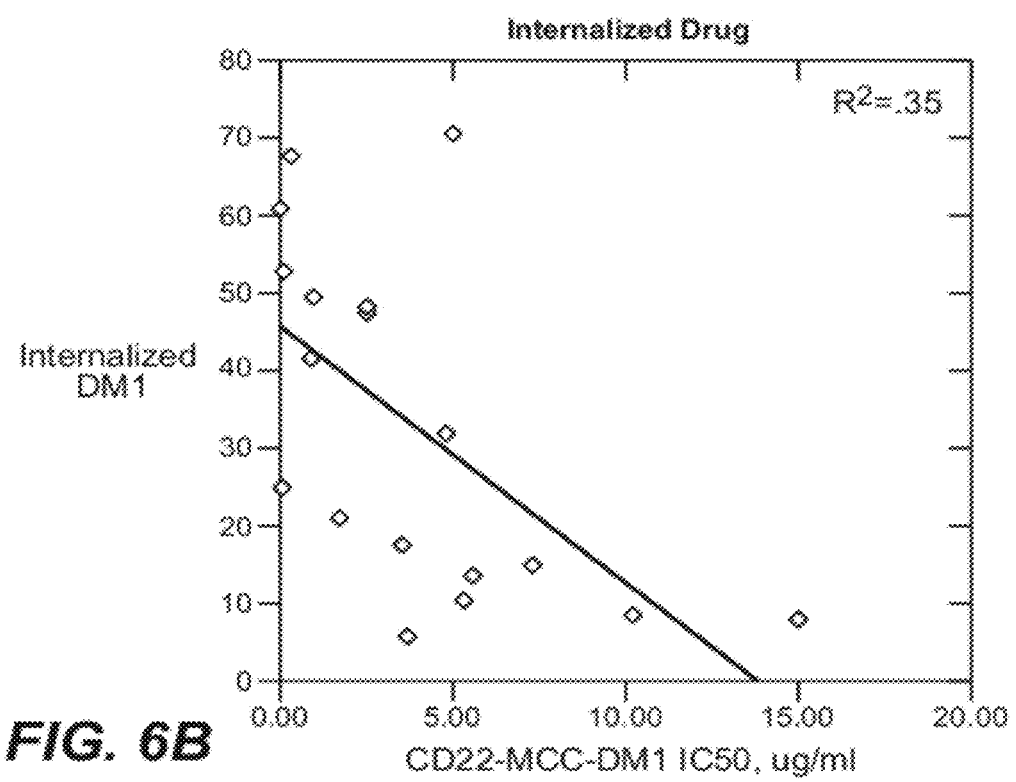
Figure 6C:
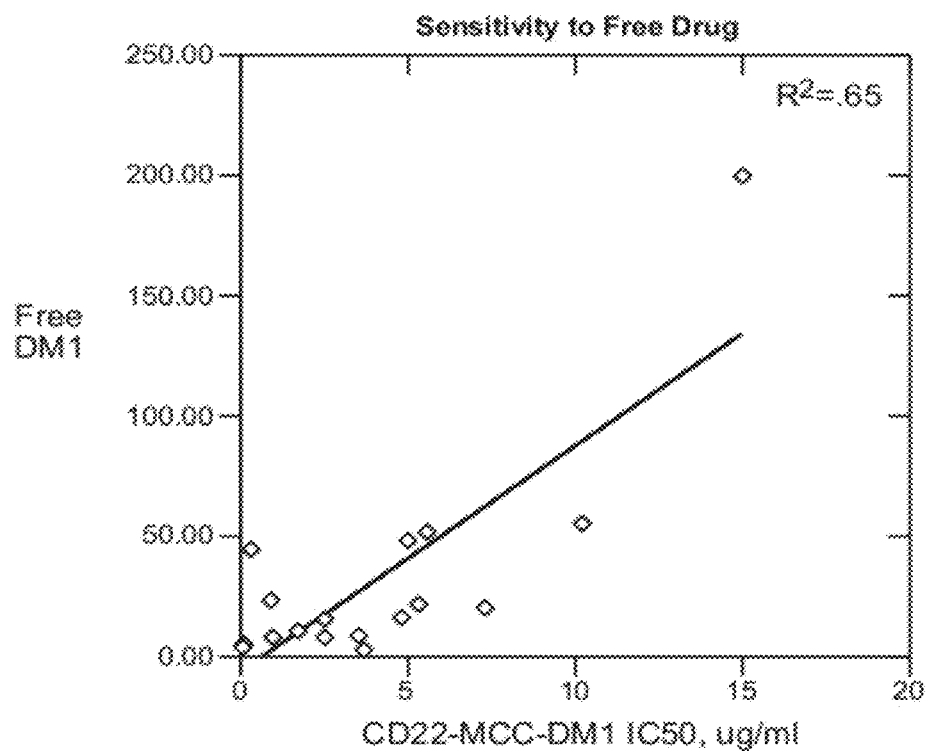
Figure 6D:
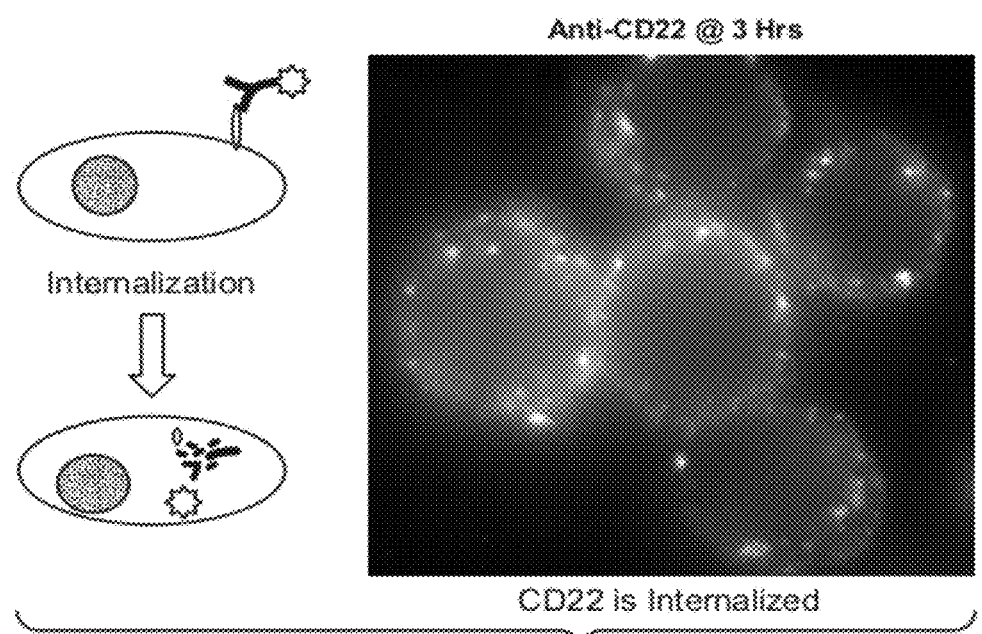

FIGS. 6A-6D show results of assays measuring various determinants of CD22 ADC efficacy in lymphoma cell lines. FIG. 6A indicates that higher cell surface CD22 levels are correlated to a lower anti-CD22-MCC-DM1 IC50 (higher efficacy). FIG. 6B indicates that increased internalization of anti-CD22-MCC-DM1 correlates with lower anti-CD22-MCC-DM1 IC50. FIG. 6C indicates that increased intrinsic sensitivity of cells to free drug correlates with lower anti-CD22-MCC-DM1 IC50. FIG. 6D is a photomicrograph showing the internalization of fluorescently labeled anti-CD22 antibody following binding to CD22 on the cell surface.

Figure 7A:
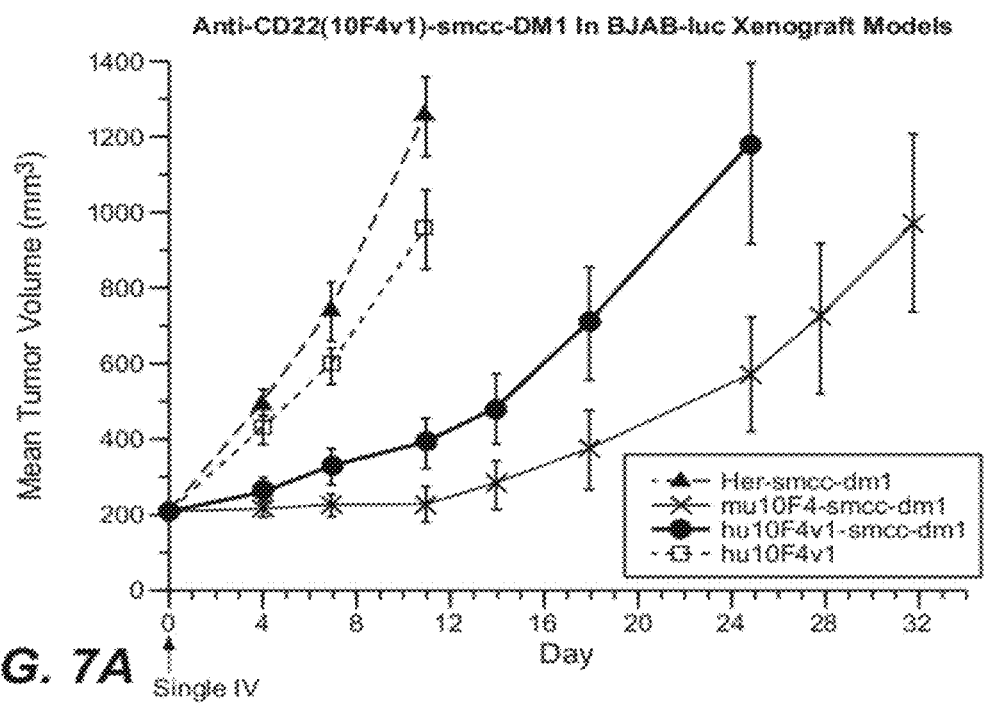
Figure 7B:
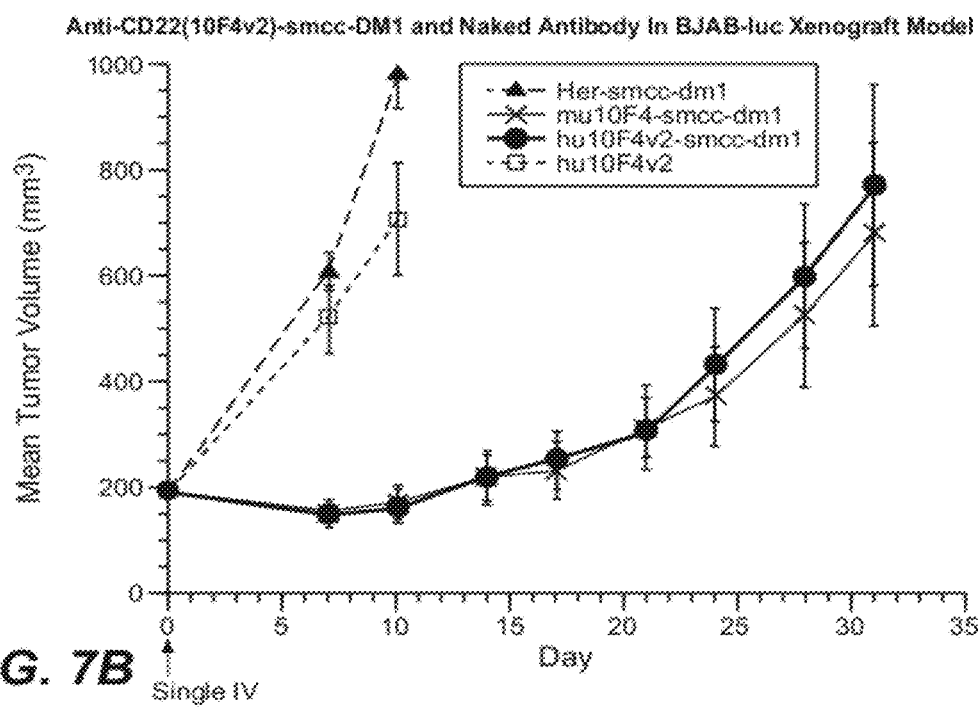
Figure 7C:
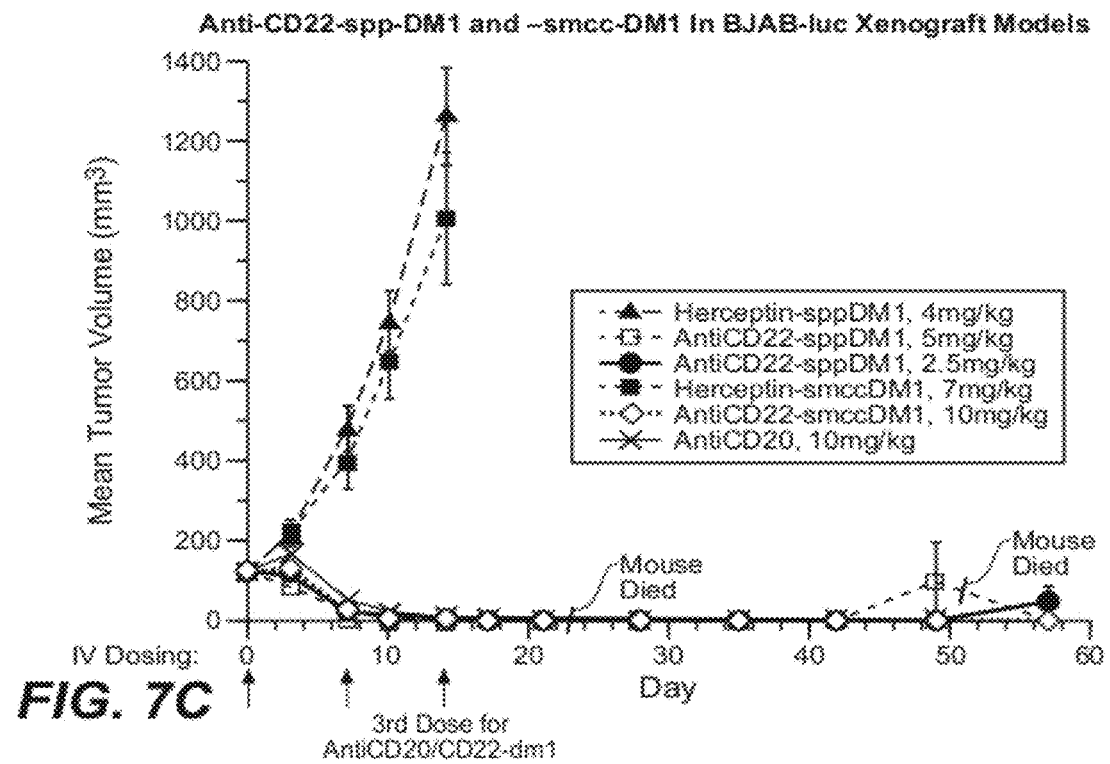

FIGS. 7A-7B: FIG. 7A is a graph of in vivo tumor volume reduction in a xenograft model which shows that administration of anti-CD22 antibody mu10F4-smcc-DM1 and hu10F4v1-smcc-DM1 to SCID mice having human B cell tumors significantly reduced tumor volume. Drug load was approximately 4 and 4.6, see Table 4. FIG. 7B is a graph of a similar study, but drug load was slightly lower at approximately 2.9 and 3.0 (see Table 5), and mu10F4-smcc-DM1 and hu10F4v2-smcc-DM1 efficacy were compared with control antibody and unconjugated mu10F4. FIG. 7C is a graph of in vivo tumor reduction in a xenograft model in which anti-CD22-spp-DM1 was administered as indicated in Table 6.

Figure 8A:
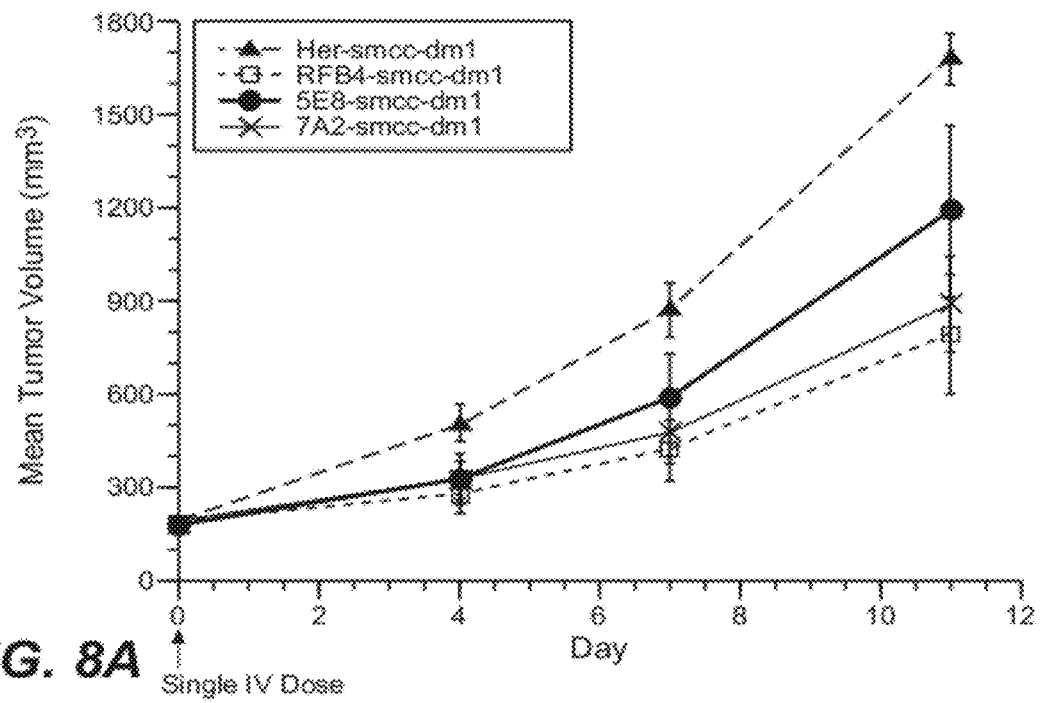
Figure 8B:
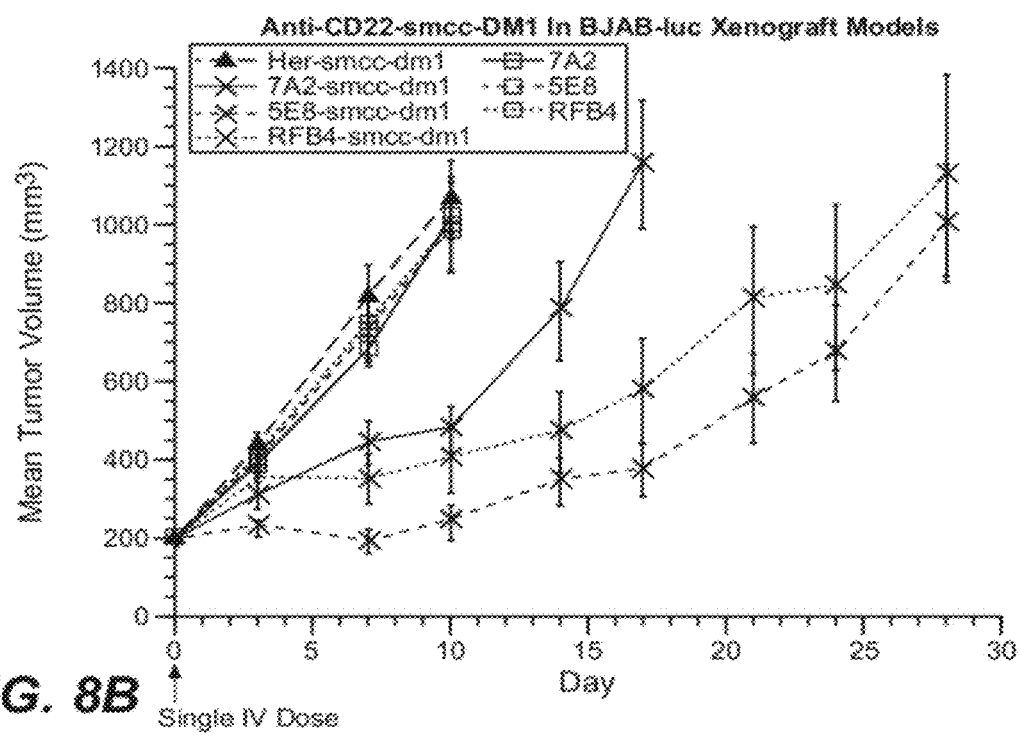

FIGS. 8A and 8B: FIG. 8A is a graph of anti-CD22 antibodies 5E8.1.8-smcc-DM1 and RFB4-smcc-DM1 administered to Ramos cell xenografts. FIG. 8B is a graph of anti-CD22 antibodies 5E8.1.8-smcc-DM1 and RFB4-smcc-DM1 administered to BJAB-luc xenografts.

Figure 9:
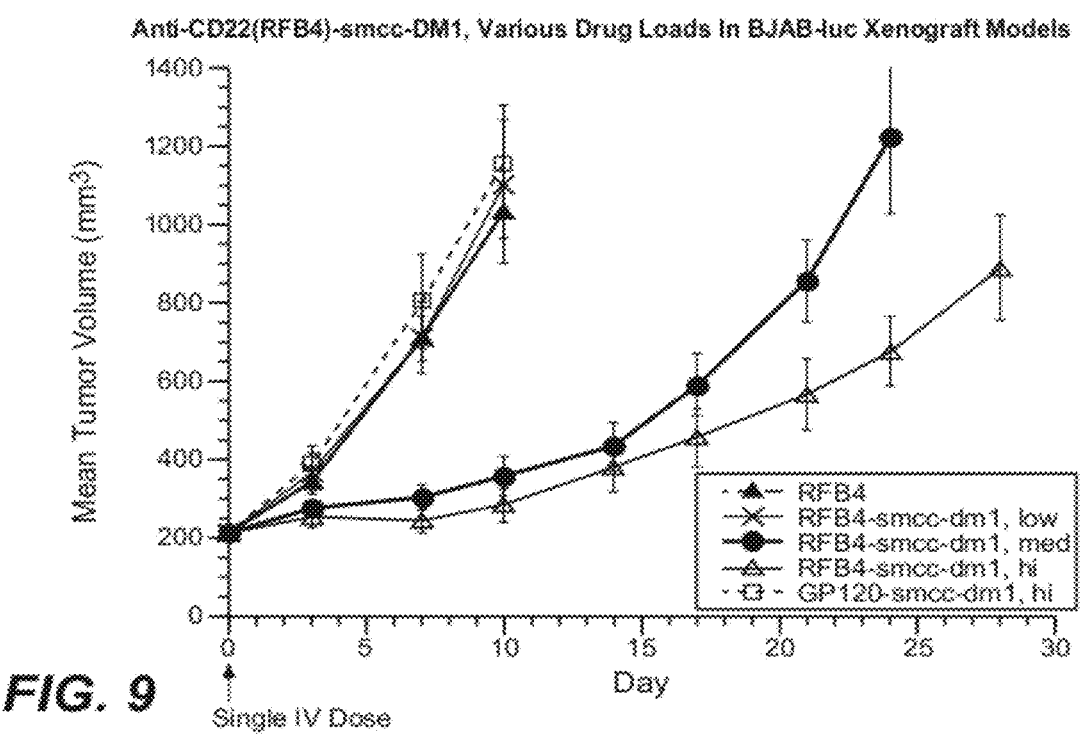

FIG. 9 is a graph showing the relative affect on tumor volume over time after administration of anti-CD22(RFB4)-smcc-DM1 at low, medium, and high drug loads.

Figure 10:
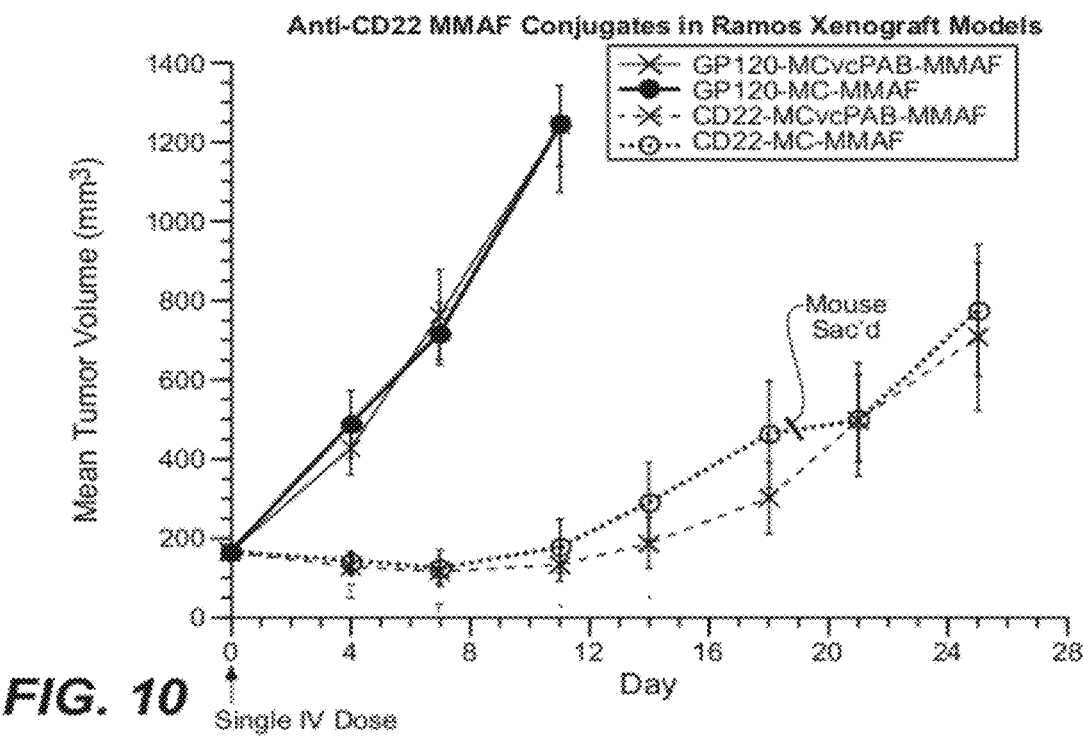

FIG. 10 is a graph showing the relative affect on tumor volume over time after administration of anti-CD22(RFB4)-MC-vcPAB-MMAF or anti-CD22(RFB4)-MC-MMAF in Ramos xenografts.

Figure 11:
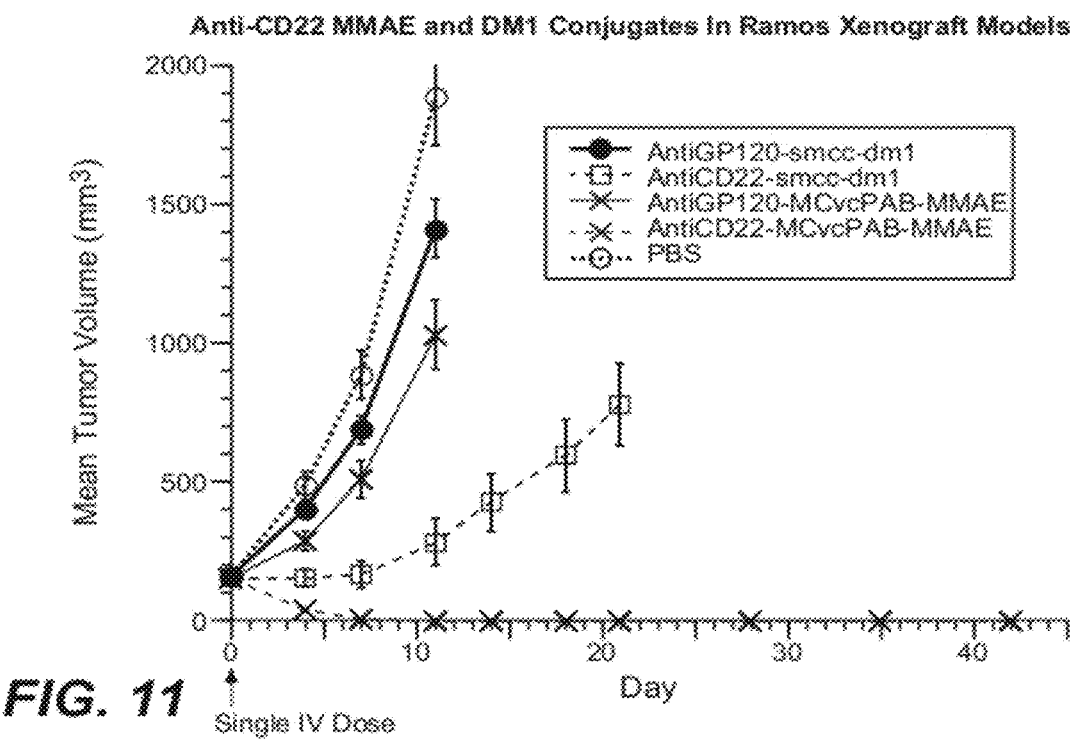

FIG. 11 is a graph showing the relative affect on tumor volume over time after administration of anti-CD22(RFB4)-smcc-DM1 or -MCvcPAB-MMAE.

Figure 12:
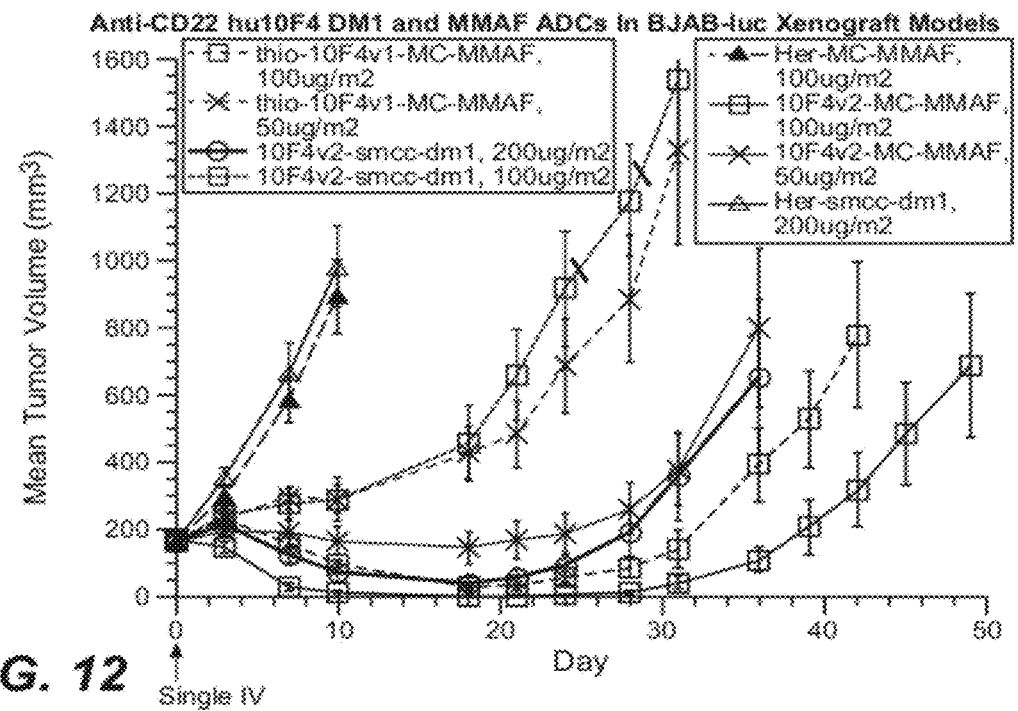

FIG. 12 is a graph showing the relative affect on tumor volume over time after administration of humanized anti-CD2210F4 variants as MMAF or DM1 immunoconjugates as disclosed in Table 12.

Figure 13A:
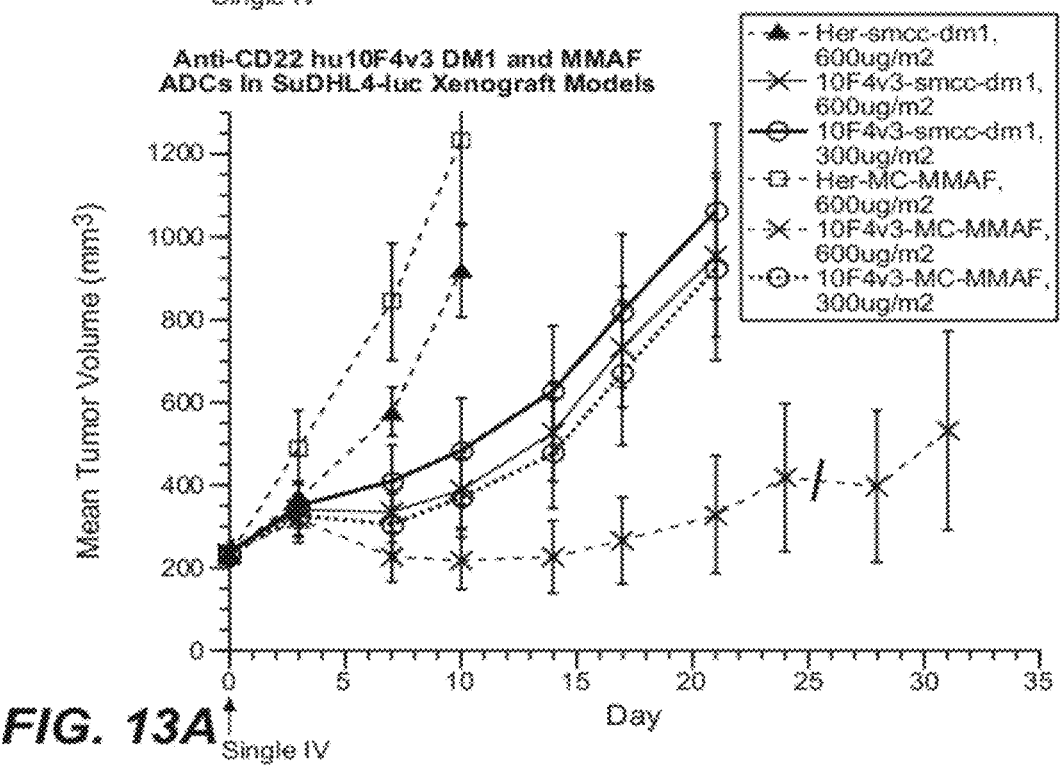

FIGS. 13A-13C are graphs showing the relative affect on tumor volume over time after administration anti-CD22-smcc-DM1 or anti-CD22-MC-MMAF in different B cell lymphoma xenograft models: SuDHL-4 (FIG. 13A), DoHH2 (FIG. 13B), and Granta-519 (FIG. 13C).

Figure 14:
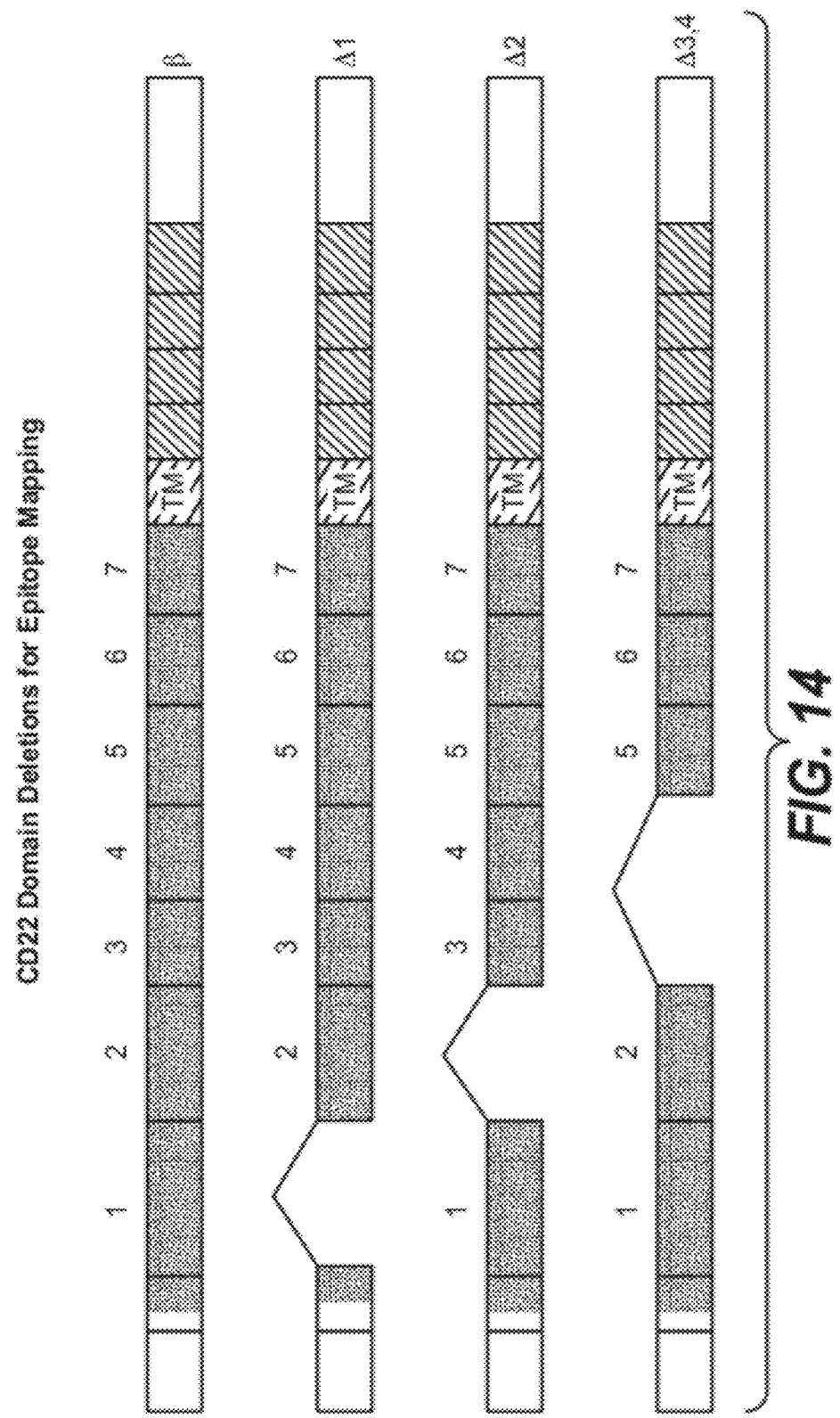

FIG. 14 shows diagrams of CD22 domains deleted for epitope mapping as described in the Examples. The domains are numbered 1-7. "TM" refers to transmembrane domain.

Figure 15:
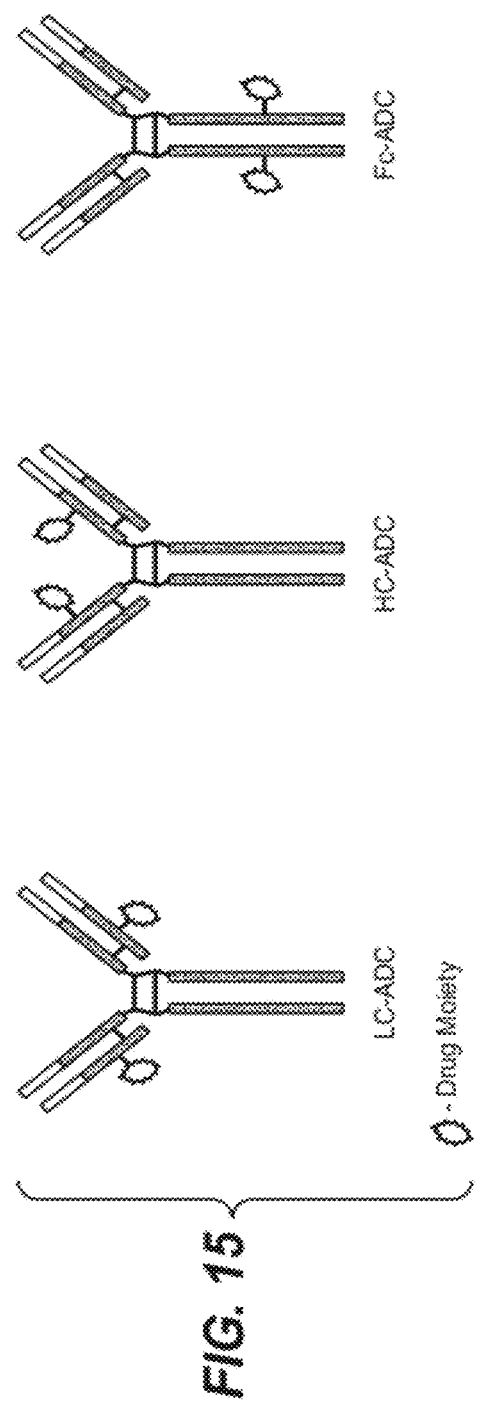

FIG. 15 shows depictions of cysteine engineered anti-CD22 antibody drug conjugates (ADC) where a drug moiety is attached to an engineered cysteine group in: the light chain (LC-ADC); the heavy chain (HC-ADC); and the Fc region (Fc-ADC).

Figure 16:
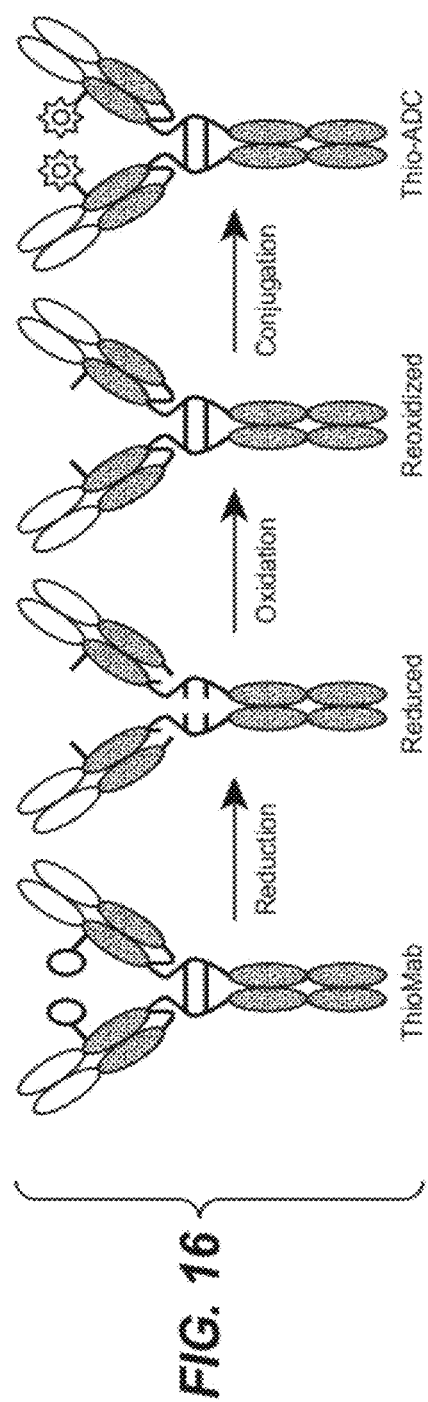
Figure 18A:
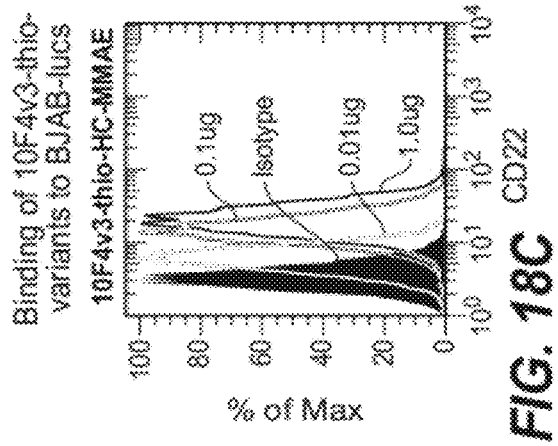
Figure 18B:
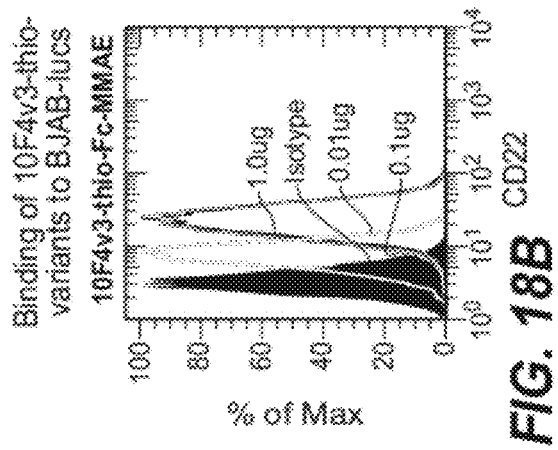
Figure 18C:
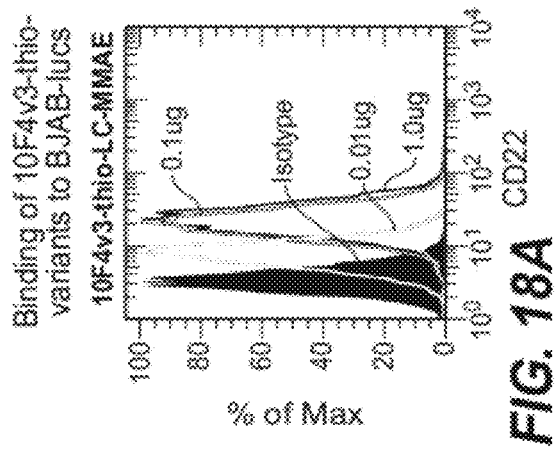
Figure 18D:
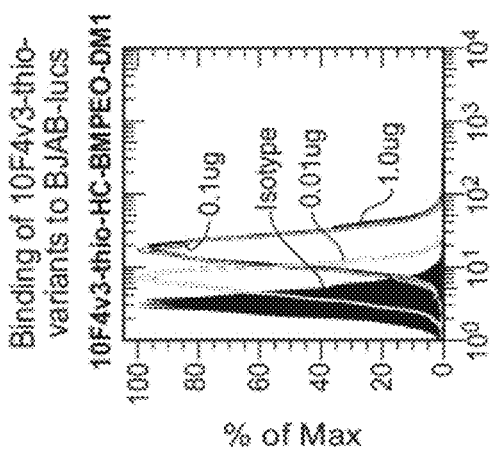
Figure 18E:
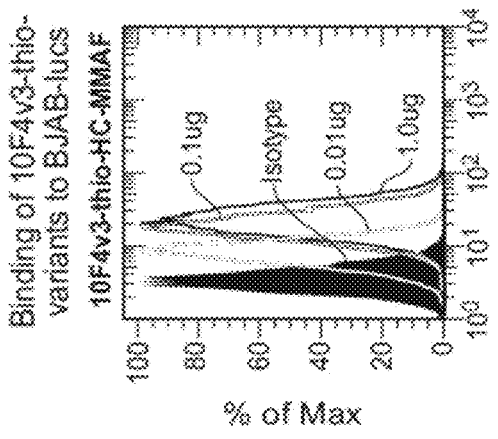

FIG. 16 shows the steps of: (i) reducing cysteine disulfide adducts and interchain and intrachain disulfides in a cysteine engineered anti-CD22 antibody (ThioMab) with reducing agent TCEP (tris(2-carboxyethyl)phosphine hydrochloride); (ii) partially oxidizing, i.e. reoxidation to reform interchain and intrachain disulfides, with dhAA (dehydroascorbic acid); and (iii) conjugation of the reoxidized antibody with a drug-linker intermediate to form a cysteine engineered anti-CD22 antibody drug conjugate (ADC).

FIGS. 17A-17C depict the amino acid sequences of the anti-CD22 cysteine engineered antibodies of the invention in which the light chain or heavy chain or Fc region is altered to engineer a cysteine at selected amino acid positions. FIG. 17A depicts the amino acid sequence of the anti-CD22 10F4 variant light chain in which a valine at Kabat position 205 (sequential position Valine 210) is altered to a Cysteine. FIG. 17B depicts the amino acid sequence of the anti-CD22 10F4 variant heavy chain in which an Alanine at EU position 118 (sequential position Alanine 121) is altered to a Cysteine. FIG. 17C depicts the amino acid sequence of the anti-CD22 10F4 variant Fc region in which a Serine at EU position 400 (sequential position Serine 403) is altered to a Cysteine. In each figure, the altered amino acid is shown in bold text with double underlining. Single underlining indicates constant regions. Variable regions are not underlined.

FIGS. 18A-18E are FACS plots indicating that binding of anti-CD22 thiomab drug conjugates (TDCs) of the invention bind to CD22 expressed on the surface of BJAB-lucs cells is similar for LC, HC and Fc thiomab variants as well as for the different drug conjugates shown.

Figure 19:
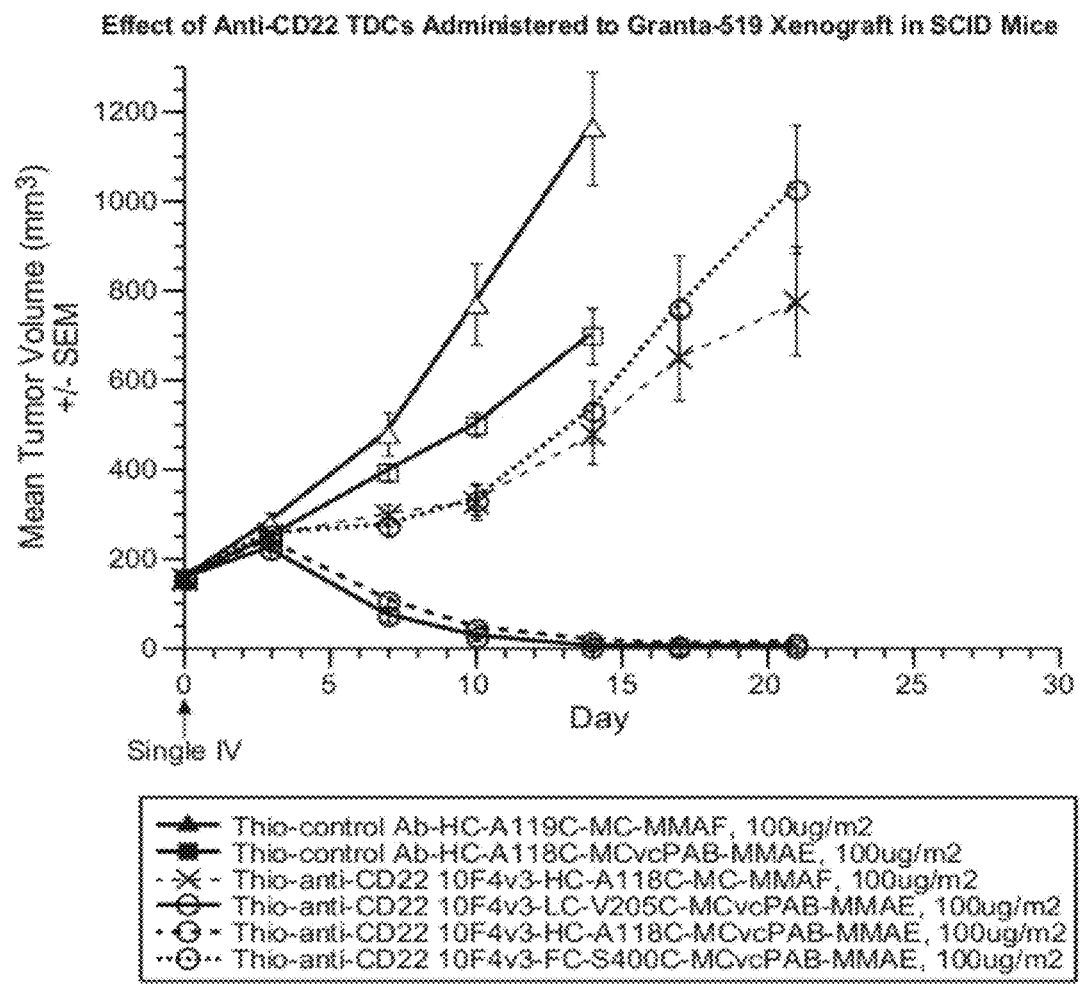

FIG. 19 is a graph plotting changes in mean tumor volume over time in a xenograft model treated with different anti-CD22 TDCs, which varied by position of the engineered cysteine (LC, HC or Fc) and/or by drug conjugate (MMAF or MMAE). Xenograft models treated with anti-CD22 TDCs 10F4-LC-V210C-MCvcPAB-MMAE and anti-CD22 10F4-HC-A121C-MCvcPAB-MMAE showed a decrease in tumor volume during the study.

Figure 20A:
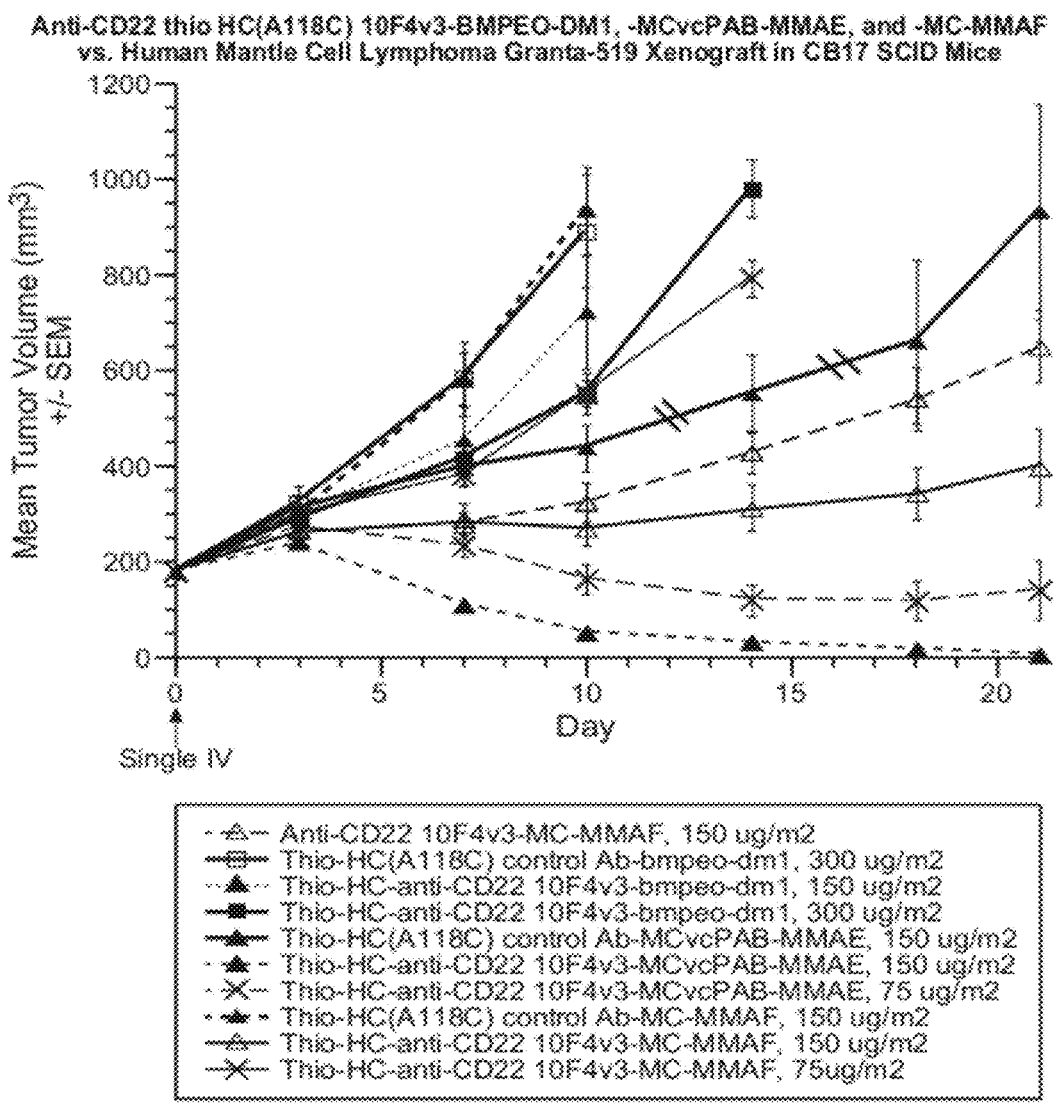
Figure 20B:
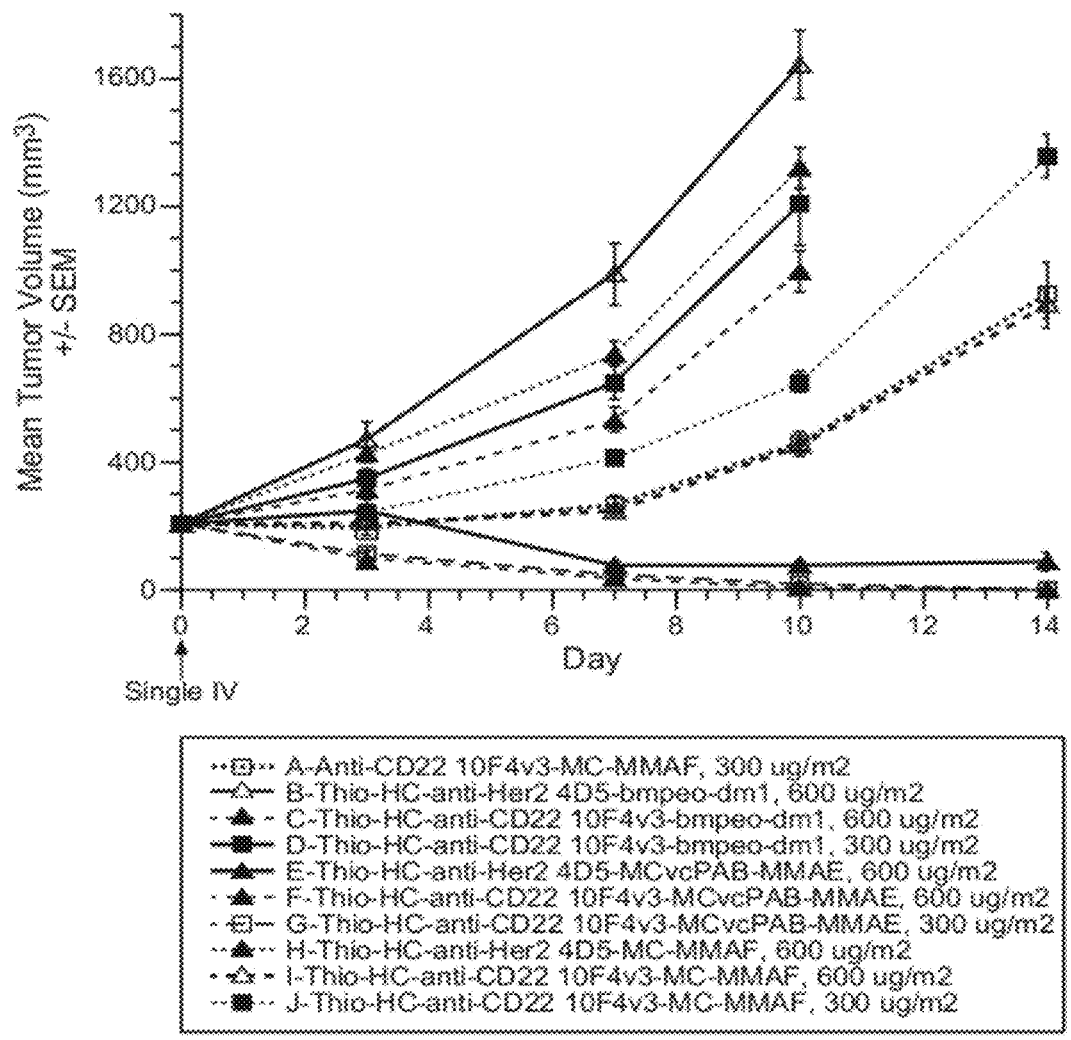
Figure 20C:
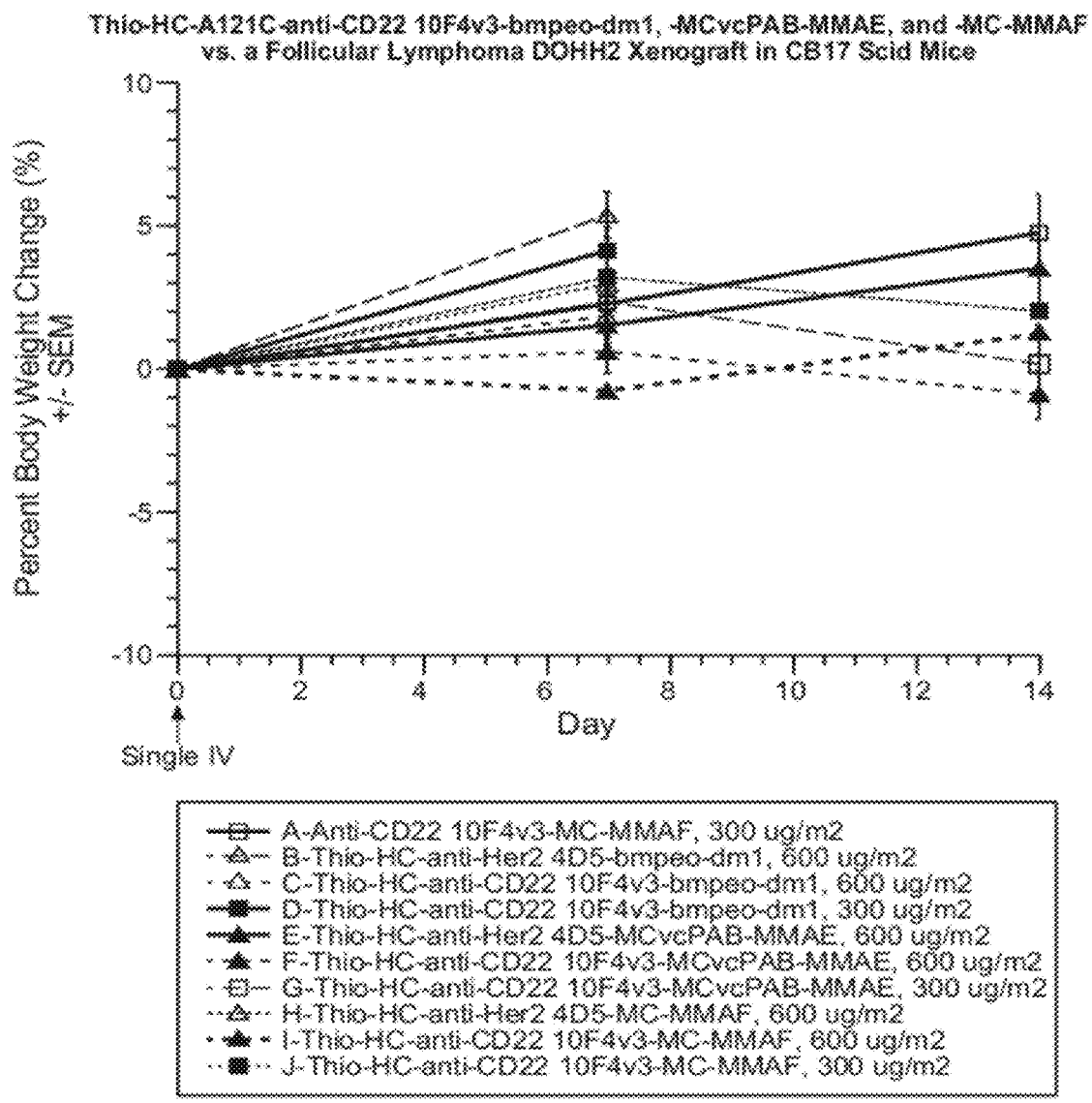

FIG. 20A is a graph plotting changes in mean tumor volume over time in a human mantle cell lymphoma Granta-519 xenograft in CB17 SCID mice treated with heavy chain A118C anti-CD22 TDCs conjugated to different linker drug moieties and/or administered at different doses as shown. The anti-CD22 10F4-HC(A118C)-MCvcPAB-MMAE TDC appeared to be the most efficacious of the test agents in this experiment. FIG. 20B is a graph plotting changes in mean tumor volume over time in a follicular lymphoma DOHH2 xenograft in CB17 SCID mice treated with the same heavy chain A118C anti-CD22 TDCs, but at higher doses. The anti-CD22 10F4-HC(A118C)-MCvcPAB-MMAE TDC appeared to be the most efficacious of the test agents in this experiment. FIG. 20C is a plot of percent weight change is the mice from the DOHH2 xenograft study showing that there was no significant change in weight during the first 14 days of the study.

Figure 21A:
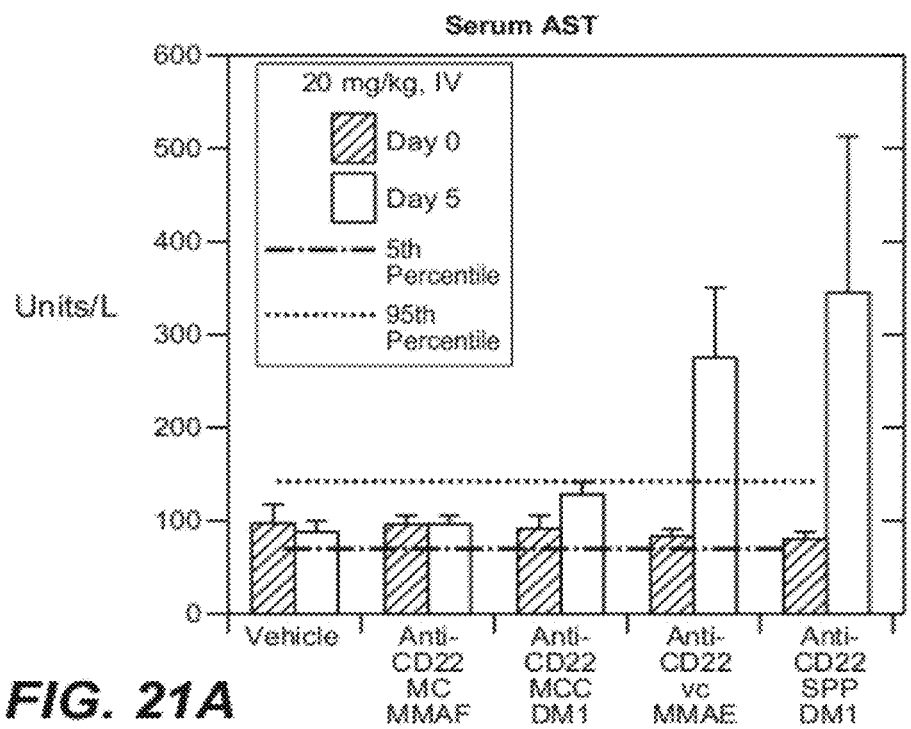
Figure 21B:
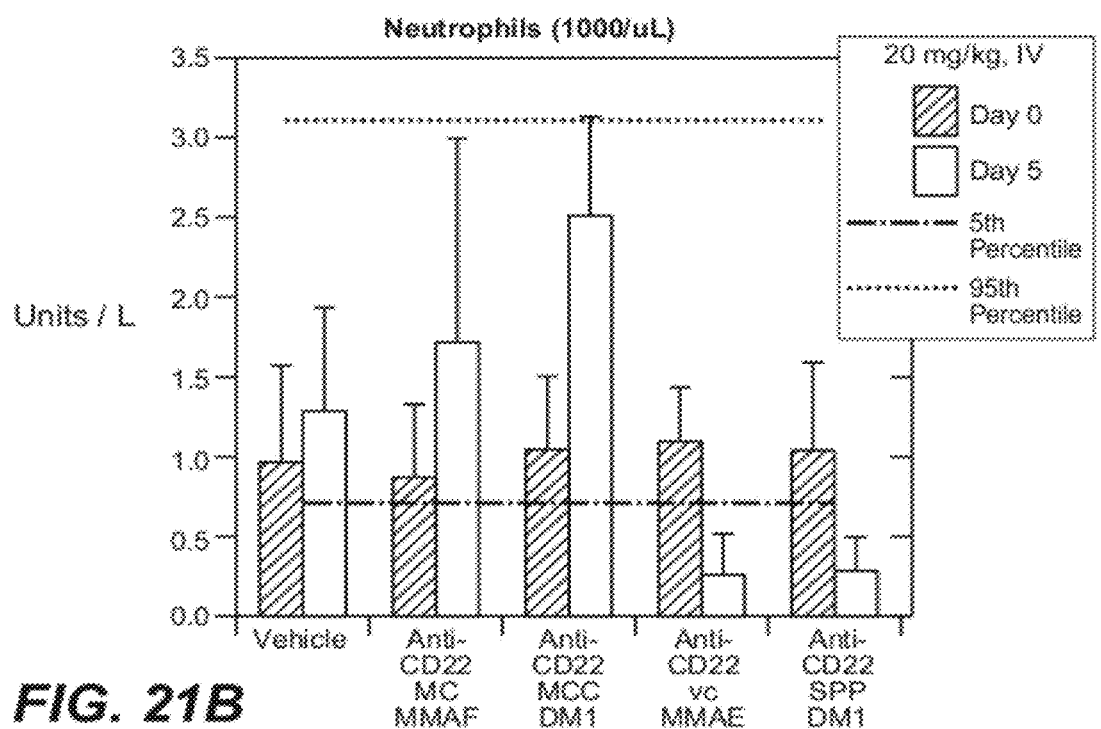

FIGS. 21A and 21B are bar graphs showing changes in serum AST (aspartate aminotransferase) (FIG. 21A) and serum neutrophils (FIG. 21B) at Days 0 and 5 where ADC comprising a cleavable and uncleavable linker was administered.

Figure 22A:
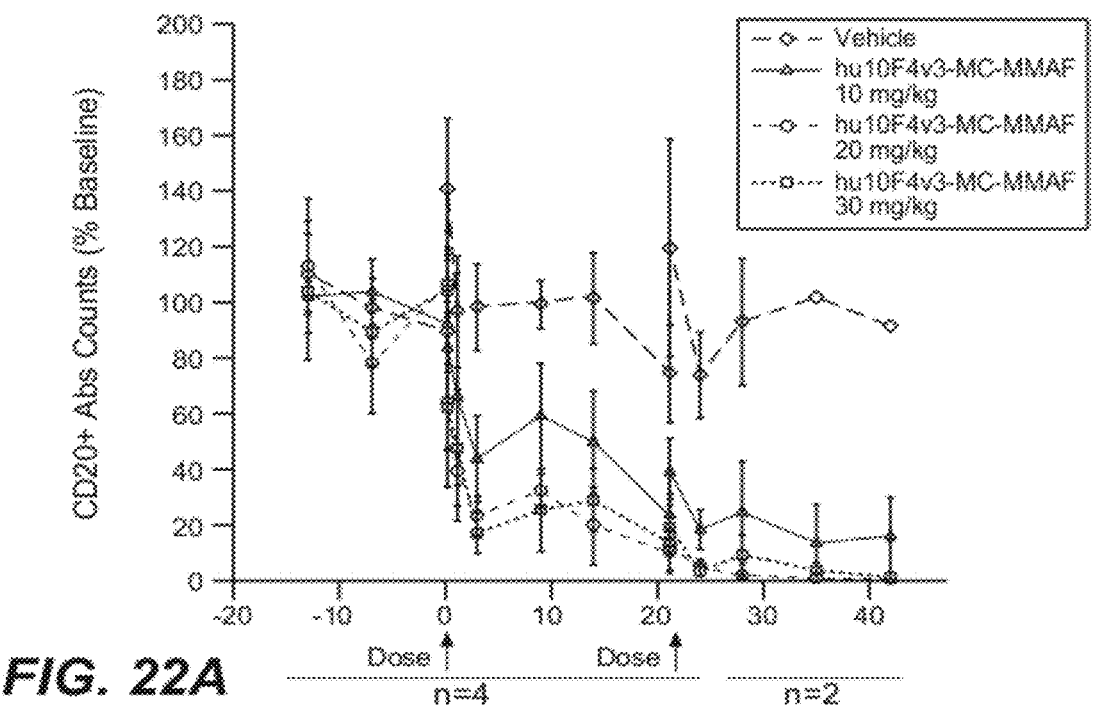
Figure 22B:
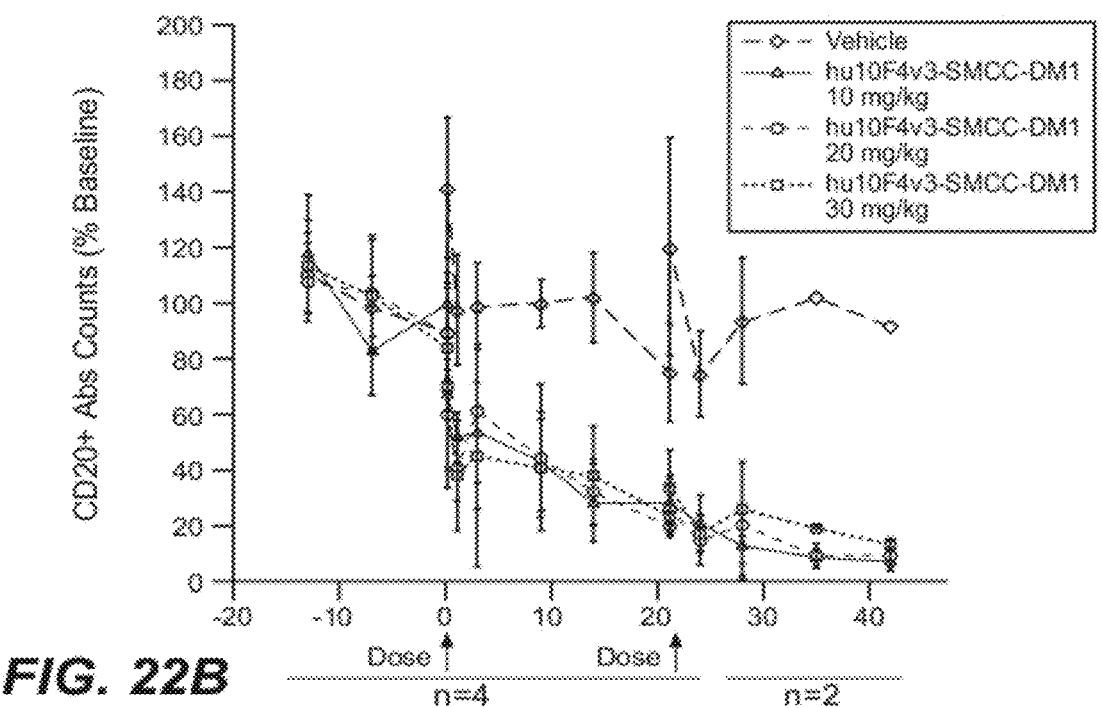

FIGS. 22A and 22B are graphs showing depletion of peripheral B cells ($CD20^+$ cells) in cynomolgus monkeys dosed with 10, 20, and 30 mg/kg anti-CD22 MMAF (FIG. 22A) and anti-CD22 DM1 (FIG. 22B).

Figure 23A:
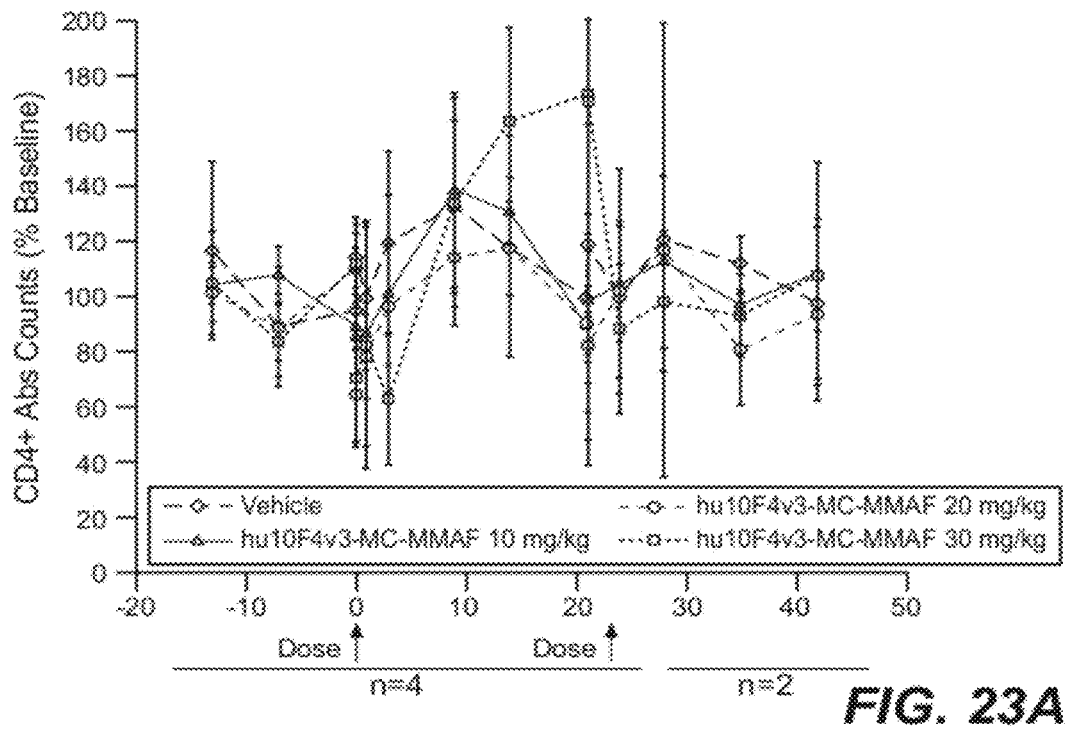
Figure 23B:
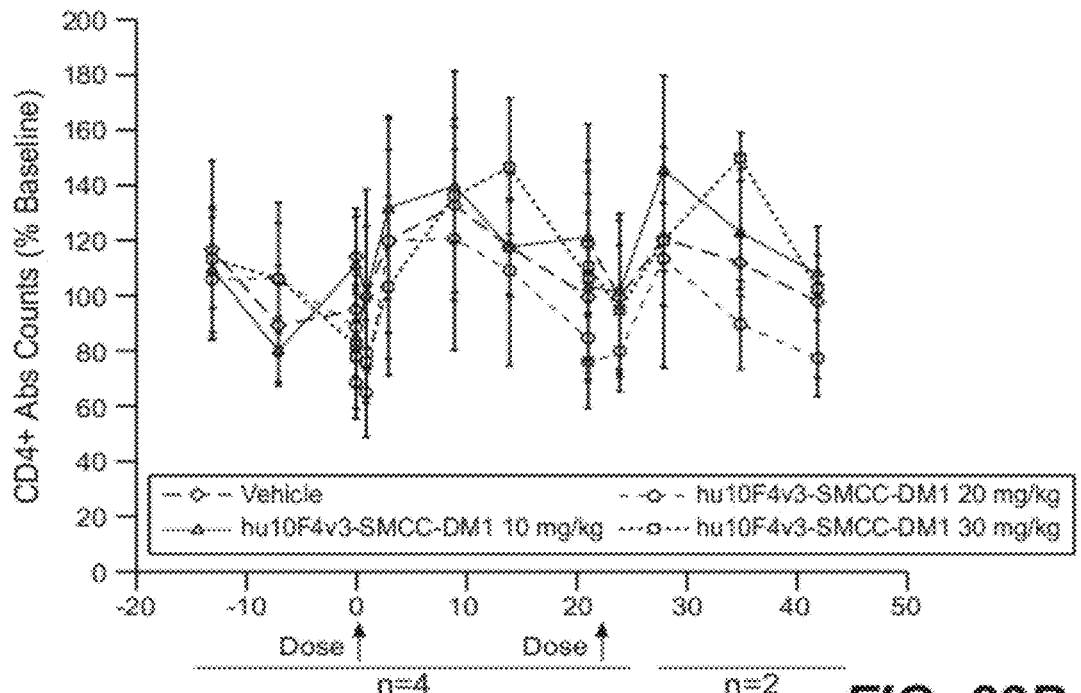

FIGS. 23A and 23B are graphs showing no significant change in $CD4^+$ lymphocytes at 10, 20, and 30 mg/kg anti-CD22 MMAF (FIG. 23A) and anti-CD22 DM1 (FIG. 23B).

Figure 24A:
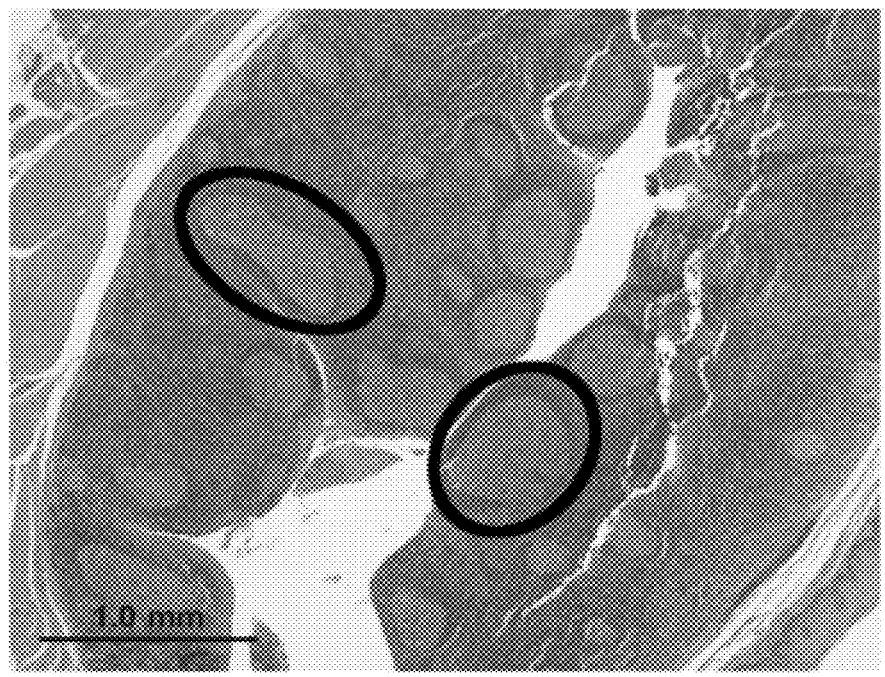
Figure 24B:
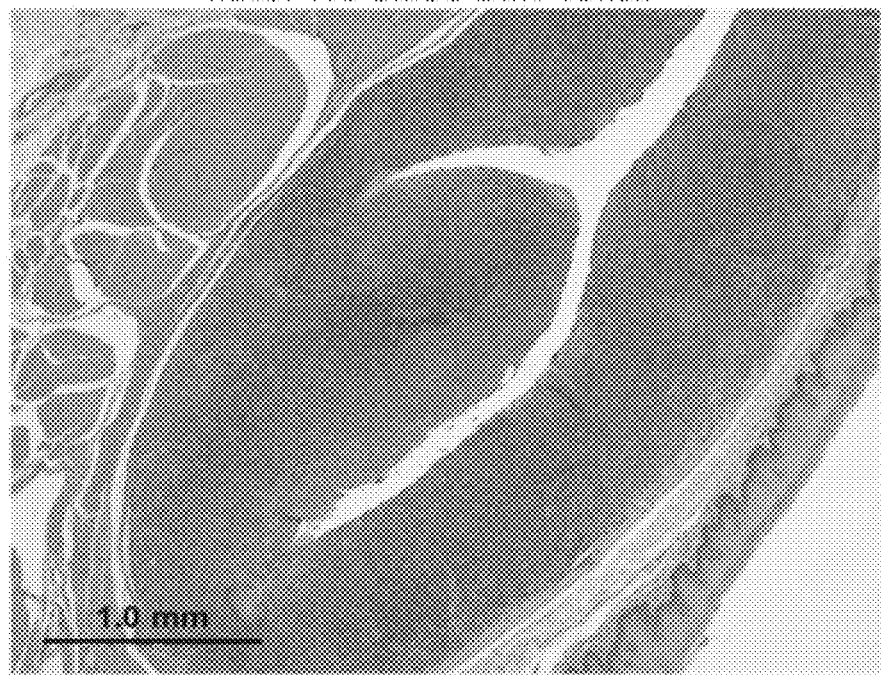

FIGS. 24A and 24B show histological samples of cynomolgus monkey tonsil tissue in which depletion of germinal center B cells, apparent in the vehicle control (FIG. 24A), are depleted in a tonsil sample from an animal dosed at 10 mg/kg hu10F4v3-SMCC-DM1.

Figure 25A:
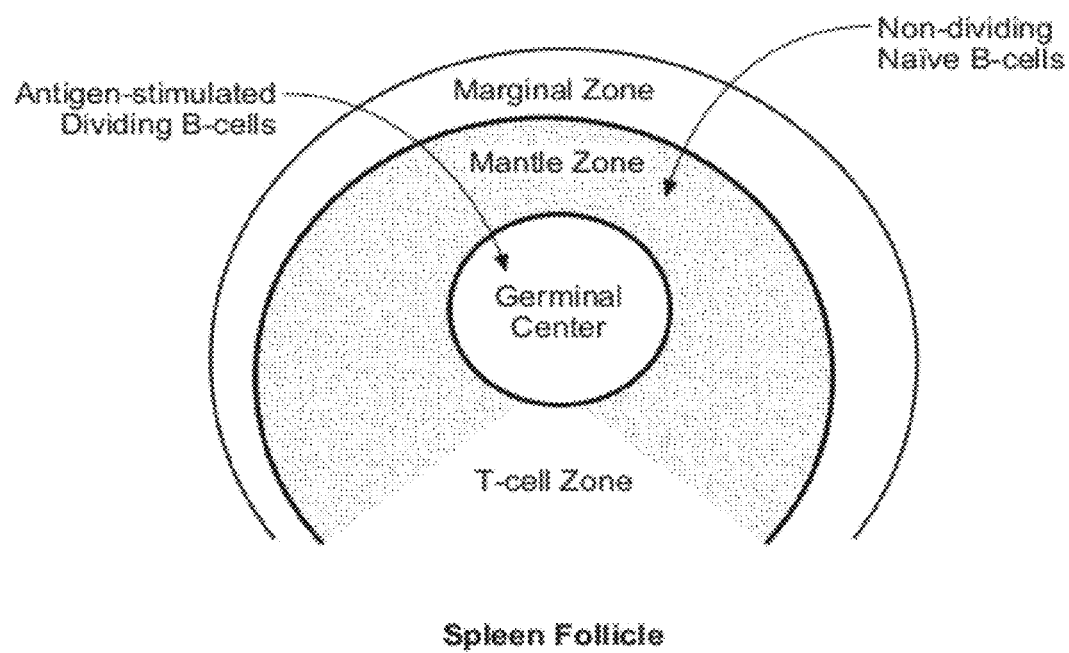

FIG. 25A is a diagram indicating the regions of spleen follicle from which tissue samples were taken for a study in which it was shown that anti-CD22 ADCs spare B cells in resting tissue in cynomolgus monkeys. Dividing cells in cyno spleen follicle germinal center were depleted in dividing germinal cells of cyno spleens from animals dosed with hu10F4v3-MC-MMAF at 10 mg/kg (FIGS. 25B and 25C). Non-dividing naïve B cells were not depleted under the same conditions (FIGS. 25D and 25E).

DETAILED DESCRIPTION OF EMBODIMENTS OF THE INVENTION

Isolated antibodies that bind to CD22 are provided. Immunoconjugates comprising anti-CD22 antibodies are further provided. Cysteine engineered anti-CD22 antibodies and immunoconjugates thereof are further provided. Antibodies and immunoconjugates of the invention are useful, e.g., for the diagnosis or treatment of disorders associated with altered expression, e.g., increased expression, of CD22. In certain embodiments, antibodies or immunoconjugates of the invention are useful for the diagnosis or treatment of a cell proliferative disorder, such as a tumor or cancer. In certain embodiments, antibodies or immunoconjugates of the invention are useful for the detection of CD22, e.g., CD22 expressed on the cell surface.

Polynucleotides encoding anti-CD22 antibodies are provided. Vectors comprising polynucleotides encoding anti-CD22 antibodies are provided, and host cells comprising such vectors are provided. Compositions, including pharmaceutical formulations, comprising any one or more of the polynucleotides, anti-CD22 antibodies, or immunoconjugates of the invention are also provided.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.):

*Pcr 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

DEFINITIONS AND ABBREVIATIONS

Definitions

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

"Purified" means that a molecule is present in a sample at a concentration of at least 95% by weight, or at least 98% by weight of the sample in which it is contained.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "B-cell surface marker" or "B-cell surface antigen" herein is an antigen expressed on the surface of a B cell that can be targeted with an antagonist that binds thereto, including but not limited to, antibodies to a B-cell surface antigen or a soluble form a B-cell surface antigen capable of antagonizing binding of a ligand to the naturally occurring B-cell antigen. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, 2$^{nd}$ Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, BAFF, BLyS, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells.

The term "CD22," as used herein, refers to any native CD22 from any vertebrate source, including mammals such as primates (e.g. humans, cynomolgus monkey (cyno)) and rodents (e.g., mice and rats), unless otherwise indicated. The term encompasses "full-length," unprocessed CD22 as well as any form of CD22 that results from processing in the cell. The term also encompasses naturally occurring variants of CD22, e.g., splice variants, allelic variants, and isoforms. The major isoform of CD22 (CD22beta) comprises 847 amino acids and seven immunoglobulin-like regions in the extracellular domain (see Wilson, G. L. et al., J. Exp. Med. 173:137-146 (1991)). A minor isoform, CD22alpha, comprises 647 amino acids and lacks immunoglobulin-like domains 3 and 4 in the extracellular domain (see Stamenkovic, I. and Seed, B., Nature 345:74-77 (1990)) and Wilson et al. (1991), supra). The amino acid sequence of CD22 beta is depicted in FIG. 1B in which the underlined portion is the extracellular domain (ECD) and the italicized portion indicates the amino acids missing from the CD22 alpha extracellular domain sequence. FIG. 1C depicts the amino acid sequence of CD22alpha in which the ECD is underlined. The amino acid sequence from amino acid 1 to amino acid 21 represents the signal sequence cleaved from the mature form of the protein. In one embodiment, CD22 is expressed on the cell surface, such as on the surface of a normal B cell or a tumor B cell. FIG. 1D depicts the amino acid sequence of CD22 from cynomolgus monkey.

"Antibodies" (Abs) and "immunoglobulins" (Igs) are glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The term "anti-CD22 antibody" or "an antibody that binds to CD22" refers to an antibody that is capable of binding CD22 with sufficient affinity such that the antibody is useful as a diagnostic and/or therapeutic agent in targeting CD22. Preferably, the extent of binding of an anti-CD22 antibody to an unrelated, non-CD22 protein is less than about 10% of the binding of the antibody to CD22 as measured, e.g., by a radioimmunoassay (RIA). In certain embodiments, an antibody that binds to CD22 has a dissociation constant (Kd) of $\leq 1$ μM, $\leq 100$ nM, $\leq 10$ nM, $\leq 1$ nM, or $\leq 0.1$ nM. In certain embodiments, an anti-CD22 antibody binds to an epitope of CD22 that is conserved among CD22 from different species.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, IgG2, IgG3, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al. (2003) Nat. Med. 9:129-134; and Hollinger et al., Proc. Natl. Acad. Sci. USA 90: 6444-6448 (1993). Triabodies and tetrabodies are also described in Hudson et al. (2003) Nat. Med. 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2$^{nd}$ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). In native antibodies, H3 and L3 display the most diversity of the six hypervariable regions, and H3 in particular is believed to play a unique role in conferring fine specificity to antibodies. Xu et al. (2000) Immunity 13:37-45; Johnson and Wu (2003) in Methods in Molecular Biology 248:1-25 (Lo, ed., Human Press, Totowa, N.J.). Indeed, naturally occurring camelid antibodies consisting of a heavy chain only are functional and stable in the absence of light chain. Hamers-Casterman et al. (1993) Nature 363:446-448; Sheriff et al. (1996) Nature Struct. Biol. 3:733-736.

A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions. The HVR-H1 and HVR-H2 hypervariable regions of the anti-CD22 10F4 antibodies of the invention are H26-H35 and H49-H65 using Kabat numbering.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5$^{th}$ Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

A "free cysteine amino acid" refers to a cysteine amino acid residue which has been engineered into a parent antibody, has a thiol functional group (—SH), and is not paired as, or otherwise part of, an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests. Thiol-reactive reagents which allow capture of the cysteine engineered antibody and comparison and quantitation of the cysteine reactivity include biotin-PEO-maleimide ((+)-biotinyl-3-maleimidopropionamidyl-3,6-dioxaoctainediamine, Oda et al (2001) Nature Biotechnology 19:379-382, Pierce Biotechnology, Inc.) Biotin-BMCC, PEO-Iodoacetyl Biotin, Iodoacetyl-LC-Biotin, and Biotin-HPDP (Pierce Biotechnology, Inc.), and Nα-(3-maleimidylpropionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

The following abbreviations are used herein and have the indicated definitions: BME is beta-mercaptoethanol, Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis (2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), nor is (1S,2R)-(+)-norephedrine, PAB is p-aminobenzylcarbamoyl, PBS is phosphate-buffered saline (pH 7), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of HVR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which mimics at least one of the functional activities of a polypeptide of interest.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

WO00/42072 (Presta) describes antibody variants with improved or diminished binding to FcRs. The content of that patent publication is specifically incorporated herein by reference. See, also, Shields et al. J. Biol. Chem. 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. J. Immunol. 164: 4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5$^{th}$ Ed. Public Health Service, National Institutes of Health, Bethesda, Md. (1991). In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences:

EVQLVESGGGLVQPGGSLRLSCAAS (FR-H1, SEQ ID NO: 1)-

HVR-H1-WVRQAPGKGLEWV (FR-H2, SEQ ID NO: 3)-HVR-

H2-RFTISADTSKNTAYLQMNSLRAEDTAVYYC (FR-H3, SEQ ID

NO: 5)-HVR-H3-WGQGTLVTVSS (FR-H4, SEQ ID NO: 7).

A "VL subgroup I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences:

DIQMTQSPSSLSASVGDRVTITC (FR-L1, SEQ ID NO: 8)-

HVR-L1-WYQQKPGKAPKLLIY (FR-L2, SEQ ID NO: 11)-

HVR-L2-GVPSRFSGSGSGTDFTLTISSLQPEDFATYYC (FR-L3,

SEQ ID NO: 13)-HVR-L3-FGQGTKVEIK (FR-L4, SEQ ID

NO: 15).

"Secretion signal sequence" or "signal sequence" refers to a nucleic acid sequence encoding a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol. Biol. 293: 865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., (1997) Cancer Res. 57:4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20;

Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates (kon) and dissociation rates (koff) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881. If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

An "on-rate," "rate of association," "association rate," or "$k_{on}$" according to this invention can also be determined as described above using a BIAcore™-2000 or a BIAcore™-3000 system (BIAcore, Inc., Piscataway, N.J.).

A "disorder" is any condition or disease that would benefit from treatment with a substance/molecule or method of the invention. This includes chronic and acute disorders including those pathological conditions which predispose the mammal to the disorder in question. Non-limiting examples of disorders to be treated herein include cancerous conditions such as B cell proliferative disorders and/or B cell tumors, e.g., lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, cancerous B cell proliferative disorders B cell proliferative disorder is selected from lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. Other cancers conditions included, for example, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A "B-cell malignancy" herein includes non-Hodgkin's lymphoma (NHL), including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, non-Hodgkin's lymphoma (NHL), lymphocyte predominant Hodgkin's disease (LPHD), small lymphocytic lymphoma (SLL), chronic lymphocytic leukemia (CLL), indolent NHL including relapsed indolent NHL and rituximab-refractory indolent NHL; leukemia, including acute lymphoblastic leukemia (ALL), chronic lymphocytic leukemia (CLL), Hairy cell leukemia, chronic myeloblastic leukemia; mantle cell lymphoma; and other hematologic malignancies. Such malignancies may be treated with antibodies directed against B-cell surface markers, such as CD22. Such diseases are contemplated herein to be treated by the administration of an antibody directed against a B cell surface marker, such as CD22, and includes the administration of an unconjugated ("naked") antibody or an antibody conjugated to a cytotoxic agent as disclosed herein. Such diseases are also contemplated herein to be treated by combination therapy including an anti-CD22 antibody or anti-CD22 antibody drug conjugate of the invention in combination with another antibody or antibody drug conjugate, another cytoxic agent, radiation or other treatment administered simultaneously or in series. In exemplary treatment method of the invention, an anti-CD22 antibody of the invention is administered in combination with an anti-CD20 antibody, immunoglobulin, or CD20 binding fragment thereof, either together or sequentially. The anti-CD20 antibody may be a naked antibody or an antibody drug conjugate. In an embodiment of the combination therapy, the anti-CD22 antibody is an antibody of the present invention and the anti-CD20 antibody is Rituxan® (rituximab).

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology (3rd edition), A. Victor Hoffbrand and John E. Pettit (eds.) (Harcourt Publishers Ltd., 2000). See, in particular, the lists in FIG. 11.57, 11.58 and 11.59. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Specific examples of other autoimmune diseases as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutate psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immunovasculitis, CNS vasculitis, cutaneous vasculitis, hypersensitivity vasculitis, necrotizing vasculitis such as fibrinoid necrotizing vasculitis and systemic necrotizing vasculitis, ANCA-negative vasculitis, and ANCA-associated vasculitis such as Churg-Strauss syndrome (CSS), Wegener's granulomatosis, and microscopic polyangiitis), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Behçet's disease/syndrome, Castleman's syndrome, Goodpasture's syndrome, Reynaud's syndrome, Sjögren's syndrome, Stevens-Johnson syndrome, pemphigoid or pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, preferably allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (opthalmopathy or thyroid-associated opthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis. Such diseases are contemplated herein to be treated by the administration of an antibody which binds to a B cell surface marker, such as CD22, and includes the administration of an unconjugated ("naked") antibody or an antibody conjugated to a cytotoxic agent as disclosed herein. Such diseases are also contemplated herein to be treated by combination therapy including an anti-CD22 antibody or anti-CD22 antibody drug conjugate of the invention in combination with another antibody or antibody drug conjugate, another cytoxic agent, radiation or other treatment administered simultaneously or in series.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $R^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, toxins, growth inhibitory agents, drug moieties, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylane; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing CD22) either in vitro or in vivo. Thus, the growth inhibitory agent may be one which significantly reduces the percentage of cells (such as a cell expressing CD22) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anti-cancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "intracellular metabolite" refers to a compound resulting from a metabolic process or reaction inside a cell on an antibody-drug conjugate (ADC). The metabolic process or reaction may be an enzymatic process, such as proteolytic cleavage of a peptide linker of the ADC, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an antibody-drug conjugate (ADC) whereby the covalent attachment, i.e. linker, between the drug moiety (D) and the antibody (Ab) is broken, resulting in the free drug dissociated from the antibody inside the cell. The cleaved moieties of the ADC are thus intracellular metabolites.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or growth inhibitory effect of an antibody-drug conjugate or an intracellular metabolite of an antibody-drug conjugate. Cytotoxic activity may be expressed as the $IC_{50}$ value, which is the concentration (molar or mass) per unit volume at which half the cells survive.

"Alkyl" is C1-C18 hydrocarbon containing normal, secondary, tertiary or cyclic carbon atoms. Examples are methyl (Me, —CH3), ethyl (Et, —CH2CH3), 1-propyl (n-Pr, n-propyl, —CH2CH2CH3), 2-propyl (i-Pr, i-propyl, —CH(CH3)2), 1-butyl (n-Bu, n-butyl, —CH2CH2CH2CH3), 2-methyl-1-propyl (i-Bu, i-butyl, —CH2CH(CH3)2), 2-butyl (s-Bu, s-butyl, —CH(CH3)CH2CH3), 2-methyl-2-propyl (t-Bu, t-butyl, —C(CH3)3), 1-pentyl (n-pentyl, —CH2CH2CH2CH2CH3), 2-pentyl (—CH(CH3)CH2CH2CH3), 3-pentyl (—CH(CH2CH3)2), 2-methyl-2-butyl (—C(CH3)2CH2CH3), 3-methyl-2-butyl (—CH(CH3)CH(CH3)2), 3-methyl-1-butyl (—CH2CH2CH(CH3)2), 2-methyl-1-butyl (—CH2CH(CH3)CH2CH3), 1-hexyl (—CH2CH2CH2CH2CH2CH3), 2-hexyl (—CH(CH3)CH2CH2CH2CH3), 3-hexyl (—CH(CH2CH3)(CH2CH2CH3)), 2-methyl-2-pentyl (—C(CH3)2CH2CH2CH3), 3-methyl-2-pentyl (—CH(CH3)CH(CH3)CH2CH3), 4-methyl-2-pentyl (—CH(CH3)CH2CH(CH3)2), 3-methyl-3-pentyl (—C(CH3)(CH2CH3)2), 2-methyl-3-pentyl (—CH(CH2CH3)CH(CH3)2), 2,3-dimethyl-2-butyl (—C(CH3)2CH(CH3)2), 3,3-dimethyl-2-butyl (—CH(CH3)C(CH3)3.

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

"Alkenyl" is C2-C18 hydrocarbon containing normal, secondary, tertiary or cyclic carbon atoms with at least one site of unsaturation, i.e. a carbon-carbon, sp$^2$ double bond. Examples include, but are not limited to: ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$)

"Alkynyl" is C2-C18 hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

A "$C_1$-$C_{10}$ alkylene" is a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

An "arylene" is an aryl group which has two covalent bonds and can be in the ortho, meta, or para configurations as shown in the following structures:

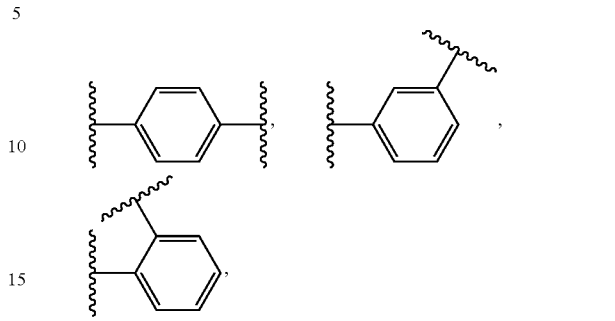

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, ═NR, —CX$_3$, —CN, —OCN, —SCN, —N═C═O, —NCS, —NO, —NO$_2$, ═N$_2$, —N$_3$, NC(═O)R, —C(═O)R, —C(═O)NR$_2$, —SO$_3^-$, —SO$_3$H, —S(═O)$_2$R, —OS(═O)$_2$OR, —S(═O)$_2$NR, —S(═O)R, —OP(═O)(OR)$_2$, —P(═O)(OR)$_2$, —PO$^-_3$, —PO$_3$H$_2$, —C(═O)R, —C(═O)X, —C(═S)R, —CO$_2$R, —CO$_2^-$, —C(═S)OR, —C(═O)SR, —C(═S)SR, —C(═O)NR$_2$, —C(═S)NR$_2$, —C(═NR)NR$_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

Abbreviations
Linker Components:
MC=6-maleimidocaproyl
Val-Cit or "vc"=valine-citrulline (an exemplary dipeptide in a protease cleavable linker)
Citrulline=2-amino-5-ureido pentanoic acid
PAB=p-aminobenzyloxycarbonyl (an example of a "self immolative" linker component)
Me-Val-Cit=N-methyl-valine-citrulline (wherein the linker peptide bond has been modified to prevent its cleavage by cathepsin B)
MC(PEG)6-OH=maleimidocaproyl-polyethylene glycol (can be attached to antibody cysteines).
SPP=N-succinimidyl-4-(2-pyridylthio)pentanoate
SPDP=N-succinimidyl-3-(2-pyridyldithio) propionate
SMCC=succinimidyl-4-(N-maleimidomethyl)cyclohexane-1-carboxylate
IT=iminothiolane
Cytotoxic Drugs:
MMAE=mono-methyl auristatin E (MW 718)
MMAF=variant of auristatin E (MMAE) with a phenylalanine at the C-terminus of the drug (MW 731.5)
MMAF-DMAEA=MMAF with DMAEA (dimethylaminoethylamine) in an amide linkage to the C-terminal phenylalanine (MW 801.5)
MMAF-TEG=MMAF with tetraethylene glycol esterified to the phenylalanine
MMAF-NtBu=N-t-butyl, attached as an amide to C-terminus of MMAF
DM1=N(2')-deacetyl-N(2')-(3-mercapto-1-oxopropyl)-maytansine
DM3=N(2')-deacetyl-N2-(4-mercapto-1-oxopentyl)-maytansine
DM4=N(2')-deacetyl-N2-(4-mercapto-4-methyl-1-oxopentyl)-maytansine Further abbreviations are as follows: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN($CH_3CN$) is acetonitrile, MeOH is methanol, Mtr is 4-anisyldiphenylmethyl (or 4-methoxytrityl), nor is (1S,2R)-(+)-norephedrine, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Compositions and Methods of Making the Same

Antibodies that bind to CD22 are provided. Immunoconjugates comprising anti-CD22 antibodies are provided. Antibodies and immunoconjugates of the invention are useful, e.g., for the diagnosis or treatment of disorders associated with altered expression, e.g., increased expression, of CD22. In certain embodiments, antibodies or immunoconjugates of the invention are useful for the diagnosis or treatment of a cell proliferative disorder, such as cancer.

Anti-CD22 Antibodies

In one aspect, the invention provides antibodies that bind to CD22. In some embodiments, antibodies are provided that bind to a mature form of human and cynomolgus monkey (cyno) CD22. In one such embodiment, a mature form of human CD22 has an amino acid sequence of SEQ ID NO:27. The mature, major human isoform has an extracellular domain comprising seven Ig-like domains and an amino acid sequence of SEQ ID NO:28. In another embodiment, a minor isoform of human CD22 lacking extracellular domains 3 and 4 has an amino acid sequence of SEQ ID NO: 29. The amino acid sequence of the extracellular domain of the minor isoform is SEQ ID NO:30. The cyno CD22 has an amino acid sequence of SEQ ID NO:31. In some embodiments, an antibody to CD22 binds to a mature form of CD22 expressed on the cell surface. In some embodiments, an antibody that binds to a mature form of CD22 expressed on the cell surface inhibits the growth of the cell. In some embodiments, an anti-CD22 antibody binds to a mature form of CD22 expressed on the cell surface and inhibits cell proliferation. In certain embodiments, an anti-CD22 antibody binds to a mature form of CD22 expressed on the cell surface and induces cell death. In some embodiments, an anti-CD22 antibody binds to a mature form of CD22 expressed on the surface of cancer cells. In some embodiments, an anti-CD22 antibody binds to a mature form of CD22 that is overexpressed on the surface of cancer cells relative to normal cells of the same tissue origin. In some embodiments, an anti-CD22 antibody is conjugated to a cytotoxin or a detectable label and binds to CD22 on a cell surface. In some embodiments, the antibody-toxin conjugate inhibits growth of the cell. In some embodiments, the antibody-detectable label conjugate causes a cell expressing CD22 on its surface to be detectable in vitro or in vivo.

In one aspect, an anti-CD22 antibody is a monoclonal antibody. In one aspect, an anti-CD22 antibody is an antibody fragment, e.g., a Fab, Fab'-SH, Fv, scFv, or (Fab')$_2$ fragment. In one aspect, an anti-CD22 antibody is a chimeric, humanized, or human antibody. In one aspect, any of the anti-CD22 antibodies described herein are purified.

Exemplary monoclonal antibodies derived from a phage library are provided herein. The antigen used for screening the library was a polypeptide having the sequence of amino acid sequences of SEQ ID NO:28 or SEQ ID NO:30, corresponding to the extracellular domains (ECDs) of CD22 beta and alpha. The antibodies resulting from the library screen are affinity matured.

In one aspect, monoclonal antibodies that compete with murine 10F4.4.1, humanized 10F4v1 and v3, and murine 5E8.1.8 for binding to CD22 are provided. Monoclonal antibodies that bind to the same epitope as murine 10F4.4.1, humanized 10F4v1 and v3, and murine 5E8.1.8 are also provided.

In one aspect of the invention, polynucleotides encoding anti-CD22 antibodies are provided. In certain embodiments, vectors comprising polynucleotides encoding anti-CD22 antibodies are provided. In certain embodiments, host cells comprising such vectors are provided. In another aspect of the invention, compositions comprising anti-CD22 antibodies or polynucleotides encoding anti-CD22 antibodies are provided. In certain embodiments, a composition of the invention is a pharmaceutical formulation for the treatment of a cell proliferative disorder, such as those enumerated herein.

Antibody Administration and Formulation

In one embodiment, the anti-CD22 antibody or anti-CD22 antibody drug conjugate (including, but not limited to, an anti-CD22 thiomab drug conjugate of the invention) of the invention is administered in combination with an antagonist of a B-cell surface antigen. Administration "in combination with" one or more further therapeutic agents includes simultaneous (concurrent) and consecutive administration in any order. In one embodiment, the administration is consecutive or sequential. In another embodiment, the administration is simultaneous, concurrent, or together in the same formulation. In one embodiment, the B-cell surface antigen antagonist is an antibody or antigen binding fragment thereof. In one embodiment, the B-cell surface antagonist is an antibody drug conjugate.

The formulations herein may contain more than one active compound as necessary for the particular indication being treated, preferably those with complementary activities that do not adversely affect each other. For example, in addition to an anti-CD22 antibody, anti-CD22 antibody drug conjugate or CD22 binding oligopeptide, it may be desirable to include in the one formulation, an additional antibody, e.g., a second anti-CD22 antibody which binds a different epitope on the CD22 polypeptide, or a second antibody that binds a different B-cell surface antigen, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

Currently, depending on the stage of the cancer, cancer treatment involves one or a combination of the following therapies: surgery to remove the cancerous tissue, radiation therapy, and chemotherapy. Anti-CD22 antibody, anti-CD22 antibody drug conjugate or oligopeptide therapy may be especially desirable in elderly patients who do not tolerate the toxicity and side effects of chemotherapy well and in metastatic disease where radiation therapy has limited usefulness. The tumor targeting anti-CD22 antibodies, anti-CD22 antibody drug conjugate or oligopeptide of the invention are useful to alleviate CD22-expressing cancers upon initial diagnosis of the disease or during relapse. For therapeutic applications, the anti-CD22 antibody, anti-CD22 antibody drug conjugate or oligopeptide can be used alone, or in combination therapy with, e.g., hormones, antiangiogens, or radiolabelled compounds, or with surgery, cryotherapy, and/or radiotherapy. Anti-CD22 antibody, anti-CD22 antibody drug conjugate or oligopeptide treatment can be administered in conjunction with other forms of conventional therapy, either consecutively with, pre- or post-conventional therapy. In the present method of the invention for treating or alleviating cancer, the cancer patient can be administered anti-CD22 antibody, anti-CD22 antibody drug conjugate or oligopeptide in conjunction with treatment with the one or more of the preceding chemotherapeutic agents. The anti-CD22 antibody, anti-CD22 antibody drug conjugate or oligopeptide will be administered with a therapeutically effective dose of the chemotherapeutic agent. In another embodiment, the anti-CD22 antibody, anti-CD22 antibody drug conjugate or oligopeptide is administered in conjunction with chemotherapy to enhance the activity and efficacy of the chemotherapeutic agent. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-CD22 antibody, anti-CD22 antibody drug conjugate or oligopeptide conjugated with a cytotoxic agent is administered to the patient. Preferably, the immunoconjugate bound to the CD22 protein is internalized by the cell, resulting in increased therapeutic efficacy of the immunoconjugate in killing the cancer cell to which it binds. In one embodiment, the cytotoxic agent targets or interferes with the nucleic acid in the cancer cell. Examples of cytotoxic agents are described above and include auristatins, maytansinoids, calicheamicins, ribonucleases and DNA endonucleases, or biologically active derivatives thereof.

The anti-CD22 antibodies, anti-CD22 antibody drug conjugates or oligopeptides or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, anti-CD22 antibody drug conjugate or oligopeptide is preferred.

Other therapeutic regimens may be combined with the administration of the anti-CD22 antibody, anti-CD22 antibody drug conjugate or oligopeptide. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-CD22 antibody or antibodies, anti-CD22 antibody drug conjugates or oligopeptides, with administration of an antibody directed against another tumor antigen or B-cell surface antigen associated with the particular cancer.

In another embodiment, the therapeutic treatment methods of the present invention involves the combined administration of an anti-CD22 antibody (or antibodies), anti-CD22 antibody drug conjugate(s) or oligopeptide(s) and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics, as well as combinations of agents such as, but not limited to, CHOP or FOLFOX. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated (see, e.g., US Patent Appln No. 2002/0009444, Grillo-Lopez, A, concerning intrathecal delivery of a CD20 antibody). Preferably, the dosing is given intravenously or subcutaneously.

A second medicament may be administered with the initial exposure and/or later exposures of the therapeutic antibody or immunoadhesin, such combined administration includes co-administration, using separate formulations or a single pharmaceutical formulation, and consecutive administration in either order, wherein preferably there is a time period while both (or all) active agents simultaneously exert their biological activities.

While the therapeutic anti-CD22 antibody, anti-CD22 antibody drug conjugate, immunoadhesin or other biologic may be administered as a single-agent to treat the autoimmune disease, generally, the therapeutic antibody or immunoadhesin will be combined with one or more second medicament(s). For example, for RA, and other autoimmune diseases, the antibody, immunoadhesin, or other biologic drug is preferably combined with any one or more of the immunosuppressive agents, chemotherapeutic agents, BAFF antagonists, integrin antagonists or antibodies, and/or cytokines listed in the definitions section above; any one or more disease-modifying antirheumatic drugs (DMARDs), such as hydroxycloroquine, sulfasalazine, methotrexate, leflunomide, azathioprine, D-penicillamine, Gold (oral), Gold (intramuscular), minocycline, cyclosporine; Staphylococcal protein A immunoadsorption; intravenous immunoglobulin (IVIG); nonsteroidal antiinflammatory drugs (NSAIDs); glucocorticoid (e.g. via joint injection); corticosteroid (e.g. methylprednisolone and/or prednisone); folate; an anti-tumor necrosis factor (TNF) antagonist, e.g. etanercept/ENBREL™, infliximab/REMICADE™, D2E7 (Knoll) or CDP-870 (Celltech); IL-1R antagonist (e.g. Kineret); IL-10 antagonist (e.g. Ilodecakin); a blood clotting modulator (e.g. WinRho); an IL-6 antagonist/anti-TNF (CBP 1011); CD40 antagonist (e.g. IDEC 131); Ig-Fc receptor antagonist (MDX33); immunomodulator (e.g. thalidomide or Immu-Dyn); anti-CD5 antibody (e.g. H5g1.1); macrophage inhibitor (e.g. MDX 33); costimulatory blocker (e.g. BMS 188667 or Tolerimab); complement inhibitor (e.g. h5G1.1, 3E10 or an anti-decay accelerating factor (DAF) antibody); IL-2 antagonist (zxSMART); EGFR inhibitor (see definition above); tyrosine kinase inhibitor (see definition above); anti-angiogenic agent (e.g. VEGF antibody such as bevacizumab); CD22 antibodies such as LL2 or epratuzumab (LYMPHOCIDE®; Immunomedics), including epratuzumab Y-90 (Juweid et al. Cancer Res 55(23 Suppl):5899s-5907s (1995)), Abiogen's CD22 antibody (Abiogen, Italy), CMC 544 (Wyeth/Celltech), combotox (UT Soutwestern), BL22 (NIH), and LympoScan Tc99 (Immunomedics); EpCAM antibody such as 17-1A (PANOREX®); αvβ3 antibody (e.g. VITAXIN®; Medimmune); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody Y-90 (USC); LIF 226 (Enhanced Lifesci.); BAFF antibody (e.g., WO 03/33658); BAFF receptor antibody (e.g., WO 02/24909); BR3 antibody; Blys antibody such as belimumab; LYMPHOSCD22-B™; anti-Lym-1 Oncolym (USC/Peregrine); ISF 154 (UCSD/Roche/Tragen); gomiliximab (Idec 152; Biogen Idec); IL-6 receptor antibody such as atlizumab (ACTEMRA™; Chugai/Roche); IL-15 antibody such as HuMax-Il-15 (Genmab/Amgen); chemokine receptor antibody, such as a CCR2 antibody (e.g. MLN1202; Millieneum); anti-complement antibody, such as C5 antibody (e.g. eculizumab, 5G1.1; Alexion); oral formulation of human immunoglobulin (e.g. IgPO; Protein Therapeutics); IL-12 antibody such as ABT-874 (CAT/Abbott); Teneliximab (BMS-224818); B cell vaccine; DN-BAFF (Xencor); CRx-119 (CombinatoRx); Amgen's BAFF antagonist; Pentostatin (Pfizer); IC-485 (ICOS); chemokine antagonist such as T-487 (Tularik) or Reticulose (AVR-118); SCO-323 (SCIOS); integrin antagonist 683699, Tanabe, NGD-2001-1 (Neurogen); SCIO-469 (SCIOS); BIRB-796 (Boehringer Ingelheim); VX702, VX850 (Vertex); Leukotriene B-4 antagonist (such as amelubunt, BIIL-284; BI); microtubule modulator (Paxceed; Angiotech); protease inhibitor (MBS561392; BMS); AGIX-4207 (Atherogenics); ISIS-104838 (ISIS/Elan); MFG-IRAP (Univ. Pitt.); IL-1 Trap (RGN-303; Regeneron/Novartis); oprelvekin (Wyeth); everolimus (Certican; Novartis); Amevive (Biogen Idec); ORG-39141 (Organon); FK-506 (Fujisawa); and IL-2 antagonist (tacrolimus; Fujisawa).

A detailed description of exemplary anti-CD22 antibodies is as follows:

1. Specific Embodiments of Anti-CD22 Antibodies

In one aspect, the invention provides an antibody comprising at least one, two, three, four, five, or six HVRs selected from (a) an HVR-H1 comprising the amino acid sequence of SEQ ID NO:2; (b) an HVR-H2 comprising the amino acid sequence of SEQ ID NO:4; (c) an HVR-H3 comprising an amino acid sequence selected from SEQ ID NO:6; (d) an HVR-L1 comprising the amino acid sequence of any one of SEQ ID NO:9, 10, 19, 20, 21, 22, 23; (e) an HVR-L2 comprising the amino acid sequence of SEQ ID NO:12; and (f) an HVR-L3 comprising an amino acid sequence selected from SEQ ID NO:14.

In one aspect, the invention provides an anti-CD22 antibody comprising at least one, at least two, or all three VH HVR sequences selected from (a) an HVR-H1 comprising the amino acid sequence of SEQ ID NO:2; (b) an HVR-H2 comprising the amino acid sequence of SEQ ID NO:4; (c) an HVR-H3 comprising an amino acid sequence selected from SEQ ID NO:6. In one aspect, the invention provides an anti-CD22 antibody comprising an HVR-H1 comprising the amino acid sequence of SEQ ID NO:2. In one aspect, the invention provides an anti-CD22 antibody comprising an HVR-H2 comprising the amino acid sequence of SEQ ID NO:4. In one aspect, the invention provides an anti-CD22 antibody comprising an HVR-H3 comprising an amino acid sequence selected from SEQ ID NO:6.

In one aspect, the invention provides an anti-CD22 antibody comprising an HVR-H3 comprising an amino acid sequence selected from SEQ ID NO:6 and an HVR-H1 comprising an amino acid sequence selected from SEQ ID NO:2.

In one aspect, the invention provides an anti-CD22 antibody comprising an HVR-H3 comprising an amino acid sequence selected from SEQ ID NO:6 and an HVR-H2 comprising an amino acid sequence selected from SEQ ID NO:4.

In one aspect, the invention provides an anti-CD22 antibody comprising an HVR-H1 comprising the amino acid sequence of SEQ ID NO:2 and an HVR-H2 comprising the amino acid sequence of SEQ ID NO:4.

In one aspect, the invention provides an anti-CD22 antibody comprising an HVR-H1 comprising the amino acid sequence of SEQ ID NO:2; an HVR-H2 comprising the amino acid sequence of SEQ ID NO:4; and an HVR-H3 comprising the amino acid sequence of SEQ ID NO:6.

In one aspect, the invention provides an anti-CD22 antibody comprising at least one, at least two, or all three VL HVR sequences selected from (a) an HVR-L1 comprising the amino acid sequence of SEQ ID NO:9 or SEQ ID NO:10; (b) an HVR-L2 comprising the amino acid sequence of SEQ ID NO:12; and (c) an HVR-L3 comprising an amino acid sequence selected from SEQ ID NO:14. In one aspect, the invention provides an anti-CD22 antibody comprising an HVR-L1 comprising an amino acid sequence selected from SEQ ID NO:9. In one aspect, the invention provides an anti-CD22 antibody comprising an HVR-L1 comprising an amino acid sequence selected from SEQ ID NO:10. In one aspect, the invention provides an anti-CD22 antibody comprising an HVR-L1 comprising an amino acid sequence selected from SEQ ID NO:19-23. In one aspect, the HVR-L1 comprises the amino acid sequence of SEQ ID NO:9 wherein N28 is replaced by V (an N28V amino acid change, which generates SEQ ID NO:10). In one aspect, the HVR-L1 comprises the amino acid sequence of SEQ ID NO:9 wherein N28 is replaced by A (an N28A amino acid change, which generates SEQ ID NO:19). In one aspect, the HVR-L1 comprises the amino acid sequence of SEQ ID NO:9 wherein N28 is replaced by Q (an N28Q amino acid change, which generates SEQ ID NO:20). In one aspect, the HVR-L1 comprises the amino acid sequence of SEQ ID NO:9 wherein N28 is replaced by S (an N28S amino acid change, which generates SEQ ID NO:21). In one aspect, the HVR-L1 comprises the amino acid sequence of SEQ ID NO:9 wherein N28 is replaced by D (an N28D amino acid change, which generates SEQ ID NO:22). In one aspect, the HVR-L1 comprises the amino acid sequence of SEQ ID NO:9 wherein N28 is replaced by I (an N28I amino acid change, which generates SEQ ID NO:23). In one aspect, the invention provides an anti-CD22 antibody comprising an HVR-L1 comprising the amino acid sequence of any one of SEQ ID NO:9, 10, 19, 20, 21, 22, 23. In one aspect, the HVR-L1 is any one of SEQ ID NO:9, 10, 19, 20, 21, 22, or 23 and the amino acid at position N30 (asparagine at position 30) is replaced by A (an N30A amino acid change). In one aspect, the HVR-L1 is any one of SEQ ID NO:9, 10, 19, 20, 21, 22, or 23 and the amino acid at position N30 (asparagine at position 30) is replaced by Q (an N30Q amino acid change).

In one aspect, the invention provides an anti-CD22 antibody comprising (a) an HVR-H3 comprising an amino acid sequence of SEQ ID NO:6 and (b) an HVR-L3 comprising an amino acid sequence of SEQ ID NO:14. In some embodiments, the CD22 antibody further comprises (a) an HVR-H1 comprising SEQ ID NO:2 and an HVR-H2 comprising SEQ ID NO:4.

In one aspect, the invention provides an anti-CD22 antibody comprising (a) an HVR-H3 comprising an amino acid sequence of SEQ ID NO:6 and (b) an HVR-L2 comprising an amino acid sequence of SEQ ID NO:12. In some embodiments, the CD22 antibody further comprises (a) an HVR-H1 comprising SEQ ID NO:2 and an HVR-H2 comprising SEQ ID NO:4.

In one aspect, the invention provides an anti-CD22 antibody comprising (a) an HVR-H3 comprising an amino acid sequence of SEQ ID NO:6 and (b) an HVR-L1 comprising an amino acid sequence selected from SEQ ID NO:9, 10, 19, 20, 21, 22, and 23. In some embodiments, the CD22 antibody further comprises (a) an HVR-H1 comprising SEQ ID NO:2 and an HVR-H2 comprising SEQ ID NO:4. In some embodiments, the amino acid sequence of SEQ ID NO:9, 10, 19, 20, 21, 22, or 23 comprises an N30A or N30Q amino acid change. In some embodiments, the CD22 antibody further comprises HVR-L2 comprising the amino acid sequence of SEQ ID NO:12. In some embodiments, the CD22 antibody further comprises HVR-L3 comprising the amino acid sequence of SEQ ID NO:14.

In one aspect, the invention provides an anti-CD22 antibody comprising (a) an HVR-H1 comprising the amino acid sequence of SEQ ID NO:2; (b) an HVR-H2 comprising the amino acid sequence of SEQ ID NO:4; (c) an HVR-H3 comprising the amino acid sequence of SEQ ID NO:6; (d) an HVR-L1 comprising the amino acid sequence selected from SEQ ID NO:9, 10, 19, 20, 21, 22, 23; (e) an HVR-L2 comprising the amino acid sequence of SEQ ID NO:12; and an HVR-L3 comprising the amino acid sequence of SEQ ID NO:14. In some embodiments, the invention further provides that the amino acid sequence SEQ ID NO:9, 10, 19, 20, 21, 22, or 23 selected as HVR-L1 is modified by an N30A or an N30Q amino acid change.

Figure 2A:
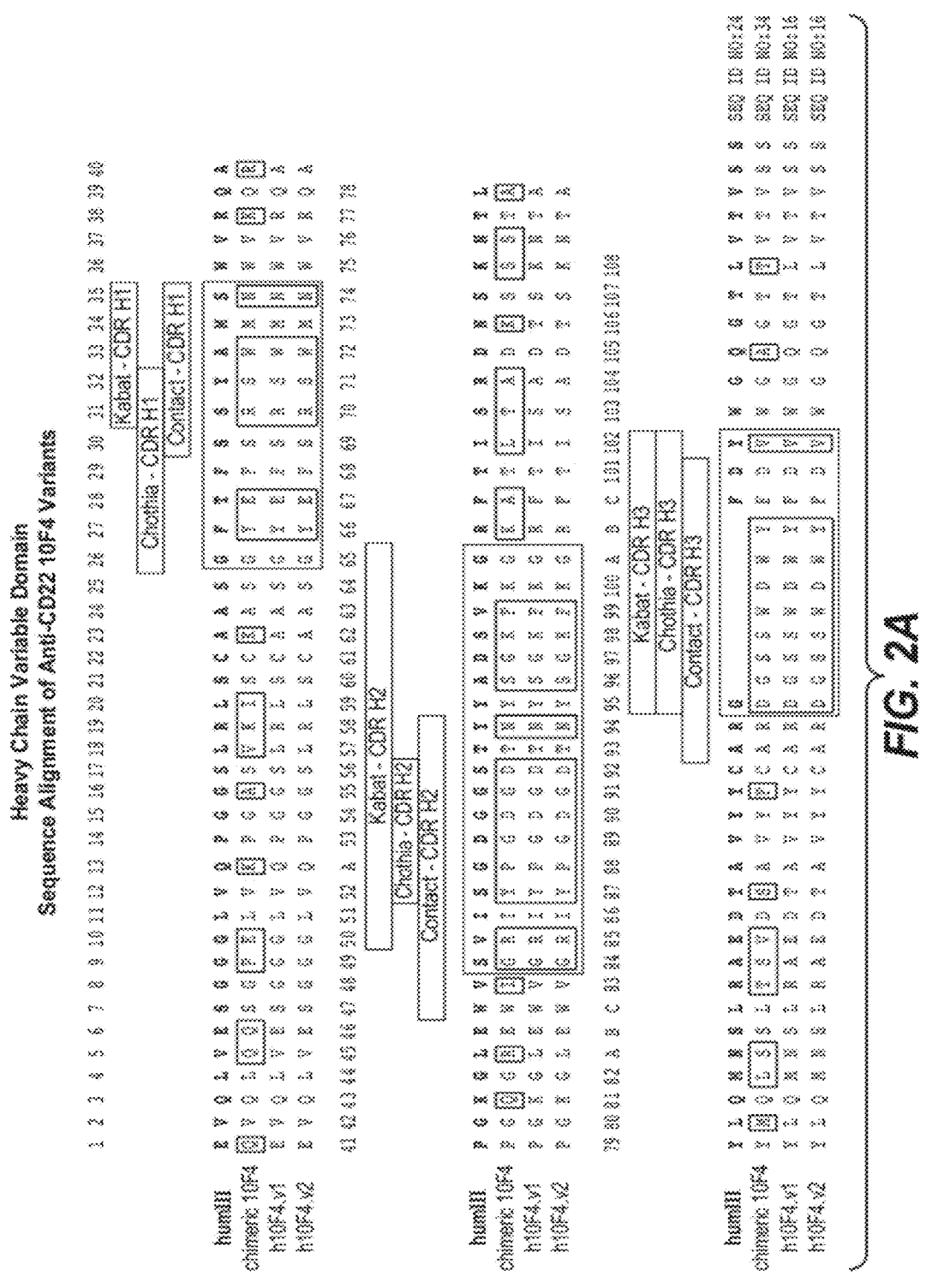

In one aspect, the invention provides an anti-CD22 antibody comprising a heavy chain variable domain comprising SEQ ID NO:16 (see FIG. 2A, h10F4v1). In one aspect, the invention provides an anti-CD22 antibody comprising a light chain variable domain comprising SEQ ID NO:17 (see FIG. 2B, h10F4v1). In one aspect, the invention provides an anti- CD22 antibody comprising a light chain variable domain comprising SEQ ID NO:18 (see FIG. 2B, h10F4v3).

In one aspect, the invention provides an anti-CD22 antibody comprising a heavy chain comprising SEQ ID NO:34 (see FIG. 2A, m10F4). In one aspect, the invention provides an anti-CD22 antibody comprising a light chain comprising SEQ ID NO:35 (see FIG. 2B, m10F4).

In one aspect, the invention provides an anti-CD22 antibody comprising 1, 2, 3, 4, 5, or 6 of the HVR sequences of the antibody 10F4.4.1 produced by the hybridoma deposited with the ATCC and having accession number PTA-7621.

In one aspect, the invention provides an anti-CD22 antibody comprising 1, 2, 3, 4, 5, or 6 of the HVR sequences of the antibody 5E8.1.8 produced by the hybridoma deposited with the ATCC and having accession number PTA-7620.

An anti-CD22 antibody may comprise any suitable framework variable domain sequence, provided that the antibody retains the ability to bind CD22. For example, in some embodiments, anti-CD22 antibodies of the invention comprise a human subgroup III heavy chain framework consensus sequence. In one embodiment of these antibodies, the heavy chain framework consensus sequence comprises substitution(s) at position 71, 73 and/or 78. In one embodiments of these antibodies, position 71 is A, position 73 is T, and/or position 78 is A. In one embodiment, these antibodies comprise a heavy chain variable domain framework sequence of huMAb4D5-8, e.g., SEQ ID NO:1, 3, 5, 7 (FR-H1, FR-H2, FR-H3, FR-H4, respectively). huMAb4D5-8 is commercially known as HERCEPTIN® anti-HER2 antibody, Genentech, Inc., South San Francisco, Calif., USA; also referred to in U.S. Pat. Nos. 6,407,213 & 5,821,337, and Lee et al., J. Mol. Biol. (2004), 340(5):1073-93. In one such embodiment, these antibodies further comprise a human □I light chain framework consensus sequence. In one such embodiment, these antibodies comprise a light chain variable domain framework sequence of huMAb4D5-8, e.g. SEQ ID NO:8, 1, 13, 15 (FR-L1, FR-L2, FR-L3, FR-L4, respectively).

In one embodiment, an anti-CD22 antibody comprises a heavy chain variable domain comprising a framework sequence and hypervariable regions, wherein the framework sequence comprises the FR-H1-FR-H4 sequences SEQ ID NO:1, 3, 5, and 7, respectively; the HVR H1 comprises the amino acid sequence of SEQ ID NO:2; the HVR-H2 comprises the amino acid sequence of SEQ ID NO:4; and the HVR-H3 comprises an amino acid sequence selected from SEQ ID NO:6. In one embodiment, an anti-CD22 antibody comprises a light chain variable domain comprising a framework sequence and hypervariable regions, wherein the framework sequence comprises the FR-L1-FR-L4 sequences of SEQ ID NO:8, 11, 13, and 15, respectively; the HVR-L1 comprises the amino acid sequence selected from SEQ ID NO:9, 10, 19, 20, 21, 22, and 23, wherein any one of SEQ ID NOS:9-10 or 19-23 may comprise a N30A or N30Q amino acid change; the HVR-L2 comprises the amino acid sequence of SEQ ID NO:12; and the HVR-L3 comprises an amino acid sequence selected from SEQ ID NO:14. In one embodiment of these antibodies, the heavy chain variable domain comprises SEQ ID NO:16 and the light chain variable domain comprises SEQ ID NO:17 or 18.

In some embodiments, the invention provides an anti-CD22 antibody comprising a heavy chain variable domain comprising an amino acid sequence having at least 90%, 91%, 92%, 93%, 94%, 95%, 96%, 97%, 98%, or 99% sequence identity to an amino acid sequence SEQ ID NO:16. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to CD22. In some embodiments, a total of 1 to 10 amino acids have been substituted, inserted, or deleted in a sequence SEQ ID NO:16. In some embodiments, the substitutions, insertions, or deletions occur in regions outside the HVRs (i.e., in the FRs). In some embodiments, an anti-CD22 antibody comprises a heavy chain variable domain comprising an amino acid sequence selected from SEQ ID NO:16.

In some embodiments, the invention provides an anti-CD22 antibody comprising a heavy chain variable domain as depicted in below.

```
                                              (SEQ ID NO: 16)
1 Glu Val Gln Leu Val Glu Ser Gly Gly Gly Leu Val

Gln Pro Gly Gly Ser Leu Arg Leu Ser Cys Ala Ala

Ser Gly Tyr Glu Phe Ser Arg Ser Trp Met Asn Trp

Val Arg Gln Ala Pro Gly Lys Gly Leu Glu Trp Val

Gly Arg Ile Tyr Pro Gly Asp Gly Asp Thr Asn Tyr

Ser Gly Lys Phe Lys Gly Lys Ala Thr Leu Thr Ala

Asp Lys Ser Ser Thr Ala Tyr Leu Gln Met Asn

Ser Leu Arg Ala Glu Asp Thr Ala Val Tyr Tyr Cys

Ala Arg Asp Gly Ser Ser Trp Asp Trp Tyr Phe Asp

Tyr Trp Gly Gln Gly Thr Leu Val Thr Val Ser Ser 113
(HVR residues are underlined).
```

In some embodiments, the heavy chain HVR and FR sequences comprise the following:

```
HVR-H1 (Gly Tyr Glu Phe Ser Arg Ser Trp Met Asn,
SEQ ID NO: 2)

HVR-H2 (Gly Arg Ile Tyr Pro Gly Asp Gly Asp Thr
Asn Tyr Ser Gly Lys Phe Lys Gly, SEQ ID NO: 4)

HVR-H3 (Asp Gly Ser Ser Trp Asp Try Tyr Phe Asp
Tyr, SEQ ID NO: 6)

FR-H1 (Glu Val Gln Leu Val Glu Ser Gly Gly Gly
Leu Val Gln Pro Gly Gly Ser Leu Arg Leu Ser Cys
Ala Ala Ser, SEQ ID NO: 1)

FR-H2 (Trp Val Arg Gln Ala Pro Gly Lys Gly Leu
Glu Trp Val, SEQ ID NO: 3)

FR-H3 (Lys Ala Thr Leu Thr Ala Asp Lys Ser Ser
Ser Thr Ala Tyr Leu Gln Met Asn Ser Leu Arg Ala
Glu Asp Thr Ala Val Tyr Tyr Cys Ala Arg, SEQ ID
NO: 5)

FR-H4 (Trp Gly Gln Gly Thr Leu Val Thr Val Ser
Ser, SEQ ID NO: 7)
```

In some embodiments, the invention provides an anti-CD22 antibody comprising a light chain variable domain as depicted in below.

(SEQ ID NO: 17)
```
1 Asp Ile Gln Met Thr Gln Ser Pro Ser Ser Leu Ser
Ala Ser Val Gly Asp Arg Val Thr Ile Thr Cys Arg
Ser Ser Gln Ser Ile Val His Ser Asn Gly Asn Thr
Phe Leu Glu Trp Tyr Gln Gln Lys Pro Gly Lys Ala
Pro Lys Leu Leu Ile Tyr Lys Val Ser Asn Arg Phe
Ser Gly Val Pro Ser Arg Phe Ser Gly Ser Arg Ser
Gly Thr Asp Phe Thr Leu Thr Ile Ser Ser Leu Gln
Pro Glu Asp Phe Ala Thr Tyr Tyr Cys Phe Gln Gly
Ser Gln Phe Pro Tyr Thr Phe Gly Gln Gly Thr Lys
Val Glu Ile Lys Arg 108
```
(HVR residues are underlined and position N28 is in bold type)
Or
(SEQ ID NO: 18)
```
1 Asp Ile Gln Met Thr Gln Ser Pro Ser Ser Leu Ser
Ala Ser Val Gly Asp Arg Val Thr Ile Thr Cys Arg
Ser Ser Gln Ser Ile Val His Ser Val Gly Asn Thr
Phe Leu Glu Trp Tyr Gln Gln Lys Pro Gly Lys Ala
Pro Lys Leu Leu Ile Tyr Lys Val Ser Asn Arg Phe
Ser Gly Val Pro Ser Arg Phe Ser Gly Ser Arg Ser
Gly Thr Asp Phe Thr Leu Thr Ile Ser Ser Leu Gln
Pro Glu Asp Phe Ala Thr Tyr Tyr Cys Phe Gln Gly
Ser Gln Phe Pro Tyr Thr Phe Gly Gln Gly Thr Lys
Val Glu Ile Lys Arg 108
```
(HVR residues are underlined and position N28V is in bold type).

In some embodiments, the light chain HVR sequences comprise the following:

HVR-L1 (Arg Ser Ser Gln Ser Ile Val His Ser Asn Gly Asn Thr Phe Leu Glu, SEQ ID NO: 9)

HVR-L1 (Arg Ser Ser Gln Ser Ile Val His Ser Val Gly Asn Thr Phe Leu Glu, SEQ ID NO: 10)

HVR-L1 (Arg Ser Ser Gln Ser Ile Val His Ser Ala Gly Asn Thr Phe Leu Glu, SEQ ID NO: 19)

HVR-L1 (Arg Ser Ser Gln Ser Ile Val His Ser Gln Gly Asn Thr Phe Leu Glu, SEQ ID NO: 20)

HVR-L1 (Arg Ser Ser Gln Ser Ile Val His Ser Ser Gly Asn Thr Phe Leu Glu, SEQ ID NO: 21)

HVR-L1 (Arg Ser Ser Gln Ser Ile Val His Ser Asp Gly Asn Thr Phe Leu Glu, SEQ ID NO: 22)

HVR-L1 (Arg Ser Ser Gln Ser Ile Val His Ser Ile Gly Asn Thr Phe Leu Glu, SEQ ID NO: 23)

HVR-L1 (Arg Ser Ser Gln Ser Ile Val His Ser Ile Gly Ala Thr Phe Leu Glu, SEQ ID NO: 32)

HVR-L1 (Arg Ser Ser Gln Ser Ile Val His Ser Ile Gly Gln Thr Phe Leu Glu, SEQ ID NO: 33)

HVR-L2 (Lys Val Ser Asn Arg Phe Ser, SEQ ID NO: 12)

HVR-L3 (Phe Gln Gly Ser Gln Phe Pro Tyr Thr, SEQ ID NO: 14).

In some embodiments, the light chain FR sequences comprise the following:

FR-L1 (Asp Ile Gln Met Thr Gln Ser Pro Ser Ser Leu Ser Ala Ser Val Gly Asp Arg Val Thr Ile Thr Cys, SEQ ID NO: 8);

FR-L2 (Trp Tyr Gln Gln Lys Pro Gly Lys Ala Pro Lys Leu Leu Ile Tyr, SEQ ID NO: 11);

FR-L3 (Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys, SEQ ID NO: 13)

FR-L4 (Phe Gly Gln Gly Thr Lys Val Glu Ile Lys Arg, SEQ ID NO: 15).

In one aspect, the invention provides an anti-CD22 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NO:17 or 18. In some embodiments, an amino acid sequence having at least 90%, 91%, 92%, 93%, 94%, 95%, 96%, 97%, 98%, or 99% sequence identity contains substitutions, additions, or deletions relative to the reference sequence, but an antibody comprising that amino acid sequence retains the ability to bind to CD22. In some embodiments, a total of 1 to 10 amino acids have been substituted, inserted, or deleted in a sequence selected from SEQ ID NO:17 or 18. In some embodiments, the substitutions, insertions, or deletions occur in regions outside the HVRs (i.e., in the FRs). In some embodiments, an anti-CD22 antibody comprises a light chain variable domain comprising an amino acid sequence selected from SEQ ID NO:17 or 18.

In one aspect, the invention provides an anti-CD22 antibody comprising (a) a heavy chain variable domain comprising an amino acid sequence having at least 90%, 91%, 92%, 93%, 94%, 95%, 96%, 97%, 98%, or 99% sequence identity to an amino acid sequence selected from SEQ ID NO:16; and (b) a light chain variable domain comprising an amino acid sequence having at least 90%, 91%, 92%, 93%, 94%, 95%, 96%, 97%, 98%, or 99% sequence identity to an amino acid sequence selected from SEQ ID NO:17 or 18. In some embodiments, an amino acid sequence having at least 90%, 91%, 92%, 93%, 94%, 95%, 96%, 97%, 98%, or 99% sequence identity contains substitutions, additions, or deletions relative to the reference sequence, but an antibody comprising that amino acid sequence retains the ability to bind to CD22. In some embodiments, a total of 1 to 10 amino acids have been substituted, inserted, or deleted in the reference sequence. In some embodiments, the substitutions, insertions, or deletions occur in regions outside the HVRs (i.e., in the FRs). In some embodiments, an anti-CD22 antibody comprises a heavy chain variable domain comprising an amino acid sequence of SEQ ID NO:16 and a light chain variable domain comprising an amino acid sequence selected from SEQ ID NO:18.

Figure 2B:
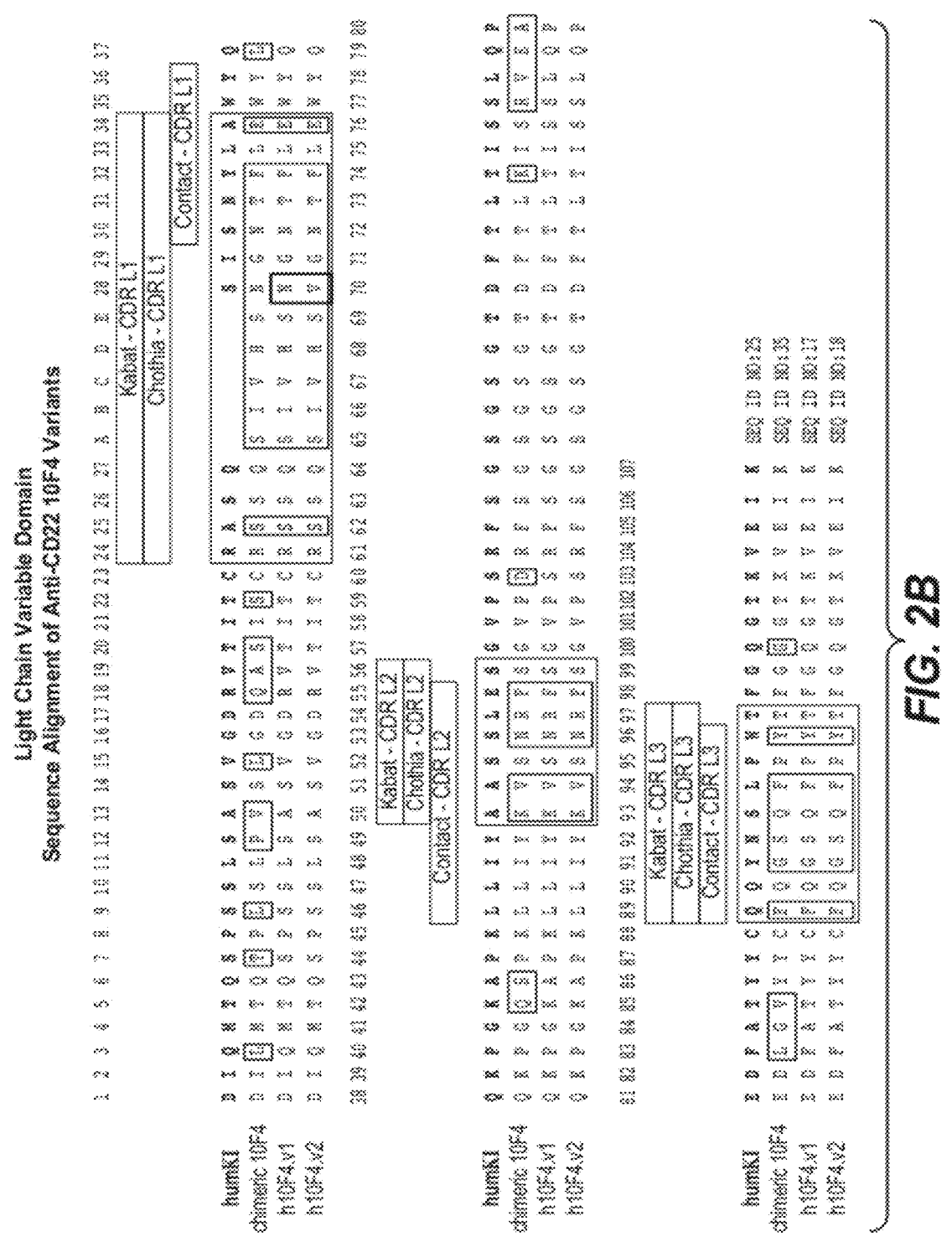

In one aspect, the invention provides an anti-CD22 antibody comprising (a) one, two, or three VH HVRs selected from those shown in FIG. 2A and/or (b) one, two, or three VL HVRs selected from those shown in FIG. 2B. In one aspect, the invention provides an anti-CD22 antibody comprising a heavy chain variable domain selected from those shown in FIG. 2A and a light chain variable domain selected from those shown in FIG. 2B.

In one aspect, the anti-CD22 antibody of the invention comprises 1, 2, 3, 4, 5, or 6 of the hypervariable regions of the 5E8.1.8 antibody produced by the hybridoma deposited with the ATCC and having accession no. PTA-7620.

2. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

3. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

4. Human Antibodies

Human anti-CD22 antibodies of the invention can be constructed by combining Fv clone variable domain sequence(s) selected from human-derived phage display libraries with known human constant domain sequences(s) as described above. Alternatively, human monoclonal anti-CD22 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

5. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for CD22 and the other is for any other antigen. In certain embodiments, bispecific antibodies may bind to two different epitopes of CD22. Bispecific antibodies may also be used to localize cytotoxic agents to cells which express CD22. These antibodies possess a CD22-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the $C_H 3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

6. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

7. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

8. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

In one embodiment, the antibody is altered to improve its serum half-life. To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. No. 6,821,505; U.S. Pat. No. 6,165,745; U.S. Pat. No. 5,624,821; U.S. Pat. No. 5,648,260; U.S. Pat. No. 6,165,745; U.S. Pat. No. 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 1 under the heading of "preferred substitutions." If such substitutions result in a desirable change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO0/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164: 4178-4184 (2000).

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

9. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Certain Methods of Making Antibodies

1. Certain Hybridoma-Based Methods

The anti-CD22 monoclonal antibodies of the invention can be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to CD22 generally are raised in animals by multiple subcutaneous (sc) or intraperitoneal (ip) injections of CD22 and an adjuvant. CD22 may be prepared using methods well-known in the art, some of which are further described herein. For example, CD22 may be produced recombinantly. In one embodiment, animals are immunized with a derivative of CD22 that contains an extracellular portion of CD22 fused to the Fc portion of an immunoglobulin heavy chain. In one embodiment, animals are immunized with an CD22-IgG1 fusion protein. In one embodiment, animals are immunized with immunogenic derivatives of CD22 in a solution with monophosphoryl lipid A (MPL)/trehalose dicorynomycolate (TDM) (Ribi Immunochem. Research, Inc., Hamilton, Mont.), and the solution is injected intradermally at multiple sites. Two weeks later the animals are boosted. Seven to fourteen days later the animals are bled, and the serum is assayed for anti-CD22 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In certain embodiments, myeloma cells are those that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies that bind to CD22. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA). The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

2. Certain Library Screening Methods

Anti-CD22 antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in Methods in Molecular Biology 178:1-37 (O'Brien et al., ed., Human Press, Totowa, N.J.), and in certain embodiments, in Lee et al. (2004) J. Mol. Biol. 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-CD22 antibodies of the invention can be obtained by designing a suitable antigen screening procedure to select for the phage clone of interest followed by construction of a full length anti-CD22 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-CD22 clones is desired, the subject is immunized with CD22 to generate an antibody response, and spleen cells and/or circulating B cells other peripheral blood lymphocytes (PBLs) are recovered for library construction. In a preferred embodiment, a human antibody gene fragment library biased in favor of anti-CD22 clones is obtained by generating an anti-CD22 antibody response in transgenic mice carrying a functional human immunoglobulin gene array (and lacking a functional endogenous antibody production system) such that CD22 immunization gives rise to B cells producing human antibodies against CD22. The generation of human antibody-producing transgenic mice is described below.

Additional enrichment for anti-CD22 reactive cell populations can be obtained by using a suitable screening procedure to isolate B cells expressing CD22-specific membrane bound antibody, e.g., by cell separation using CD22 affinity chromatography or adsorption of cells to fluorochrome-labeled CD22 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which CD22 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$ M or less.

Screening of the libraries can be accomplished by various techniques known in the art. For example, CD22 can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized CD22 under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by CD22 antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for CD22. However, random mutation of a selected antibody (e.g. as performed in some affinity maturation techniques) is likely to give rise to many mutants, most binding to antigen, and a few with higher affinity. With limiting CD22, rare high affinity phage could be competed out. To retain all higher affinity mutants, phages can be incubated with excess biotinylated CD22, but with the biotinylated CD22 at a concentration of lower molarity than the target molar affinity constant for CD22. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-CD22 clones may be selected based on activity. In certain embodiments, the invention provides anti-CD22 antibodies that bind to living cells that naturally express CD22. In one embodiment, the invention provides anti-CD22 antibodies that block the binding between a CD22 ligand and CD22, but do not block the binding between a CD22 ligand and a second protein. Fv clones corresponding to such anti-CD22 antibodies can be selected by (1) isolating anti-CD22 clones from a phage library as described above, and optionally amplifying the isolated population of phage clones by growing up the population in a suitable bacterial host; (2) selecting CD22 and a second protein against which blocking and non-blocking activity, respectively, is desired; (3) adsorbing the anti-CD22 phage clones to immobilized CD22; (4) using an excess of the second protein to elute any undesired clones that recognize CD22-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-CD22 antibody derived from a hybridoma of the invention can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

3. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB− strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.* In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli,* the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from Staphylococcus aureas which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

Origin of Replication

Generally, an origin of replication component is not needed for mammalian expression vectors. For example, the SV40 origin may typically be used only because it contains the early promoter.

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl) benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Immunoconjugates

The invention also provides immunoconjugates (interchangeably referred to as "antibody-drug conjugates," or "ADCs") comprising any of the anti-CD22 antibodies of the invention conjugated to one or more cytotoxic agents, such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In certain embodiments, an immunoconjugate comprises an anti-CD22 antibody and a chemotherapeutic agent or other toxin. Chemotherapeutic agents useful in the generation of immunoconjugates are described herein (e.g., above). Enzymatically active toxins and fragments thereof can also be used and are described herein.

In certain embodiments, an immunoconjugate comprises an anti-CD22 antibody and one or more small molecule toxins, including, but not limited to, small molecule drugs such as a calicheamicin, maytansinoid, dolastatin, auristatin, trichothecene, and CC1065, and the derivatives of these drugs that have cytotoxic activity. Examples of such immunoconjugates are discussed in further detail below.

1. Exemplary Immunoconjugates—Antibody Drug Conjugates

An immunoconjugate (or "antibody-drug conjugate" ("ADC")) of the invention may be of Formula I, below, wherein an anti-CD22 antibody is conjugated (i.e., covalently attached) to one or more drug moieties (D) through an optional linker (L).

$$Ab\text{-}(L\text{-}D)_p \qquad \text{Formula I}$$

Accordingly, the anti-CD22 antibody may be conjugated to the drug either directly or via a linker. In Formula I, p is the average number of drug moieties per antibody, which can range, e.g., from about 1 to about 20 drug moieties per antibody, and in certain embodiments, from 1 to about 8 drug moieties per antibody.

Exemplary Linkers

Exemplary linkers and drug moieties are disclosed herein. A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio)pentanoate ("SPP"), N-succinimidyl 4-(N-maleimidomethyl)cyclohexane-1 carboxylate ("SMCC"), and N-Succinimidyl (4-iodo-acetyl)aminobenzoate ("SIAB"). Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used.

In some embodiments, a linker component may comprise a "stretcher unit" that links an antibody to another linker component or to a drug moiety. Exemplary stretcher units are shown below (wherein the wavy line indicates sites of covalent attachment to an antibody):

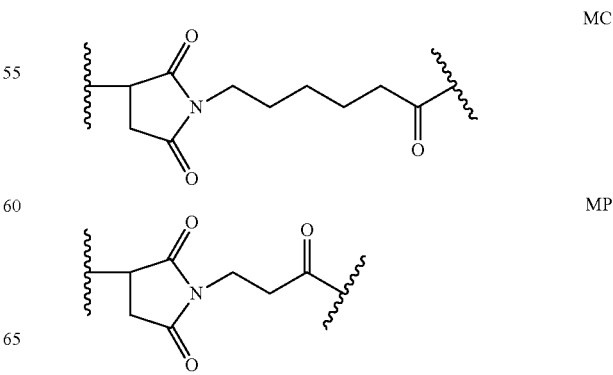

MPEG

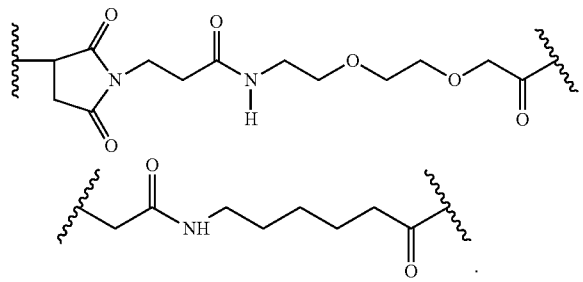

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the antibody to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al. (2005) Expert Opin. Ther. Patents (2005) 15:1087-1103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1), such as 2-aminoimidazol-5-methanol derivatives (Hay et al. (1999) Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223); appropriately substituted bicyclo[2.2.1] and bicyclo[2.2.2] ring systems (Storm, et al., J. Amer. Chem. Soc., 1972, 94, 5815); and 2-aminophenylpropionic acid amides (Amsberry, et al., J. Org. Chem., 1990, 55, 5867). Elimination of amine-containing drugs that are substituted at the a-position of glycine (Kingsbury, et al., J. Med. Chem., 1984, 27, 1447) are also examples of self-immolative spacers useful in ADCs.

In one embodiment, a spacer unit is a branched bis(hydroxymethyl)styrene (BHMS) unit as depicted below, which can be used to incorporate and release multiple drugs.

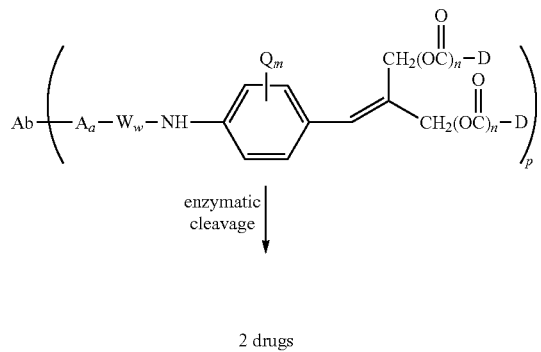

2 drugs wherein Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

A linker may comprise any one or more of the above linker components. In certain embodiments, a linker is as shown in brackets in the following ADC Formula II Ab-([Aa-Ww-Yy]-D)$_p$   Formula II wherein A is a stretcher unit, and a is an integer from 0 to 1; W is an amino acid unit, and w is an integer from 0 to 12; Y is a spacer unit, and y is 0, 1, or 2; and Ab, D, and p are defined as above for Formula I. Exemplary embodiments of such linkers are described in US 20050238649 A1, which is expressly incorporated herein by reference.

Exemplary linker components and combinations thereof are shown below in the context of ADCs of Formula II:

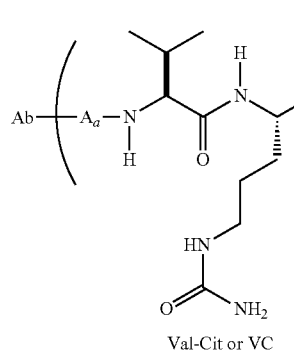
Val-Cit or VC

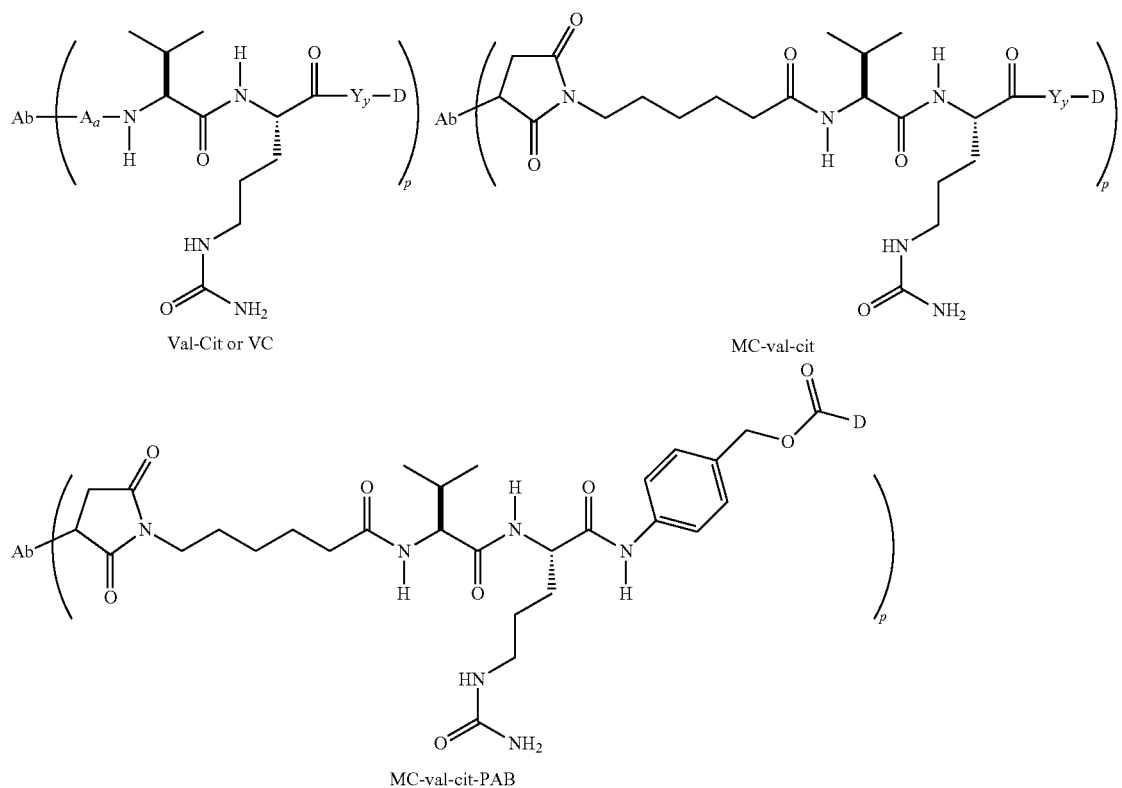

MC-val-cit-PAB

Linkers components, including stretcher, spacer, and amino acid units, may be synthesized by methods known in the art, such as those described in US 2005-0238649 A1.

Exemplary Drug Moieties

Maytansine and Maytansinoids

In some embodiments, an immunoconjugate comprises an antibody of the invention conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Maytansine compounds suitable for use as maytansinoid drug moieties are well known in the art and can be isolated from natural sources according to known methods or produced using genetic engineering techniques (see Yu et al (2002) PNAS 99:7968-7973). Maytansinol and maytansinol analogues may also be prepared synthetically according to known methods.

Exemplary embodiments of maytansinoid drug moieties include: DM1; DM3; and DM4, as disclosed herein.

Auristatins and Dolastatins

In some embodiments, an immunoconjugate comprises an antibody of the invention conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

A peptidic drug moiety may be selected from Formulas $D_E$ and $D_F$ below:

$D_E$

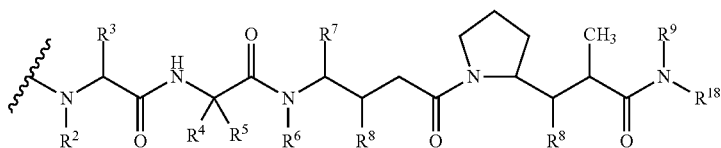

$D_F$

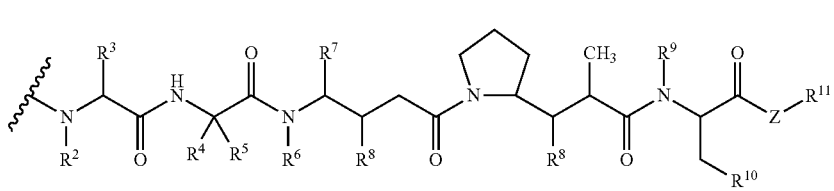

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{10}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

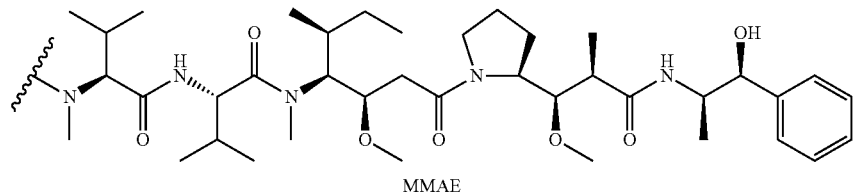

MMAE

An exemplary auristatin embodiment of formula $D_F$ is MMAF, wherein the wavy line indicates the covalent attachment to a linker (L) of an antibody-drug conjugate (see US 2005/0238649 and Doronina et al. (2006) *Bioconjugate Chem.* 17:114-124):

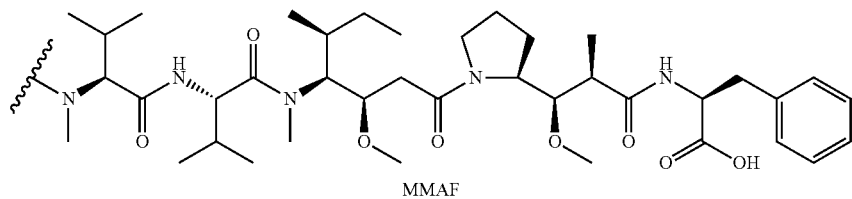
MMAF
Other drug moieties include the following MMAF derivatives, wherein the wavy line indicates the covalent attachment to a linker (L) of an antibody-drug conjugate:
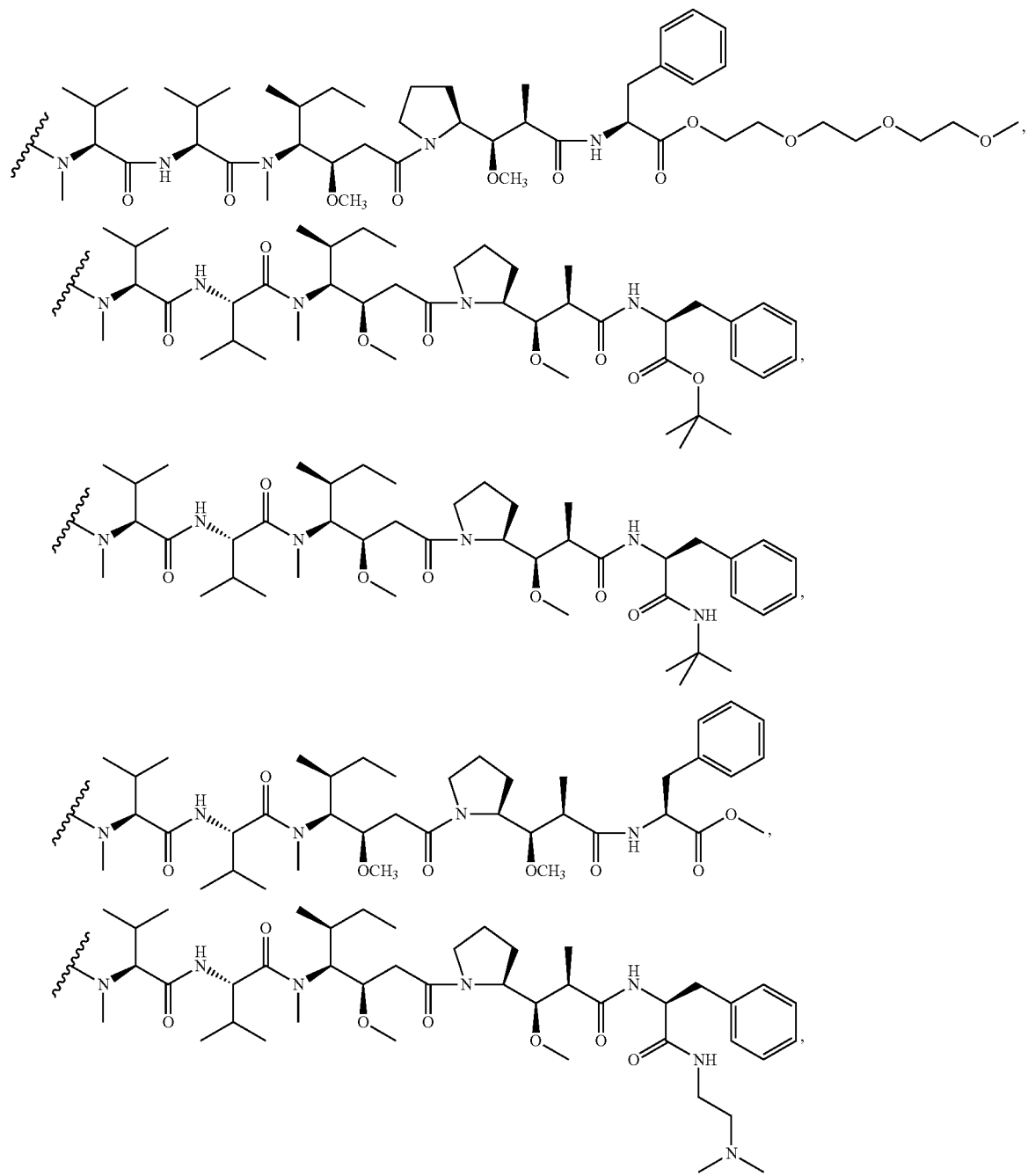

-continued

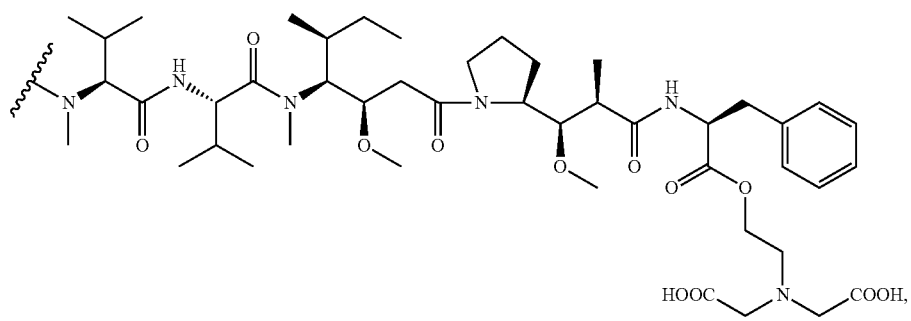

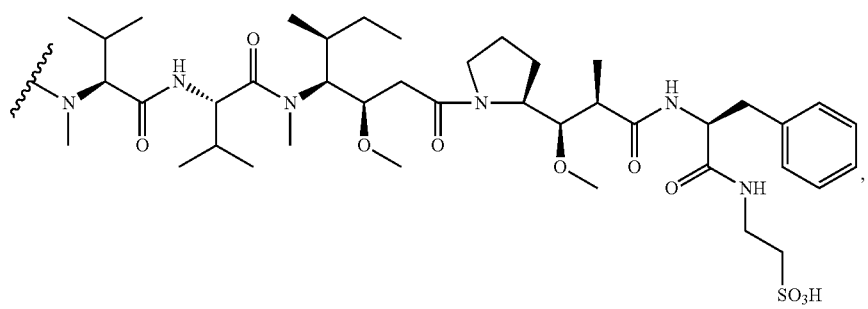

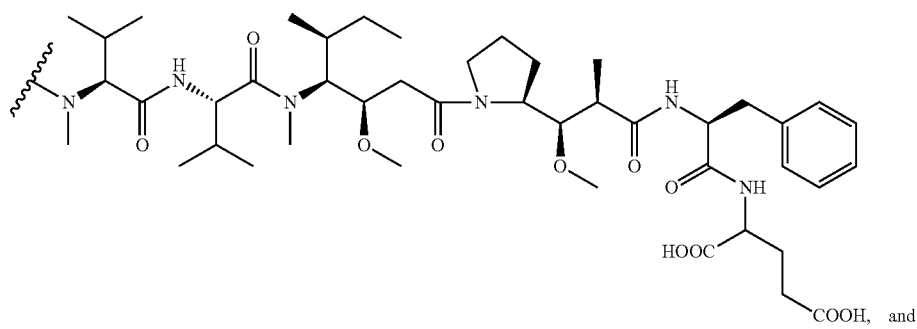

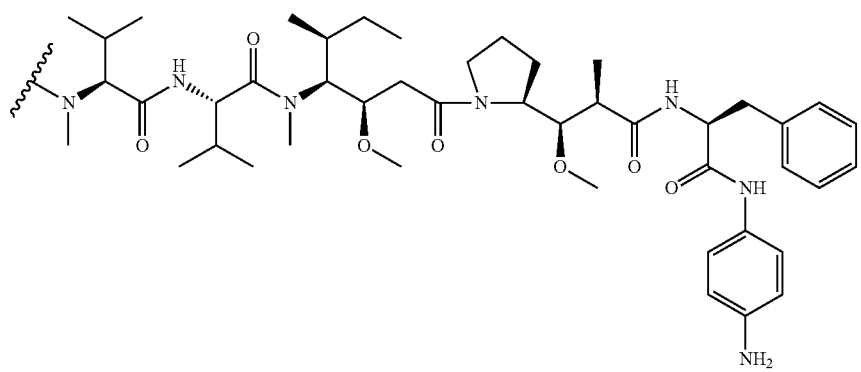

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs of Formula I comprising an auristatin/dolastatin or derivative thereof are described in US 2005-0238649 A1 and Doronina et al. (2006) Bioconjugate Chem. 17:114-124, which is expressly incorporated herein by reference. Exemplary embodiments of ADCs of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

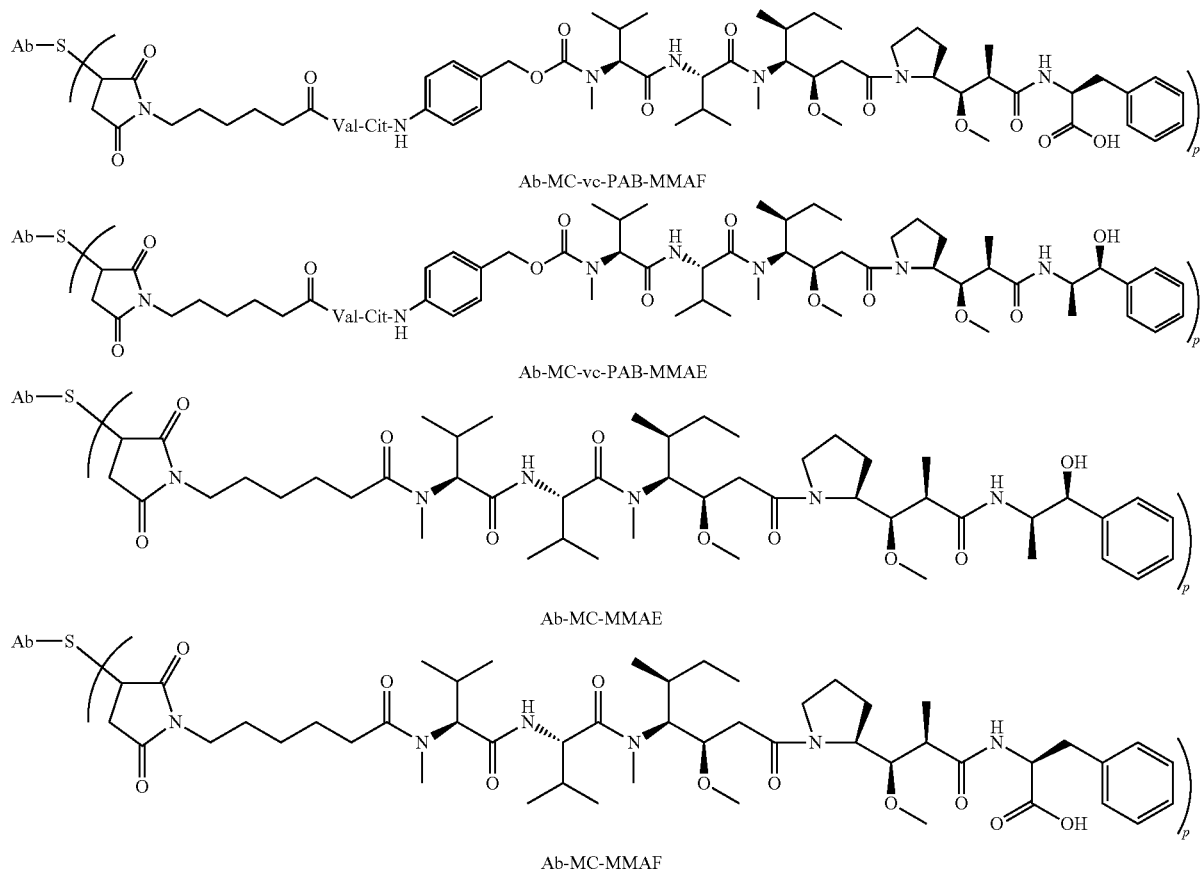

Exemplary embodiments of ADCs of Formula I comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) Bioconjugate Chem. 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. Auristatin/dolastatin drug moieties may be prepared according to the methods of: US 2005-0238649 A1; U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat. Biotechnol. 21(7):778-784.

In particular, auristatin/dolastatin drug moieties of formula $D_F$, such as MMAF and derivatives thereof, may be prepared using methods described in US 2005-0238649 A1 and Doronina et al. (2006) Bioconjugate Chem. 17:114-124. Auristatin/dolastatin drug moieties of formula $D_E$, such as MMAE and derivatives thereof, may be prepared using methods described in Doronina et al. (2003) Nat. Biotech. 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) Nat. Biotech. 21:778-784, and Patent Application Publication No. US 2005/0238649 A1, and then conjugated to an antibody of interest.

Drug Loading

Drug loading is represented by p and is the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g.

p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in US 20050238649 A1, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Alternatively, sulfhydryl groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic subsituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The compounds of the invention expressly contemplate, but are not limited to, ADC prepared with the following cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A; see pages 467-498, 2003-2004 Applications Handbook and Catalog.

Immunoconjugates comprising an antibody and a cytotoxic agent may also be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Alternatively, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

2. Exemplary Immunoconjugates—Thio-Antibody Drug Conjugates

Preparation of Cysteine Engineered Anti-CD22 Antibodies

DNA encoding an amino acid sequence variant of the cysteine engineered anti-CD22 antibodies and parent anti-CD22 antibodies of the invention is prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733), and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993).

Phage display technology (McCafferty et al (1990) Nature 348:552-553) can be used to produce anti-CD22 human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell (Johnson et al (1993) Current Opinion in Structural Biology 3:564-571; Clackson et al (1991) Nature, 352:624-628; Marks et al (1991) J. Mol. Biol. 222:581-597; Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275).

Anti-CD22 antibodies may be chemically synthesized using known oligopeptide synthesis methodology or may be prepared and purified using recombinant technology. The appropriate amino acid sequence, or portions thereof, may be produced by direct peptide synthesis using solid-phase techniques (Stewart et al., *Solid-Phase Peptide Synthesis*, (1969) W.H. Freeman Co., San Francisco, Calif.; Merrifield, (1963) J. Am. Chem. Soc., 85:2149-2154). In vitro protein synthesis may be performed using manual techniques or by automation. Automated solid phase synthesis may be accomplished, for instance, employing t-BOC or Fmoc protected amino acids and using an Applied Biosystems Peptide Synthesizer (Foster City, Calif.) using manufacturer's instructions. Various portions of the anti-CD22 antibody or CD22 polypeptide may be chemically synthesized separately and combined using chemical or enzymatic methods to produce the desired anti-CD22 antibody or CD22 polypeptide.

Various techniques have been developed for the production of antibody fragments. Traditionally, these fragments were derived via proteolytic digestion of intact antibodies (Morimoto et al (1992) Journal of Biochemical and Biophysical Methods 24:107-117; and Brennan et al (1985) Science, 229:81), or produced directly by recombinant host cells. Fab, Fv and ScFv anti-CD22 antibody fragments can all be expressed in and secreted from *E. coli*, thus allowing the facile production of large amounts of these fragments. Antibody fragments can be isolated from the antibody phage libraries discussed herein. Alternatively, Fab'-SH fragments can be directly recovered from *E. coli* and chemically coupled to form F(ab')₂ fragments (Carter et al (1992) Bio/Technology 10: 163-167), or isolated directly from recombinant host cell culture. The anti-CD22 antibody may be a (scFv) single chain Fv fragment (WO 93/16185; U.S. Pat. No. 5,571,894; U.S. Pat. No. 5,587,458). The anti-CD22 antibody fragment may also be a "linear antibody" (U.S. Pat. No. 5,641,870). Such linear antibody fragments may be monospecific or bispecific.

The description below relates primarily to production of anti-CD22 antibodies by culturing cells transformed or transfected with a vector containing anti-CD22 antibody-encoding nucleic acid. DNA encoding anti-CD22 antibodies may be obtained from a cDNA library prepared from tissue believed to possess the anti-CD22 antibody mRNA and to express it at a detectable level. Accordingly, human anti-CD22 antibody or CD22 polypeptide DNA can be conveniently obtained from a cDNA library prepared from human tissue. The anti-CD22 antibody-encoding gene may also be obtained from a genomic library or by known synthetic procedures (e.g., automated nucleic acid synthesis).

The design, selection, and preparation methods of the invention enable cysteine engineered anti-CD22 antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

The Pheselector (Phage ELISA for Selection of Reactive Thiols) Assay allows for detection of reactive cysteine groups in antibodies in an ELISA phage format thereby assisting in the design of cysteine engineered antibodies (WO 2006/034488). The cysteine engineered antibody is coated on well surfaces, followed by incubation with phage particles, addition of HRP labeled secondary antibody, and absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA4 4AD, United Kingdom, Fax: (+44) 1925 603825, or by internet: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements.

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100. Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide. The fractional surface accessibility for every amino acid in an antibody may be calculated using available crystal structure information (Eigenbrot et al. (1993) J Mol Biol. 229:969-995).

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells.

After design and selection, cysteine engineered antibodies, e.g. ThioFabs, with the engineered, highly reactive unpaired Cys residues, may be produced by: (i) expression in a bacterial, e.g. E. coli, system (Skerra et al (1993) Curr. Opinion in Immunol. 5:256-262; Pluckthun (1992) Immunol. Revs. 130: 151-188) or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

The engineered Cys thiol groups react with electrophilic linker reagents and drug-linker intermediates to form cysteine engineered antibody drug conjugates and other labelled cysteine engineered antibodies. Cys residues of cysteine engineered antibodies, and present in the parent antibodies, which are paired and form interchain and intrachain disulfide bonds do not have any reactive thiol groups (unless treated with a reducing agent) and do not react with electrophilic linker reagents or drug-linker intermediates. The newly engineered Cys residue, can remain unpaired, and able to react with, i.e. conjugate to, an electrophilic linker reagent or drug-linker intermediate, such as a drug-maleimide. Exemplary drug-linker intermediates include: MC-MMAE, MC-MMAF, MC-vc-PAB-MMAE, and MC-vc-PAB-MMAF. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) starting at the N-terminus, differs from the Kabat numbering scheme (bottom row) by insertions noted by a,b,c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes.

In one embodiment, the cysteine engineered anti-CD22 antibody is prepared by a process comprising:
(a) replacing one or more amino acid residues of a parent anti-CD22 antibody by cysteine; and
(b) determining the thiol reactivity of the cysteine engineered anti-CD22 antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another embodiment of the invention provides a method of preparing (making) a cysteine engineered anti-CD22 antibody, comprising:
(a) introducing one or more cysteine amino acids into a parent anti-CD22 antibody in order to generate the cysteine engineered anti-CD22 antibody; and
(b) determining the thiol reactivity of the cysteine engineered antibody with a thiol-reactive reagent;
wherein the cysteine engineered antibody is more reactive than the parent antibody with the thiol-reactive reagent.

Step (a) of the method of preparing a cysteine engineered antibody may comprise:
(i) mutagenizing a nucleic acid sequence encoding the cysteine engineered antibody;
(ii) expressing the cysteine engineered antibody; and
(iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:
(i) reacting the cysteine engineered antibody with a thiol-reactive affinity reagent to generate an affinity labelled, cysteine engineered antibody; and
(ii) measuring the binding of the affinity labelled, cysteine engineered antibody to a capture media.

Another embodiment of the invention is a method of screening cysteine engineered antibodies with highly reactive, unpaired cysteine amino acids for thiol reactivity comprising:
(a) introducing one or more cysteine amino acids into a parent antibody in order to generate a cysteine engineered antibody;
(b) reacting the cysteine engineered antibody with a thiol-reactive affinity reagent to generate an affinity labelled, cysteine engineered antibody; and
(c) measuring the binding of the affinity labelled, cysteine engineered antibody to a capture media; and
(d) determining the thiol reactivity of the cysteine engineered antibody with the thiol-reactive reagent.

Step (a) of the method of screening cysteine engineered antibodies may comprise:
(i) mutagenizing a nucleic acid sequence encoding the cysteine engineered antibody;
(ii) expressing the cysteine engineered antibody; and
(iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:
(i) reacting the cysteine engineered antibody with a thiol-reactive affinity reagent to generate an affinity labelled, cysteine engineered antibody; and
(ii) measuring the binding of the affinity labelled, cysteine engineered antibody to a capture media.

Cysteine Engineering of Anti-CD22 10F4 IgG Variants

Cysteine was introduced at the heavy chain 118 (EU numbering) (equivalent to heavy chain position 121, sequential numbering) site into the full-length, chimeric parent monoclonal anti-CD22 antibodies by the cysteine engineering methods described herein.

The parent antibody, "std Anti-CD22 Hu 10F4v3 Fc" (Heavy Chain sequence: SEQ ID NO:88, Light Chain sequence: SEQ ID NO:87, FIG. 5B) was cysteine engineered to give "A118C thio hu anti-CD22 10F4v3" (Heavy Chain sequence: SEQ ID NO:92, Light Chain sequence: SEQ ID NO:91, FIG. 17), "S400C thio hu anti-CD22 10F4v3" (Heavy Chain sequence: SEQ ID NO:93, Light Chain sequence: SEQ ID NO:91, FIG. 17), or "V205C thio anti-CD22 10F4v3" (Heavy Chain sequence: SEQ ID NO:88, Light Chain sequence: SEQ ID NO:91, FIGS. 5B and 17).

These cysteine engineered monoclonal antibodies were expressed in CHO (Chinese Hamster Ovary) cells by transient fermentation in media containing 1 mM cysteine.

Labelled Cysteine Engineered Anti-CD22 Antibodies

Cysteine engineered anti-CD22 antibodies may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive reagents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The thiol-reactive reagent may be a drug moiety, a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Uses of Cysteine Engineered Anti-CD22 Antibodies

Cysteine engineered anti-CD22 antibodies, and conjugates thereof may find use as therapeutic and/or diagnostic agents. The present invention further provides methods of preventing, managing, treating or ameliorating one or more symptoms associated with a B-cell related disorder. In particular, the present invention provides methods of preventing, managing, treating, or ameliorating one or more symptoms associated with a cell proliferative disorder, such as cancer, e.g., lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. The present invention still further provides methods for diagnosing a CD22 related disorder or predisposition to developing such a disorder, as well as methods for identifying antibodies, and antigen-binding fragments of antibodies, that preferentially bind B cell-associated CD22 polypeptides.

Another embodiment of the present invention is directed to the use of a cysteine engineered anti-CD22 antibody for the preparation of a medicament useful in the treatment of a condition which is responsive to a B cell related disorder.

Cysteine Engineered Antibody Drug Conjugates (Thio-Antibody Drug Conjugates)

Another aspect of the invention is an antibody-drug conjugate compound comprising a cysteine engineered anti-CD22 antibody (Ab), and an auristatin drug moiety (D) wherein the cysteine engineered antibody is attached through one or more free cysteine amino acids by a linker moiety (L) to D; the compound having Formula I:

$$Ab-(L-D)_p \qquad\qquad I$$

where p is 1, 2, 3, or 4; and wherein the cysteine engineered antibody is prepared by a process comprising replacing one or more amino acid residues of a parent anti-CD22 antibody by one or more free cysteine amino acids.

FIG. 10 shows embodiments of cysteine engineered anti-CD22 antibody drug conjugates (ADC) where an auristatin drug moiety is attached to an engineered cysteine group in: the light chain (LC-ADC); the heavy chain (HC-ADC); and the Fc region (Fc-ADC).

Potential advantages of cysteine engineered anti-CD22 antibody drug conjugates include improved safety (larger therapeutic index), improved PK parameters, the antibody inter-chain disulfide bonds are retained which may stabilize the conjugate and retain its active binding conformation, the sites of drug conjugation are defined, and the preparation of cysteine engineered antibody drug conjugates from conjugation of cysteine engineered antibodies to drug-linker reagents results in a more homogeneous product.

Linkers

"Linker", "Linker Unit", or "link" means a chemical moiety comprising a covalent bond or a chain of atoms that covalently attaches an antibody to a drug moiety. In various embodiments, a linker is specified as L. A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with an electrophilic functional group of a linker reagent, a drug moiety or drug-linker intermediate.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Linkers include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example x.

The linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy —$CH_2CH_2O$— as one or more repeating units ("EO" or "PEO"). Additional linker components are known in the art and some are described herein.

In one embodiment, linker L of an ADC has the formula:

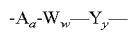

wherein:
-A- is a Stretcher unit covalently attached to a cysteine thiol of the antibody (Ab);
a is 0 or 1;
each —W— is independently an Amino Acid unit;
w is independently an integer ranging from 0 to 12;
—Y— is a Spacer unit covalently attached to the drug moiety; and
y is 0, 1 or 2.

Stretcher Unit

The Stretcher unit (-A-), when present, is capable of linking an antibody unit to an amino acid unit (—W—). In this regard an antibody (Ab) has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the antibody functional groups are sulfhydryl or amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent. In one embodiment, an antibody (Ab) has a free cysteine thiol group that can form a bond with an electrophilic functional group of a Stretcher Unit. Exemplary stretcher units in Formula I conjugates are depicted by Formulas II and III, wherein Ab-, —W—, —Y—, -D, w and y are as defined above, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_3$-$C_8$ heterocyclyl), —$(C_3$-$C_8$ heterocyclyl)-$(CH_2)_r$, —$(CH_2)_rC(O)NR(CH_2)_r$—, —$(CH_2CH_2O)_r$—, —$(CH_2CH_2O)_rCH_2$—, —$(CH_2)_rC(O)NR^b(CH_2CH_2O)_r$—, —$(CH_2)_rC(O)NR^b(CH_2CH_2O)_rCH_2$—, —$(CH_2CH_2O)_rC(O)NR^b(CH_2CH_2O)_rCH_2$—, and —$(CH_2CH_2O)_rC(O)NR^b(CH_2)_r$; where $R^b$ is H, $C_1$-$C_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from the aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as II-VI, that even where not denoted expressly, from 1 to 4 drug moieties are linked to an antibody (p=1-4), depending on the number of engineered cysteine residues.

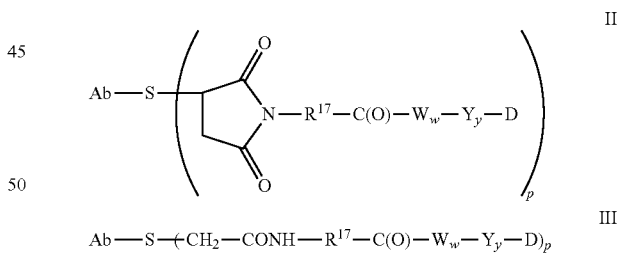

An illustrative Formula II Stretcher unit is derived from maleimido-caproyl (MC) wherein $R^{17}$ is —$(CH_2)_5$—:

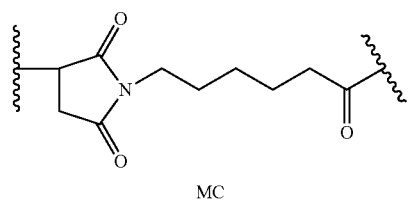

MC

An illustrative Stretcher unit of Formula II, and is derived from maleimido-propanoyl (MP) wherein $R^{17}$ is —$(CH_2)_2$—:

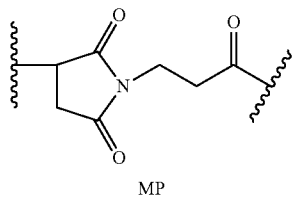

MP

Another illustrative Stretcher unit of Formula II wherein $R^{17}$ is —$(CH_2CH_2O)_r$—$CH_2$— and r is 2:

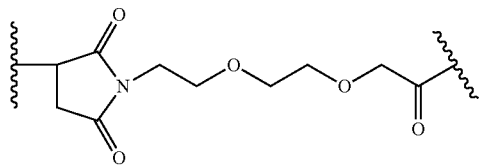

Another illustrative Stretcher unit of Formula II wherein $R^{17}$ is —$(CH_2)_rC(O)NR^b(CH_2CH_2O)_r$—$CH_2$— where $R^b$ is H and each r is 2:

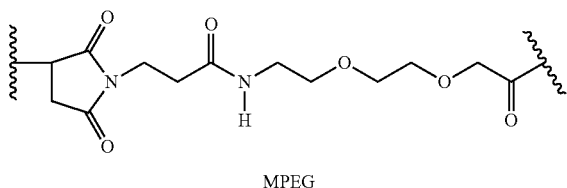

MPEG

An illustrative Stretcher unit of Formula III wherein $R^{17}$ is —$(CH_2)_5$—:

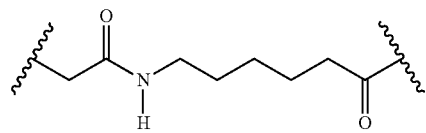

In another embodiment, the Stretcher unit is linked to the cysteine engineered anti-CD22 antibody via a disulfide bond between the engineered cysteine sulfur atom of the antibody and a sulfur atom of the Stretcher unit. A representative Stretcher unit of this embodiment is depicted by Formula IV, wherein $R^{17}$, Ab-, —W—, —Y—, -D, w and y are as defined above.

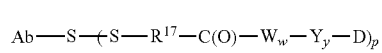

IV

In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted by Formulas Va and Vb, wherein —$R^{17}$—, Ab-, —W—, —Y—, -D, w and y are as defined above;

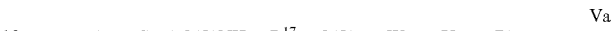
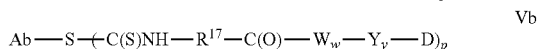

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the cysteine engineered antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

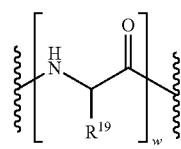

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

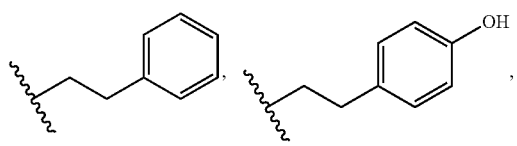

-continued

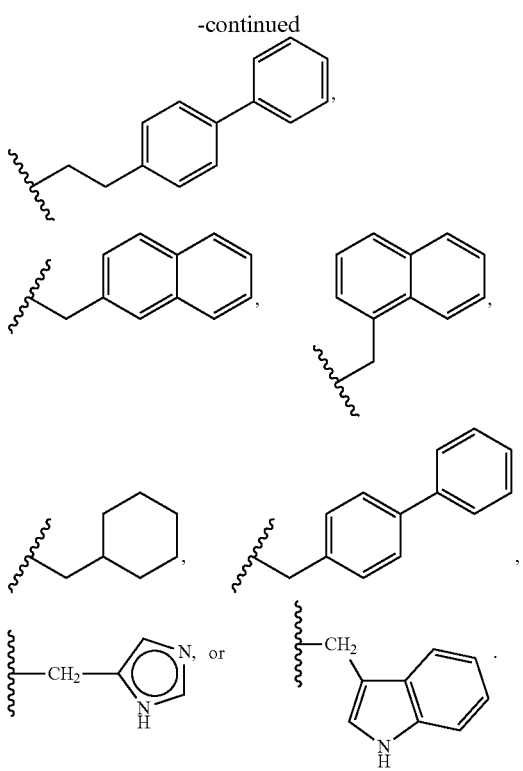

When R[19] is other than hydrogen, the carbon atom to which R[19] is attached is chiral. Each carbon atom to which R[19] is attached is independently in the (S) or (R) configuration, or a racemic mixture. Amino acid units may thus be enantiomerically pure, racemic, or diastereomeric.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline.

The Amino Acid unit can be enzymatically cleaved by one or more enzymes, including a tumor-associated protease, to liberate the Drug moiety (-D), which in one embodiment is protonated in vivo upon release to provide a Drug (D). Amino acid linker components can be designed and optimized in their selectivity for enzymatic cleavage by a particular enzymes, for example, a tumor-associated protease, cathepsin B, C and D, or a plasmin protease.

Spacer Unit

The Spacer unit (—Y—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-Ww-. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —$W_w$— via the amino nitrogen atom of the PAB group, and connected directly to -D via a carbonate, carbamate or ether group, where the ADC has the exemplary structure:

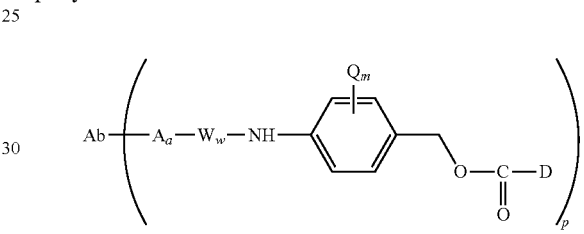

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237), heterocyclic PAB analogs (US 2005/0256030), beta-glucuronide (WO 2007/011968), and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

Exemplary Spacer units (—$Y_y$—) are represented by Formulas X-XII:

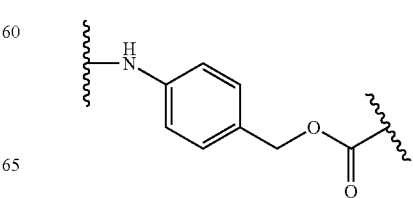

X

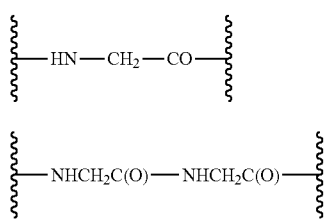

XI

XII

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker. Exemplary embodiments of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125: 15688-15689; Shamis et al (2004) J. Amer. Chem. Soc. 126: 1726-1731; Amir et al (2003) Angew. Chem. Int. Ed. 42:4494-4499).

In one embodiment, the Spacer unit is a branched bis (hydroxymethyl)styrene (BHMS), which can be used to incorporate and release multiple drugs, having the structure:

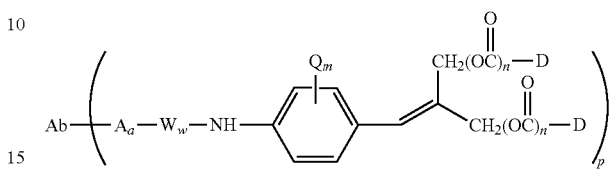

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Exemplary embodiments of the Formula I antibody-drug conjugate compounds include XIIIa (MC), XIIIb (val-cit), XIIIc (MC-val-cit), and XIIId (MC-val-cit-PAB):

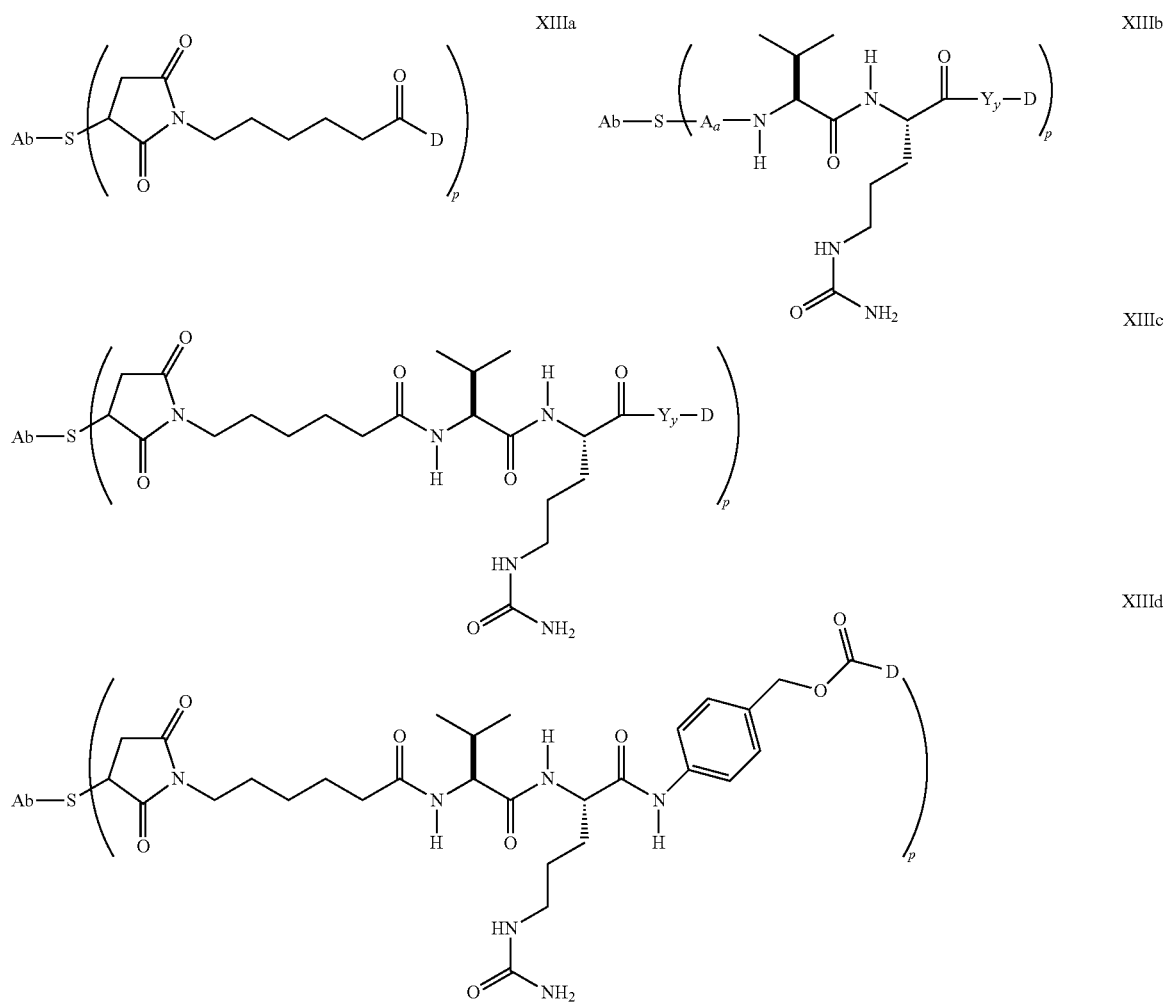

Other exemplary embodiments of the Formula Ia antibody-drug conjugate compounds include XIVa-e:

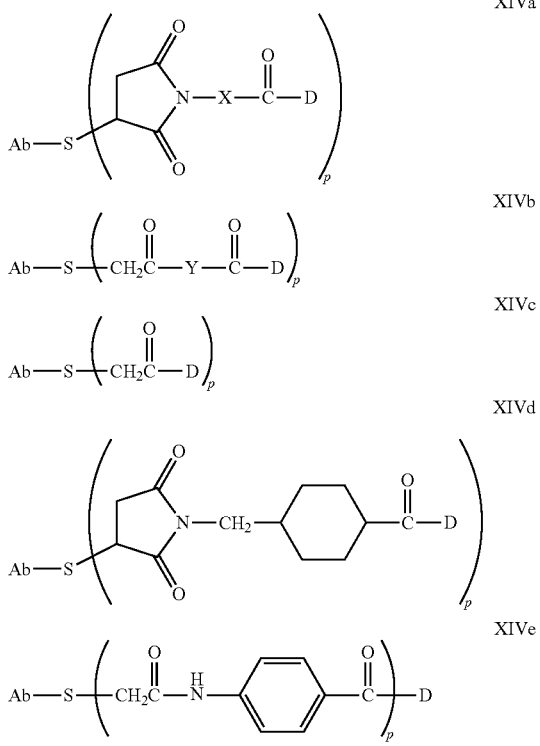

where X is:

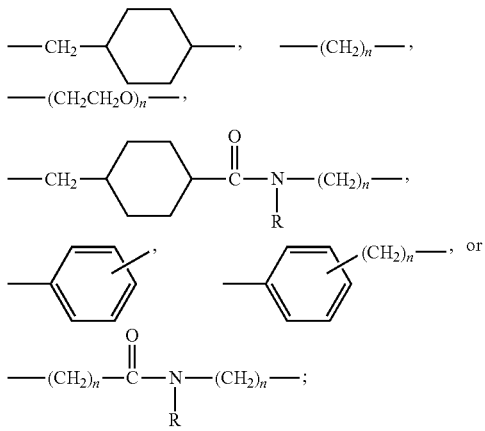

Y is

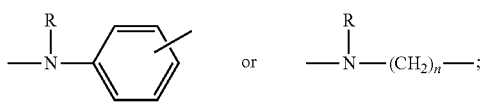

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to carboxyls, hydroxyls, para-nitrophenylcarbonate, isothiocyanate, and leaving groups, such as O-mesyl, O-tosyl, —Cl, —Br, —I; or maleimide.

In another embodiment, the Linker may be substituted with groups which modulated solubility or reactivity. For example, a charged substituent such as sulfonate (—$SO_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

Linker Reagents

Conjugates of the antibody and auristatin may be made using a variety of bifunctional linker reagents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugates may also be prepared with linker reagents: BMPEO, BMPS, EMCS, GMBS, HBVS, LC-SMCC, MBS, MPBH, SBAP, SIA, SIAB, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 U.S.A, U.S.A 1-800-874-3723, International +815-968-0747. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

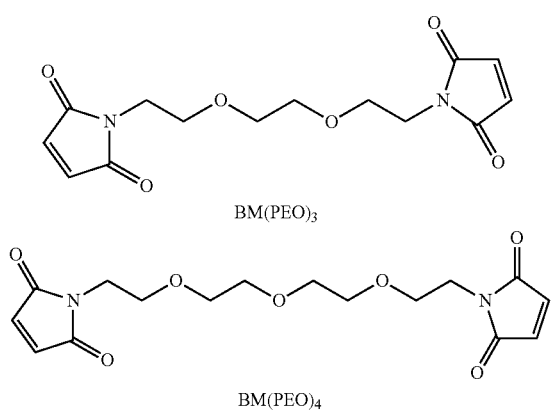

BM(PEO)₃

BM(PEO)₄

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Stretchers of formula (IIIa) can be introduced into a Linker by reacting the following linker reagents with the N-terminus of an Amino Acid unit:

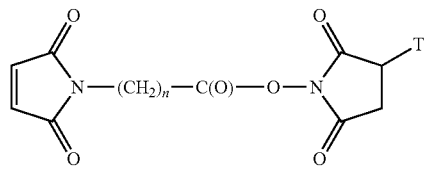

where n is an integer ranging from 1-10 and T is —H or —SO₃Na;

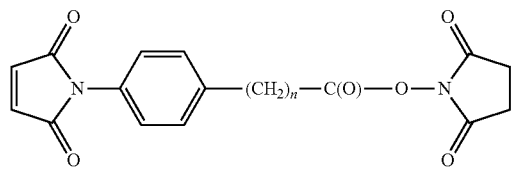

where n is an integer ranging from 0-3;

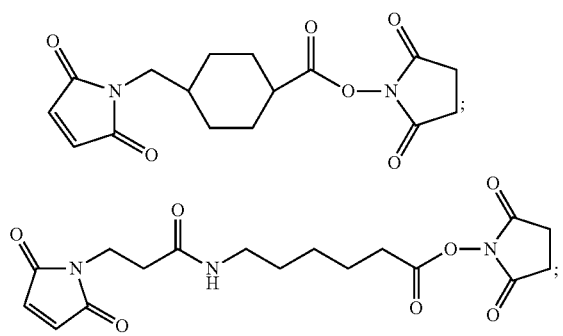

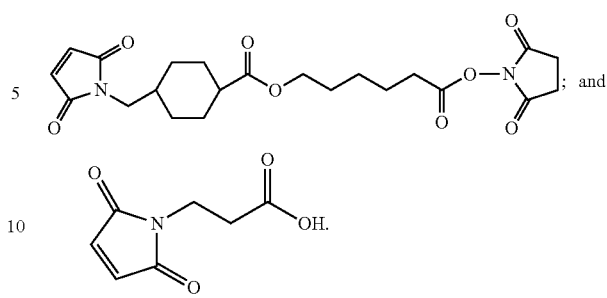

Stretcher units of can be introduced into a Linker by reacting the following bifunctional reagents with the N-terminus of an Amino Acid unit:

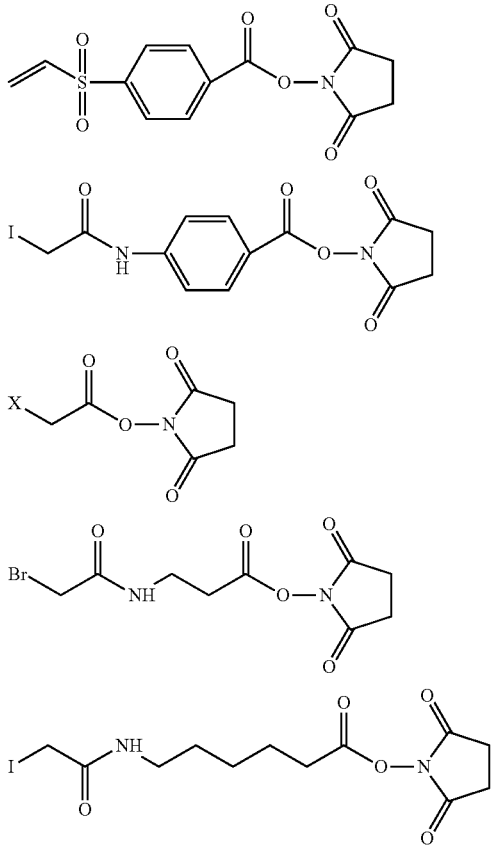

where X is Br or I.

Stretcher units of formula can also be introduced into a Linker by reacting the following bifunctional reagents with the N-terminus of an Amino Acid unit:

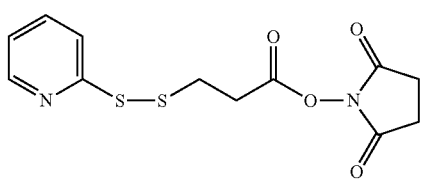

-continued

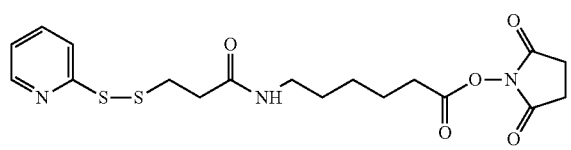

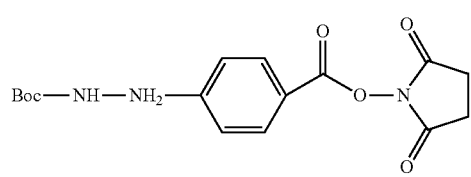

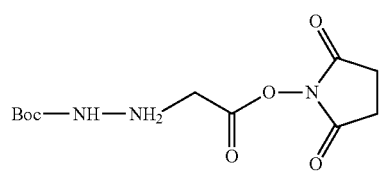

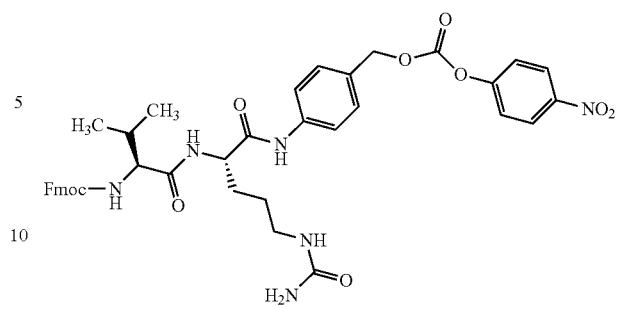

An exemplary phe-lys(Mtr, mono-4-methoxytrityl) dipeptide linker reagent having a maleimide Stretcher unit and a PAB self-immolative Spacer unit can be prepared according to Dubowchik, et al. (1997) Tetrahedron Letters, 38:5257-60, and has the structure:

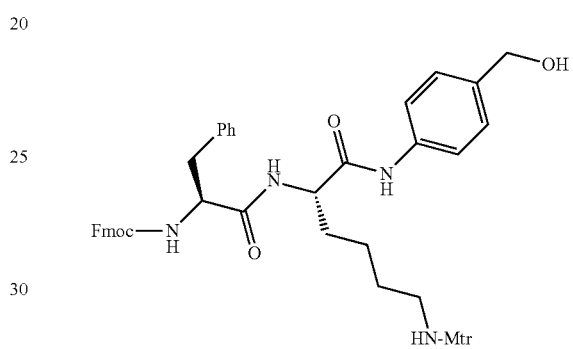

An exemplary valine-citrulline (val-cit or vc) dipeptide linker reagent having a maleimide Stretcher and a para-aminobenzylcarbamoyl (PAB) self-immolative Spacer has the structure:

Exemplary antibody-drug conjugate compounds of the invention include:

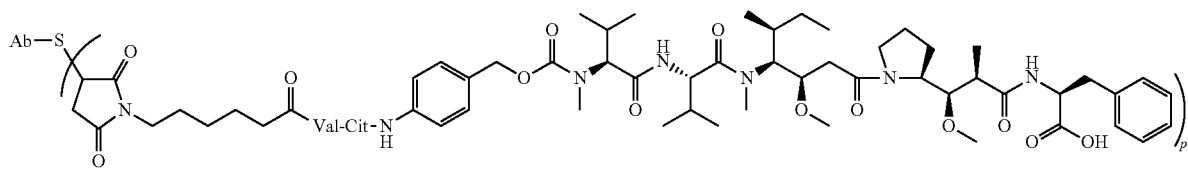

Ab-MC-vc-PAB-MMAF

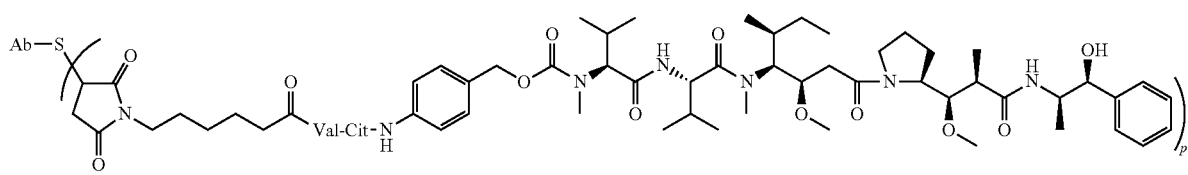

Ab-MC-vc-PAB-MMAE

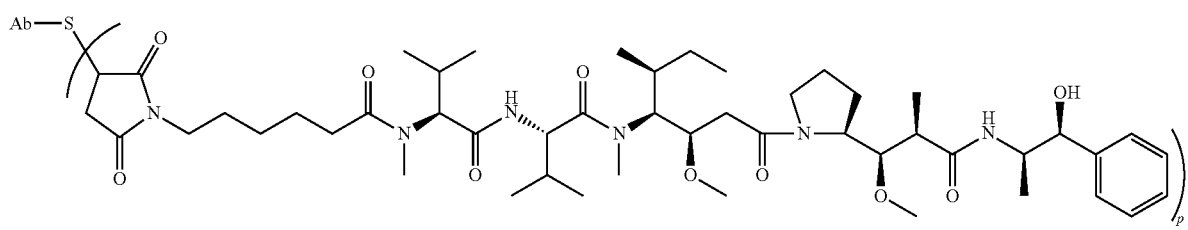

Ab-MC-MMAE

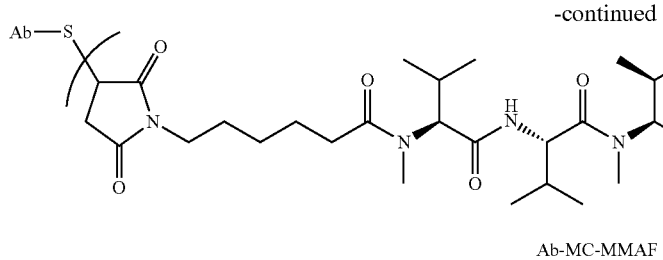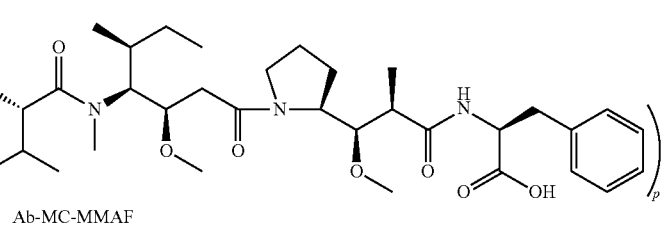

Ab-MC-MMAF where Val is valine; Cit is citrulline; p is 1, 2, 3, or 4; and Ab is a cysteine engineered anti-CD22 antibody.

Preparation of Cysteine Engineered Anti-CD22 Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.), followed by reoxidation to reform interchain and intrachain disulfide bonds (Example x). For example, full length, cysteine engineered monoclonal antibodies (ThioMabs) expressed in CHO cells are reduced with about a 50 fold excess of TCEP for 3 hrs at 37° C. to reduce disulfide bonds in cysteine adducts which may form between the newly introduced cysteine residues and the cysteine present in the culture media. The reduced ThioMab is diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate (CuSO$_4$) at room temperature, overnight. Alternatively, dehydroascorbic acid (DHAA) is an effective oxidant to reestablish the intrachain disulfide groups of the cysteine engineered antibody after reductive cleavage of the cysteine adducts. Other oxidants, i.e. oxidizing agents, and oxidizing conditions, which are known in the art may be used. Ambient air oxidation is also effective. This mild, partial reoxidation step forms intrachain disulfides efficiently with high fidelity and preserves the thiol groups of the newly introduced cysteine residues. An approximate 10 fold excess of drug-linker intermediate, e.g. MC-vc-PAB-MMAE, was added, mixed, and let stand for about an hour at room temperature to effect conjugation and form the 10F4v3 anti-CD22 antibody-drug conjugate. The conjugation mixture was gel filtered and loaded and eluted through a HiTrap S column to remove excess drug-linker intermediate and other impurities.

FIG. 12 shows the general process to prepare a cysteine engineered antibody expressed from cell culture for conjugation. When the cell culture media contains cysteine, disulfide adducts can form between the newly introduced cysteine amino acid and cysteine from media. These cysteine adducts, depicted as a circle in the exemplary ThioMab (left) in FIG. 12, must be reduced to generate cysteine engineered antibodies reactive for conjugation. Cysteine adducts, presumably along with various interchain disulfide bonds, are reductively cleaved to give a reduced form of the antibody with reducing agents such as TCEP. The interchain disulfide bonds between paired cysteine residues are reformed under partial oxidation conditions with copper sulfate, DHAA, or exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs are treated with the reduction and reoxidation procedures as described in Example x to produce reactive ThioMabs. These ThioMabs are used to conjugate with maleimide containing cytotoxic drugs, fluorophores, and other labels.

Methods of Screening

Yet another embodiment of the present invention is directed to a method of determining the presence of a CD22 polypeptide in a sample suspected of containing the CD22 polypeptide, wherein the method comprises exposing the sample to a cysteine engineered anti-CD22 antibody, or antibody drug conjugate thereof, that binds to the CD22 polypeptide and determining binding of the cysteine engineered anti-CD22 antibody, or antibody drug conjugate thereof, to the CD22 polypeptide in the sample, wherein the presence of such binding is indicative of the presence of the CD22 polypeptide in the sample. Optionally, the sample may contain cells (which may be cancer cells) suspected of expressing the CD22 polypeptide. The cysteine engineered anti-CD22 antibody, or antibody drug conjugate thereof, employed in the method may optionally be detectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with a cysteine engineered anti-CD22 antibody, or antibody drug conjugate thereof, that binds to a CD22 polypeptide and (b) detecting the formation of a complex between the cysteine engineered anti-CD22 antibody, or antibody drug conjugate thereof, and the CD22 polypeptide in the test sample, wherein the formation of a complex is indicative of the presence of a tumor in the mammal. Optionally, the cysteine engineered anti-CD22 antibody, or antibody drug conjugate thereof, is detectably labeled, attached to a solid support, or the like, and/or the test sample of tissue cells is obtained from an individual suspected of having a cancerous tumor.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}$C or $^{3}$H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Pharmaceutical Formulations

Administration of Antibody-Drug Conjugates, Including Thio-Antibody Drug Conjugates The antibody-drug conjugates (ADC), including thio-antibody drug conjugates (TDC), of the invention may be administered by any route appropriate to the condition to be treated. The ADC will typically be administered parenterally, i.e. infusion, subcutaneous, intramuscular, intravenous, intradermal, intrathecal and epidural.

For treating these cancers, in one embodiment, the antibody-drug conjugate is administered via intravenous infusion. The dosage administered via infusion is in the range of about 1 μg/m$^2$ to about 10,000 μg/m$^2$ per dose, generally one dose per week for a total of one, two, three or four doses. Alternatively, the dosage range is of about 1 μg/m$^2$ to about 1000 μg/m$^2$, about 1 μg/m$^2$ to about 800 μg/m$^2$, about 1 μg/m$^2$ to about 600 μg/m$^2$, about 1 μg/m$^2$ to about 400 μg/m$^2$, about 10 μg/m$^2$ to about 500 μg/m$^2$, about 10 μg/m$^2$ to about 300 μg/m$^2$, about 10 μg/m$^2$ to about 200 μg/m$^2$, and about 1 μg/m$^2$ to about 200 μg/m$^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the lymphoma, leukemia being treated. Administration may continue after remission or relief of symptoms is achieved where such remission or relief is prolonged by such continued administration.

The invention also provides a method of alleviating an autoimmune disease, comprising administering to a patient suffering from the autoimmune disease, a therapeutically effective amount of a humanized 10F4 antibody-drug conjugate of any one of the preceding embodiments. In preferred embodiments the antibody is administered intravenously or subcutaneously. The antibody-drug conjugate is administered intravenously at a dosage in the range of about 1 μg/m$^2$ to about 100 mg/m$^2$ per dose and in a specific embodiment, the dosage is 1 μg/m$^2$ to about 500 μg/m$^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until relief from or alleviation of symptoms of the autoimmune disease being treated. Administration may continue after relief from or alleviation of symptoms is achieved where such alleviation or relief is prolong by such continued administration.

The invention also provides a method of treating a B cell disorder comprising administering to a patient suffering from a B cell disorder, such as a B cell proliferative disorder (including without limitation lymphoma and leukemia) or an autoimmune disease, a therapeutically effective amount of a humanized 10F4 antibody of any one of the preceding embodiments, which antibody is not conjugated to a cytotoxic molecule or a detectable molecule. The antibody will typically be administered in a dosage range of about 1 μg/m$^2$ to about 1000 mg/m$^2$.

In one aspect, the invention further provides pharmaceutical formulations comprising at least one anti-CD22 antibody of the invention and/or at least one immunoconjugate thereof and/or at least one anti-CD22 antibody-drug conjugate of the invention. In some embodiments, a pharmaceutical formulation comprises 1) an anti-CD22 antibody and/or an anti-CD22 antibody-drug conjugate and/or an immunoconjugate thereof, and 2) a pharmaceutically acceptable carrier. In some embodiments, a pharmaceutical formulation comprises 1) an anti-CD22 antibody and/or an immunoconjugate thereof, and optionally, 2) at least one additional therapeutic agent.

Pharmaceutical formulations comprising an antibody or immunoconjugate of the invention or the antibody-drug conjugate of the invention are prepared for storage by mixing the antibody or antibody-drug conjugate having the desired degree of purity with optional physiologically acceptable carriers, excipients or stabilizers (Remington's Pharmaceutical Sciences 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished by filtration through sterile filtration membranes.

Active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies or immunoconjugates remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The ADC compounds which are identified in the animal models and cell-based assays can be further tested in tumor-bearing higher primates and human clinical trials. Human clinical trials can be designed to test the efficacy of the anti-CD22 monoclonal antibody or immunoconjugate of the invention in patients experiencing a B cell proliferative disorder including without limitation lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is a hyperproliferative disease such as a B cell proliferative disorder and/or a B cell cancer. Examples of cancer to be treated herein include, but are not limited to, B cell proliferative disorder is selected from lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

The cancer may comprise CD22-expressing cells, such that the ADC of the present invention are able to bind to the cancer cells. To determine CD22 expression in the cancer, various diagnostic/prognostic assays are available. In one embodiment, CD22 overexpression may be analyzed by IHC. Parrafin-embedded tissue sections from a tumor biopsy may be subjected to the IHC assay and accorded a CD22 protein staining intensity criteria with respect to the degree of staining and in what proportion of tumor cells examined.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-ErbB2 antibody. Other dosage regimens may be useful. The progress of this therapy is easily monitored by conventional techniques and assays.

Combination Therapy

An antibody-drug conjugate (ADC) of the invention may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, or a DNA binder.

In one aspect, the first compound is an anti-CD22 ADC of the invention and the second compound is an anti-CD20 antibody (either a naked antibody or an ADC). In one embodiment the second compound is an anti-CD20 antibody rituximab (Rituxan®) or 2H7 (Genentech, Inc., South San Francisco, Calif.). Another antibodies useful for combined immunotherapy with anti-CD22 ADCs of the invention includes without limitation, anti-VEGF (e.g, Avastin®).

Other therapeutic regimens may be combined with the administration of an anticancer agent identified in accordance with this invention, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-CD20 (e.g., Rituxan®) or anti-VEGF (e.g., Avastin®). The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. 14C or 3H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Further Methods of Using Anti-CD22 Antibodies and Immunoconjugates

Diagnostic Methods and Methods of Detection

In one aspect, anti-CD22 antibodies and immunoconjugates of the invention are useful for detecting the presence of CD22 in a biological sample. The term "detecting" as used herein encompasses quantitative or qualitative detection. In certain embodiments, a biological sample comprises a cell or tissue. In certain embodiments, such tissues include normal and/or cancerous tissues that express CD22 at higher levels relative to other tissues, for example, B cells and/or B cell associated tissues.

In one aspect, the invention provides a method of detecting the presence of CD22 in a biological sample. In certain embodiments, the method comprises contacting the biological sample with an anti-CD22 antibody under conditions permissive for binding of the anti-CD22 antibody to CD22, and detecting whether a complex is formed between the anti-CD22 antibody and CD22.

In one aspect, the invention provides a method of diagnosing a disorder associated with increased expression of CD22. In certain embodiments, the method comprises contacting a test cell with an anti-CD22 antibody; determining the level of expression (either quantitatively or qualitatively) of CD22 by the test cell by detecting binding of the anti-CD22 antibody to CD22; and comparing the level of expression of CD22 by the test cell with the level of expression of CD22 by a control cell (e.g., a normal cell of the same tissue origin as the test cell or a cell that expresses CD22 at levels comparable to such a normal cell), wherein a higher level of expression of CD22 by the test cell as compared to the control cell indicates the presence of a disorder associated with increased expression of CD22. In certain embodiments, the test cell is obtained from an individual suspected of having a disorder associated with increased expression of CD22. In certain embodiments, the disorder is a cell proliferative disorder, such as a cancer or a tumor.

Exemplary cell proliferative disorders that may be diagnosed using an antibody of the invention include a B cell disorder and/or a B cell proliferative disorder including, but not limited to, lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In certain embodiments, a method of diagnosis or detection, such as those described above, comprises detecting binding of an anti-CD22 antibody to CD22 expressed on the surface of a cell or in a membrane preparation obtained from a cell expressing CD22 on its surface. In certain embodiments, the method comprises contacting a cell with an anti-CD22 antibody under conditions permissive for binding of the anti-CD22 antibody to CD22, and detecting whether a complex is formed between the anti-CD22 antibody and CD22 on the cell surface. An exemplary assay for detecting binding of an anti-CD22 antibody to CD22 expressed CD22 on the surface of a cell is a "FACS" assay.

Certain other methods can be used to detect binding of anti-CD22 antibodies to CD22. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CD22 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-CD22 antibodies are immobilized on an insoluble matrix. Immobilization entails separating the anti-CD22 antibody from any CD22 that remains free in solution. This conventionally is accomplished by either insolubilizing the anti-CD22 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-CD22 antibody after formation of a complex between the anti-CD22 antibody and CD22, e.g., by immunoprecipitation.

Any of the above embodiments of diagnosis or detection may be carried out using an immunoconjugate of the invention in place of or in addition to an anti-CD22 antibody.

Therapeutic Methods

An antibody or immunoconjugate of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-CD22 antibody or immunoconjugate thereof under conditions permissive for binding of the immunoconjugate to CD22. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a B cell. In certain embodiments, the cell is a xenograft, e.g., as exemplified herein.

In one aspect, an antibody or immunoconjugate of the invention is used to treat or prevent a B cell proliferative disorder. In certain embodiments, the cell proliferative disorder is associated with increased expression and/or activity of CD22. For example, in certain embodiments, the B cell proliferative disorder is associated with increased expression of CD22 on the surface of a B cell. In certain embodiments, the B cell proliferative disorder is a tumor or a cancer. Examples of B cell proliferative disorders to be treated by the antibodies or immunoconjugates of the invention include, but are not limited to, lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides methods for treating a B cell proliferative disorder comprising administering to an individual an effective amount of an anti-CD22 antibody or immunoconjugate thereof. In certain embodiments, a method for treating a B cell proliferative disorder comprises administering to an individual an effective amount of a pharmaceutical formulation comprising an anti-CD22 antibody or anti-CD22 immunoconjugate and, optionally, at least one additional therapeutic agent, such as those provided below. In certain embodiments, a method for treating a cell proliferative disorder comprises administering to an individual an effective amount of a pharmaceutical formulation comprising 1) an immunoconjugate comprising an anti-CD22 antibody and a cytotoxic agent; and optionally, 2) at least one additional therapeutic agent, such as those provided below.

In one aspect, at least some of the antibodies or immunoconjugates of the invention can bind CD22 from species other than human. Accordingly, antibodies or immunoconjugates of the invention can be used to bind CD22, e.g., in a cell culture containing CD22, in humans, or in other mammals having a CD22 with which an antibody or immunoconjugate of the invention cross-reacts (e.g. chimpanzee, baboon, marmoset, cynomolgus and rhesus monkeys, pig or mouse). In one embodiment, an anti-CD22 antibody or immunoconjugate can be used for targeting CD22 on B cells by contacting the antibody or immunoconjugate with CD22 to form an antibody or immunoconjugate-antigen complex such that a conjugated cytotoxin of the immunoconjugate accesses the interior of the cell. In one embodiment, the CD22 is human CD22.

In one embodiment, an anti-CD22 antibody or immunoconjugate can be used in a method for binding CD22 in an individual suffering from a disorder associated with increased CD22 expression and/or activity, the method comprising administering to the individual the antibody or immunoconjugate such that CD22 in the individual is bound. In one embodiment, the bound antibody or immunoconjugate is internalized into the B cell expressing CD22. In one embodiment, the CD22 is human CD22, and the individual is a human individual. Alternatively, the individual can be a mammal expressing CD22 to which an anti-CD22 antibody binds. Still further the individual can be a mammal into which CD22 has been introduced (e.g., by administration of CD22 or by expression of a transgene encoding CD22).

An anti-CD22 antibody or immunoconjugate can be administered to a human for therapeutic purposes. Moreover, an anti-CD22 antibody or immunoconjugate can be administered to a non-human mammal expressing CD22 with which the antibody cross-reacts (e.g., a primate, pig, rat, or mouse) for veterinary purposes or as an animal model of human disease. Regarding the latter, such animal models may be useful for evaluating the therapeutic efficacy of antibodies or immunoconjugates of the invention (e.g., testing of dosages and time courses of administration).

Antibodies or immunoconjugates of the invention can be used either alone or in combination with other compositions in a therapy. For instance, an antibody or immunoconjugate of the invention may be co-administered with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-CD20 (e.g., Rituxan®) or anti-VEGF (e.g., Avastin®), wherein the combination therapy is useful in the treatment of cancers and/or B cell disorders such as B cell proliferative disorders including lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or immunoconjugate is suitably administered by pulse infusion, particularly with declining doses of the antibody or immunoconjugate. Dosing can be by any suitable route, e.g. by injections, such as intravenous or subcutaneous injections, depending in part on whether the administration is brief or chronic.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents, such as chemotherapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 100 mg/kg (e.g. 0.1 mg/kg-20 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) of antibody or immunoconjugate may be administered to the patient. Such doses may be administered intermittently, e.g. every week or every three weeks (e.g. such that the patient receives from about two to about twenty, or e.g. about six doses of the antibody or immunoconjugate). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Assays

Anti-CD22 antibodies and immunoconjugates of the invention may be characterized for their physical/chemical properties and/or biological activities by various assays known in the art.

Activity Assays

In one aspect, assays are provided for identifying anti-CD22 antibodies or immunoconjugates thereof having biological activity. Biological activity may include, e.g., the ability to inhibit cell growth or proliferation (e.g., "cell killing" activity), or the ability to induce cell death, including programmed cell death (apoptosis). Antibodies or immunoconjugates having such biological activity in vivo and/or in vitro are also provided.

In certain embodiments, an anti-CD22 antibody or immunoconjugate thereof is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602, 677. The assay may be conducted in 96- or 384-well format, making it amenable to automated high-throughput screening (HTS). See Cree et al (1995) AntiCancer Drugs 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-CD22 antibody is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3 \times 10^6$ per dish in 100×20 mm dishes and allowed to attach overnight. The medium is removed and replaced with fresh medium alone or medium containing various concentrations of the antibody or immunoconjugate. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples are analyzed using a FACSCAN™ flow cytometer and FACSCONVERT™ CellQuest software (Becton Dickinson). Antibodies or immunoconjugates which induce statistically significant levels of cell death as determined by PI uptake are thus identified.

In one aspect, an anti-CD22 antibody or immunoconjugate is tested for its ability to induce apoptosis (programmed cell death) in vitro. An exemplary assay for antibodies or immunoconjugates that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 µg/ml of the antibody or immunoconjugate. Following a three-day incubation period, monolayers are washed with PBS and detached by trypsinization. Cells are then centrifuged, resuspended in $Ca^{2+}$ binding buffer, and aliquoted into tubes as discussed in the preceding paragraph. Tubes then receive labeled annexin (e.g. annexin V-FITC) (1 µg/ml). Samples are analyzed using a FACSCAN™ flow cytometer and FACSCONVERT™ CellQuest software (BD Biosciences). Antibodies or immunoconjugates that induce statistically significant levels of annexin binding relative to control are thus identified. Another exemplary assay for antibodies or immunoconjugates that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express CD22 or that have been engineered to express CD22. Such cells include tumor cells that overexpress CD22 relative to normal cells of the same tissue origin. Such cells also include cell lines (including tumor cell lines) that express CD22 and cell lines that do not normally express CD22 but have been transfected with nucleic acid encoding CD22.

In one aspect, an anti-CD22 antibody or immunoconjugate thereof is tested for its ability to inhibit cell growth or proliferation in vivo. In certain embodiments, an anti-CD22 antibody or immunoconjugate thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An antibody or immunoconjugate of the invention is administered to the animal. The ability of the antibody or immunoconjugate to inhibit or decrease tumor growth is measured. In certain embodiments of the above xenograft system, the human tumor cells are tumor cells from a human patient. Such cells useful for preparing xenograft models include human leukemia and lymphoma cell lines, which include without limitation the BJAB-luc cells (an EBV-negative Burkitt's lymphoma cell line transfected with the luciferase reporter gene), Ramos cells (ATCC, Manassas, Va., CRL-1923), Raji cells (ATCC, Manassas, Va., CCL-86), SuDHL-4 cells (DSMZ, Braunschweig, Germany, AAC 495), DoHH2 cells (see Kluin-Neilemans, H. C. et al., Leukemia 5:221-224 (1991), and Kluin-Neilemans, H. C. et al., Leukemia 8:1385-1391 (1994)), Granta-519 cells (see Jadayel, D. M. et al, Leukemia 11(1):64-72 (1997)). In certain embodiments, the human tumor cells are introduced into a suitably immunocompromised non-human animal by subcutaneous injection or by transplantation into a suitable site, such as a mammary fat pad.

Binding Assays and Other Assays

In one aspect, an anti-CD22 antibody is tested for its antigen binding activity. For example, in certain embodiments, an anti-CD22 antibody is tested for its ability to bind to CD22 expressed on the surface of a cell. A FACS assay may be used for such testing.

In one aspect, competition assays may be used to identify a monoclonal antibody that competes with murine 10F4.4.1 antibody, humanized 10F4v1 antibody, humanized 10F4v3 antibody and/or murine 5E8.1.8 antibody for binding to CD22. In certain embodiments, such a competing antibody binds to the same epitope (e.g., a linear or a conformational epitope) that is bound by murine 10F4.4.1 antibody, humanized 10F4v1 antibody, humanized 10F4v3 antibody and/or murine 5E8.1.8 antibody. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized CD22 is incubated in a solution comprising a first labeled antibody that binds to CD22 (e.g., murine 10F4.4.1 antibody, humanized 10F4v1 antibody, humanized 10F4v3 antibody and/or murine 5E8.1.8 antibody) and a second unlabeled antibody that is being tested for its ability to compete with the first antibody for binding to CD22. The second antibody may be present in a hybridoma supernatant. As a control, immobilized CD22 is incubated in a solution comprising the first labeled antibody but not the second unlabeled antibody. After incubation under conditions permissive for binding of the first antibody to CD22, excess unbound antibody is removed, and the amount of label associated with immobilized CD22 is measured. If the amount of label associated with immobilized CD22 is substantially reduced in the test sample relative to the control sample, then that indicates that the second antibody is competing with the first antibody for binding to CD22. In certain embodiments, immobilized CD22 is present on the surface of a cell or in a membrane preparation obtained from a cell expressing CD22 on its surface.

In one aspect, purified anti-CD22 antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

EXAMPLES

The following are examples of methods and compositions of the invention. It is understood that various other embodiments may be practiced, given the general description provided above.

Example 1

Preparation of Murine Anti-Human CD22 Monoclonal Antibody

Murine monoclonal antibodies capable of specifically binding human CD22 was prepared. BALB/c female mice, age six weeks, were immunized in their foot pads with purified human CD22 his-8 tagged extracellular domain lacking domains 3 and 4 (SEQ ID NO:30 (ECD) plus the sequence GRAHHHHHHHH at the C-terminus) or CD22 his-8 tagged extracellular domain comprising domains 1-7 (SEQ ID NO:28 (ECD) plus the above His sequence tag) in Ribi's adjuvant. Subsequent injections were performed in the same manner at one and three weeks after the initial immunizations. Three days after the final injection, the inguinal and popliteal lymph nodes were removed and pooled, and a single cell suspension was made by passing the tissue through steel gauze. The cells were fused at a 4:1 ratio with mouse myeloma such as P3×63-Ag8.653 (ATCC CRL 1580) in high glucose (DMEM) containing 50% w/v polyethylene glycol 4000. The fused cells were then plated at a density of 2×105 per well in 96 well tissue culture plates. After 24 hours HAT selective medium (hypoxanthine/aminopterin/thymidine, Sigma, #H0262) was added. Fifteen days after the fusion, supernatants of growing cells were tested for the presence of antibodies specific for human CD22 using an enzyme-linked immunosorbent assay (ELISA).

The murine anti-human CD22 10F4.4.1 (mu 10F4) and 5E8.1.8 (mu 5E8) monoclonal antibodies were selected for further study based on cell-based assays and plate assays which showed the antibodies to bind specifically to human CD22. The assays are described in the following paragraphs.

ELISA-based assays: Anti-CD22 antibody screening by ELISA is performed as follows, with all incubations done at room temperature. Test plates (Nunc Immunoplate) were coated for 2 hours with purified CD22 in 50 mM sodium carbonate buffer, pH 9.6, then blocked with 0.5% bovine serum albumin in phosphate buffered saline (PBS) for 30 minutes, then washed four times with PBS containing 0.05% Tween 20 (PBST). Test antibody supernatants are added and incubated two hours with shaking, then washed four times with PBST. The plates are developed by adding 100 µl/well of a solution containing 10 mg of o-phenylenediamine dihydrochloride (Sigma, #P8287) and 10 µl of a 30% hydrogen peroxide solution in 25 ml phosphate citrate buffer, pH 5.0, and incubating for 15 minutes. The reaction is stopped by adding 100 µl/well of 2.5 M sulfuric acid. Data is obtained by reading the plates in an automated ELISA plate reader at an absorbance of 490 nm.

Example 2

FACS Based Assays for Analysis of Anti-Human CD22 Monoclonal Antibodies (MAbs)

CHO cells expressing human CD22 on their surface were incubated with anti-CD22 hybridoma supernatant in 100 µl FACS buffer (0.1% BSA, 10 mM sodium azide in PBS, pH 7.4) for 30 minutes at 4° C. followed by one wash with FACS buffer. The amount of anti-CD22 binding was determined by incubating an aliquot of the antibody/cell mixture with a polyclonal FITC conjugated goat or rabbit anti-mouse IgG (Accurate Chem. Co., Westbury, N.Y.) (for murine test antibodies) or goat or rabbit anti-human IgG (for humanized antibodies) for 30 minutes at 4° C. followed by three washes with FACS buffer.

Example 3

Preparation of Humanized Anti-CD22 Antibodies

Humanized 10F4 antibodies were generated wherein hypervariable region (HVR) amino acid residues (interchangeably referred to as complementarity determining regions or CDRs) were modified via site-directed mutagenesis (Kunkel et al., Methods Enzymol. (1987), 154:367-382) to arrive at two variants, humanized 10F4v1 and humanized 10F4v2 (also referred to herein as "10F4v1," "hu10F4v1," "10F4v2," or "hu10F4v2," respectively). A third version, humanized 10F4v3 ("10F4v3" or "hu10Fv3"), used in some studies disclosed herein has the same light and heavy chain amino acid sequences for the mature protein as hu10F4v2, but comprises a different signal sequence in the vector used for protein expression.

Figure 3A:
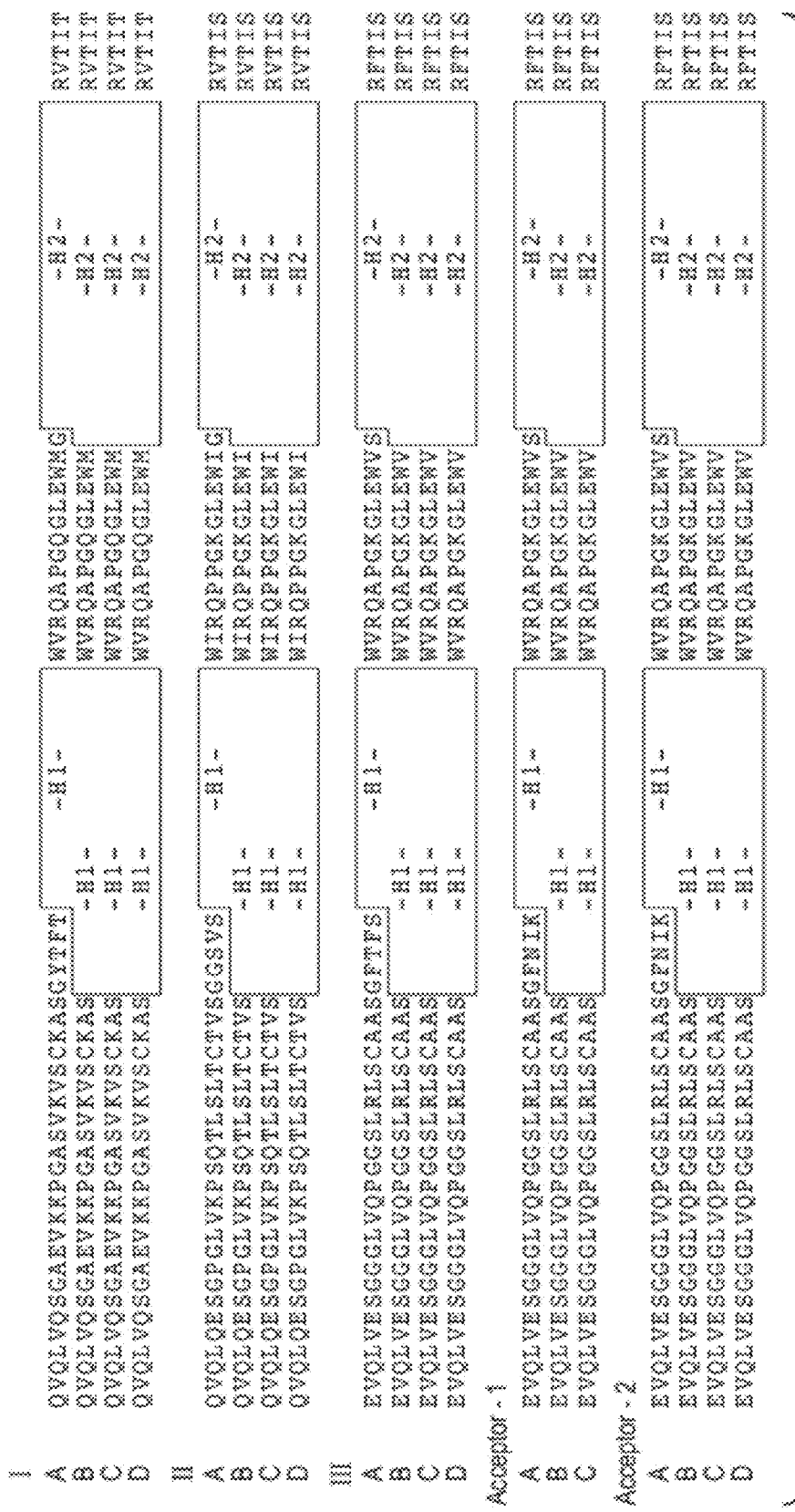
FIGS. 3A and 3B show exemplary acceptor human variable heavy (VH) consensus framework sequences for use in practicing the instant invention with sequence identifiers as follows, where the FR SEQ ID NOs are listed in the order FR-H1, FR-H2, FR-H3, FR-H4.
Figure 3B:
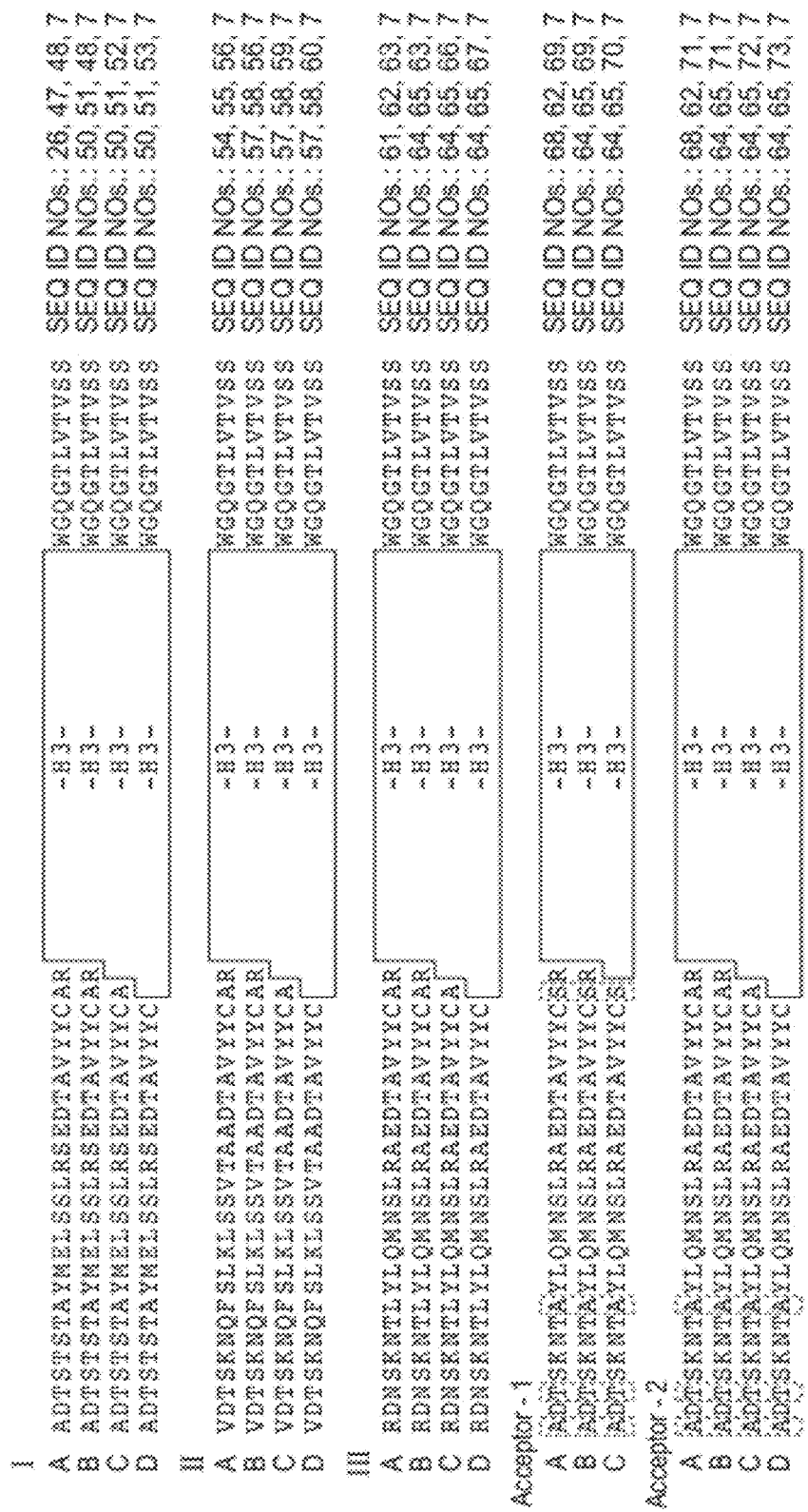

Humanization of the murine 10F4 antibody was preformed as disclosed herein. Briefly, the hypervariable regions of the light and heavy chains of murine 10F4 were cloned into modified consensus framework sequences to generate the light and heavy chain variable regions amino acid sequences shown in FIGS. 2A and 2B. Alternative light and heavy chain framework sequences that may be used as framework sequences of antibodies of the invention are shown in FIGS. 3 and 4.

A monovalent Fab-g3 display vector (pV0350-2B) phagemid having two open reading frames under control of the phoA promoter, essentially as described in Lee et al., J. Mol. Biol. 340:1073-93 (2004), was used in the humanization of the 10F4 antibody. The first open reading frame comprised the E. coli heat stable STII signal sequence for protein secretion fused to the VL and CH1 domains of the acceptor light chain sequence. The second open reading frame comprised the STII signal sequence fused to the VH and CH1 domains of the acceptor heavy chain sequence followed by a truncated minor phage coat protein P3.

The VH and VL domains from murine 10F4 (SEQ ID NOs:89 and 90, respectively) were aligned with the human subgroup III consensus VH (huIII) domain (SEQ ID NO:24) and human consensus kappaI (huK1) domain (SEQ ID NO:25), respectively. The amino acid sequences of the hypervariable regions (HVRs, interchangeably referred to herein as complimentary determining regions (CDRs)) of the murine anti-human CD22 MAb 10F4 were inserted into consensus framework sequences as follows. The light chain HVRs (HVR-L1 (Kabat positions 24-34), HVR-L2 (Kabat positions 50-56), and HVR-L3 (Kabat positions 89-97) of the mu 10F4 antibody were engineered into a human kappa I (huKI) consensus sequence antibody framework to produce the humanized 10F4v1 light chain (SEQ ID NO:17, FIG. 2B). The heavy chain HVRs (HVR-H1 (Kabat positions 26-35), HVR-H2 (Kabat positions 49-65), and HVR-H3 (Kabat positions 95-102) of the mu 10F4 antibody were engineered into a modified human subgroup III (humIII) consensus VH domain which differs from the humIII sequence at three positions: R71A, N73T, and L78A were used (see Carter et all, Proc. Natl. Acad. Sci. USA 89:4285 (1992)) to produce the humanized 10F4v1 heavy chain variable region (SEQ ID NO:16, FIG. 2A). Genetic engineering of HVRs into the acceptor frameworks was performed by Kunkel mutagenesis using a separate oligonucleotide for each hypervariable region. The sequence of each clone was determined by standard DNA sequencing techniques. Hypervariable regions and framework regions shown in FIGS. 2A and 2B are numbered according to Kabat numbering (Kabat et al. (1991), supra). The light and heavy chains were sequenced and the amino acid sequences of the variable regions (including HVRs and framework regions (FRs)) of the huKI, the humIII, murine 10F4, humanized 10F4v1 and humanized 10F4v2 are shown in FIGS. 2A and 2B. Humanized 10F4v3 antibody has the identical amino acid sequence as 10F4v2.

Nucleic acid molecules encoding amino acid sequence variants of the antibody, antibody fragment, VL domain or VH domain are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody, antibody fragment, VL domain or VH domain. For example, libraries can be created by targeting VL accessible amino acid positions in VH, and optionally in one or more CDRs, for amino acid substitution with variant amino acids using the Kunkel method. See, for e.g., Kunkel et al., Methods Enzymol. (1987), 154:367-382 and the examples herein. Generation of randomized sequences is also described below in the Examples.

The sequence of oligonucleotides includes one or more of the designed codon sets for a particular position in a CDR (HVR) or FR region of a polypeptide of the invention. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al, 1987, Nucleic Acids Res. 10:6487-6504. Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

Oligonucleotide sets can be used in a polymerase chain reaction using a variable domain nucleic acid template sequence as the template to create nucleic acid cassettes. The variable domain nucleic acid template sequence can be any portion of the heavy immunoglobulin chains containing the target nucleic acid sequences (ie., nucleic acid sequences encoding amino acids targeted for substitution). The variable region nucleic acid template sequence is a portion of a double stranded DNA molecule having a first nucleic acid strand and complementary second nucleic acid strand. The variable domain nucleic acid template sequence contains at least a portion of a variable domain and has at least one CDR. In some cases, the variable domain nucleic acid template sequence contains more than one CDR. An upstream portion and a downstream portion of the variable domain nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (ie., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes (i.e., PCR reaction products) into an expression vector having additional antibody sequence. In one embodiment, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated via the PCR reaction. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

When a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acids sequences, such as sequences that encode viral coat proteins and therefore allow production of a fusion protein.

Example 4

Variable Region Sequence Determination

The nucleic acid and amino acid sequences of the murine and humanized 10F4 monoclonal antibodies were determined by standard procedures. Total RNA was extracted from hybridoma cells producing the mouse anti-human CD22 10F4.4.1 monoclonal antibodies using the RNeasy® (Mini Kit (Qiagen, Germany). The variable light (VL) and variable heavy (VH) domains were amplified using RT-PCR with degenerate primers. The forward primers were specific for the N-terminal amino acid sequences of the VL and VH regions of the antibody. Respectively, the light chain and heavy chain reverse primers were designed to anneal to a region in the constant light (CL) and constant heavy domain 1 (CH1), which is highly conserved across species. Amplified VH and VL were cloned into a pRK mammalian cell expression vector (Shields et al., J. Biol. Chem. 276:659-04 (2000)). The polynucleotide sequence of the inserts was determined using routine sequencing methods. The amino acid sequences of the murine chimeric 10F4 and humanized 10F4v1 and humanized 10F4v2 light and heavy chain variable regions are shown in FIGS. 2A and 2B.

Humanized 10F4v1 was further modified at HVR-L1 position 28 (N28) (SEQ ID NO:9) (see FIG. 2B. The asparagine residue at that position was replaced with a valine residue (N28V) to generate HVR-L1 (SEQ ID NO:10) for the hu10F4v2 and hu10F4v3 variants, which showed improved binding affinity. These variants comprise the same variable and constant domain sequences of the mature antibody and differ only in a signal sequence not found in the mature antibody of the invention.

Additional amino acid sequence modifications were generated at one or both of amino acids Asn28 (N28) and/or Asn30 (N30) of the HVR-L1 hypervariable region (see FIG. 2B) of hu10F4v1. Because N28 and N30 are possible sites for deamination, amino acid changes at these sites were tested. For example, Asparagine at position 28 (N28) was replaced alternatively with A, Q, S, D, V, or I, and Asparagine at position 30 (N30) was replaced alternatively with A or Q. Amino acid sequence changes in the HVR-L1 domain according to the invention are provided in Table 2 along with their binding affinities as tested by competition analysis in a phage ELISA assay (IC50) using standard procedures.

TABLE 2

Substitution Variants of hu 10F4v1 antibody

| Amino Acid Change In HVR-L1 FIG. 2B | HVR-L1 SEQ ID NO | Binding Affinity (nM) |
|---|---|---|
| No change (N28, N30) | 9 | 8 |
| N28A, N30 | 19 | 8 |
| N28Q, N30 | 20 | 7.3 |
| N28S, N30 | 21 | 12 |
| N28D, N30 | 22 | 12 |
| N28V, N30 | 10 | 7.3 |
| N28I, N30 | 23 | 9.8 |
| N28, N30A | 32 | 7.7 |
| N28, N30Q | 33 | 10 |

For generation of full-length human IgG1 versions of humanized 10F4 antibody, the heavy and light chains are subcloned separately into previously described pRK plasmids (Gorman, C. M. et al. (1990), DNA Protein Eng. Tech. 2: 3). Appropriate heavy and light chain plasmids (depending upon the sequence change(s) desired) are cotransfected into an adenovirus-transformed human embryonic kidney cell line, known as 293 (Graham, F. L. et al. (1977), J. Gen. Virol. 36: 59), using a high efficiency procedure (Graham et al., supra & Gorman, C. M., Science 221: 551). Media is changed to serum free and harvested daily for up to 5 days. Antibodies are purified from the pooled supernatants using protein A-Sepharose CL-4B (Pharmacia). The eluted antibody is buffer exchanged into PBS by G25 gel filtration, concentrated by ultrafiltration using a Centriprep-30 or Centricon-100 (Millipore), and stored at 4° C. The concentration of antibody is determined using total IgG-binding ELISA.

Exemplary heavy chain IgG1 constant domains according to the invention are depicted in FIG. 5A. An exemplary human light chain κ constant domain comprises, for example, RTVAAPSVFIFPPSDEQLKSGTASV-VCLLNNFYPREAKVQWKVDNALQSGNSQESV TEQDSKDSTYSLSSTLTLSKADYEKHD-VYACEVTHQGLSSPVTKSFNRGEC (SEQ ID NO:37). The full length amino acid sequence of h10F4v2 is shown in FIG. 5B in which the constant regions of the light and heavy chains are indicated by underlining. The h10F4v1, v2, and v3 antibodies are IgG1 isotype.

Characterization of Anti-CD22 Antibodies

Example 5

Epitope Mapping

The epitopes of CD22 to which 10F4.4.1 and 5E8.1.8 antibodies bound were determined according to the following procedures. CD22 sequences lacking various of the seven immunoglobulin-like domains of the major CD22 isoform (CD22beta) were cloned and transformed into cells for stable expression. For example, CD22 variants lacking domain 1 (Δ1), domain 2 (Δ2), or domains 3 and 4 (Δ3,4) were cloned, transformed into CHO cells, and expressed on the cells. Control cells expressed CD22beta. Deletions were performed using Stratagene QuikChange XL™ reagent kit. Deletion of domain 1 was performed by deletion of amino acids 22-138; deletion of domain 2 was performed by deletion of amino acids 139-242; and deleted domains 3 and 4 were available as the minor isoform CD22alpha (deletion of amino acids 241-417). All amino acid numbers refer to the numbering of full length precursor CD22beta by Wilson, G. L. et al. (see FIG. 1 in Wilson, G. L. et al., J. Exp. Med. 173:137-146 (1991)). FIG. 14 is a diagram of the deleted domains. Binding was determined by flow cytometry using an isotype control. Binding of 10F4.4.1 was detected using goat anti-mouse IgG Alexa 488. Binding of 5E8.1.8 was detected using biotinylated goat anti-mouse IgG plus streptavidin PE. An adverse affect on the binding of murine 10F4.4.1 or murine 5E8.1.8 antibodies in the absence of particular ECD domains indicated that the antibody bound those domains. Murine 10F4.4.1 and 5E8.1.8 showed the same binding characteristics under these conditions. Neither bound CD22 lacking domain 1 or domain 2, and both bound CD22 comprising domains 1 and 2, but lacking domains 3 and 4. Using this method, it was determined that 10F4.4.1 and 5E8.1.8 bind to domains 1 and 2 of human CD22, within the sequence from amino acid 22 to amino acid 240 of SEQ ID NO:27 (see Wilson, G. L. et al., (1991) supra).

Example 6

Characterization of Binding Affinity to Soluble Antigen

The binding affinity of murine and humanized 10F4 antibody for soluble CD22 extracellular domain (ECD) was determined by surface plasmon resonance measurement using a BIACOR® 3000 system (Biacore, Inc., Piscataway, N.J.). Briefly, carboxymethylated dextran biosensor chips (CM5, Biacore Inc.) were activated with N-ethyl-N'-(3-dimethylaminopropyl)-carbodiimide hydrochloride (EDC) and N-hydroxysuccinimide (NHS) according to the supplier's instructions. These activated chips were coated with anti-CD22 IgG1 antibody 10F4 (murine or humanized) by dilution to 5 μg/ml with 10 mM sodium acetate, pH 4.8, before injection at a flow rate of 5 μl/minute to achieve approximately 500 response units (RU) of coupled antibody. Next, 1M ethanolamine was injected to block unreacted groups. For kinetics measurements, two-fold serial dilutions of human CD22-beta-ECD-His tagged soluble antigen (approximately 500 nM to approximately 7.8 nM) were injected in PBS with 0.05% Tween 20 at 25° C. at a flow rate of 30 μl/min. Association rates ($k_{on}$) and dissociation rates ($k_{off}$) were calculated using a simple one-to-one Langmuir binding model (BIAevaluation Software version 3.2). The equilibrium dissociation constant (Kd) was calculated as the ratio $k_{off}/k_{on}$. Anti-CD22 antibody, RFB4, was used as a control (Chemicon International, Inc., Temecula, Calif., catalog no. CBL147). The results of this experiment are shown in Table 2 below.

TABLE 2

Anti-CD22 Binding Affinity to Soluble Human CD22 (BIACORE ® analysis)

| Clone | $k_{on}/10^5$ | $k_{off}/10^{-4}$ | Kd (nM) |
|---|---|---|---|
| Murine 10F4 | 0.19 | 2.8 | 15 |
| Chimeric 10F4 | 0.26 | 4.2 | 16 |
| Humanized 10F4v1 | 0.18 | 3.5 | 19 |
| Humanized 10F4v2 | 0.32 | 2.5 | 7.8 |
| Control RFB4 | 0.33 | 1.4 | 4.2 |

Example 7

Characterization of Binding Affinity to Cell Surface Antigen

The binding affinity of murine 10F4.4.1 and humanized 10F4v1 and 10F4v2 for human and cynomolgus monkey (cyno) CD22 expressed on the surface of CHO cells was examined using a competition assay. Briefly, CHO cells stably expressing full length human CD22 (SEQ ID NO:27) or cynomolgus monkey (cyno) CD22 (SEQ ID NO:31). Anti-CD22 antibody (murine or humanized 10F4v1 or v2) was iodinated with Iodogen® [$^{125}$I] reagent to a specific activity of approximately 10 μCi/μg. A cell-based, competitive binding assay was performed using serially diluted, unlabeled anti-CD22 antibody. Antibodies were allowed to bind to the cells for 4 hours at 4° C. Binding affinity, $K_D$, of the antibodies was determined in accordance with standard Scatchard analysis performed utilizing a non-linear curve fitting program (see, for example, Munson et al., Anal Biochem, 107: 220-239, 1980). The results of this experiment are shown in Table 3 below.

TABLE 3

| 10F4 MAb Binding Affinity for Human and Cyno CD22 | | |
|---|---|---|
| Antibody | Human CD22 Kd (nM) | Cyno CD22 Kd (nM) |
| Mu 10F4.4.1 | 2.4 | 2.3 |
| Hu 10F4v1* | 1.1, 1.7 | 1.4, 1.8 |
| Hu 10F4v2 | 1.6 | 2.1 |

*repeated assays

The results indicate that murine and humanized 10F4 bind human and cyno CD22 expressed on the surface of CHO cells with approximately equivalent affinity.

Example 8

Production of Anti-CD22 Antibody Drug Conjugates

Anti-CD22 ADCs were produced by conjugating anti-CD22 antibodies RFB4, murine 5E8, murine 10F4, humanized 10F4v1, humanized thioMAb 10F4v1 (thio-10F4v1), humanized 10F4v2, and humanized 10F4v3 to the following drug-linker moieties: spp-DM1, smcc-DM1, MC-vc-PAB-MMAE; MC-vc-PAB-MMAF; MC-MMAE and MC-MMAF, which drug and linker moieties are disclosed herein as well as in WO 2004/010957, published Feb. 5, 2004, and WO2006/034488, published Sep. 9, 2005 (each of which patent applications is herein incorporated by reference in its entirety). Prior to conjugation, the antibodies were partially reduced with TCEP using standard methods in accordance with the methodology described in WO 2004/010957. The partially reduced antibodies were conjugated to the above drug-linker moieties using standard methods in accordance with the methodology described in Doronina et al. (2003) Nat. Biotechnol. 21:778-784 and US 2005/0238649 A1. Briefly, the partially reduced antibodies were combined with the drug linker moieties to allow conjugation of the moieties to cysteine residues. The conjugation reactions were quenched, and the ADCs were purified. The drug load (average number of drug moieties per antibody) for each ADC was determined by HPLC. Other useful linkers for the preparation of ADCs include, without limitation, BMPEO, BMPS, EMCS, GMBS, HBVS, LC-SMCC, MBS, MPBH, SBAP, SIA, SIAB, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$.

Anti-CD22 ADCs are also produced by conjugation to lysine residues of the antibody. Lysines of the antibody are converted to sulfhydryl groups using, for example, Traut's reagent (Pierce Chemical Co.) as disclosed herein. The resultant sulfhydryl groups are reactive with linkers or linker drug molecules for the preparation of ADCs. Alternatively, ADC's are produced by reacting a lysine on an anti-CD22 antibody with the linker, SPP (N-succinimidyl 4-(2'-pyridyldithio) pentanoate, which may be already attached to a drug molecule or may be subsequently reacted with a drug molecule, such as a maytansinoid. For example, an antibody is modified by reaction with SPP, followed by conjugation with f as disclosed in Wang, L. et al., Protein Science 14:2436-2446 (2005), which reference is hereby incorporated by reference in its entirety. Lysine residues on an anti-CD22 antibody may also be reacted with the linker, SMCC (Pierce Chemical Co.), at pH 7-9 such that the amine-reactive N-hydroxysuccinimide (NHS ester) of SMCC forms a stable amide bond with the antibody. The sulfhydryl-reactive maleimide group of SMCC is reacted with the sulfhydryl group of DM1 at pH 6.5-7.5 (see Pierce Chemical Co., piercenet.com) to form the ADC. Lysine or cysteine residues are reacted with linker-drug to produce ADCs comprising an average drug load of approximately 1-8 linker drug molecules per antibody, alternatively 1-6, 1-4, 1-3 or 1-2 linker drug molecules per antibody.

ADCs anti-CD22(RFB4)-SMCC-DM1 and anti-GP120-SMCC-DM1 were prepared according to this method, where RFB4-smcc-DM1 was prepared at low (1.95), medium (3.7) and high (6.75) drug loads. Anti-GP120-smcc-DM1 was prepared at high (6.1) drug load. These ADCs were shown to be efficacious in vivo, as shown in Example 9 and Table 9, herein below.

Example 9

Efficacy of Anti-CD22 Antibody Drug Conjugates

In Vitro Studies of Efficacy Determinants.

The determinants of anti-CD22 ADC (or TDC) efficacy in a lymphoma cell line were determined. It is known that CD22 expressed on the surface of B cells is internalized upon binding of its ligand(s) or antibodies (Sato, S. et al., Immunity 5:551-562 (1996)). To test whether and how the level of B cell surface expression of CD22 and/or internalization of CD22 affect efficacy, the following in vitro studies were performed.

Surface expression of human CD22 on multiple lymphoma cell lines. Nineteen lymphoma cell lines expressing varying amounts of CD22 on their surface were cultured and harvested in log phase growth. Cells were resuspended in FACS wash buffer (PBS; 0.5% bovine serum albumin; 0.1% sodium azide) containing 100 µg/ml each normal mouse IgG and normal human IgG and maintained on ice. Approximately 1×10^6 cells/100 µl were stained with anti-huCD22 APC (mIgG1, clone RFB4, Southern Biotech #9361-11) or murine IgG1 APC isotype (BD Pharmingen #555751) for 30 minutes on ice. Dead cells were stained with 7-AAD (BD Pharmingen #559925). Data were acquired on a BD FacsCalibur™ flow cytometer and analyzed with FlowJo™ software. The IC50 determination for hu10F4v3-SMCC-DM1 or each free drug (DM1, MMAF, or MMAE) were determined by culturing lymphoma cells as above, harvesting the cultured cells in log phase and seeding 5,000 cells in 90 µl culture medium per well in 96 well plate. ADC and free drug were diluted serially within the detection range (starting at 300 µg/ml for ADC, or 90 nM for free drug and diluting to essentially zero assay target). Aliquots of 101 diluted ADC or free drug were added to replicate wells containing cells and incubated for 3 days at 37° C. To each well, 100 µl CellTiter Glo™ was added and incubated for 30 min. Chemiluminescence was detected and data were analyzed using Prism™ software. The results are shown in FIG. 6A, in which high surface CD22 levels correlate with low IC50 (higher efficacy) of hu10F4v3-SMCC-DM1. FIG. 6C indicates that a stronger correlation exists between the intrinsic sensitivity of the cells to free drug and the IC50 of the ADC.

Internalization of hu10F4v3-SMCC-DM1 was determined by FACS assay. Briefly, lymphoma cells were stained by standard FACS techniques with CD22-FITC (RFB4) in the presence of hu10F4v3-SMCC-DM1 and incubated on ice for 20-30 minutes. To determine CD22 levels on the cell surface after the initial staining, cells were washed in cold RPMI/10% FBS media and 200 µl pre-warmed RPMI/10% FBS was added and incubated at 37° C. for 15 minutes. 80 µl staining buffer and 20 µl heat-inactivated normal mouse serum (HI NMS) were added, followed by incubation on ice for 15 minutes. Anti-DM1-Alexa-647 was added, incubated on ice for 20-30 minutes and cells were washed and fixed with 200 µl PBS/1% paraformaldehyde prior to FACS analysis. To determine surface and internal staining of CD22 after the initial staining, cells were washed with cold RPMI/10% FBS, pre-warmed RPMI/10% FBS was added and the cells incubated for 15 minutes at 37° C. Cells were then washed with FACS Wash and fixed with Fix Reagent A (Dako™ #k2311) at room temperature for 15 minutes, and the step was repeated with Fix Reagent B (Dako™). Staining buffer and HI NMS were added and the cell mixture was incubated on ice for 15 min. Fix Reagent B was added, followed by anti-DM1-Alexa-647 and incubated at room temperature for 20-30 minutes. Cells were washed in FACS Wash and fixed in PBS/1% paraformaldehyde. FACS analysis was performed on each cell mixture (surface, surface post-internalization, and internal staining) using a BD FacsCalibur™ flow cytometer and analyzed with FlowJo™ software. The results are shown in FIG. 6B in which high amounts of internalized DM1 correlated with low IC50 (high efficacy); and in FIG. 6D in which internalized DM1 is visualized by fluorescent microscopy.

In Vivo Efficacy Studies.

To test the efficacy of toxin-conjugated or unconjugated anti-CD22 monoclonal antibodies for the ability to reduce tumor volume in vivo, the following protocol was employed.

SCID mice were each inoculated subcutaneously in the flank with 2×10$^7$ a human B-cell lymphoma cell line. The human cell lines included human Burkitt lymphoma cell lines Daudi, Ramos, and Raji cells (available from the American Type Culture Collection, Manassas, Va., USA), and other B-cell lines including U-698-M cells and Su-DHL-4 cells (available from DSMZ, Braunschweig, Germany; Su-DHL-4 cells were transfected with the luciferase reporter gene), DoHH2 cells (Kluin-Neilemans, H. C. (1991), supra), and Granta-519 (Mantle cell lymphoma cells, Jadayel, D. M. et al., Leukemia 11(1):64-72 (1997)), and BJAB-luc cells (BJAB human B-cell lymphoblastoid cell line which expresses reporter gene luciferase. When the tumors reached a mean tumor volume of between 100-200 mm3, the mice were divided into groups, and treated on day 0 by intravenous injection with toxin-conjugated antibody or unconjugated antibody as shown in Tables 4-16, below.

Anti-CD22 Maytansine Drug Conjugates Reduce B-Cell Tumor Volume

Sixty-five SCID mice were injected with $2\times10^7$ BJAB-luc cells subcutaneously in a volume of 0.2 ml per mouse in the flank. Cells were suspended in HBSS. When the mean tumor size reached 100-200 mm^3, mice were randomly grouped into four groups of 9 mice each and given a single I.V. treatment (via the tail vein) of the anti-CD22 or control antibody indicated in Table 4, below.

TABLE 4

In Vivo Tumor Volume Reduction
Antibody Administration

| Antibody administered | TI | PR | CR | Dose Ab (mg/kg) | Dose DM1 ($\mu g/m^2$) | Drug ratio (Drug moieties/Ab) |
|---|---|---|---|---|---|---|
| anti-Her2-smcc-DM1 | 9/9 | 0 | 0 | 4.2 | 200 | 3.2 |
| mu10F4-smcc-DM1 | 9/9 | 2 | 0 | 3.0 | 200 | 4.6 |
| hu10F4v2-smcc-DM1 | 9/9 | 0 | 0 | 3.4 | 200 | 4.0 |
| hu10F4v1 | 9/9 | 0 | 0 | 3.4 | — | — |

"TI" - tumor incidence at the last time point of each group; the numerator refers to the number of tumor-bearing animals and the denominator refers to total number of animals.
"PR" refers to the number of animals with tumor regressed 50-99% from its initial volume.
"CR" refers to the number of animals attaining complete remission.

Mean tumor volume was monitored in each treatment group for 32 days post-antibody injection. Tumor measurements were taken with calipers. Efficacy of the toxin-conjugated anti-CD22 antibodies was determined by comparison to the control and unconjugated antibodies. The results are shown in FIG. 7A. The murine and humanized 10F4v1-smcc-DM1 monoclonal antibodies significantly slowed tumor growth relative to unconjugated anti-CD22 antibody and non-specific control antibody.

Using the same protocol as above, an assay was performed comparing toxin-conjugated humanized 10F4v2 to toxin-conjugated murine and naked humanized antibody as indicated in Table 5, below.

TABLE 5

In Vivo Tumor Volume Reduction
Antibody Administration

| Antibody administered | TI | PR | CR | Dose Ab (mg/kg) | Dose DM1 ($\mu g/m^2$) | Drug ratio (Drug moieties/Ab) |
|---|---|---|---|---|---|---|
| anti-Her2-smcc-DM1 | 9/9 | 0 | 0 | 4.2 | 200 | 3.2 |
| mu10F4-smcc-DM1 | 7/9 | 1 | 2 | 4.7 | 200 | 2.9 |

TABLE 5-continued

In Vivo Tumor Volume Reduction
Antibody Administration

| Antibody administered | TI | PR | CR | Dose Ab (mg/kg) | Dose DM1 ($\mu g/m^2$) | Drug ratio (Drug moieties/Ab) |
|---|---|---|---|---|---|---|
| hu10F4v2-smcc-DM1 | 8/9 | 1 | 1 | 4.5 | 200 | 3.0 |
| hu10F4v2 | 9/9 | 0 | 0 | 4.5 | — | — |

"TI" - tumor incidence at the last time point of each group; the numerator refers to the number of tumor-animals in the study group and the denominator refers to total number of animals.
"PR" refers to the number of animals with tumor regressed 50-99% from its initial volume.
"CR" refers to the number of animals attaining complete remission.

Mean tumor volume was monitored in each treatment group for 32 days post-antibody injection. Tumor measurements were taken with calipers. Efficacy of the toxin-conjugated anti-CD22 antibodies was determined by comparison to the control and unconjugated antibodies. The results are shown in FIG. 7B. The murine 10F4-smcc-DM1 and humanized 10F4v2-smcc-DM1 monoclonal antibodies significantly slowed tumor growth relative to unconjugated anti-CD22 antibody and non-specific control antibody.

Anti-CD22 antibody was conjugated to DM1 via the spp linker or the smcc linker according to conjugation methods disclosed herein. The naked anti-CD20 antibody was used as a positive control and the toxin conjugates, anti-HER2-spp-DM1 and anti-HER2-smcc-DM1, were used as negative controls. Eighty SCID mice were injected with $2\times10^7$ BJAB-luc cells subcutaneously in a volume of 0.2 ml per mouse in the flank. Cells were suspended in HBSS. When the mean tumor size reached 100-200 mm^3, the mice were randomly grouped into six groups of 10 mice each and intravenous injection of test or control antibodies was performed. Doses were repeated once each week for a total of three doses. See Table 6.

TABLE 6

In Vivo Tumor Volume Reduction
Antibody Administration

| Antibody administered | Dose Ab (mg/kg) | Dose DM1 ($\mu g/m^2$) |
|---|---|---|
| anti-Her2-spp-DM1* | 4 | 214 |
| anti-Her2-smcc-DM1** | 6.9 | 405 |
| anti-CD22-spp-DM1* | 5 | 214 |
| anti-CD22-spp-DM1 | 2.5 | 107 |
| anti-CD22-smcc-DM1** | 10 | 405 |
| naked anti-CD22 | 10 | — |

*Matched drug load
**Matched drug load

Mean tumor volume was monitored twice each week for 3 weeks and then once each week thereafter for a total of 8 weeks. Changes in tumor volume over time (FIG. 7C) show that the anti-CD22-spp-DM1 dosed at 214 and 107 $\mu g/m^2$ DM1 and anti-CD22-smcc-DM1 dosed at 405 $\mu g/m^2$ showed robust and comparable anti-tumor activity in BJAB-luc xenograft tumors. All anti-CD22 ADC groups showed complete responses.

The anti-CD22 antibodies, RFB4, 5E8, and 7A2 were conjugated to DM1 via the smcc linker according to conjugation methods disclosed herein. The toxin conjugate, anti-HER2-smcc-DM1 (referred to interchangeably herein as HER-smcc-DM1 or HER2-smcc-DM1), was used as negative control.

The ability of these antibodies to reduce tumor volume in various xenografts in SCID mice was examined. The human B-cell lymphoma cell lines used to generate xenograft tumors in mice were Ramos cells and BJAB-luc cells. For each xenograft, SCID mice were injected with 5×10^6 human B-cell lymphoma Ramos cells subcutaneously in a volume of 0.1 ml per mouse in the flank (or 2×10^7 BJAB-luc cells in 0.2 ml). Cells were suspended in HBSS. When the mean tumor size reached 100-200 mm^3, the mice were randomly grouped into groups of 8-10 mice each, and each mouse was given a single intravenous injection of test or control antibody. DM1 drug loading was normalized to 200 µg/m² for each group to provide the dose of DM1 administered. Mean tumor volume was monitored twice each week for 4 weeks. The results are shown below in Tables 7 and 8 and plotted in FIGS. 8A and 8B, respectively.

TABLE 7

In Vivo Tumor Volume Reduction, Ramos Xenograft Antibody Administration

| Antibody administered | Dose Ab (mg/kg) | Dose DM1 (µg/m²) |
|---|---|---|
| anti-HER2-smcc-DM1 | 4.2 | 200 |
| Anti-CD22(7A2)-smcc-DM1 | 3.8 | 200 |
| anti-CD22(5E8)-smcc-DM1 | 3.8 | 200 |
| Anti-CD22(RFB4)-smcc-DM1 | 3.2 | 200 |

TABLE 8

In Vivo Tumor Volume Reduction, BJAB-luc Xenograft Antibody Administration

| Antibody administered | Dose Ab (mg/kg) | Dose DM1 (µg/m²) | Drug ratio (Drug moieties/Ab) |
|---|---|---|---|
| anti-HER2-smcc-DM1 | 4.2 | 200 | 3.2 |
| Anti-CD22(7A2)-smcc-DM1 | 3.8 | 200 | 3.6 |
| Anti-CD22(5E8)-smcc-DM1 | 3.8 | 200 | 3.6 |
| Anti-CD22(RFB4)-smcc-DM1 | 3.2 | 200 | 4.25 |

These results show that anti-CD22-smcc-DM1 antibody drug conjugates significantly reduce B-cell tumor volume in Ramos, and BJAB-luc xenografts relative to control antibody or naked anti-CD22 antibody.

The affect of antibody drug load (average number of drug molecules conjugated per antibody in a population of antibodies) on the ability of anti-CD22-smcc-DM1 antibody drug conjugates to reduce tumor volume in BJAB-luc SCID mouse xenografts was examined. One hundred forty SCID mice were injected with 2×10^7 BJAB-luc cells subcutaneously in a volume of 0.2 ml per mouse in the flank. Cells were suspended in HBSS. When the mean tumor size reached 100-200 mm^3, the mice were randomly grouped into groups of 8-10 mice each, and each mouse was given a single intravenous injection of test or control antibody. Populations of anti-CD22(RFB4)-smcc-DM1 having relative low, medium or high drug loads (average drug loads 1.95, 3.7, or 6.75 conjugated DM1 molecules per antibody, respectively) were administered as the test antibodies. Naked RFB4 antibody and anti-GP120-smcc-DM1 (high drug load) were the controls. The doses of antibody drug conjugates (test and control) were normalized to a dose of 5 mg/kg protein level. Linker conjugate attachment to the antibodies was via lysine residues. See Table 9.

TABLE 9

In Vivo Tumor Volume Reduction, BJAB-luc Xenograft Anti-CD22(RFB4)-smcc-DM1 Administration

| Antibody administered | Dose Ab (mg/kg) | Dose DM1 (µg/m²) | Drug ratio (Drug moieties/Ab) |
|---|---|---|---|
| anti-CD22(RFB4) (naked antibody) | 10 | — | — |
| anti-CD22(RFB4)-smcc-DM1 (low) | 5 | 144 | 1.95 |
| anti-CD22(RFB4)-smcc-DM1 (medium) | 5 | 273 | 3.7 |
| anti-CD22(RFB4)-smcc-DM1 (high) | 5 | 497 | 6.75 |
| anti-GP120-smcc-DM1 (high) | 5 | 449 | 6.1 |

When dosed at a matching protein level (5 mg/kg), anti-CD22(RFB4)-smcc-DM1 loaded with a high drug load (6.75 DM1 molecules per antibody molecule) reduced tumor volume slightly more than the antibody drug conjugate with a medium load of 3.7, whereas the affects of the antibody drug conjugate with a low drug load was not different from control conjugate or naked antibody. The results are plotted in FIG. 9.

Anti-CD22 Auristatin Drug Conjugates Reduce B-Cell Tumor Volume

The affect of anti-CD22 auristatin MMAF drug conjugates on tumor volume in mouse xenografts was examined. Anti-CD22(RFB4) and control antibody anti-GP120 were conjugated to MMAF via a MC-vcPAB linker or a MC linker according to methods disclosed herein. SCID mice were injected with 5×10^6 Ramos cells subcutaneously in a volume of 0.2 ml per mouse in the flank. Cells were suspended in HBSS. When the mean tumor size reached 100-200 mm^3, the mice were randomly grouped into groups of 8-10 mice each, and each mouse was given a single intravenous injection of test or control antibody. Drug dose, drug load (drug ratio) and antibody dose administered to the mice are shown in Table 10.

TABLE 10

In Vivo Tumor Volume Reduction, Ramos Xenograft Anti-CD22(RFB4) MMAF Conjugate Administration

| Antibody administered | Dose MMAF (µg/m²) | Dose Ab (mg/kg) | Drug ratio (Drug moieties/Ab) |
|---|---|---|---|
| anti-CD22(RFB4)-MCvcPAB-MMAF | 405 | 6.6 | 4.2 |

TABLE 10-continued

In Vivo Tumor Volume Reduction, Ramos Xenograft
Anti-CD22(RFB4) MMAF Conjugate Administration

| Antibody administered | Dose MMAF (μg/m²) | Dose Ab (mg/kg) | Drug ratio (Drug moieties/Ab) |
|---|---|---|---|
| anti-CD22(RFB4)-MC-MMAF | 405 | 6.9 | 4.0 |
| anti-GP120-MCvcPAB-MMAF | 405 | 5.8 | 4.8 |
| anti-GP120-MC-MMAF | 405 | 5.9 | 4.7 |

Anti-CD22-MC-MMAF showed comparable activity compared to anti-CD22-MC-vc-PAB-MMAF in Ramos RA1 xenografts. The results are plotted in FIG. 10.

The affect of anti-CD22 auristatin MMAE and DM1 drug conjugates on tumor volume in mouse xenografts was examined. Anti-CD22(RFB4) and control antibody anti-GP120 were conjugated to MMAE via a MC-vcPAB linker or a MC linker or to DM1 via a smcc linker according to methods disclosed herein. SCID mice were injected with 5×10^6 Ramos cells subcutaneously in a volume of 0.1 ml per mouse in the flank. Cells were suspended in HBSS. PBS was administered as a control. When the mean tumor size reached 100-200 mm^3, the mice were randomly grouped into groups of 8-10 mice each, and each mouse was given a single intravenous injection of test or control antibody. Drug dose, drug load (drug ratio) and antibody dose administered to the mice are shown in Table 11.

TABLE 11

In Vivo Tumor Volume Reduction, Ramos Xenograft
Anti-CD22(RFB4) MMAE and DM1 Conjugate Administration

| Antibody administered | Dose MMAE or DM1 (μg/m²) | Dose Ab (mg/kg) | Drug ratio (Drug moieties/Ab) |
|---|---|---|---|
| Anti-GP120-smcc-DM1 | 405 | 6.7 | 4.1 |
| Anti-CD22(RFB4)-smcc-DM1 | 405 | 6.5 | 4.25 |
| Anti-GP120-MCvcPAB-MMAE | 405 | 6.0 | 4.7 |
| antiCD22(RFB4)-MCvcPAB-MMAE | 405 | 6.3 | 4.5 |
| PBS | — | — | — |

Anti-CD22-MCvcPAB-MMAE showed potent anti-tumor activity in Ramos RA1 xenografts. The anti-CD22-MCvc-PAB-MMAE showed superior activity compared to antiCD22-smcc-DM1. The ADC control, anti-GP120-MCvcPAB-MMAE, did not show significant activity. The results are plotted in FIG. 11.

The affect of anti-CD22 auristatin MMAF and DM1 drug conjugates on tumor volume in mouse xenografts was examined. Anti-CD22 hu10F4v2-MC-MMAF, hu10F4v2-smcc-DM1 and thio-10F4v1-MC-MMAF were administered and compared for affect on tumor volume. Control antibodies were anti-Her2-MC-MMAF and anti-Her2-smcc-DM1. SCID mice were injected with 2×10^7 BJAB-luc cells subcutaneously in a volume of 0.2 ml per mouse in the flank. Cells were suspended in HBSS. When the mean tumor size reached 100-200 mm^3, the mice were randomly grouped into groups of 8-10 mice each, and each mouse was given a single intravenous injection of test or control antibody. "Thio" refers to a thioMab, as disclosed herein, in which the linker-drug moiety is conjugated to the antibody via a cysteine engineered site on the antibody. Drug dose, drug load (drug ratio) and antibody dose administered to the mice are shown in Table 12.

TABLE 12

In Vivo Tumor Volume Reduction, BJAB-luc Xenograft
Hu10F4 MMAF and DM1 Conjugate Administration

| Antibody administered | Dose MMAF or DM1 (μg/m²) | Dose Ab (mg/kg) | Drug ratio (Drug moieties/Ab) |
|---|---|---|---|
| Anti-Her2-MC-MMAF | 100 | 1.1 | 6.3 |
| Hu10F4v2-MC-MMAF | 100 | 2.0 | 3.4 |
| Hu10F4v2-MC-MMAF | 50 | 1.0 | 3.4 |
| Thio-hu10F4v1-MC-MMAF | 100 | 4.6 | 1.5 |
| Thio-hu10F4v1-MC-MMAF | 50 | 2.3 | 1.5 |
| Anti-Her2-smcc-DM1 | 200 | 4.2 | 3.2 |
| Hu10F4v2-smcc-DM1 | 200 | 4.5 | 3.0 |
| Hu10F4v2-smcc-DM1 | 100 | 2.3 | 3.0 |

Hu10F4v2 ADCs showed potent anti-tumor activity in BJAB-luc xenografts. The results are plotted in FIG. 12.

Using procedures as disclosed in the above experiments, hu10F4v3-smcc-DM1 and -MC-MMAF ADC efficacy in different xenografts at different doses was examined. Xenografts of SuDHL4-luc, DoHH2, and Granta-519 xenografts were prepared as disclosed herein, above. When the tumor size reached 100-200 mm^3, the mice were randomly grouped into groups of 8-10 mice each, and each mouse was given a single intravenous injection of test or control antibody. Drug dose, drug load (drug ratio) and antibody dose administered to the mice are shown in Tables 13A-13C and the results are shown in FIGS. 13A-13C.

TABLE 13A

In Vivo Tumor Volume Reduction,
Hu10F4v3 MMAF and DM1 Conjugate Administration
In SuDHL-4-luc Xenografts

| Antibody administered | Dose MMAF or DM1 (μg/m²) | Dose Ab (mg/kg) | Drug ratio (Drug/Ab) |
|---|---|---|---|
| Anti-Her2-smcc-DM1 | 600 | 11.9 | 3.3 |
| Hu10F4v3-smcc-DM1 | 600 | 13.6 | 2.9 |
| Hu10F4v3-smcc-DM1 | 300 | 6.8 | 2.9 |
| Anti-Her2-MC-MMAF | 600 | 9.9 | 4.0 |
| Hu10F4v3-MC-MMAF | 600 | 13.3 | 3.0 |
| Hu10F4v3-MC-MMAF | 300 | 6.6 | 3.0 |

TABLE 13B

In Vivo Tumor Volume Reduction,
Hu10F4v3 MMAF and DM1 Conjugate Administration
In DoHH2 Xenografts

| Antibody administered | Dose MMAF or DM1 (µg/m²) | Dose Ab (mg/kg) | Drug ratio (Drug/Ab) |
|---|---|---|---|
| Anti-Her2-smcc-DM1 | 600 | 11.9 | 3.3 |
| Hu10F4v3-smcc-DM1 | 600 | 11.8 | 3.35 |
| Hu10F4v3-smcc-DM1 | 300 | 5.9 | 3.35 |
| Anti-Her2-MC-MMAF | 600 | 9.9 | 4.0 |
| Hu10F4v3-MC-MMAF | 600 | 13.1 | 3.04 |
| Hu10F4v3-MC-MMAF | 300 | 6.6 | 3.04 |
| Naked hu10F4v3 | — | 13.1 | — |

TABLE 13C

In Vivo Tumor Volume Reduction,
Hu10F4v3 MMAF and DM1 Conjugate Administration
In Granta-519 Xenografts

| Antibody administered | Dose MMAF or DM1 (µg/m²) | Dose Ab (mg/kg) | Drug ratio (Drug/Ab) |
|---|---|---|---|
| Anti-Her2-smcc-DM1 | 300 | 5.9 | 3.3 |
| Hu10F4v3-smcc-DM1 | 300 | 5.9 | 3.35 |
| Hu10F4v3-smcc-DM1 | 150 | 2.9 | 3.35 |
| Anti-Her2-MC-MMAF | 300 | 4.9 | 4.0 |
| Hu10F4v3-MC-MMAF | 300 | 6.6 | 3.04 |
| Hu10F4v3-MC-MMAF | 150 | 3.3 | 3.04 |
| Naked hu10F4v3 | — | 6.6 | — |

Anti-CD22 hu10F4v3-smcc-DM1 and -MC-MMAF ADCs showed potent tumor reduction in all of the xenograft models tested.

Example 10

Preparation of Cysteine Engineered Anti-CD22 Antibodies

Preparation of cysteine engineered anti-CD22 antibodies was performed as disclosed herein. DNA encoding the 10F4v3 antibody, having the same variable and constant region sequences as 10F4v2 (light chain, SEQ ID NO:87; and heavy chain, SEQ ID NO:88, FIG. 5B), was mutagenized by methods disclosed herein to modify the light chain, the heavy chain or the Fc region of the heavy chain. DNA encoding the light chain was mutagenized to substitute cysteine for valine at Kabat position 205 in the light chain (sequential position 210) as shown in FIG. 17A (light chain SEQ ID NO:91 of humanized antibody 10F4v3 thiomab). DNA encoding the heavy chain was mutagenized to substitute cysteine for alanine at EU position 118 in the heavy chain (sequential position 121) as shown in FIG. 17B (heavy chain SEQ ID NO:92 of humanized antibody 10F4v3 thiomab). The Fc region was mutagenized to substitute cysteine for serine at EU position 400 in the heavy chain Fc region (sequential position 403) as shown in FIG. 17C (heavy chain SEQ ID NO:93).

Preparation of Cysteine Engineered Anti-CD22 Antibodies for Conjugation by Reduction and Reoxidation.

Full length, cysteine engineered anti-CD22 monoclonal antibodies (ThioMabs) expressed in CHO cells are dissolved in 500 mM sodium borate and 500 mM sodium chloride at about pH 8.0 and reduced with about a 50-100 fold excess of 1 mM TCEP (tris(2-carboxyethyl)phosphine hydrochloride; Getz et al (1999) Anal. Biochem. Vol 273:73-80; Soltec Ventures, Beverly, Mass.) for about 1-2 hrs at 37° C. The reduced ThioMab is diluted and loaded onto a HiTrap S column in 10 mM sodium acetate, pH 5, and eluted with PBS containing 0.3M sodium chloride. The eluted reduced ThioMab is treated with 2 mM dehydroascorbic acid (dhAA) at pH 7 for 3 hours, or 2 mM aqueous copper sulfate ($CuSO_4$) at room temperature overnight. Ambient air oxidation may also be effective. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Example 11

Preparation of Cysteine Engineered Anti-CD22 Antibody Drug Conjugates by Conjugation of Cysteine Engineered Anti-CD22 Antibodies and Drug-Linker Intermediates After the reduction and reoxidation procedures of Example 10, the cysteine engineered anti-CD22 antibody is dissolved in PBS (phosphate buffered saline) buffer and chilled on ice. About 1.5 molar equivalents relative to engineered cysteines per antibody of an auristatin drug linker intermediate, such as MC-MMAE (maleimidocaproyl-monomethyl auristatin E), MC-MMAF, MC-val-cit-PAB-MMAE, or MC-val-cit-PAB-MMAF, with a thiol-reactive functional group such as maleimido, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered anti-CD22 antibody drug conjugate is purified and desalted by elution through G25 resin in PBS, filtered through 0.2 µm filters under sterile conditions, and frozen for storage.

Preparation of hu 10F4v3 HC(A118C) thiomab-BMPEO-DM1 was performed as follows. The free cysteine on hu 10F4v3 HC(A118C) thiomab was modified by the bis-maleimido reagent BM(PEO)4 (Pierce Chemical), leaving an unreacted maleimido group on the surface of the antibody. This was accomplished by dissolving BM(PEO)4 in a 50% ethanol/water mixture to a concentration of 10 mM and adding a tenfold molar excess of BM(PEO)4 to a solution containing hu4D5Fabv8-(V110C) ThioFab in phosphate buffered saline at a concentration of approximately 1.6 mg/ml (10 micromolar) and allowing it to react for 1 hour. Excess BM(PEO)4 was removed by gel filtration (HiTrap column, Pharmacia) in 30 mM citrate, pH 6 with 150 mM NaCl buffer. An approximate 10 fold molar excess DM1 dissolved in dimethyl acetamide (DMA) was added to the hu4D5Fabv8-(V110C) ThioFab-BMPEO intermediate. Dimethylformamide (DMF) may also be employed to dissolve the drug moiety reagent. The reaction mixture was allowed to react overnight before gel filtration or dialysis into PBS to remove unreacted drug. Gel filtration on S200 columns in PBS was used to remove high molecular weight aggregates and furnish purified hu 10F4v3 HC(A118C) thiomab-BMPEO-DM1.

By the same protocols, control HC (A118C) MAb-MC-MMAF, control HC ThioMAb-MC-MMAF, control HCThioMAb-MCvcPAB-MMAE, and control HC ThioMab-BMPEO-DM1 were prepared.

By the procedures above, the following cysteine engineered anti-CD22 antibody drug conjugates were prepared and tested:

thio hu thio-HC-10F4v3-MC-MMAF by conjugation of A118C thio hu 10F4v3 and MC-MMAF;

thio hu thio-HC-10F4v3-MC-val-cit-PAB-MMAE by conjugation of A118C thio hu 10F4v3 and MC-val-cit-PAB-MMAE;

thio hu HC-10F4v3-bmpeo-DM1 by conjugation of A118C thio hu HC-10F4v3 and bmpeo-DM1;

thio hu LC-10F4v3-MC-val-cit-PAB-MMAE by conjugation of V205C thio hu LC-10F4v3 and MC-val-cit-PAB-MMAE; and thio hu Fc-10F4v3-MC-val-cit-PAB-MMAE by conjugation of S400C thio hu Fc-10F4v3 and MC-val-cit-PAB-MMAE.

Example 12

Characterization of Binding Affinity of Cysteine Engineered ThioMAb Drug Conjugates to Cell Surface Antigen The binding affinity of thio hu 10F4v3 drug conjugates to CD22 expressed on BJAB-lucs cells was determined by FACS analysis. Briefly, approximately 1×10^6 cells in 100 µl were contacted with varying amounts of one of the following anti-CD22 ThioMAb drug conjugates: thio hu LC(V205C) 10F4v3-MCvcPAB-MMAE, thio hu Fc(S400C) 10F4v3-MCvcPAB-MMAE, thio hu HC(A118C) 10F4v3-MCvcPAB-MMAE, thio hu HC(A118C) 10F4v3-MC-MMAF, or thio hu HC(A118C) 10F4v3-BMPEO-DM1 (see FIGS. 18A-18E, respectively). Anti-CD22 antibody bound to the cell surface was detected using biotinylated goat anti-huFc plus Streptavidin-PE. The plots of FIGS. 18A-18E indicate that antigen binding was approximately the same for all of the thiomab drug conjugates tested.

Example 13

Assay for In Vivo Tumor Volume Reduction by Anti-CD22 ThioMab Drug Conjugates

The ability of the thiomab drug conjugates prepared according to Example 11 to reduce B-cell tumor volume in xenograft models was tested according to the procedure disclosed in Example 9, herein. To SCID mice having Granta-519 cell xenograft tumors, control and anti-CD22 humanized 10F4v3 thiomab drug conjugates were administered at Day 0 in the doses shown in Table 14, below. The control HC(A118C) thiomab was anti-HER2 4D5 antibody.

TABLE 14

In Vivo Tumor Volume Reduction, Thio Hu10F4v3 MMAE and MMAF Conjugate Administration In Granta-519 Xenografts

| Antibody administered | Dose MMAF or DM1 (µg/m$^2$) | Dose Ab (mg/kg) | Drug ratio (Drug/Ab) |
|---|---|---|---|
| Thio Control HC(A118C)-MC-MMAF | 100 | 3.99 | 1.65 |
| Thio Control HC(A118C)-MCvcPAB-MMAE | 100 | 4.33 | 1.55 |
| Thio 10F4v3-HC(A118C)-MC-MMAF | 100 | 3.41 | 1.95 |
| Thio 10F4v3-LC(V205C)-MCvcPAB-MMAE | 100 | 4.23 | 1.6 |
| Thio 10F4v3-HC(A118C)-MCvcPAB-MMAE | 100 | 3.76 | 1.8 |
| Thio 10F4v3-Fc(S400C)-MCvcPAB-MMAE | 100 | 4.23 | 1.6 |

The results of this experiment are shown in FIG. 19. Administration of the thio 10F4v3-LC-(V205C)-MCvcPAB-MMAE and thio 10F4v3-HC(A118C)-MCvcPAB-MMAE thiomab drug conjugates at the doses shown in Table 14 caused a reduction in mean tumor volume for the duration of the study.

Additional thiomab drug conjugates were tested in Granta-519 xenografts in CB17 SCID mice using the same protocol, although different drug doses were tested. The control antibody or control thiomab was anti-HER2 4D5 antibody or HC(A118C) thiomab. The results are shown in Table 15, below.

TABLE 15

In Vivo Tumor Volume Reduction, Thio Hu10F4v3 MMAE, MMAF, and DM1 Conjugate Administration In Granta-519 Xenografts

| Antibody administered | Dose MMAF or DM1 (µg/m$^2$) | Dose Ab (mg/kg) | Drug ratio (Drug/Ab) |
|---|---|---|---|
| 10F4v3-MC-MMAF | 150 | 3.2 | 3.1 |
| Thio Control HC(A118C)-BMPEO-DM1 | 300 | 10.3 | 1.9 |
| Thio 10F4v3-HC(A118C)-BMPEO-DM1 | 150 | 5.2 | 1.9 |
| Thio 10F4v3-HC(A118C)-BMPEO-DM1 | 300 | 10.4 | 1.9 |
| Thio Control HC(A118C)-MCvcPAB-MMAE | 150 | 6.5 | 1.55 |
| Thio 10F4v3-HC(A118C)-MCvcPAB-MMAE | 150 | 5.3 | 1.9 |
| Thio 10F4v3-HC(A118C)-MCvcPAB-MMAE | 75 | 2.7 | 1.9 |
| Thio Control HC(A118C)-MC-MMAF | 150 | 5.2 | 1.9 |
| Thio 10F4v3-HC(A118C)-MC-MMAF | 150 | 5.1 | 1.95 |
| Thio 10F4v3-HC(A118C)-MC-MMAF | 75 | 2.6 | 1.95 |

The results of this experiment are shown in FIG. 20A. Administration of the thio 10F4v3-HC(A118C)-MCvcPAB-MMAE thiomab drug conjugate at 150 and 75 µg/m$^2$ caused a reduction in mean tumor volume for the duration of the study. In the same study, the percent body weight change in the first 7 days was determined in each dosage group. The results plotted in FIG. 20B indicate administration of these thiomab drug conjugates did not cause weight loss during this time.

In a similar study, using the same xenograft study protocol as disclosed in the above examples, varying the TDCs and doses administered, the efficacy of TDCs in follicular lymphoma DOHH2 xenografts in CB17 SCID mice was studied. The TDCs and doses are shown in Table 16, below.

TABLE 16

In Vivo Tumor Volume Reduction,
Thio Hu10Fv3 MMAE, MMAF, and DM1 Conjugate Administration
In DOHH2 Xenografts

| Antibody administered | Dose MMAF or DM1 (μg/m²) | Dose Ab (mg/kg) | Drug ratio (Drug/Ab) |
|---|---|---|---|
| 10F4v3-MC-MMAF | 300 | 6.4 | 3.1 |
| Thio Control HC(A118C)-BMPEO-DM1 | 600 | 21.9 | 1.79 |
| Thio 10F4v3-HC(A118C)-BMPEO-DM1 | 600 | 20.8 | 1.9 |
| Thio 10F4v3-HC(A118C)-BMPEO-DM1 | 300 | 10.4 | 1.9 |
| Thio Control HC(A118C)-MCvcPAB-MMAE | 600 | 26.0 | 1.55 |
| Thio 10F4v3-HC(A118C)-MCvcPAB-MMAE | 600 | 21.4 | 1.9 |
| Thio 10F4v3-HC(A118C)-MCvcPAB-MMAE | 300 | 10.7 | 1.9 |
| Thio Control HC(A118C)-MC-MMAF | 600 | 20.8 | 1.9 |
| Thio 10F4v3-HC(A118C)-MC-MMAF | 600 | 20.4 | 1.95 |
| Thio 10F4v3-HC(A118C)-MC-MMAF | 300 | 10.2 | 1.95 |

FIG. 20C is a graph plotting changes in mean tumor volume over time in the follicular lymphoma DOHH2 xenograft in CB17 SCID mice treated with the same heavy chain A118C anti-CD22 TDCs, but at higher doses as shown in Table 16. The anti-CD22 10F4v3-HC(A118C)-MCvcPAB-MMAE TDC appeared to be the most efficacious of the test agents in this study. However, at the increased dose levels in this experiment, some efficacy was noted in the anti-HER2-HC(A118C)-MCvcPAB-MMAE controls. This activity is possibly attributable to release of the drug from the ADC in circulation. The anti-CD22 hu10F4-HC(A118C)-MC-MMAF and -BMPEO-DM1 test agents showed intermediate efficacy and, consistent with the increased stability of these linkers, the non-binding anti-HER2 controls showed little activity. FIG. 20D is a plot of percent weight change in the mice from the DOHH2 xenograft study showing that there was no significant change in weight during the first 14 days of the study.

Example 14

Safety of Anti-CD22 Drug Conjugates in Rats and Cynomolgus Monkeys

The hu10F4 anti-CD22 antibody cross-reacts with cynomolgus (cyno) monkey CD22 with an affinity equivalent to human CD22. The hu10F4 anti-CD22 antibody does not cross-react with rat CD22. As a result, the target-independent and target-dependent safety and toxicity of anti-CD22 drug conjugates were assessed in rat and cyno, respectively.

Safety and Toxicity in Rats.

For safety and toxicity studies in rats, two studies were performed. In one study, rats were dosed intravenously on Day 1 with hu10F4v3-SMCC-DM1, -SPP-DM1, -MC-vc-PAB-MMAE, or -MC-MMAF conjugates in which the drug was linked via a cleavable (-vc- or -spp-) or uncleavable (MC or SMCC (also referred to as MCC)) linker. Vehicle was administered as the control. Blood samples were collected on Day 5 for pharmacokinetic analysis, and on Day 12 (at necropsy). Clinical observations and body weight recordings were conducted at least three times per week. Serum AST (aspartate aminotransferase) was monitored as an indication of toxicity. Serum AST levels were increased at Day 5 relative to Day 0 in rats dosed with 20 mg/kg hu10F4v3-vcMMAE and hu10F4v3-SPP-DM1 comprising cleavable linkers (FIG. 21A). Neutrophil levels were increased at Day 5 relative to Day 0 in rats dosed with 20 mg/kg hu10F4v3-MC-MMAF or hu10F4v3-MCC-DM1 (uncleavable linkers, FIG. 21B). Neutrophil levels were decreased at Day 5 relative to Day 0 in rats dosed with hu10F4v3-vc-MMAE or hu10F4v3-SPP-DM1. Increased serum AST and decreased neutrophils in rats dosed with ADCs comprising cleavable linkers indicates increased toxicity of such ADCs In the same rat study, six animals per group were dosed with 20, 40, or 60 mg/kg hu10F4v3-MC-MMAF or hu10F4v3-SMCC-DM1 at Day 1 and monitored for twelve days. In animals dosed with hu10F4v3-MC-MMAF, there were no observations in the following indicators: decreased body weight, increases in serum liver enzymes, decreases in platelets, or decreases in neutrophils. In rats dosed with hu10F4v3-SMCC-DM1, reversible decreased body weight and reversible increases in serum liver enzymes were observed at dose levels of 40 and 60 mg/kg, whereas reversible decreases in neutrophils and transient decreases in platelets were observed at 60 mg/kg doses.

Safety and Toxicity in Cynomolgus Monkeys.

To assess safety and toxicity of anti-CD22 ADCs in a primate model, thirty cyno monkeys were assigned to the following treatment groups: vehicle control (6 animals), hu10F4v3-SMCC-DM1 at doses of 2, 4, and 6 mg/m^2 drug dose (equivalent to 0, 10, 20, and 30 mg/kg antibody dose; 4 animals per dosage group), and hu10F4v3-MC-MMAF at doses of 2, 4, and 6 mg/m^2 (4 animals per dosage group). Animals were dosed intravenously on Day 1 and Day 22. The animals were evaluated for changes in body weight, food consumption, and pathology indices. Blood samples were collected and assayed to assess toxicological, pharmacodynamic, and anti-drug antibody effects. One-half of the animals in each group were euthanized at each of Day 25 and Day 43 and tissue samples were collected.

No noticeable body weight changes were noted in either ADC group. Levels of serum liver enzymes AST (aspartate aminotransferase), ALT (aminotransferase) and GGT (gamma-glutamyltranspeptidase) were assayed according to standard methods well known in the relevant arts. Reversible increases in serum liver enzymes were observed in animals dosed at 30 mg/kg with either ADC, although ALT was elevated in the DM1 group, whereas AST and GGT were elevated in the MMAF group. Sciatic nerve degeneration was minimal to mild in the DM1 group in 2 of 4 animals at a dose of 20 mg/kg and in 4 of 4 animals at a dose of 30 mg/kg. Sciatic nerve degeneration was minimal in the MMAF group in 1 of 4 animals at a dose of 30 mg/kg. Tissue from various organs was examined microscopically. Two of four animals in the 30 mg/kg MMAF group had lung lesions of unknown significance, whereas none were observed in the DM1 group.

Depletion of peripheral B cells by the hu10F4v3-MC-MMAF and —SMCC-DM1 ADCs was determined by measuring CD20$^+$ cell levels in blood over 43 days in cyno monkeys dosed at Day 0 and Day 22. Blood collected periodically during the study was assayed by FACS using a fluorescently labeled anti-CD20 antibody. The anti-CD22 MMAF and DM1 ADCs deplete cyno peripheral B cells as shown in FIG. 22A (MMAF group) and FIG. 22B (DM1 group). No significant effects of MMAF or DM1 ADCs were observed for other lymphocyte populations as shown in FIGS. 23A and 23B in which it is shown that CD4$^+$ cells were not significantly depleted over the same time period.

Hu10F4v3-SMCC-DM1 depleted germinal center B cells in the cyno monkey tonsil samples relative to control as shown in the photomicrographs in FIGS. 24A and 24B. Exemplary germinal centers are circled in FIG. 24A. Complete ablation of germinal center B cells was observed at the 10 mg/kg dose level as shown if FIG. 24B. The same results were obtained following administration of the hu10F4v3-MC-MMAF ADC under the same conditions.

Hu10F4v3-MC-MMAF dosed at 10 mg/kg depleted dividing B cells from the spleen follicle germinal centers of cyno monkeys. See the diagram in FIG. 25A and the tissue photomicrographs in FIGS. 25B and 25C. The same results were obtained when the hu10F4v3-SMCC-DM1 ADC was tested under the same conditions. Germinal centers appear as dark regions in FIG. 25B using Ki-67 stain and as unstained areas surrounded by dark regions when stained with detectably labeled anti-IgD in FIG. 25D. Loss of the germinal centers due to depletion of germinal center B cells by anti-10F4v3-MC-MMAF is shown in FIGS. 25C and 25E. Thus, these anti-mitotic drugs have an impact on proliferating B cell populations.

The following hybridoma has been deposited with the American Type Culture Collection, PO Box 1549, Manassas, Va., 20108, USA (ATCC):

| Cell Lines | ATCC Accession No. | Deposit Date |
| --- | --- | --- |
| Hybridoma 10F4.4.1 | PTA-7621 | May 26, 2006 |
| Hybridoma 5E8.1.8 | PTA-7620 | May 26, 2006 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. An antibody that binds to CD22, comprising:
   (a) an HVR-L1 sequence of SEQ ID NO:10;
   (b) an HVR-H1 sequence of SEQ ID NO:2;
   (c) an HVR-H2 sequence of SEQ ID NO:4;
   (d) an HVR-H3 sequence of SEQ ID NO:6;
   (e) an HVR-L2 sequence of SEQ ID NO:12; and
   (f) an HVR-L3 sequence of SEQ ID NO:14.

2. The antibody of claim 1, wherein the antibody comprises a heavy chain variable domain sequence of SEQ ID NO:16.

3. The antibody of claim 1, wherein the antibody comprises a light chain variable domain sequence of SEQ ID NO:18.

4. The antibody of claim 3, further comprising a light chain variable domain sequence of SEQ ID NO:18.

5. The antibody of claim 1, wherein the antibody comprises a heavy chain sequence of SEQ ID NO:88.

6. The antibody of claim 1, wherein the antibody comprises a light chain sequence of SEQ ID NO:87.

7. The antibody of claim 1, wherein the antibody comprises a heavy chain sequence of SEQ ID NO:88 and a light chain sequence of SEQ ID NO:87.

8. The antibody of claim 1, wherein the antibody is humanized.

9. The antibody of claim 1, wherein the antibody binds to an epitope within a region of CD22 from amino acid 22-240 of SEQ ID NO:27.

10. The antibody of claim 1, wherein the antibody is a monoclonal antibody.

11. An immunoconjugate comprising the antibody of claim 1 wherein the antibody is covalently attached to the group consisting of a cytotoxic agent.

12. The immunoconjugate of claim 11, wherein the cytotoxic agent is selected from a toxin, a chemotherapeutic agent, a drug moiety, an antibiotic, a radioactive isotope, and a nucleolytic enzyme.

13. The immunoconjugate of claim 12, the immunoconjugate having wherein the formula Ab-(L-D)p, wherein:
(a) Ab is the antibody of claim 1;
(b) L is a linker;
(c) D is a drug moiety; and
(d) p ranges from about 1 to 8.

14. The immunoconjugate of claim 13, wherein L is selected from the group consisting of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), and N-Succinimidyl (4-iodo-acetyl)aminobenzoate (SIAB).

15. The immunoconjugate of claim 13, wherein D is selected from an auristatin and dolostantin.

16. The immunoconjugate of claim 11, having in vitro or in vivo cell killing activity.

17. The immunoconjugate of claim 13, wherein the linker is attached to the antibody through a thiol group on the antibody.

18. The immunoconjugate of claim 13, wherein the linker is cleavable by a protease.

19. The immunoconjugate of claim 14, wherein the linker comprises a val-cit dipeptide.

20. The immunoconjugate of claim 13, wherein the linker comprises a p-aminobenzyl unit.

21. The immunoconjugate of claim 14, wherein the linker is 6-maleimidocaproyl.

22. The immunoconjugate of claim 13, wherein the drug is selected from the group consisting of Monomethyl auristatin E (MMAE) and Monomethyl auristatin F (MMAF).

23. The immunoconjugate of claim 22, wherein the drug is MMAE.

24. The immunoconjugate of claim 22, wherein the drug is MMAF.

25. A pharmaceutical composition comprising the immunoconjugate of claim 11 and a pharmaceutically acceptable carrier.

* * * * *

UNITED STATES PATENT AND TRADEMARK OFFICE
CERTIFICATE OF CORRECTION

PATENT NO. : 8,226,945 B2  Page 1 of 1
APPLICATION NO. : 12/939533
DATED : July 24, 2012
INVENTOR(S) : Ebens et al.

It is certified that error appears in the above-identified patent and that said Letters Patent is hereby corrected as shown below:

In the claims:

Claim 4. Under column 255, line 1, please delete "claim 3" and insert --claim 2--;

Claim 11. Under column 255, line 18-19, please delete "the group consisting of".

Claim 13. Under column 255, line 25, please delete "wherein" after "having".

Signed and Sealed this
Fourteenth Day of October, 2014

Michelle K. Lee
*Deputy Director of the United States Patent and Trademark Office*